United States Patent
Meng et al.

(10) Patent No.: US 12,168,655 B2
(45) Date of Patent: *Dec. 17, 2024

(54) APELIN RECEPTOR AGONISTS AND METHODS OF USE

(71) Applicant: BRISTOL-MYERS SQUIBB COMPANY, Princeton, NJ (US)

(72) Inventors: Wei Meng, Pennington, NJ (US); Hannguang J. Chao, Nashua, NH (US); Heather Finlay, Skillman, NJ (US); R. Michael Lawrence, Yardley, PA (US); Michael C. Myers, Newtown, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 22 days.

This patent is subject to a terminal disclaimer.

(21) Appl. No.: 17/836,596

(22) Filed: Jun. 9, 2022

(65) Prior Publication Data

US 2022/0315569 A1 Oct. 6, 2022

Related U.S. Application Data

(62) Division of application No. 15/779,194, filed as application No. PCT/US2016/064562 on Dec. 2, 2016, now Pat. No. 11,390,616.

(60) Provisional application No. 62/263,106, filed on Dec. 4, 2015.

(51) Int. Cl.
| | |
|---|---|
| *C07D 413/10* | (2006.01) |
| *C07D 239/54* | (2006.01) |
| *C07D 401/10* | (2006.01) |
| *C07D 401/12* | (2006.01) |
| *C07D 401/14* | (2006.01) |
| *C07D 403/10* | (2006.01) |
| *C07D 413/06* | (2006.01) |
| *C07D 417/06* | (2006.01) |
| *C07D 417/14* | (2006.01) |

(52) U.S. Cl.
CPC ......... *C07D 413/10* (2013.01); *C07D 239/54* (2013.01); *C07D 401/10* (2013.01); *C07D 401/12* (2013.01); *C07D 401/14* (2013.01); *C07D 403/10* (2013.01); *C07D 413/06* (2013.01); *C07D 417/06* (2013.01); *C07D 417/14* (2013.01)

(58) Field of Classification Search
CPC .................................................. C07D 413/10
USPC ..................................................... 514/235.8
See application file for complete search history.

(56) References Cited

U.S. PATENT DOCUMENTS

| | | |
|---|---|---|
| 6,310,069 B1 | 10/2001 | Lohray et al. |
| 11,390,616 B2 | 7/2022 | Meng et al. |
| 2014/0005181 A1 | 1/2014 | Smith et al. |

FOREIGN PATENT DOCUMENTS

| | | |
|---|---|---|
| EP | 0 693 477 A1 | 1/1996 |
| EP | 1 903 052 A2 | 3/2008 |
| GB | 2 263 639 A | 8/1993 |
| WO | WO1996/37481 A1 | 11/1996 |
| WO | WO1999/08501 A2 | 2/1999 |
| WO | WO2002/06242 A2 | 1/2002 |
| WO | WO2003/072107 A1 | 9/2003 |
| WO | WO2004/094408 A1 | 11/2004 |
| WO | WO2005/026148 A1 | 3/2005 |
| WO | WO2005/060654 A2 | 7/2005 |
| WO | WO2007/043835 A1 | 4/2007 |
| WO | WO2007/064797 A2 | 6/2007 |
| WO | WO2012/020742 A1 | 2/2012 |
| WO | WO2014/031928 A2 | 2/2014 |
| WO | WO2014/044738 A1 | 3/2014 |
| WO | WO2016/196771 A1 | 12/2016 |
| WO | WO2017/066402 A1 | 4/2017 |
| WO | WO2017/106396 A1 | 6/2017 |
| WO | WO2017/165640 A1 | 9/2017 |
| WO | WO2017/218617 A1 | 12/2017 |
| WO | WO2017/218633 A1 | 12/2017 |
| WO | WO2018/071622 A1 | 4/2018 |

OTHER PUBLICATIONS

Cao, Jiangang et al., "Targeting Drugs to APJ Receptor: The Prospect of Treatment of Hypertension and Other Cardiovascular Diseases", Current Drug Targets, vol. 16, pp. 148-155 (2015).
Kappe, Thomas et al., "1,4-Dipolare Cycloadditionen an mesoionische 1,3-Thiazine", Chem Ber. vol. 109, pp. 3668-3674 (1976).

(Continued)

*Primary Examiner* — Taofiq A Solola
(74) *Attorney, Agent, or Firm* — Hong Liu

(57) ABSTRACT

The present invention provides compounds of Formula (I):

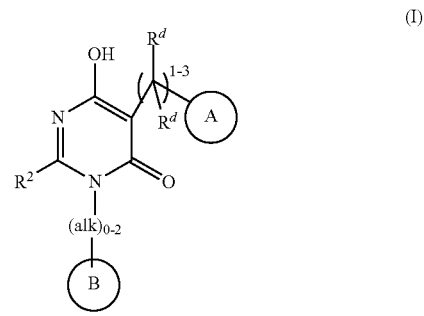

wherein all variables are as defined in the specification, and compositions comprising any of such novel compounds. These compounds are APJ agonists which may be used as medicaments.

14 Claims, No Drawings

(56) References Cited

OTHER PUBLICATIONS

Schindler, et al., "Mesoionic six-membered heterocycles, VI. Rearrangement reactions of heterocycles, IV. Thermal rearrangement of mesoionic N-benzylpyrimidines", Anorganische Chemie, Organische Chemie, vol. 31B(4), pp. 500-504 (1976).
Chemical Abstracts Compounds report listing compounds 1-136.
NCBI:SID 58283610 (May 27, 2009) XP055335443.
Ncbi: SID 58283605 (May 27, 2009) XP055335452.
NCBI:SID 58283610 (May 27, 2009) XP055335455.
Chemical Abstract Registry RN896947-37-8 "4(3H)-Pyrimidinone, 3-[(2-chlorophenyl)methyl]-6-hydroxy-2-phenyl-5-(phenylmethyl)-" XP55335892 (Jul. 20, 2006).

APELIN RECEPTOR AGONISTS AND METHODS OF USE

CROSS REFERENCE TO RELATED APPLICATIONS

This application is a divisional application of patent application Ser. No. 15/779,194, filed May 25, 2018, (now allowed) which is a 371 International Application of PCT/US2016/064562, filed Dec. 2, 2016, which claims the priority benefit of U.S. Provisional Application No. 62/263,106, filed Dec. 4, 2015, which is incorporated herein in its entirety.

FIELD OF THE INVENTION

The present invention provides substituted hydroxypyrimidinones, and their analogues thereof, which are APJ agonists, compositions containing them, and methods of using them, for example, for the treatment or prophylaxis of heart failure, atherosclerosis, ischemic heart disease and related conditions.

BACKGROUND OF THE INVENTION

Heart failure (HF) and related complications constitute major health burden in developed countries with an estimated prevalence of 5,700,000 in the United States alone (Roger, V. L. et al., *Circulation*, 125(1):e2-e220 (2012)). Despite considerable advances in recent two decades, the prognosis remains very poor, with survival rates of only ~50% within 5-years of diagnosis (Roger, V. L. et al., *JAMA*, 292(3):344-350 (2004)). In addition to poor survival, the impaired quality of life and recurrent hospitalizations constitute clear unmet medical need for development of novel treatment options.

HF is a clinical syndrome characterized by the inability of the heart to deliver sufficient supply of blood and oxygen to meet the metabolic demands of organs in the body. Main symptoms associated with HF include shortness of breath due to pulmonary edema, fatigue, reduced tolerance to exercise and lower extremity edemas. The etiology of HF is highly complex with multiple associated risk factors and potential causes.

Among the leading causes of HF are coronary artery disease and cardiac ischemia, acute myocardial infarction, intrinsic cardiomyopathies and chronic uncontrolled hypertension. HF can develop either acutely (functional impairment post myocardial infarction) or as a chronic condition, characterized by long-term maladaptive cardiac tissue remodeling, hypertrophy and cardiac dysfunction (for example due to uncontrolled long-term hypertension). According to the diagnostic criteria and type of ventricular dysfunction, HF is classified to two major groups, HF with "reduced ejection fraction" (HFrEF) or HF with "preserved ejection fraction" (HFpEF). Both types are associated with similar signs and symptoms, but differ in the type of ventricular functional impairment (Borlaug, B. A. et al., *Eur. Heart J.*, 32(6):670-679 (2011)).

APJ receptor (APLNR) and its endogenous peptidic ligand apelin have been implicated as important modulators of cardiovascular function and candidates for therapeutic intervention in HF (for review see Japp, A. G. et al., *Biochem. Pharmacol.*, 75(10):1882-1892 (2008)).

Accumulated evidence from preclinical disease models and human heart failure patients have implicated apelin and APJ agonism as beneficial in the setting of HF. Mice lacking Apelin or APJ gene have impaired myocyte contractility (Charo, D. N. et al., *Am. J. Physiol. Heart Circ. Physiol.*, 297(5):H1904-H1913 (2009)). Apelin knockout (KO) mice develop progressive cardiac dysfunction with aging and are more susceptible to HF in the model of trans-aortic constriction (TAC) (Kuba, K. et al., *Circ. Res.*, 101(4):e32-42 (2007)). The functional impairment in chronic HF is a result of prolonged demand on the heart and is associated with maladaptive cardiac remodeling, manifested by the cardiac hypertrophy, increased inflammation and interstitial fibrosis which eventually lead to decrease in cardiac performance.

Acute administration of apelin increases cardiac output in rodents under normal conditions and also in models of heart failure (Berry, M. F., *Circulation*, 110(11 Suppl. 1):II187-II193 (2004)). Increased cardiac output is a result of direct augmentation of cardiac contractility and reduced peripheral vascular resistance in the arterial and venous beds (Ashley, E. A., *Cardiovasc. Res.*, 65(1):73-82 (2005)). Reduction in the vascular resistance leads to lower pre-load and after-load on the heart and thus lesser work load (Cheng, X. et al., *Eur. J. Pharmacal.*, 470(3):171-175 (2003)). Similar to rodent studies, acute infusion of apelin to healthy human subjects and patients with heart failure produces similar hemodynamic responses with increased cardiac output and increased vasodilatory response in peripheral and coronary arteries (Japp, A. G. et al., *Circulation*, 121(16):1818-1827 (2010)).

The mechanisms underlying inotropic action of apelin are not well understood, but appear to be distinct from clinically used $\beta_1$-adrenergic agonists (dobutamine) due to lack of increase in heart rate. The vasodilatory action of apelin is primarily mediated via endothelial nitric oxide synthase pathways (Tatemoto, K., *Regul. Pept.*, 99(2-3):87-92 (2001)). Apelin is induced under hypoxic conditions, promotes angiogenesis and has been shown to limit the infarct size in ischemia-reperfusion models (Simpkin, J. C., *Basic Res. Cardiol.*, 102(6):518-528 (2007)).

In addition to aforementioned studies evaluating acute administration of apelin, several studies have clearly demonstrated beneficial effects of prolonged administration of apelin in a number of chronic rodent models of HF, including the angiotensin II model, TAC model and rat Dahl salt-sensitive model (Siddiquee, K. et al., *J. Hypertens.*, 29(4):724-731 (2011); Scimia, M. C. et al., *Nature*, 488 (7411):394-398 (2012); Koguchi, W. et al., *Circ. J.*, 76(1): 137-144 (2012)). In these studies, prolonged apelin infusion reduced cardiac hypertrophy and cardiac fibrosis, and was associated with improvement in cardiac performance.

Genetic evidence is also emerging that polymorphisms in the APJ gene are associated with slower progression of HF (Sarzani, R. et al., *J. Card. Fail.*, 13(7):521-529 (2007)). Importantly, while expression of APJ and apelin can be reduced or vary considerably with HF progression, the cardiovascular hemodynamic effects of apelin are sustained in patients with developed HF and receiving standard of care therapy (Japp, A. G. et al., *Circulation*, 121(16):1818-1827 (2010)).

In summary, there is a significant amount of evidence to indicate that APJ receptor agonism plays a cardioprotective role in HF and would be of potential benefit to HF patients. Apelin's very short half life in circulation limits its therapeutic utility, and consequently, there is a need for APJ receptor agonists with improved pharmacokinetic and signaling profile while maintaining or enhancing the beneficial effects of endogenous APJ agonist apelin.

SUMMARY OF THE INVENTION

The present invention provides substituted hydroxypyrimidinones, and their analogues thereof, which are useful as APJ agonists, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of multiple diseases or disorders associated with APJ, such as heart failure, coronary artery disease, cardiomyopathy, diabetes and related conditions including but not limited to acute coronary syndrome, myocardial ischemia, hypertension, pulmonary hypertension, coronary vasospasm, cerebral vasospasm, ischemia/reperfusion injury, angina, renal disease, metabolic syndrome and insulin resistance.

The compounds of the invention may be used in therapy.

The compounds of the invention may be used for the manufacture of a medicament for the treatment and/or prophylaxis of multiple diseases or disorders associated with APJ.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present disclosure provides, inter alia, a compound of Formula (I):

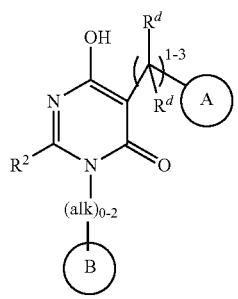

(I)

or a stereoisomer, an enantiomer, a diastereoisomer and, a tautomer, a pharmaceutically acceptable salt, or a solvate thereof, wherein:
  alk is $C_{1-6}$ alkyl substituted with 1-5 $R^4$;
  ring A is independently selected from 5- or 6-membered aryl and heteroaryl comprising carbon atoms and 1-4 heteroatoms selected from N, $NR^{3a}$, O, and S, each substituted with 1-4 $R^3$;
  ring B is independently selected from aryl, heteroaryl, and cycloalkyl, each substituted with 1-4 $R^1$;
  $R^1$ is independently selected from H, halogen, $NO_2$, $-(CH_2)_nOR^b$, $(CH_2)_nS(O)_pR_c$, $-(CH_2)_nC(=O)R^b$, $-(CH_2)_nNR^aR^a$, $-(CH_2)_nCN$, $-(CH_2)_nC(=O)NR^aR^a$, $-(CH_2)_nNR^aC(=O)R^b$, $-(CH_2)_nNR^aC(=O)NR^aR^a$, $-(CH_2)_nNR^aC(=O)OR^b$, $-(CH_2)_nOC(=O)NR^aR^a$, $-(CH_2)_nC(=O)OR^b$, $-(CH_2)_nS(O)_pNR^aR^a$, $-(CH_2)_nNR^aS(O)_pNR^aR^a$, $-(CH_2)_nNR^aS(O)_pR^c$, $C_{1-4}$ alkyl substituted with 0-3 $R^e$, $-(CH_2)_n-C_{3-6}$ carbocyclyl substituted with 0-3 $R^e$, and $-(CH_2)_n$-heterocyclyl substituted with 0-3 $R^e$;

$R^2$ is independently selected from $C_{1-5}$ alkyl substituted with 0-3 $R^e$; $C_{1-5}$ alkenyl substituted with 0-3 $R^e$, aryl substituted with 0-3 $R^e$, heterocyclyl substituted with 0-3 $R^e$, and $C_{3-6}$ cycloalkyl substituted with 0-3 $R^e$; provided when $R^2$ is $C_{1-5}$ alkyl, the carbon atom and the groups attached thereto except the one attached to the pyrimidine ring may be replaced by O, N, and S;
  $R^3$ is independently selected from H, halogen, $-(CH_2)_nOR^b$, $-(CH_2)_nS(O)_pR_c$, $-(CH_2)_nC(=O)R^b$, $-(CH_2)_nNR^aR^a$, $-(CH_2)_nCN$, $-(CH_2)_nC(=O)NR^aR^a$, $-(CH_2)_nNR^aC(=O)R^b$, $-(CH_2)_nNR^aC(=O)NR^aR^a$, $-(CH_2)_nNR^aC(=O)OR^b$, $-(CH_2)_nOC(=O)NR^aR^a$, $-(CH_2)_nC(=O)OR^b$, $-(CH_2)_nS(O)_pNR^aR^a$, $-(CH_2)_nNR^aS(O)_pNR^aR^a$, $-(CH_2)_nNR^aS(O)_pR^c$, $C_{1-5}$ alkyl substituted with 0-3 $R^e$, $(CH_2)_n-C_{3-6}$ carbocyclyl substituted with 0-3 $R^e$, and $-(CH_2)_n$-heterocyclyl substituted with 0-3 $R^e$;
  $R^{3a}$ is independently selected from H, $-S(O)_pR_c$, $-C(=O)R^b$, $-C(=O)NR^aR^a$, $-C(=O)OR^b$, $-S(O)_pNR^aR^a$, $C_{1-5}$ alkyl substituted with 0-3 $R^e$, $-(CH_2)_n-C_{3-6}$ carbocyclyl substituted with 0-3 $R^e$, and $-(CH_2)_n$-heterocyclyl substituted with 0-3 $R^e$;
  $R^4$ is independently selected from $C_{1-5}$ alkyl substituted with 0-3 $R^e$, $(CH_2)_n-C_{3-6}$ carbocyclyl substituted with 0-3 $R^e$, and $-(CH_2)_n$-heterocyclyl substituted with 0-3 $R^e$;
  $R^a$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, $-(CH_2)_n-C_{3-10}$carbocyclyl substituted with 0-5 $R^e$, and $-(CH_2)_n$-heterocyclyl substituted with 0-5 $R^e$; or $R^a$ and $R^a$ together with the nitrogen atom to which they are both attached form a heterocyclic ring substituted with 0-5 $R^e$;
  $R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, $-(CH_2)_n-C_{3-10}$carbocyclyl substituted with 0-5 $R^e$, and $-(CH_2)_n$-heterocyclyl substituted with 0-5 $R^e$;
  $R^c$, at each occurrence, is independently selected from $C_{1-6}$ alkyl substituted with 0-5 $R^e$, $C_{2-6}$alkenyl substituted with 0-5 $R^e$, $C_{2-6}$alkynyl substituted with 0-5 $R^e$, $C_{3-6}$carbocyclyl, and heterocyclyl;
  $R^d$, at each occurrence, is independently selected from H and $C_{1-6}$ alkyl substituted with 0-5 $R^e$;
  $R^e$, at each occurrence, is independently selected from $C_{1-6}$ alkyl substituted with 0-5 $R_f$, $C_{2-6}$ alkenyl, $C_{2-6}$ alkynyl, $-(CH_2)_n-C_{3-6}$ cycloalkyl, $-(CH_2)_n-C_{4-6}$ heterocyclyl, $-(CH_2)_n$-aryl, $-(CH_2)_n$-heteroaryl, F, Cl, Br, CN, $NO_2$, $=O$, $CO_2H$, $-(CH_2)_nOR_f$, $S(O)_pR^f$, $C(=O)NR^fR^f$, $NR^fC(=O)R^f$, $S(O)_pNR^fR^f$, $NR^fS(O)_pR^f$, $NR^fC(=O)OR^f$, $OC(=O)NR^fR^f$ and $-(CH_2)_nNR^fR^f$;
  $R^f$, at each occurrence, is independently selected from H, F, Cl, Br, CN, OH, $C_{1-5}$alkyl (optionally substituted with halogen and OH), $C_{3-6}$ cycloalkyl, and phenyl, or $R^f$ and $R^f$ together with the nitrogen atom to which they are both attached form a heterocyclic ring optionally substituted with $C_{1-4}$alkyl;

n is independently selected from zero, 1, 2, and 3; and p, at each occurrence, is independently selected from zero, 1, and 2.

In a second aspect, the present disclosure provides a compound of Formula (I), or a stereoisomer, an enantiomer, a diastereoisomer, a tautomer, a pharmaceutically acceptable salt, or a solvate thereof, within the scope of any of the first aspect, wherein:

ring A is independently selected from

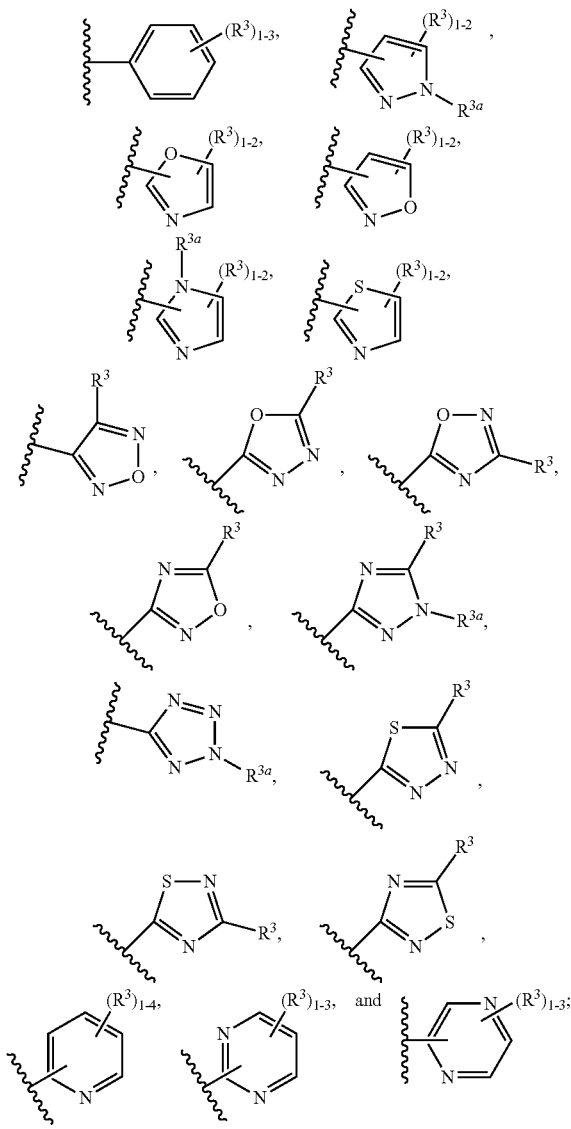

ring B is independently selected from

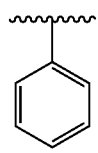

and 6-membered heteroaryl, each substituted with 1-4 $R^1$;

$R^1$ is independently selected from H, F, Cl, Br, $NO_2$, —$(CH_2)_nOR^b$, —$(CH_2)_nS(O)_pR^c$, —$(CH_2)_nC(=O)R^b$, —$(CH_2)_nNR^aR^a$, —$(CH_2)_nC(=O)NR^aR^a$, —$(CH_2)_nNR^aC(=O)R^b$, $C_{1-4}$ alkyl substituted with 0-3 $R^e$ and $C_{3-6}$ cycloalkyl substituted with 0-3 $R^e$;

$R^2$ is independently selected from $C_{2-5}$ alkyl substituted with 0-3 $R^e$; $C_{2-5}$ alkenyl, aryl substituted with 1-3 $R^e$, heterocyclyl substituted with 0-3 $R^e$, and $C_{3-6}$ cycloalkyl; provided when $R^2$ is $C_{1-5}$ alkyl, the carbon atom and the groups attached thereto except the one attached to the pyrimidine ring may be replaced by O, N, and S;

$R^3$ is independently selected from H, halogen, —$(CH_2)_nOR^b$, $(CH_2)_nS(O)_pR^c$, —$(CH_2)_nC(=O)R^b$, —$(CH_2)_nNR^aR^a$, —$(CH_2)_nCN$, —$(CH_2)_nC(=O)NR^aR^a$, —$(CH_2)_nNHC(=O)R^b$, —$(CH_2)_nNHC(=O)NR^aR^a$, —$(CH_2)_nNHC(=O)OR^b$, —$(CH_2)_nOC(=O)NR^aR^a$, —$(CH_2)_nC(=O)OR^b$, —$(CH_2)_nS(O)_pNR^aR^a$, —$(CH_2)_nNHS(O)_pNR^aR^a$, —$(CH_2)_nNHS(O)_pR^c$, $C_{1-5}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^{3a}$ is independently selected from H, $C_{1-4}$ alkyl, —$(CH_2)_n$-aryl substituted with 0-3 $R^e$, and —$(CH_2)_n$-heterocyclyl substituted with 0-3 $R^e$;

$R^a$, at each occurrence, is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^e$, at each occurrence, is independently selected from $C_{1-6}$ alkyl substituted with 0-5 $R_f$, $C_{2-6}$ alkenyl, $C_{2-6}$ alkynyl, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$, —$(CH_2)_nOR^f$, $S(O)_pR^f$, $C(=O)NR^fR^f$, $NR^fC(=O)R^f$, $S(O)_pNR^fR^f$, $NR^fS(O)_pR^f$, $NR^fC(=O)OR^f$, $OC(=O)NR^fR^f$ and —$(CH_2)_nNR^fR^f$;

$R^f$, at each occurrence, is independently selected from H, F, Cl, Br, CN, OH, $C_{1-5}$alkyl (optionally substituted with halogen and OH), $C_{3-6}$ cycloalkyl, and phenyl;

n is independently selected from zero, 1, 2, and 3; and p, at each occurrence, is independently selected from zero, 1, and 2.

In a third aspect, the present disclosure provides a compound of Formula (II):

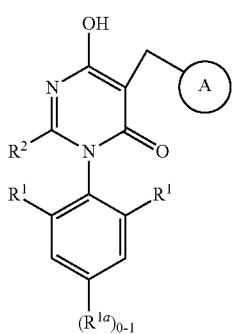

or a stereoisomer, an enantiomer, a diastereoisomer, a tautomer, a pharmaceutically acceptable salt, or a solvate thereof, within the scope of the first or second aspect, wherein:

ring A is independently selected from

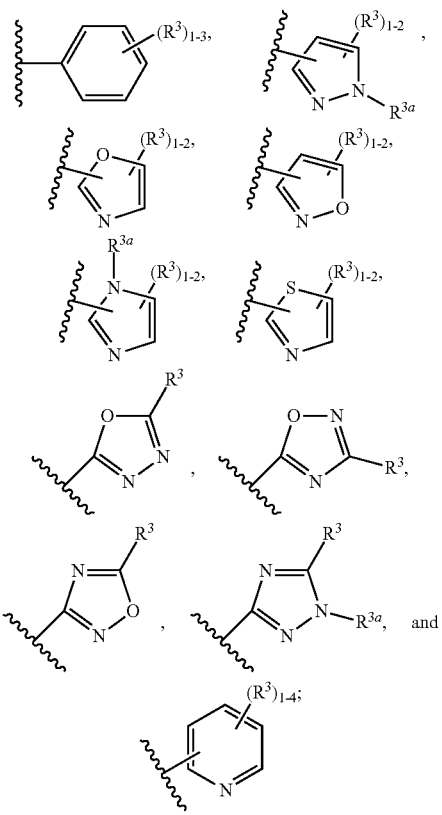

R[1] is independently selected from F, Cl, OH, and $OC_{1-4}$ alkyl;

R[1a] is independently selected from F, Cl, and $C_{1-2}$ alkyl;

R[2] is independently selected from $C_{2-5}$ alkyl substituted with 0-3 $R^e$; $C_{2-5}$ alkenyl, aryl substituted with 1-3 $R^e$, heteroaryl substituted with 0-3 $R^e$, $C_{3-6}$ cycloalkyl and —$(CH_2)_{1-4}OC_{1-5}$alkyl, and —$(CH_2)_{1-3}OC_{3-6}$cycloalkyl;

R[3] is independently selected from H, F, Cl, Br, —$OR^b$, —$(CH_2)_nC(=O)R^b$, $(CH_2)_nS(O)_pR_c$, —$(CH_2)_nC(=O)OR^b$, —$(CH_2)_nNR^aR^a$, CN, —$(CH_2)_nC(=O)NR^aR^a$, —$(CH_2)_nNHC(=O)R^b$, $C_{1-4}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$.

R[3a] is independently selected from H, $CH_3$, —$(CH_2)_n$-aryl substituted with 0-3 $R^e$, and —$(CH_2)_n$-heterocyclyl substituted with 0-3 $R^e$;

R[a], at each occurrence, is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

R[b], at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$.

R[e], at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, and $CO_2H$; and n is independently selected from zero, 1, 2, and 3.

In a fourth aspect, the present disclosure provides a compound of Formula (III):

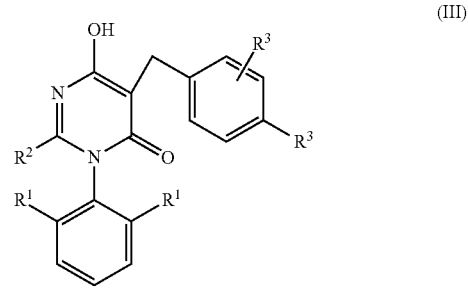

or a stereoisomer, an enantiomer, a diastereoisomer, a tautomer, a pharmaceutically acceptable salt, or a solvate thereof, within the scope of any of the first, second and third aspects, wherein:

R[2] is independently selected from $C_{2-5}$ alkyl substituted with 0-3 $R^e$; $C_{2-5}$ alkenyl, phenyl substituted with 1-3 $R^e$, 6-membered heteroaryl substituted with 0-3 $R^e$, $C_{3-6}$ cycloalkyl and $CH_2O(CH_2)_{1-3}CH_3$;

R[3] is independently selected from H, F, Cl, Br, —$OC_{1-4}$alkyl, $S(O)_2C_{1-4}$alkyl $R_c$, —$(CH_2)_nC(=O)R^b$, —$(CH_2)_nC(=O)OR^b$, —$(CH_2)_nNR^aR^a$, —$C(=O)NR^aR^a$, —$NHC(=O)R^b$, $C_{1-4}$ alkyl substituted with 0-3 $R^e$, and heterocyclyl selected from

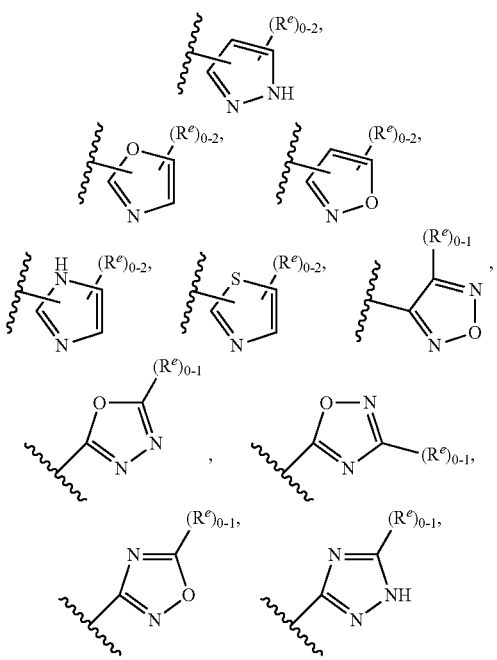

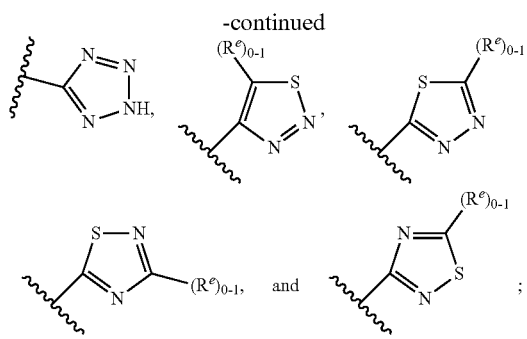

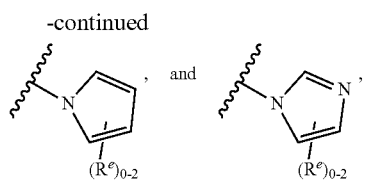

$R^a$, at each occurrence, is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, and $CO_2H$; and n is independently selected from zero, 1, 2, and 3.

In a fifth aspect, the present disclosure provides a compound of Formula (III), or a stereoisomer, an enantiomer, a diastereoisomer, a tautomer, a pharmaceutically acceptable salt, or a solvate thereof, within the scope of any of the first, second, third, and fourth aspects, wherein:

$R^3$ is independently selected from H and —$(CH_2)_{0-1}NR^aR^a$;

$R^a$ and $R^a$ together with the nitrogen atom to which they are both attached form a heterocyclic ring selected from

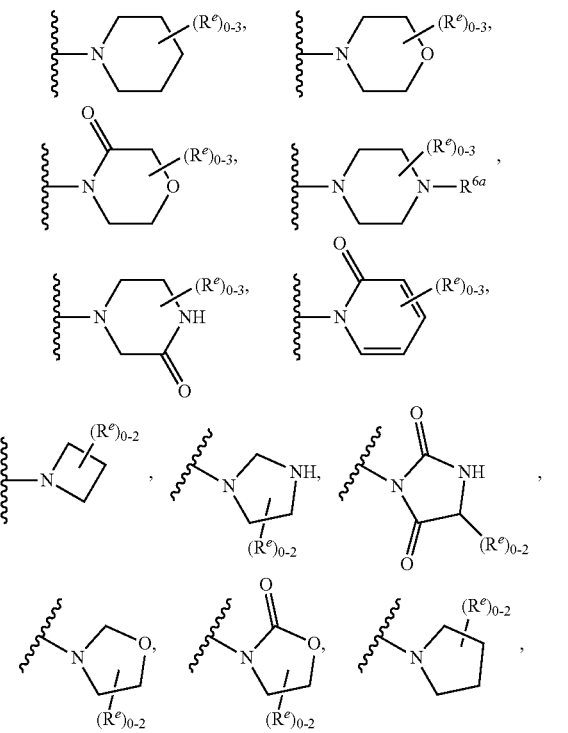

$R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, and $CO_2H$.

In a sixth aspect, the present disclosures provides a compound of Formula (III), or a stereoisomer, an enantiomer, a diastereoisomer, a tautomer, a pharmaceutically acceptable salt, or a solvate thereof, within the scope of any of the first, second and third aspects, wherein:

ring A is independently selected from

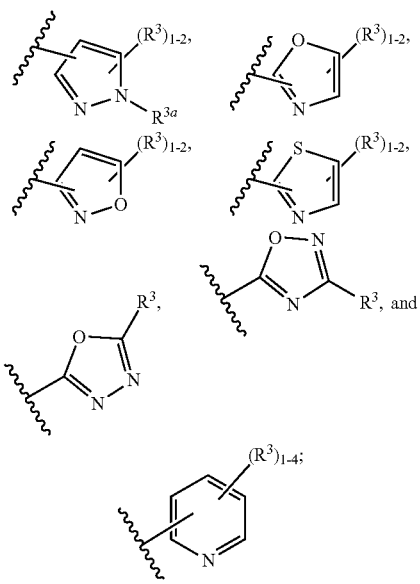

$R^1$ is independently selected from F, Cl, OH, and $OC_{1-4}$ alkyl;

$R^{1a}$ is independently selected from F, Cl, and $C_{1-2}$ alkyl;

$R^2$ is independently selected from $C_{2-5}$ alkyl substituted with 0-3 $R^e$; $C_{2-5}$ alkenyl, phenyl substituted with 1-3 $R^e$, 6-membered heteroaryl substituted with 0-3 $R^e$, $C_{3-6}$ cycloalkyl, and $CH_2O(CH_2)_{1-3}CH_3$;

$R^3$ is independently selected from H, $C_{1-4}$ alkyl substituted with 0-3 $R^e$, and phenyl substituted with 0-3 $R^e$;

$R^{3a}$ is independently selected from H, $CH_3$, and —$(CH_2)_n$-phenyl substituted with 0-3 $R^e$; and $R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, and $CO_2H$.

In a seventh aspect, the present disclosures provides a compound of Formula (IV):

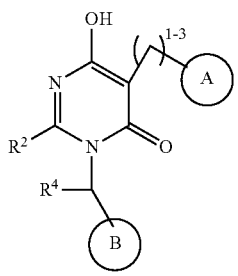

(IV)

or a stereoisomer, an enantiomer, a diastereoisomer, a tautomer, a pharmaceutically acceptable salt, or a solvate thereof, within the scope of the first aspect, wherein:

ring A is independently selected from

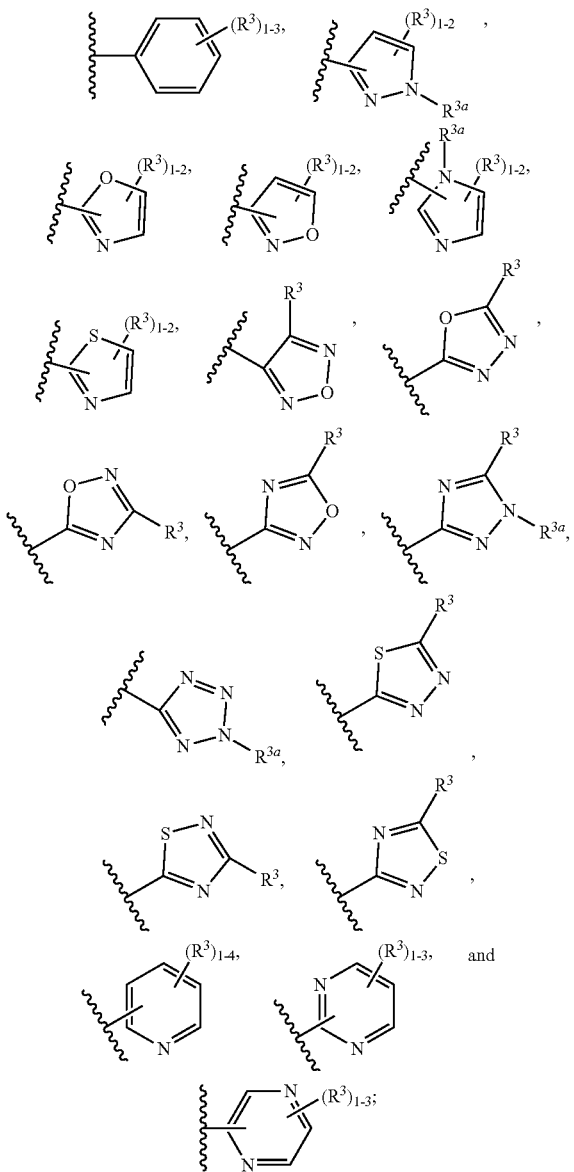

ring B is independently selected from

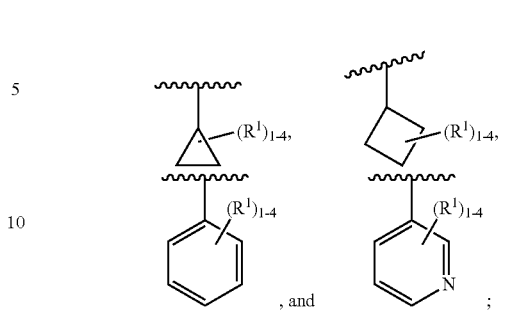

$R^1$ is independently selected from H, F, Cl, Br, $OC_{1-4}$ alkyl, CN, and $C_{1-4}$ alkyl;

$R^2$ is independently selected from $C_{2-5}$ alkyl substituted with 0-3 $R^e$; $C_{2-5}$ alkenyl, phenyl substituted with 1-3 $R^e$, 6-membered heteroaryl substituted with 0-3 $R^e$, $C_{3-6}$ cycloalkyl and $CH_2O(CH_2)_{1-3}CH_3$;

$R^3$ is independently selected from H, F, Cl, Br, $—OR^b$, $—(CH_2)_nC(=O)R^b$, $(CH_2)_nS(O)_pR_c$, $—(CH_2)_nC(=O)OR^b$, $—(CH_2)_nNR^aR^a$, CN, $—(CH_2)_nC(=O)NR^aR^a$, $—(CH_2)_nNHC(=O)R^b$, $C_{1-4}$ alkyl substituted with 0-3 $R^e$, $(CH_2)_n—C_{3-6}$ carbocyclyl substituted with 0-3 $R^e$, and $—(CH_2)_n$-heterocyclyl substituted with 0-3 $R^e$.

$R^{3a}$ is independently selected from H, $CH_3$, $—(CH_2)_n$-aryl substituted with 0-3 $R^e$, and $—(CH_2)_n$-heterocyclyl substituted with 0-3 $R^e$;

$R^4$ is independently selected from $CH_3$, $CH_2CH_3$, $CH_2CH_2CH_3$, $CH(CH_3)_2$, and $CH_2OCH_3$;

$R^a$, at each occurrence, is independently selected from H, $C_{1-6}$ alkyl substituted with 0-5 $R^e$, $—(CH_2)_n—C_{3-10}$carbocyclyl substituted with 0-5 $R^e$, and $—(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, $—(CH_2)_n—C_{3-10}$carbocyclyl substituted with 0-5 $R^e$, and $—(CH_2)_n$-heterocyclyl substituted with 0-5 $R^e$.

$R^e$, at each occurrence, is independently selected from $C_{1-6}$ alkyl (optionally substituted with F and Cl), OH, $OCH_3$, $OCF_3$, $—(CH_2)_n—C_{3-6}$ cycloalkyl, $—(CH_2)_n—C_{4-6}$ heterocyclyl, $—(CH_2)_n$-aryl, $—(CH_2)_n$-heteroaryl, F, Cl, Br, CN, $NO_2$, $=O$, and $CO_2H$; and n is independently selected from zero, 1, 2, and 3.

In an eighth aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the eighth aspect.

In another aspect, the present invention provides compounds of Formula (Ia):

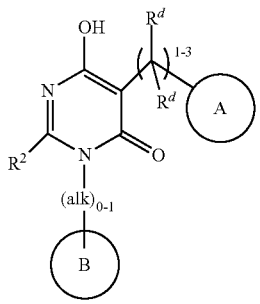

(Ia)

or stereoisomers, enantiomers, diastereoisomers, tautomers, pharmaceutically acceptable salts, solvates, or prodrugs thereof, wherein:

alk is $C_{1-6}$ alkyl substituted with 1-5 $R^4$;

ring A is independently selected from 5- or 6-membered aryl and heteroaryl comprising carbon atoms and 1-4 heteroatoms selected from N, $NR^{3a}$, O, and S, each substituted with 1-4 $R^3$;

ring B is independently selected from aryl, heteroaryl, and cycloalkyl, each substituted with 1-4 $R^1$;

$R^1$ is independently selected from H, halogen, $NO_2$, $-(CH_2)_nOR^b$, $(CH_2)_nS(O)_pR_c$, $-(CH_2)_nC(=O)R^b$, $-(CH_2)_nNR^aR^a$, $-(CH_2)_nCN$, $-(CH_2)_nC(=O)NR^aR^a$, $-(CH_2)_nNR^aC(=O)R^b$, $-(CH_2)_nNR^aC(=O)NR^aR^a$, $-(CH_2)_nNR^aC(=O)OR^b$, $-(CH_2)_nOC(=O)NR^aR^a$, $-(CH_2)_nC(=O)OR^b$, $-(CH_2)_nS(O)_pNR^aR^a$, $-(CH_2)_nNR^aS(O)_pNR^aR^a$, $-(CH_2)_nNR^aS(O)_pR^c$, $C_{1-4}$ alkyl substituted with 0-3 $R^e$, $-(CH_2)_n-C_{3-6}$ carbocyclyl substituted with 0-3 $R^e$, and $-(CH_2)_n$-heterocyclyl substituted with 0-3 $R^e$;

$R^2$ is independently selected from $C_{2-5}$ alkyl substituted with 0-3 $R^e$; $C_{2-5}$ alkenyl substituted with 0-3 $R^e$, aryl substituted with 0-3 $R^e$, heterocyclyl substituted with 0-3 $R^e$, and $C_{3-6}$ cycloalkyl substituted with 1-3 $R^e$; provided when $R^2$ is $C_{1-5}$ alkyl, the carbon atom and the groups attached thereto except the one attached to the pyrimidine ring may be replaced by O, N, and S;

$R^3$ is independently selected from H, halogen, $-(CH_2)_nOR^b$, $-(CH_2)_nS(O)_pR_c$, $-(CH_2)_nC(=O)R^b$, $-(CH_2)_nNR^aR^a$, $-(CH_2)_nCN$, $-(CH_2)_nC(=O)NR^aR^a$, $-(CH_2)_nNR^aC(=O)R^b$, $-(CH_2)_nNR^aC(=O)NR^aR^a$, $-(CH_2)_nNR^aC(=O)OR^b$, $-(CH_2)_nOC(=O)NR^aR^a$, $-(CH_2)_nC(=O)OR^b$, $-(CH_2)_nS(O)_pNR^aR^a$, $-(CH_2)_nNR^aS(O)_pNR^aR^a$, $-(CH_2)_nNR^aS(O)_pR^c$, $C_{1-5}$ alkyl substituted with 0-3 $R^e$, $(CH_2)_n-C_{3-6}$ carbocyclyl substituted with 0-3 $R^e$, and $-(CH_2)_n$-heterocyclyl comprising carbon atoms and 1-4 heteroatoms selected from N, $NR^{3a}$, O, S, and substituted with 0-3 $R^e$;

$R^{3a}$ is independently selected from H, $-S(O)_pR_c$, $-C(=O)R^b$, $-C(=O)NR^aR^a$, $-C(=O)OR^b$, $-S(O)_pNR^aR^a$, $C_{1-5}$ alkyl substituted with 0-3 $R^e$, $-(CH_2)_n-C_{3-6}$ carbocyclyl substituted with 0-3 $R^e$, and $-(CH_2)_n$-heterocyclyl substituted with 0-3 $R^e$;

$R^4$ is independently selected from $C_{1-5}$ alkyl substituted with 0-3 $R^e$, $(CH_2)_n-C_{3-6}$ carbocyclyl substituted with 0-3 $R^e$, and $-(CH_2)_n$-heterocyclyl substituted with 0-3 $R^e$;

$R^a$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, $-(CH_2)_n-C_{3-10}$carbocyclyl substituted with 0-5 $R^e$, and $-(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, $-(CH_2)_n-C_{3-10}$carbocyclyl substituted with 0-5 $R^e$, and $-(CH_2)_n$-heterocyclyl substituted with 0-5 $R^e$;

$R^c$, at each occurrence, is independently selected from $C_{1-6}$ alkyl substituted with 0-5 $R^e$, $C_{2-6}$alkenyl substituted with 0-5 $R^e$, $C_{2-6}$alkynyl substituted with 0-5 $R^e$, $C_{3-6}$carbocyclyl, and heterocyclyl;

$R^d$, at each occurrence, is independently selected from H and $C_{1-6}$ alkyl substituted with 0-5 $R^e$;

$R^e$, at each occurrence, is independently selected from $C_{1-6}$ alkyl (optionally substituted with halogen, OH, and CN), $C_{2-6}$ alkenyl, $C_{2-6}$ alkynyl, $-(CH_2)_n-C_{3-6}$ cycloalkyl, $-(CH_2)_n-C_{4-6}$ heterocyclyl, $-(CH_2)_n$-aryl, $-(CH_2)_n$-heteroaryl, F, Cl, Br, CN, $NO_2$, $=O$, $CO_2H$, $-(CH_2)_nOR_f$, $S(O)_pR^f$, $C(=O)NR^fR^f$, $NR^fC(=O)R^f$, $S(O)_pNR^fR^f$, $NR^fS(O)_pR^f$, $NR^fC(=O)OR^f$, $OC(=O)NR^fR^f$ and $-(CH_2)_nNR^fR^f$;

$R^f$, at each occurrence, is independently selected from H, $C_{1-5}$alkyl (optionally substituted with halogen and OH), $C_{3-6}$ cycloalkyl, and phenyl, or $R^f$ and $R^f$ together with the nitrogen atom to which they are both attached form a heterocyclic ring optionally substituted with $C_{1-4}$alkyl;

n is independently selected from zero, 1, 2, and 3; and p, at each occurrence, is independently selected from zero, 1, and 2.

In another aspect, the present invention provides compounds of Formula (Ia), or stereoisomers, enantiomers, diastereoisomers, tautomers, pharmaceutically acceptable salts, solvates, or prodrugs thereof, wherein:

ring A is independently selected from

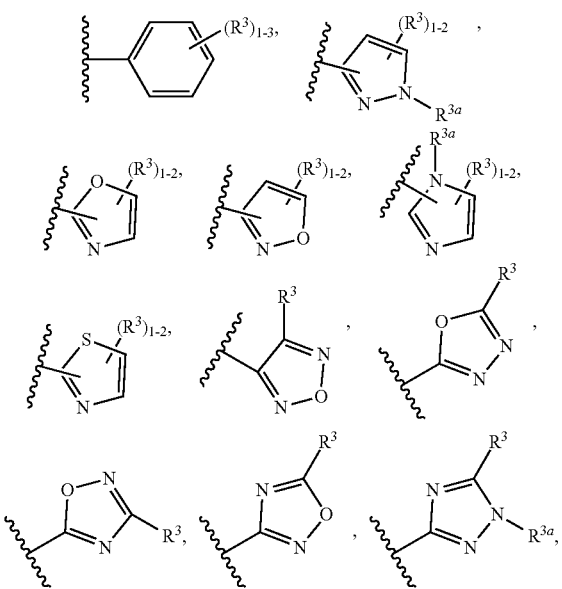

-continued

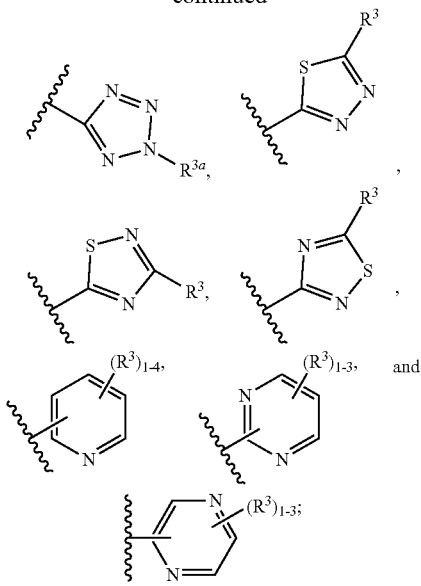

ring B is independently selected from

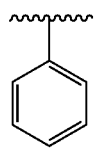 [SMILES: *c1ccccc1]

and 6-membered heteroaryl, each substituted with 1-4 $R^1$;

$R^1$ is independently selected from H, F, Cl, Br, $NO_2$, —$(CH_2)_nOR^b$, —$(CH_2)_nS(O)_pR_c$, —$(CH_2)_nC(=O)R^b$, —$(CH_2)_nNR^aR^a$, —$(CH_2)_nC(=O)NR^aR^a$, —$(CH_2)_nNR^aC(=O)R^b$, $C_{1-4}$ alkyl substituted with 0-3 $R^e$ and $C_{3-6}$ cycloalkyl substituted with 0-3 $R^e$;

$R^2$ is independently selected from $C_{2-5}$ alkyl substituted with 0-3 $R^e$; $C_{2-5}$ alkenyl, aryl substituted with 1-3 $R^e$, heterocyclyl substituted with 0-3 $R^e$, and $C_{3-6}$ cycloalkyl; provided when $R^2$ is $C_{1-5}$ alkyl, the carbon atom and the groups attached thereto except the one attached to the pyrimidine ring may be replaced by O, N, and S;

$R^3$ is independently selected from H, halogen, —$(CH_2)_nOR^b$, $(CH_2)_nS(O)_pR_c$, —$(CH_2)_nC(=O)R^b$, —$(CH_2)_nNR^aR^a$, —$(CH_2)_nCN$, —$(CH_2)_nC(=O)NR^aR^a$, —$(CH_2)_nNHC(=O)R^b$, —$(CH_2)_nNHC(=O)NR^aR^a$, —$(CH_2)_nNHC(=O)OR^b$, —$(CH_2)_nOC(=O)NR^aR^a$, —$(CH_2)_nC(=O)OR^b$, —$(CH_2)_nS(O)_pNR^aR^a$, —$(CH_2)_nNHS(O)_pNR^aR^a$, —$(CH_2)_nNHS(O)_pR^c$, $C_{1-5}$ alkyl substituted with 0-3 $R^e$, $(CH_2)_n$—$C_{3-6}$ carbocyclyl substituted with 0-3 $R^e$, and —$(CH_2)_n$-heterocyclyl comprising carbon atoms and 1-4 heteroatoms selected from N, $NR^{3a}$, O, S, and substituted with 0-3 $R^e$;

$R^{3a}$ is independently selected from H, $C_{1-4}$ alkyl, —$(CH_2)_n$-aryl substituted with 0-3 $R^e$, and —$(CH_2)_n$-heterocyclyl substituted with 0-3 $R^e$;

$R^a$, at each occurrence, is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$.

$R^e$, at each occurrence, is independently selected from $C_{1-6}$ alkyl (optionally substituted with halogen, OH, and CN), $C_{2-6}$ alkenyl, $C_{2-6}$ alkynyl, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$, —$(CH_2)_nOR_f$, $S(O)_pR^f$, $C(=O)NR^fR^f$, $NR^fC(=O)R^f$, $S(O)_pNR^fR^f$, $NR^fS(O)_pR^f$, $NR^fC(=O)OR^f$, $OC(=O)NR^fR^f$ and —$(CH_2)_nNR^fR^f$;

$R^f$, at each occurrence, is independently selected from H, $C_{1-5}$alkyl (optionally substituted with halogen and OH), $C_{3-6}$ cycloalkyl, and phenyl;

n is independently selected from zero, 1, 2, and 3; and p, at each occurrence, is independently selected from zero, 1, and 2.

In another aspect, the present invention provides compounds of Formula (II):

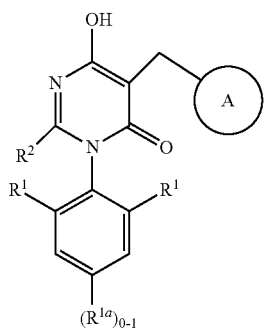

(II)

or stereoisomers, enantiomers, diastereoisomers, tautomers, pharmaceutically acceptable salts, solvates, or prodrugs thereof, wherein:

ring A is independently selected from

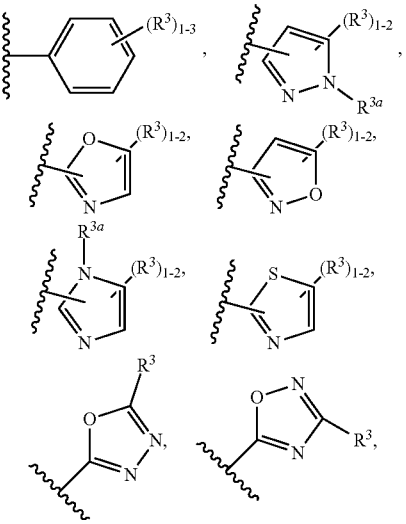

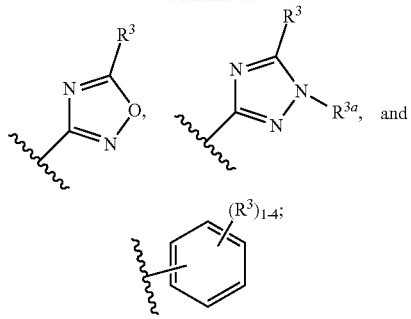

R[1] is independently selected from F, Cl, OH, $C_{1-3}$ alkyl, and $OC_{1-3}$ alkyl;

R[1a] is independently selected from F, Cl, and $C_{1-2}$ alkyl;

R[2] is independently selected from $C_{1-5}$ alkyl substituted with 0-3 R[e]; $C_{2-5}$ alkenyl, aryl substituted with 1-3 R[e], heteroaryl substituted with 0-3 R[e], $C_{3-6}$ cycloalkyl and —$(CH_2)_{1-4}OC_{1-5}$alkyl, and —$(CH_2)_{1-3}OC_{3-6}$cycloalkyl;

R[3] is independently selected from H, F, Cl, Br, —OR[b], —$(CH_2)_n$C(=O)R[b], —$(CH_2)_n$S(O)$_p$R[c], —$(CH_2)_n$C(=O)OR[b], —$(CH_2)_n$NR[a]R[a], CN, —$(CH_2)_n$C(=O)NR[a]R[a], —$(CH_2)_n$NHC(=O)R[b], $C_{1-4}$ alkyl substituted with 0-3 R[e], $(CH_2)_n$—$C_{3-6}$ carbocyclyl substituted with 0-3 R[e], and —$(CH_2)_n$-heterocyclyl comprising carbon atoms and 1-4 heteroatoms selected from N, NR[3a], O, S, and substituted with 0-3 R[e];

R[3a] is independently selected from H, CH$_3$, —$(CH_2)_n$-aryl substituted with 0-3 R[e], and —$(CH_2)_n$-heterocyclyl substituted with 0-3 R[e];

R[a], at each occurrence, is independently selected from H, $C_{1-6}$ alkyl substituted with 0-5 R[e], —$(CH_2)_n$—$C_{3-10}$carbocyclyl substituted with 0-5 R[e], —$(CH_2)_n$-heterocyclyl substituted with 0-5 R[e]; or R[a] and R[a] together with the nitrogen atom to which they are both attached form a heterocyclic ring substituted with 0-5 R[e];

R[b], at each occurrence, is independently selected from H, $C_{1-6}$ alkyl substituted with 0-5 R[e], $C_{2-6}$ alkenyl substituted with 0-5 R[e], $C_{2-6}$ alkynyl substituted with 0-5 R[e], —$(CH_2)_n$—$C_{3-10}$carbocyclyl substituted with 0-5 R[e], and —$(CH_2)_n$-heterocyclyl substituted with 0-5 R[e];

R[e], at each occurrence, is independently selected from $C_{1-6}$ alkyl (optionally substituted with F and Cl), OH, OCH$_3$, OCF$_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, NO$_2$, =O, CO$_2$H, and CONH$_2$; and n is independently selected from zero, 1, 2, and 3.

In another aspect, the present invention provides compounds of Formula (III):

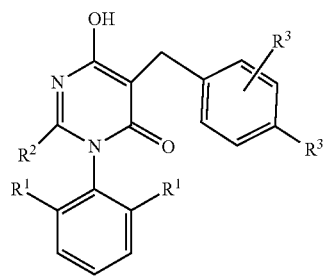

(III)

or stereoisomers, enantiomers, diastereoisomers, tautomers, pharmaceutically acceptable salts, solvates, or prodrugs thereof, wherein:

R[1] is independently selected from $C_{1-3}$ alkyl and —$OC_{1-3}$ alkyl;

R[2] is independently selected from $C_{2-5}$ alkyl substituted with 0-3 R[e]; $C_{2-5}$ alkenyl, aryl substituted with 1-3 R[e], heteroaryl substituted with 0-3 R[e], $C_{3-6}$ cycloalkyl, —$(CH_2)_{1-4}OC_{1-5}$alkyl, and —$(CH_2)_{1-3}OC_{3-6}$cycloalkyl;

R[3] is independently selected from H, F, Cl, Br, —$OC_{1-4}$alkyl, $S(O)_2C_{1-4}$alkyl R$_c$, —$(CH_2)_n$C(=O)R[b], —$(CH_2)_n$C(=O)OR[b], —$(CH_2)_n$NR[a]R[a], —C(=O)NR[a]R[a], —NHC(=O)R[b], $C_{1-4}$ alkyl substituted with 0-3 R[e], $C_{3-6}$ carbocyclyl selected from

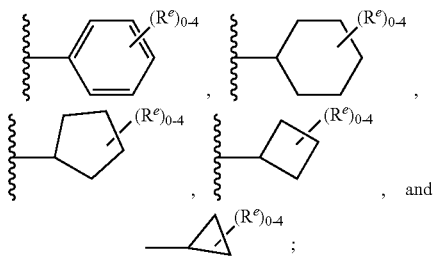

and heterocyclyl selected from

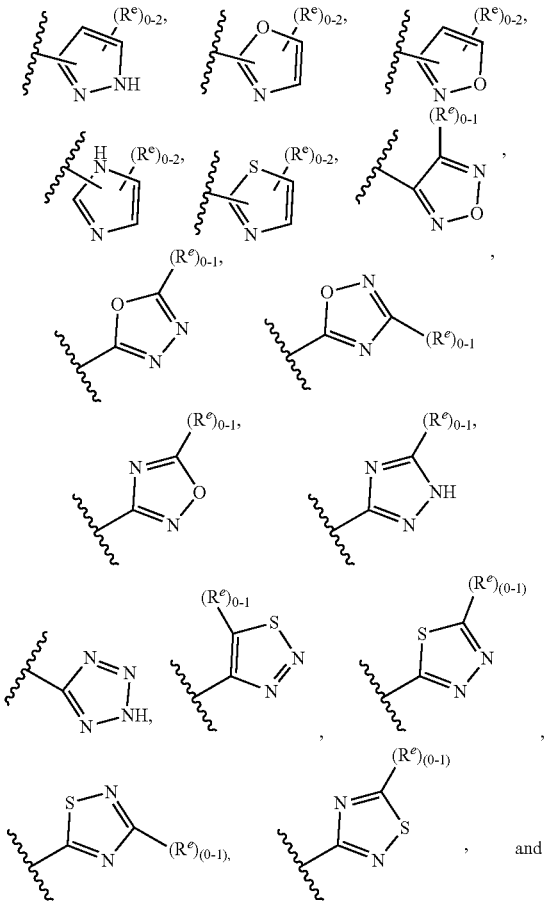

-continued

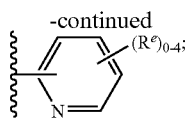

$R^a$, at each occurrence, is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, and $CO_2H$, and $CONH_2$; and n is independently selected from zero, 1, 2, and 3.

In another aspect, the present invention provides compounds of Formula (IIIa):

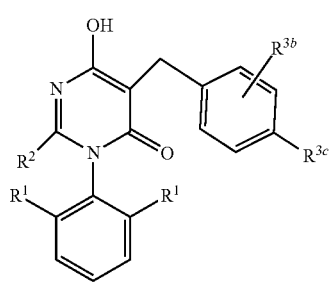

(IIIa)

or stereoisomers, enantiomers, diastereoisomers, tautomers, pharmaceutically acceptable salts, solvates, or prodrugs thereof, wherein:

$R^1$ is independently selected from $C_{1-3}$ alkyl and —$OC_{1-3}$ alkyl;

$R^2$ is independently selected from $C_{2-5}$ alkyl substituted with 0-3 $R^e$, phenyl substituted with 1-3 $R^e$, 5-membered heteroaryl substituted with 0-3 $R^e$, $C_{3-6}$ cycloalkyl, —$(CH_2)_{1-4}OC_{1-5}$alkyl, and —$(CH_2)_{1-3}OC_{3-6}$cycloalkyl;

$R^{3b}$ is independently selected from H, F, Cl, and Br;

$R^{3c}$ is independently selected from H, —$(CH_2)_nNR^aR^a$,

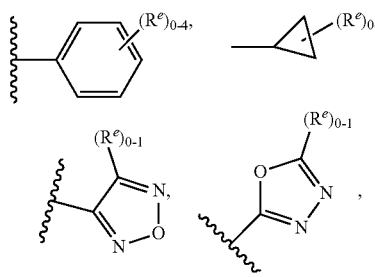

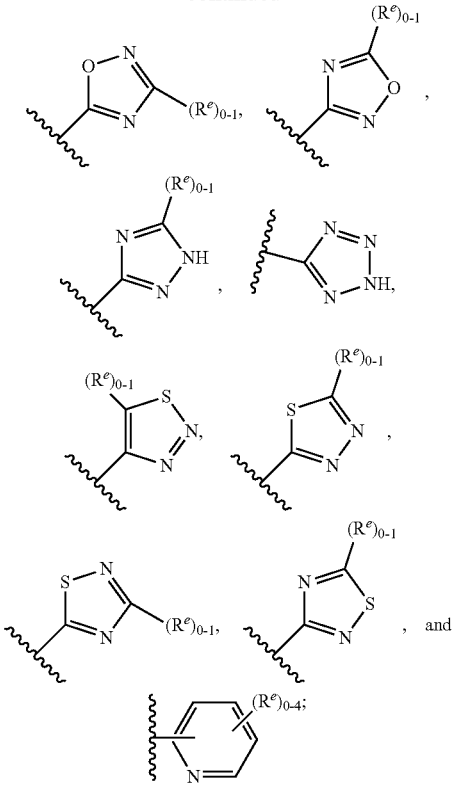

$R^a$, at each occurrence, is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$, and $CONH_2$; and n is independently selected from zero, 1, 2, and 3.

In another aspect, the present invention provides compounds of Formula (IIIa), or stereoisomers, enantiomers, diastereoisomers, tautomers, pharmaceutically acceptable salts, solvates, or prodrugs thereof, wherein:

$R^1$ is independently selected from $C_{1-3}$ alkyl and —$OC_{1-3}$ alkyl;

$R^2$ is independently selected from $C_{2-5}$ alkyl substituted with 0-3 $R^e$; $C_{2-5}$ alkenyl, phenyl substituted with 1-3 $R^e$, 5-membered heteroaryl substituted with 0-3 $R^e$, $C_{3-6}$ cycloalkyl and $CH_2O(CH_2)_{1-3}CH_3$;

$R^3$ is independently selected from H and —$(CH_2)_{0-1}NR^aR^a$;

$R^a$ and $R^a$ together with the nitrogen atom to which they are both attached form a heterocyclic ring selected from

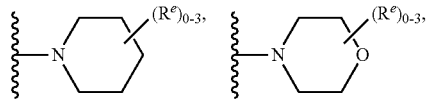

-continued

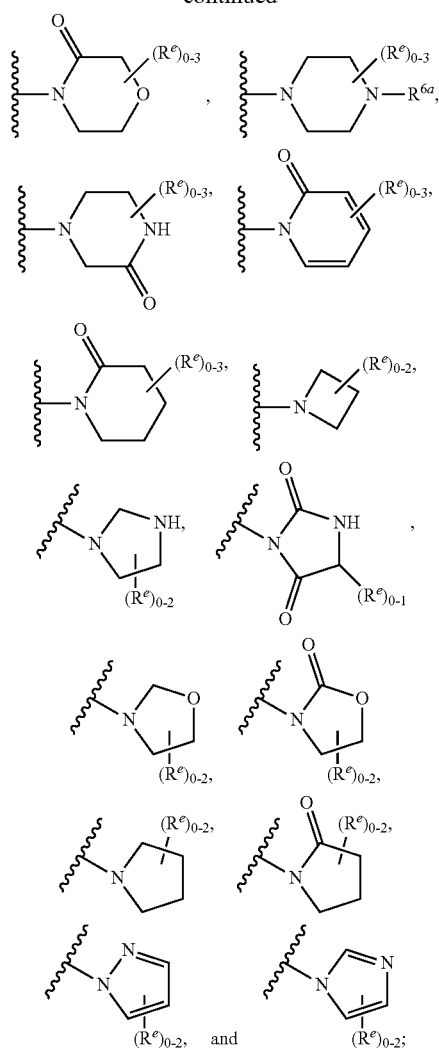

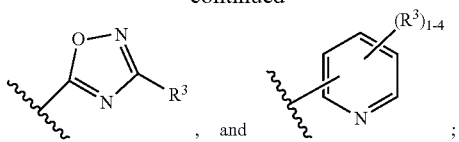

, and

R[1] is independently selected from F, Cl, OH, and $OC_{1-4}$ alkyl;
R[1a] is independently selected from F, Cl, and $C_{1-2}$ alkyl;
R[2] is independently selected from $C_{2-5}$ alkyl substituted with 0-3 $R^e$; $C_{2-5}$ alkenyl, phenyl substituted with 1-3 $R^e$, 5- or 6-membered heteroaryl substituted with 0-3 $R^e$, $C_{3-6}$ cycloalkyl and $CH_2O(CH_2)_{1-3}CH_3$;
R[3] is independently selected from H, $C_{1-4}$ alkyl substituted with 0-3 $R^e$, and phenyl substituted with 0-3 $R^e$;
R[3a] is independently selected from H, $CH_3$, and $-(CH_2)_n$-phenyl substituted with 0-3 $R^e$; and
$R^e$, at each occurrence, is independently selected from $C_{1-6}$ alkyl (optionally substituted with F and Cl), OH, $OCH_3$, $OCF_3$, $-(CH_2)_n-C_{3-6}$ cycloalkyl, $-(CH_2)_n-C_{4-6}$ heterocyclyl, $-(CH_2)_n$-aryl, $-(CH_2)_n$-heteroaryl, F, Cl, Br, CN, $NO_2$, =O, and $CO_2H$;
and other variables are as defined in Formula (IIIa).

In another aspect, the present invention provides compounds of Formula (IV):

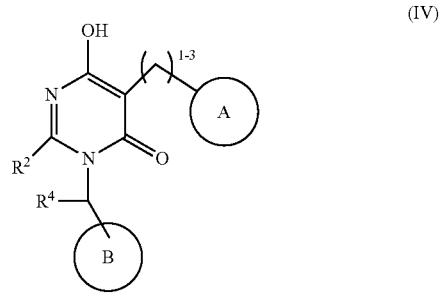

(IV)

or stereoisomers, enantiomers, diastereoisomers, tautomers, pharmaceutically acceptable salts, solvates, or prodrugs thereof, wherein:
ring A is independently selected from

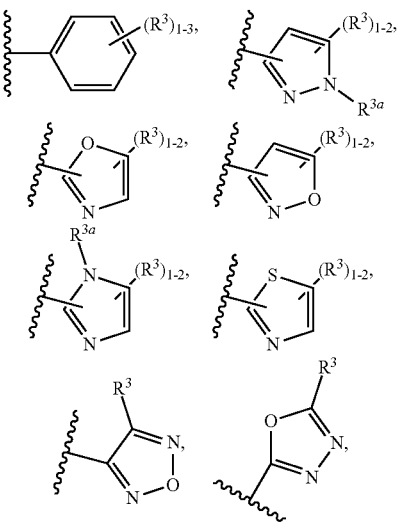

$R^e$, at each occurrence, is independently selected from $C_{1-6}$ alkyl (optionally substituted with F and Cl), OH, $OCH_3$, $OCF_3$, $-(CH_2)_n-C_{3-6}$ cycloalkyl, $-(CH_2)_n-C_{4-6}$ heterocyclyl, $-(CH_2)_n$-aryl, $-(CH_2)_n$-heteroaryl, F, Cl, Br, CN, $NO_2$, =O, and $CO_2H$.

In another aspect, the present invention provides compounds of Formula (IIIa), or stereoisomers, enantiomers, diastereoisomers, tautomers, pharmaceutically acceptable salts, solvates, or prodrugs thereof, wherein:
ring A is independently selected from

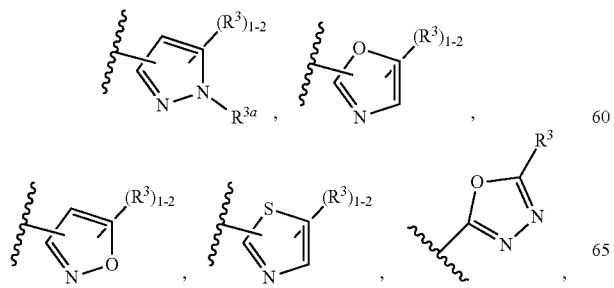

-continued

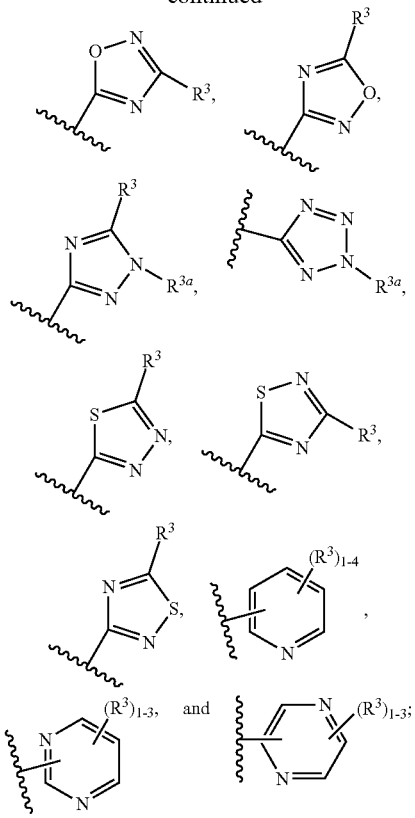

ring B is independently selected from

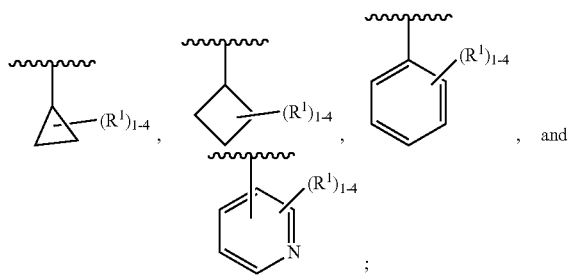

$R^1$ is independently selected from H, F, Cl, Br, $OC_{1-4}$ alkyl, CN, and $C_{1-4}$ alkyl;
$R^2$ is independently selected from $C_{2-5}$ alkyl substituted with 0-3 $R^e$; $C_{2-5}$ alkenyl, phenyl substituted with 1-3 $R^e$, 5- or 6-membered heteroaryl substituted with 0-3 $R^e$, $C_{3-6}$ cycloalkyl and $CH_2O(CH_2)_{1-3}CH_3$;
$R^3$ is independently selected from H, F, Cl, Br, —$OR^b$, —$(CH_2)_nC(=O)R^b$, $(CH_2)_nS(O)_pR_c$, —$(CH_2)_nC(=O)OR^b$, —$(CH_2)_nNR^aR^a$, CN, —$(CH_2)_nC(=O)NR^aR^a$, —$(CH_2)_nNHC(=O)R^b$, $C_{1-4}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;
$R^{3a}$ is independently selected from H, $CH_3$, —$(CH_2)_n$-aryl substituted with 0-3 $R^e$, and —$(CH_2)_n$-heterocyclyl substituted with 0-3 $R^e$;
$R^4$ is independently selected from $CH_3$, $CH_2CH_3$, $CH_2CH_2CH_3$, $CH(CH_3)_2$, and $CH_2OCH_3$;
$R^a$, at each occurrence, is independently selected from H, $C_{1-6}$ alkyl substituted with 0-5 $R^e$, —$(CH_2)_n$—$C_{3-10}$ carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;
$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$ carbocyclyl substituted with 0-5 $R^e$, and —$(CH_2)_n$-heterocyclyl substituted with 0-5 $R^e$;
$R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$, and $CONH_2$; and
n is independently selected from zero, 1, 2, and 3.

In another aspect, the present invention provides compounds of Formula (V):

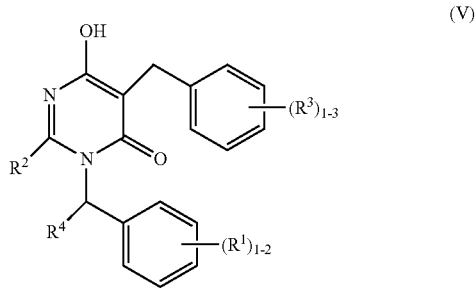

(V)

or a stereoisomer, an enantiomer, a diastereoisomer, a tautomer, or a pharmaceutically acceptable salt thereof, wherein:
$R^1$ is independently selected from H, F, Cl, Br, $OC_{1-4}$ alkyl, CN, and $C_{1-4}$ alkyl;
$R^2$ is independently selected from —$CH_2(CH_2)_{1-3}CH_3$, —$CH_2OCH(CH_3)_2$, —$(CH_2)_{1-3}C_{3-6}$cycloalkyl,

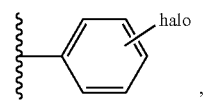

5-membered heteroaryl selected from

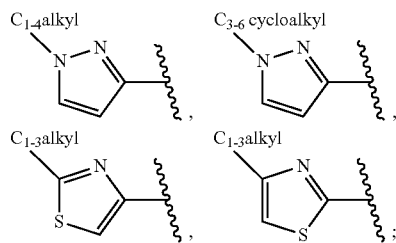

and $CH_2O(CH_2)_{1-3}CH_3$;
$R^3$ is independently selected from H, F, Cl, Br, $C_{3-6}$alkyl, phenyl substituted with 0-3 $R^e$, and 5- or 6-membered heteroaryl substituted with 0-3 $R^e$;
$R^4$ is independently selected from $CH_3$, $CH_2CH_3$, $CH_2CH_2CH_3$, $CH(CH_3)_2$, and $CH_2OCH_3$;

$R^e$, at each occurrence, is independently selected from $C_{1-6}$ alkyl (optionally substituted with F and Cl), OH, OCH$_3$, OCF$_3$, —(CH$_2$)$_n$—$C_{3-6}$ cycloalkyl, —(CH$_2$)$_n$—$C_{4-6}$ heterocyclyl, —(CH$_2$)$_n$-aryl, —(CH$_2$)$_n$-heteroaryl, F, Cl, Br, CN, NO$_2$, =O, CO$_2$H, and CONH$_2$; and n is independently selected from zero, 1, 2, and 3.

In another aspect, the present invention provides compounds of Formula (VI):

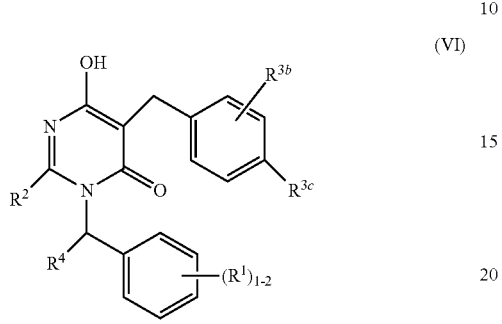

(VI)

or stereoisomers, enantiomers, diastereoisomers, tautomers, pharmaceutically acceptable salts, solvates, or prodrugs thereof, wherein:

$R^1$ is independently selected from H, F, Cl, Br, OC$_{1-4}$ alkyl, CN, and C$_{1-4}$ alkyl;

$R^2$ is independently selected from —CH$_2$(CH$_2$)$_{1-3}$CH$_3$, —CH$_2$OCH(CH$_3$)$_2$, —(CH$_2$)$_{1-3}$C$_{3-6}$cycloalkyl,

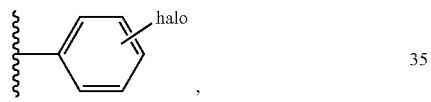

5-membered heteroaryl selected from

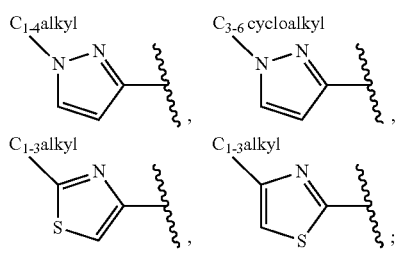

and CH$_2$O(CH$_2$)$_{1-3}$CH$_3$;

$R^{3b}$ is independently selected from H and F;

$R^{3c}$ is independently selected from

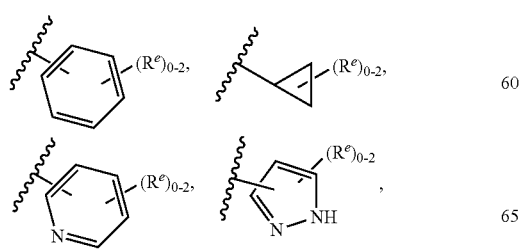

$R^4$ is independently selected from CH$_3$, CH$_2$CH$_3$, CH$_2$CH$_2$CH$_3$, CH(CH$_3$)$_2$, and CH$_2$OCH$_3$;

$R^e$, at each occurrence, is independently selected from $C_{1-6}$ alkyl (optionally substituted with F and Cl), OH, OCH$_3$, OCF$_3$, —(CH$_2$)$_n$—$C_{3-6}$ cycloalkyl, —(CH$_2$)$_n$—$C_{4-6}$ heterocyclyl, —(CH$_2$)$_n$-aryl, —(CH$_2$)$_n$-heteroaryl, F, Cl, Br, CN, NO$_2$, =O, CO$_2$H, and CONH$_2$; and n is independently selected from zero, 1, 2, and 3.

In one non-limiting embodiment of Formula (IIIa), ring A is

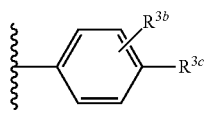

ring B is

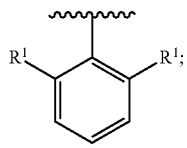

$R^1$ is independently selected from Et and OMe; $R^2$ is independently selected from —CH$_2$CH$_2$CH$_2$CH$_3$, —CH$_2$CH$_2$CH(CH$_3$)$_2$, —CH$_2$OCH(CH$_3$)$_2$, —CH$_2$OC$_{3-6}$ cycloalkyl, —CH$_2$CH$_2$C$_{3-6}$ cycloalkyl, C$_{3-6}$ cycloalkyl,

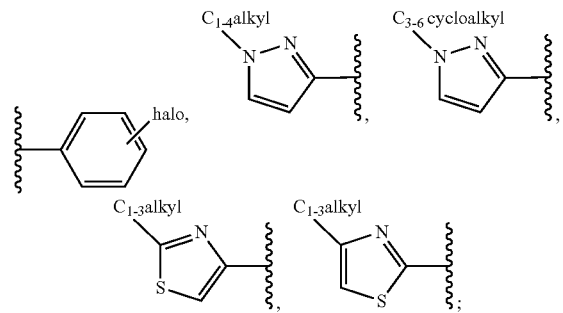

$R^{3b}$ is independently selected from H, F, Cl, and Br; $R^{3c}$ is independently selected from H, —OC$_{1-4}$alkyl, NH$_2$C(═O)C$_{1-4}$alkyl, —C(═O)NHC$_{1-4}$alkyl, —S(O)$_2$C$_{1-3}$ alkyl, —S(O)$_2$NH$_2$, C$_{1-4}$ alkyl substituted with 0-3 $R^e$,

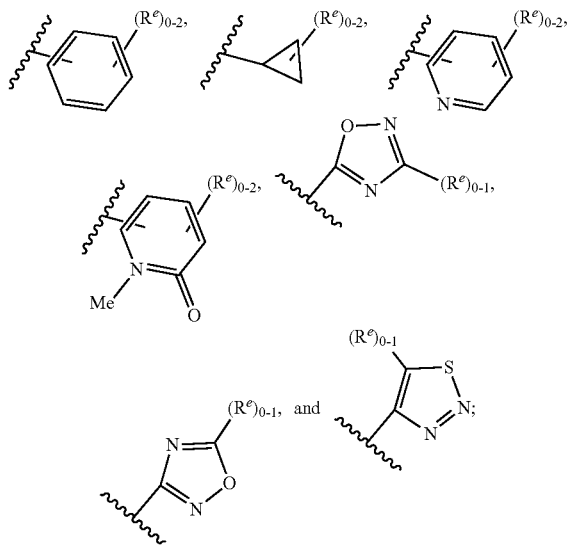

$R^e$, at each occurrence, is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, ═O, CO$_2$H, and CONH$_2$; and n is independently selected from zero, 1, 2, and 3.

In another non-limiting embodiment of Formula (IIIa), ring A is

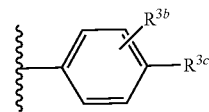

ring B is

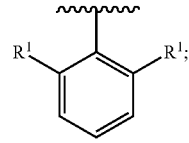

$R^1$ is independently selected from Et and OMe; $R^2$ is independently selected from —CH$_2$CH$_2$CH$_2$CH$_3$, —CH$_2$CH$_2$CH(CH$_3$)$_2$, —CH$_2$OCH(CH$_3$)$_2$, —CH$_2$OC$_{3-6}$ cycloalkyl, —CH$_2$CH$_2$C$_{3-6}$ cycloalkyl, C$_{3-6}$ cycloalkyl,

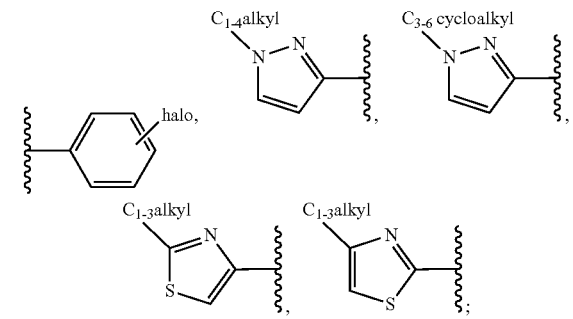

$R^{3b}$ is independently selected from H, F, Cl, and Br; $R^{3c}$ is —(CH$_2$)$_{0-1}$NR$^a$R$^a$ wherein R$^a$ and R$^a$ together with the nitrogen atom to which they are both attached form a heterocyclic ring selected from

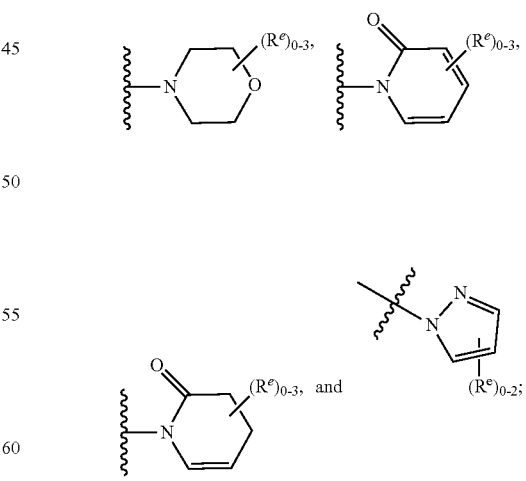

$R^e$, at each occurrence, is independently selected from C$_{1-3}$ alkyl, F, Cl, and Br.

In another non-limiting embodiment of Formula (IIIa), ring A is

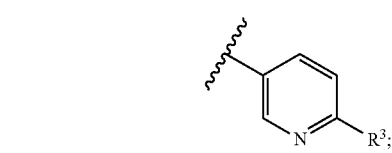

ring B is

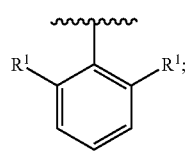

$R^1$ is independently selected from Et and OMe; $R^2$ is independently selected from —CH$_2$CH$_2$CH$_2$CH$_3$, —CH$_2$CH$_2$CH(CH$_3$)$_2$, —CH$_2$OCH(CH$_3$)$_2$, —CH$_2$OC$_{3-6}$ cycloalkyl, —CH$_2$CH$_2$C$_{3-6}$ cycloalkyl, C$_{3-6}$ cycloalkyl,

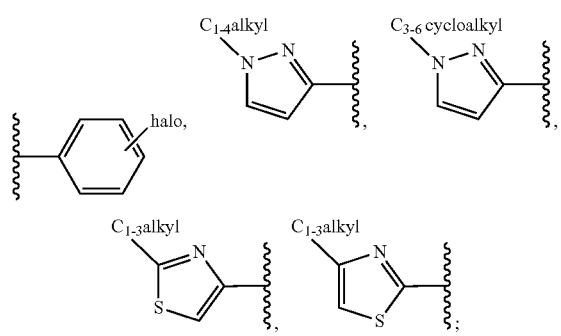

$R^3$ is

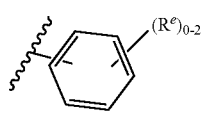

$R^e$, at each occurrence, is independently selected from C$_{1-6}$ alkyl (optionally substituted with F and Cl), OH, OCH$_3$, OCF$_3$, F, Cl, Br, and CN.

In another non-limiting embodiment of Formula (IIIa), ring A is independently selected from

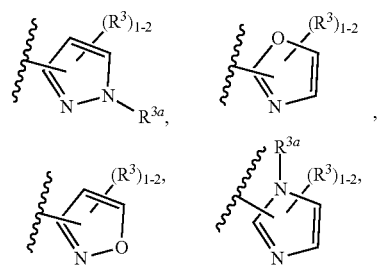

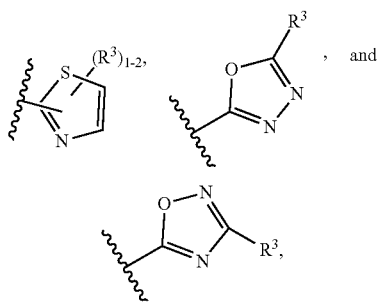

, and

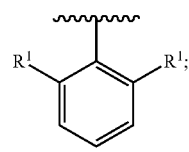

$R^1$ is independently selected from Et and OMe; $R^2$ is independently selected from —CH$_2$CH$_2$CH$_2$CH$_3$, —CH$_2$CH$_2$CH(CH$_3$)$_2$, —CH$_2$OCH(CH$_3$)$_2$, —CH$_2$OC$_{3-6}$ cycloalkyl, —CH$_2$CH$_2$C$_{3-6}$ cycloalkyl, C$_{3-6}$ cycloalkyl,

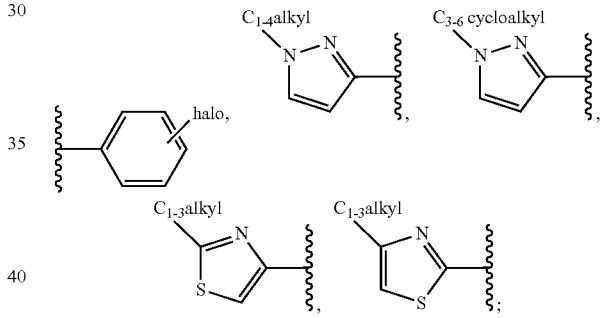

$R^3$ and $R^{3a}$ are independently selected from H, C$_{1-4}$ alkyl, and

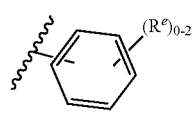

$R^e$, at each occurrence, is independently selected from C$_{1-6}$ alkyl (optionally substituted with F and Cl), OH, OCH$_3$, OCF$_3$, F, Cl, Br, and CN.

In one non-limiting embodiment of Formula (VI), ring A is

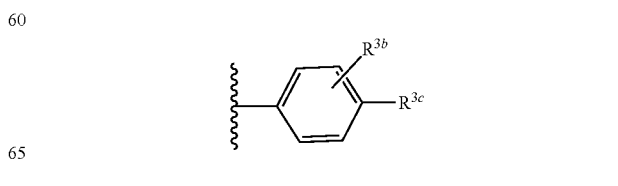

ring B is

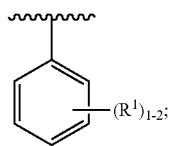

R¹ is independently selected from H, F, Cl, Br, $OC_{1-4}$ alkyl, CN, and $C_{1-4}$ alkyl; R² is independently selected from —$CH_2CH_2CH_2CH_3$, —$CH_2CH_2CH(CH_3)_2$, —$CH_2OCH(CH_3)_2$, —$CH_2OC_{3-6}$ cycloalkyl, —$CH_2CH_2C_{3-6}$ cycloalkyl, $C_{3-6}$ cycloalkyl,

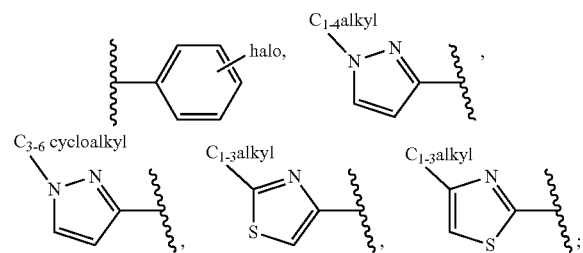

$R^{3b}$ is independently selected from H, F, Cl, and Br; $R^{3c}$ is independently selected from H, —$OC_{1-4}$alkyl, $NH_2C(=O)C_{1-4}$alkyl, —$C(=O)NHC_{1-4}$alkyl, —$S(O)_2C_{1-3}$ alkyl, —$S(O)_2NH_2$, $C_{1-4}$ alkyl substituted with 0-3 $R^e$,

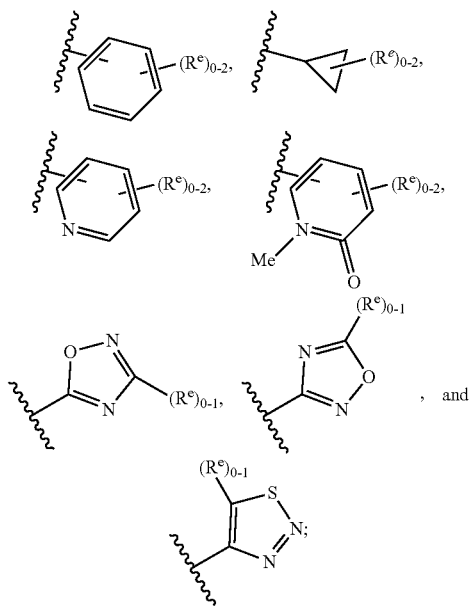

$R^4$ is independently selected from $CH_3$, $CH_2CH_3$, $CH_2CH_2CH_3$, $CH(CH_3)_2$, and $CH_2OCH_3$; $R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$, and $CONH_2$; and n is independently selected from zero, 1, 2, and 3.

In another aspect, the present invention provides a compound selected from 3-(2,6-dimethoxyphenyl)-6-hydroxy-2-(3-methylbutyl)-5-{[4-(2-oxo-1,2-dihydropyridin-1-yl)phenyl]methyl}-3,4-dihydropyrimidin-4-one (1),
2-butyl-3-(2,6-dimethoxyphenyl)-6-hydroxy-5-[(4-methoxyphenyl)methyl]-3,4-dihydropyrimidin-4-one (2),
2-butyl-6-hydroxy-3-(2-methoxyphenyl)-5-[(4-methoxyphenyl)methyl]-3,4-dihydropyrimidin-4-one (3),
2-butyl-3-(2,6-dimethoxyphenyl)-6-hydroxy-5-{[4-(1,2,4-oxadiazol-3-yl)phenyl]methyl}-3,4-dihydropyrimidin-4-one (4),
2-butyl-3-(2,6-dimethoxyphenyl)-6-hydroxy-5-{[4-(1H-pyrazol-1-yl)phenyl]methyl}-3,4-dihydropyrimidin-4-one (5),
2-butyl-3-(2,6-dimethoxyphenyl)-5-{[2-fluoro-4-(1,2,4-oxadiazol-3-yl)phenyl]methyl}-6-hydroxy-3,4-dihydropyrimidin-4-one (6),
2-butyl-3-(2,6-dimethoxyphenyl)-6-hydroxy-5-[(4-methanesulfonylphenyl)methyl]-3,4-dihydropyrimidin-4-one (7),
2-butyl-3-(2,6-dimethoxyphenyl)-6-hydroxy-5-[(5-methyl-1,2-oxazol-3-yl)methyl]-3,4-dihydropyrimidin-4-one (8),
N-(4-{[2-butyl-1-(2,6-dimethoxyphenyl)-4-hydroxy-6-oxo-1,6-dihydropyrimidin-5-yl]methyl}phenyl)acetamide (9),
2-butyl-3-(2,6-dimethoxyphenyl)-6-hydroxy-5-{[4-(3-methyl-1,2,4-oxadiazol-5-yl)phenyl]methyl}-3,4-dihydropyrimidin-4-one (10),
2-butyl-5-{[2-(4-chlorophenyl)-1,3-oxazol-4-yl]methyl}-3-(2,6-dimethoxyphenyl)-6-hydroxy-3,4-dihydropyrimidin-4-one (11),
2-butyl-3-(2,6-dimethoxyphenyl)-6-hydroxy-5-{[4-(1,2,3-thiadiazol-4-yl)phenyl]methyl}-3,4-dihydropyrimidin-4-one (12),
2-butyl-3-(2,6-dimethoxyphenyl)-5-{[3-fluoro-4-(1,2,4-oxadiazol-3-yl)phenyl]methyl}-6-hydroxy-3,4-dihydropyrimidin-4-one (13),
2-butyl-5-{[6-(4-chlorophenyl)pyridin-3-yl]methyl}-3-(2,6-dimethoxyphenyl)-6-hydroxy-3,4-dihydropyrimidin-4-one (14),
4-{[2-butyl-1-(2,6-dimethoxyphenyl)-4-hydroxy-6-oxo-1,6-dihydropyrimidin-5-yl]methyl}-N-ethylbenzamide (15),
N-(4-{[1-(2,6-dimethoxyphenyl)-4-hydroxy-2-(3-methylbutyl)-6-oxo-1,6-dihydropyrimidin-5-yl]methyl}phenyl)acetamide (16),
3-(2,6-dimethoxyphenyl)-6-hydroxy-2-(3-methylbutyl)-5-{[4-(1,2,4-oxadiazol-3-yl)phenyl]methyl}-3,4-dihydropyrimidin-4-one (17),
5-{[2-(4-chlorophenyl)-1,3-oxazol-4-yl]methyl}-3-(2,6-dimethoxyphenyl)-6-hydroxy-2-(3-methylbutyl)-3,4-dihydropyrimidin-4-one (18),
5-benzyl-2-butyl-3-(2,6-dimethoxyphenyl)-6-hydroxy-3,4-dihydropyrimidin-4-one (19),
2-butyl-3-(2,6-dimethoxyphenyl)-6-hydroxy-5-({3-[4-(trifluoromethyl)phenyl]-1,2,4-oxadiazol-5-yl}methyl)-3,4-dihydropyrimidin-4-one (20),
3-(2,6-dimethoxyphenyl)-6-hydroxy-2-(3-methylbutyl)-5-{[5-(4-methylphenyl)-1,3,4-oxadiazol-2-yl]methyl}-3,4-dihydropyrimidin-4-one (21),
2-butyl-5-{[2-(4-chlorophenyl)-1,3-thiazol-4-yl]methyl}-3-(2,6-dimethoxyphenyl)-6-hydroxy-3,4-dihydropyrimidin-4-one (22),
2-butyl-3-(2,6-dimethoxyphenyl)-6-hydroxy-5-{[2-(4-methylphenyl)-1,3-thiazol-4-yl]methyl}-3,4-dihydropyrimidin-4-one (23),
2-butyl-5-{[1-(4-chlorophenyl)-1H-pyrazol-3-yl]methyl}-3-(2,6-dimethoxyphenyl)-6-hydroxy-3,4-dihydropyrimidin-4-one (24), 2-butyl-3-(2,6-dimethoxyphenyl)-6-hydroxy-5-{[1-(4-methylphenyl)-1H-pyrazol-4-yl]methyl}-3,4-dihydropyrimidin-4-one (25), 2-butyl-5-{[2-(4-chlorophenyl)-1,3-thiazol-5-yl]methyl}-3-(2,6-dimethoxyphenyl)-6-hydroxy-3,4-dihydropyrimidin-4-one (26), 2-butyl-3-(2,6-dimethoxyphenyl)-6-hydroxy-5-{[4-(1H-pyrazol-1-ylmethyl)phenyl]methyl}-3,4-dihydropyrimidin-4-one (27), 2-butyl-3-(2,6-dimethoxyphenyl)-6-hydroxy-5-{[4-(2-oxo-1,2-dihydropyridin-1-yl)phenyl]methyl}-3,4-dihydropyrimidin-4-one (28), 2-butyl-3-(2,6-dimethoxyphenyl)-6-hydroxy-5-{[6-(4-methoxyphenyl)pyridin-3-yl]methyl}-3,4-dihydropyrimidin-4-one (29), 5-[(1-benzyl-1H-pyrazol-4-yl)methyl]-2-butyl-3-(2,6-dimethoxyphenyl)-6-hydroxy-3,4-dihydropyrimidin-4-one (30), 5-{[1-(4-chlorophenyl)-1H-pyrazol-3-yl]methyl}-3-(2,6-dimethoxyphenyl)-2-(ethoxymethyl)-6-hydroxy-3,4-dihydropyrimidin-4-one (31), 3-(2,6-dimethoxyphenyl)-2-(ethoxymethyl)-6-hydroxy-5-{[4-(1,2,4-oxadiazol-3-yl)phenyl]methyl}-3,4-dihydropyrimidin-4-one (32), 5-{[2-(4-chlorophenyl)-1,3-oxazol-4-yl]methyl}-3-(2,6-dimethoxyphenyl)-2-(ethoxymethyl)-6-hydroxy-3,4-dihydropyrimidin-4-one (33), 3-(2,6-dimethoxyphenyl)-6-hydroxy-2-(3-methylbutyl)-5-{[4-(2-oxo-1,2-dihydropyridin-1-yl)phenyl]methyl}-3,4-dihydropyrimidin-4-one (34), 2-butyl-3-(2,6-dimethoxyphenyl)-6-hydroxy-5-{[4-(2-oxopiperidin-1-yl)phenyl]methyl}-3,4-dihydropyrimidin-4-one (35), 2-butyl-3-(2,6-dimethoxyphenyl)-6-hydroxy-5-{[4-(morpholin-4-yl)phenyl]methyl}-3,4-dihydropyrimidin-4-one (36), 3-(2,6-dimethoxyphenyl)-5-(4-(5-fluoro-2-oxopyridin-1(2H)-yl)benzyl)-2-(4-fluorophenyl)-6-hydroxypyrimidin-4(3H)-one (37), 2-cyclopentyl-3-(2,6-dimethoxyphenyl)-6-hydroxy-5-{[4-(2-oxo-1,2-dihydropyridin-1-yl)phenyl]methyl}-3,4-dihydropyrimidin-4-one (38), 2-(cyclobutoxymethyl)-3-(2,6-dimethoxyphenyl)-6-hydroxy-5-{[4-(2-oxo-1,2-dihydropyridin-1-yl)phenyl]methyl}-3,4-dihydropyrimidin-4-one (39), 2-(cyclopropoxymethyl)-3-(2,6-dimethoxyphenyl)-6-hydroxy-5-{[4-(2-oxo-1,2-dihydropyridin-1-yl)phenyl]methyl}-3,4-dihydropyrimidin-4-one (40), 2-(2-cyclopropylethyl)-3-(2,6-dimethoxyphenyl)-6-hydroxy-5-{[4-(2-oxo-1,2-dihydropyridin-1-yl)phenyl]methyl}-3,4-dihydropyrimidin-4-one (41), 2-butyl-5-{[4-(4-chloro-2-oxo-1,2-dihydropyridin-1-yl)phenyl]methyl}-3-(2,6-dimethoxyphenyl)-6-hydroxy-3,4-dihydropyrimidin-4-one (42), 2-butyl-3-(2,6-dimethoxyphenyl)-6-hydroxy-5-{[4-(4-methyl-2-oxo-1,2-dihydropyridin-1-yl)phenyl]methyl}-3,4-dihydropyrimidin-4-one (43), 2-butyl-3-(2,6-dimethoxyphenyl)-6-hydroxy-5-{[4-(6-methylpyridin-3-yl)phenyl]methyl}-3,4-dihydropyrimidin-4-one (44), 5-({[1,1'-biphenyl]-4-yl}methyl)-2-butyl-3-(2,6-dimethoxyphenyl)-6-hydroxy-3,4-dihydropyrimidin-4-one (45), 2-butyl-5-{[4-(5-chloropyridin-2-yl)phenyl]methyl}-3-(2,6-dimethoxyphenyl)-6-hydroxy-3,4-dihydropyrimidin-4-one (46), 2-butyl-3-(2,6-dimethoxyphenyl)-5-{[4-(5-fluoro-2-oxo-1,2-dihydropyridin-1-yl)phenyl]methyl}-6-hydroxy-3,4-dihydropyrimidin-4-one (47), 2-butyl-3-(2,6-dimethoxyphenyl)-6-hydroxy-5-{[4-(2-methoxypyridin-3-yl)phenyl]methyl}-3,4-dihydropyrimidin-4-one (48), 2-butyl-5-{[4-(5-chloro-2-oxo-1,2-dihydropyridin-1-yl)phenyl]methyl}-3-(2,6-dimethoxyphenyl)-6-hydroxy-3,4-dihydropyrimidin-4-one (49), 2-butyl-3-(2,6-dimethoxyphenyl)-6-hydroxy-5-{[4-(5-methyl-2-oxo-1,2-dihydropyridin-1-yl)phenyl]methyl}-3,4-dihydropyrimidin-4-one (50), 2-cyclopentyl-3-(2,6-dimethoxyphenyl)-5-{[4-(5-fluoro-2-oxo-1,2-dihydropyridin-1-yl)phenyl]methyl}-6-hydroxy-3,4-dihydropyrimidin-4-one (51), 3-(2,6-dimethoxyphenyl)-5-{[4-(5-fluoro-2-oxo-1,2-dihydropyridin-1-yl)phenyl]methyl}-6-hydroxy-2-(3-methylbutyl)-3,4-dihydropyrimidin-4-one (52), 5-{[4-(5-chloro-2-oxo-1,2-dihydropyridin-1-yl)phenyl]methyl}-3-(2,6-dimethoxyphenyl)-6-hydroxy-2-(3-methylbutyl)-3,4-dihydropyrimidin-4-one (53), 3-(2,6-dimethoxyphenyl)-6-hydroxy-5-{[4-(5-methyl-2-oxo-1,2-dihydropyridin-1-yl)phenyl]methyl}-2-(3-methylbutyl)-3,4-dihydropyrimidin-4-one (54), 2-(2-cyclopropylethyl)-3-(2,6-dimethoxyphenyl)-6-hydroxy-5-{[4-(5-methyl-2-oxo-1,2-dihydropyridin-1-yl)phenyl]methyl}-3,4-dihydropyrimidin-4-one (55), 2-(2-cyclopropylethyl)-3-(2,6-dimethoxyphenyl)-5-{[4-(5-fluoro-2-oxo-1,2-dihydropyridin-1-yl)phenyl]methyl}-6-hydroxy-3,4-dihydropyrimidin-4-one (56), 5-{[4-(5-chloro-2-oxo-1,2-dihydropyridin-1-yl)phenyl]methyl}-2-(2-cyclopropylethyl)-3-(2,6-dimethoxyphenyl)-6-hydroxy-3,4-dihydropyrimidin-4-one (57), 3-(2,6-dimethoxyphenyl)-6-hydroxy-5-{[4-(5-methyl-2-oxo-1,2-dihydropyridin-1-yl)phenyl]methyl}-2-[(propan-2-yloxy)methyl]-3,4-dihydropyrimidin-4-one (58), 3-(2,6-dimethoxyphenyl)-5-{[4-(5-fluoro-2-oxo-1,2-dihydropyridin-1-yl)phenyl]methyl}-6-hydroxy-2-[(propan-2-yloxy)methyl]-3,4-dihydropyrimidin-4-one (59), 5-{[4-(5-chloro-2-oxo-1,2-dihydropyridin-1-yl)phenyl]methyl}-3-(2,6-dimethoxyphenyl)-6-hydroxy-2-[(propan-2-yloxy)methyl]-3,4-dihydropyrimidin-4-one (60), 2-(1-cyclopropyl-1H-pyrazol-3-yl)-1-(2,6-diethylphenyl)-5-(3-fluoro-4-(2-fluoro-3-methylpyridin-4-yl)benzyl)-6-hydroxypyrimidin-4(1H)-one (61), 1-(2,6-dimethoxyphenyl)-2-(1-ethyl-1H-pyrazol-3-yl)-6-hydroxy-5-{[4-(3-methylpyridin-4-yl)phenyl]methyl}-1,4-dihydropyrimidin-4-one (62), 1-(2,6-dimethoxyphenyl)-2-(1-ethyl-1H-pyrazol-3-yl)-5-{[4-(2-fluoro-3-methylpyridin-4-yl)phenyl]methyl}-6-hydroxy-1,4-dihydropyrimidin-4-one (63), 2-butyl-1-(2,6-diethylphenyl)-5-{[4-(6-fluoro-2-methylpyridin-3-yl)phenyl]methyl}-6-hydroxy-1,4-dihydropyrimidin-4-one (64), 2-butyl-1-(2,6-diethylphenyl)-5-{[4-(6-fluoropyridin-3-yl)phenyl]methyl}-6-hydroxy-1,4-dihydropyrimidin-4-one (65), 2-butyl-1-(2,6-diethylphenyl)-5-{[4-(2-fluoro-3-methylpyridin-4-yl)phenyl]methyl}-6-hydroxy-1,4-dihydropyrimidin-4-one (66), 2-butyl-5-[(4-cyclopropylphenyl)methyl]-1-(2,6-diethylphenyl)-6-hydroxy-1,4-dihydropyrimidin-4-one (67), 5-({[1,1'-biphenyl]-4-yl}methyl)-2-butyl-1-(2,6-diethylphenyl)-6-hydroxy-1,4-dihydropyrimidin-4-one (68), 1-(2,6-diethylphenyl)-5-{[3-fluoro-4-(6-fluoro-2-methylpyridin-3-yl)phenyl]methyl}-6-hydroxy-2-(1-methyl-1H-pyrazol-3-yl)-1,4-dihydropyrimidin-4-one (69), 1-(2,6-diethylphenyl)-5-{[3-fluoro-4-(3-methylpyridin-4-yl)phenyl]methyl}-6-hydroxy-2-(1-methyl-1H-pyrazol-3-yl)-1,4-dihydropyrimidin-4-one (70),
1-(2,6-diethylphenyl)-5-{[3-fluoro-4-(2-fluoro-3-methylpyridin-4-yl)phenyl]methyl}-6-hydroxy-2-(1-methyl-1H-pyrazol-3-yl)-1,4-dihydropyrimidin-4-one (71),
1-(2,6-diethylphenyl)-5-{[3-fluoro-4-(6-fluoro-2-methylpyridin-3-yl)phenyl]methyl}-6-hydroxy-2-(2-methyl-1,3-thiazol-4-yl)-1,4-dihydropyrimidin-4-one (72),
1-(2,6-diethylphenyl)-5-{[3-fluoro-4-(2-fluoro-3-methylpyridin-4-yl)phenyl]methyl}-6-hydroxy-2-(4-methyl-1,3-thiazol-2-yl)-1,4-dihydropyrimidin-4-one (73),
1-(2,6-diethylphenyl)-5-{[3-fluoro-4-(3-methylpyridin-4-yl)phenyl]methyl}-6-hydroxy-2-(2-methyl-1,3-thiazol-4-yl)-1,4-dihydropyrimidin-4-one (74),
1-(2,6-diethylphenyl)-5-{[3-fluoro-4-(3-methylpyridin-4-yl)phenyl]methyl}-6-hydroxy-2-(4-methyl-1,3-thiazol-2-yl)-1,4-dihydropyrimidin-4-one (75),
1-(2,6-diethylphenyl)-2-(1-ethyl-1H-pyrazol-3-yl)-5-{[3-fluoro-4-(3-methylpyridin-4-yl)phenyl]methyl}-6-hydroxy-1,4-dihydropyrimidin-4-one (76),
1-(2,6-diethylphenyl)-2-(1-ethyl-1H-pyrazol-3-yl)-5-{[3-fluoro-4-(2-fluoro-3-methylpyridin-4-yl)phenyl]methyl}-6-hydroxy-1,4-dihydropyrimidin-4-one (77),
1-(2,6-diethylphenyl)-5-{[3-fluoro-4-(2-fluoro-3-methylpyridin-4-yl)phenyl]methyl}-6-hydroxy-2-(2-methyl-1,3-thiazol-4-yl)-1,4-dihydropyrimidin-4-one (78),
1-(2,6-diethylphenyl)-5-{[3-fluoro-4-(6-fluoro-2-methylpyridin-3-yl)phenyl]methyl}-6-hydroxy-2-(4-methyl-1,3-thiazol-2-yl)-1,4-dihydropyrimidin-4-one (79),
1-(2,6-diethylphenyl)-2-(1-ethyl-1H-pyrazol-3-yl)-5-{[3-fluoro-4-(6-fluoro-2-methylpyridin-3-yl)phenyl]methyl}-6-hydroxy-1,4-dihydropyrimidin-4-one (80),
4'-{[1-(2,6-diethylphenyl)-2-(1-ethyl-1H-pyrazol-3-yl)-6-hydroxy-4-oxo-1,4-dihydropyrimidin-5-yl]methyl}-2',5-difluoro-[1,1'-biphenyl]-2-carboxamide (81),
4'-{[1-(2,6-diethylphenyl)-6-hydroxy-2-(4-methyl-1,3-thiazol-2-yl)-4-oxo-1,4-dihydropyrimidin-5-yl]methyl}-2',4-difluoro-[1,1'-biphenyl]-2-carboxamide (82),
1-(2,6-diethylphenyl)-5-{[3-fluoro-4-(1-methyl-2-oxo-1,2-dihydropyridin-3-yl)phenyl]methyl}-6-hydroxy-2-(4-methyl-1,3-thiazol-2-yl)-1,4-dihydropyrimidin-4-on (83),
4'-{[1-(2,6-diethylphenyl)-6-hydroxy-4-oxo-2-[1-(propan-2-yl)-1H-pyrazol-3-yl]-1,4-dihydropyrimidin-5-yl]methyl}-2',4-difluoro-[1,1'-biphenyl]-2-carboxamide (84),
1-(2,6-diethylphenyl)-5-{[3-fluoro-4-(2-fluoro-3-methylpyridin-4-yl)phenyl]methyl}-6-hydroxy-2-[1-(propan-2-yl)-1H-pyrazol-3-yl]-1,4-dihydropyrimidin-4-one (85),
1-(2,6-diethylphenyl)-5-{[2-fluoro-4-(2-fluoro-3-methylpyridin-4-yl)phenyl]methyl}-6-hydroxy-2-(1-methyl-1H-pyrazol-3-yl)-1,4-dihydropyrimidin-4-one (86),
1-(2,6-diethylphenyl)-5-{[3-fluoro-4-(1-methyl-2-oxo-1,2-dihydropyridin-3-yl)phenyl]methyl}-6-hydroxy-2-[1-(propan-2-yl)-1H-pyrazol-3-yl]-1,4-dihydropyrimidin-4-one (87),
1-(2,6-diethylphenyl)-5-{[2-fluoro-4-(1-methyl-2-oxo-1,2-dihydropyridin-3-yl)phenyl]methyl}-6-hydroxy-2-(1-methyl-1H-pyrazol-3-yl)-1,4-dihydropyrimidin-4-one (88),
4'-{[1-(2,6-diethylphenyl)-6-hydroxy-2-(1-methyl-1H-pyrazol-3-yl)-4-oxo-1,4-dihydropyrimidin-5-yl]methyl}-3',4-difluoro-[1,1'-biphenyl]-2-carboxamide (89),
1-(2,6-diethylphenyl)-5-{[3-fluoro-4-(1-methyl-2-oxo-1,2-dihydropyridin-3-yl)phenyl]methyl}-6-hydroxy-2-[1-(2-methylpropyl)-1H-pyrazol-3-yl]-1,4-dihydropyrimidin-4-one (90),
1-(2,6-diethylphenyl)-5-{[3-fluoro-4-(2-fluoro-3-methylpyridin-4-yl)phenyl]methyl}-6-hydroxy-2-[1-(2-methylpropyl)-1H-pyrazol-3-yl]-1,4-dihydropyrimidin-4-one (91),
4'-{[1-(2,6-diethylphenyl)-6-hydroxy-2-[1-(2-methylpropyl)-1H-pyrazol-3-yl]-4-oxo-1,4-dihydropyrimidin-5-yl]methyl}-2',4-difluoro-[1,1'-biphenyl]-2-carboxamide (92),
2-(1-cyclopropyl-1H-pyrazol-3-yl)-1-(2,6-diethylphenyl)-5-{[3-fluoro-4-(1-methyl-2-oxo-1,2-dihydropyridin-3-yl)phenyl]methyl}-6-hydroxy-1,4-dihydropyrimidin-4-one (93),
4'-{[2-(1-cyclopropyl-1H-pyrazol-3-yl)-1-(2,6-diethylphenyl)-6-hydroxy-4-oxo-1,4-dihydropyrimidin-5-yl]methyl}-2',4-difluoro-[1,1'-biphenyl]-2-carboxamide (94),
(S)-3-(1-(2-butyl-5-(4-(6-fluoro-2-methylpyridin-3-yl)benzyl)-6-hydroxy-4-oxopyrimidin-1(4H)-yl)propyl)benzonitrile (95),
3-[(1S)-1-(2-butyl-6-hydroxy-5-{[4-(2-methylpyridin-3-yl)phenyl]methyl}-4-oxo-1,4-dihydropyrimidin-1-yl)propyl]benzonitrile (96),
3-[(1S)-1-(2-butyl-5-{[4-(6-fluoropyridin-3-yl)phenyl]methyl}-6-hydroxy-4-oxo-1,4-dihydropyrimidin-1-yl)propyl]benzonitrile (97),
3-[(1S)-1-(2-butyl-6-hydroxy-5-{[4-(3-methylpyridin-4-yl)phenyl]methyl}-4-oxo-1,4-dihydropyrimidin-1-yl)propyl]benzonitrile (98),
3-[(1S)-1-(2-butyl-5-{[4-(2-fluoro-3-methylpyridin-4-yl)phenyl]methyl}-6-hydroxy-4-oxo-1,4-dihydropyrimidin-1-yl)propyl]benzonitrile (99),
3-[(1S)-1-(2-butyl-5-{[4-(5-chloro-2-oxo-1,2-dihydropyridin-1-yl)phenyl]methyl}-6-hydroxy-4-oxo-1,4-dihydropyrimidin-1-yl)propyl]benzonitrile (100),
3-[(1S)-1-{2-butyl-5-[(4-cyclopropylphenyl)methyl]-6-hydroxy-4-oxo-1,4-dihydropyrimidin-1-yl}propyl]benzonitrile (101),
3-[(1S)-1-{2-butyl-5-[(4-cyclopropylphenyl)methyl]-6-hydroxy-4-oxo-1,4-dihydropyrimidin-1-yl}propyl]benzonitrile (102),
2-butyl-5-{[4-(2-fluoro-3-methylpyridin-4-yl)phenyl]methyl}-1-[(1S)-1-(3-fluorophenyl)propyl]-6-hydroxy-1,4-dihydropyrimidin-4-one (103),
2-butyl-5-{[4-(6-fluoro-2-methylpyridin-3-yl)phenyl]methyl}-1-[(1S)-1-(3-fluorophenyl)propyl]-6-hydroxy-1,4-dihydropyrimidin-4-one (104),
2-butyl-1-[(1S)-1-(3-fluorophenyl)propyl]-6-hydroxy-5-{[4-(2-methylpyridin-3-yl)phenyl]methyl}-1,4-dihydropyrimidin-4-one (105),
2-butyl-1-[(1S)-1-(3-fluorophenyl)propyl]-6-hydroxy-5-{[4-(3-methylpyridin-4-yl)phenyl]methyl}-1,4-dihydropyrimidin-4-one (106),
2-(2-cyclopropylethyl)-1-[(1S)-1-(3,5-difluorophenyl)propyl]-5-{[4-(6-fluoro-2-methylpyridin-3-yl)phenyl]methyl}-6-hydroxy-1,4-dihydropyrimidin-4-one (107),
1-[(1S)-1-(3,5-difluorophenyl)propyl]-5-{[4-(2-fluoro-3-methylpyridin-4-yl)phenyl]methyl}-6-hydroxy-2-[(propan-2-yloxy)methyl]-1,4-dihydropyrimidin-4-one (108),
2-(2-cyclopropylethyl)-1-[(1S)-1-(3,5-difluorophenyl)propyl]-6-hydroxy-5-{[4-(2-methylpyridin-3-yl)phenyl]methyl}-1,4-dihydropyrimidin-4-one (109),
2-(2-cyclopropylethyl)-1-[(1S)-1-(3,5-difluorophenyl)propyl]-6-hydroxy-5-{[4-(3-methylpyridin-4-yl)phenyl]methyl}-1,4-dihydropyrimidin-4-one (110),
1-[(1S)-1-(3,5-difluorophenyl)propyl]-6-hydroxy-5-{[4-(2-methylpyridin-3-yl)phenyl]methyl}-2-[(propan-2-yloxy)methyl]-1,4-dihydropyrimidin-4-one (111), 1-[(1S)-1-(3,5-difluorophenyl)propyl]-5-{[4-(6-fluoro-2-methylpyridin-3-yl)phenyl]methyl}-6-hydroxy-2-[(propan-2-yloxy)methyl]-1,4-dihydropyrimidin-4-one (112), 2-(2-cyclopropylethyl)-1-[(1S)-1-(3,5-difluorophenyl)propyl]-5-{[4-(2-fluoro-3-methylpyridin-4-yl)phenyl]methyl}-6-hydroxy-1,4-dihydropyrimidin-4-one (113), 1-[(1S)-1-(3,5-difluorophenyl)propyl]-6-hydroxy-5-{[4-(3-methylpyridin-4-yl)phenyl]methyl}-2-[(propan-2-yloxy)methyl]-1,4-dihydropyrimidin-4-one (114), 1-[(1S)-1-(3,5-difluorophenyl)-2-methylpropyl]-6-hydroxy-5-{[4-(2-methylpyridin-3-yl)phenyl]methyl}-2-[(propan-2-yloxy)methyl]-1,4-dihydropyrimidin-4-one (115), 4'-({1-[(1S)-1-(3,5-difluorophenyl)-2-methylpropyl]-6-hydroxy-4-oxo-2-[(propan-2-yloxy)methyl]-1,4-dihydropyrimidin-5-yl}methyl)-4-fluoro-[1,1'-biphenyl]-2-carboxamide (116), 4'-{[2-(2-cyclopropylethyl)-1-[(1S)-1-(3,5-difluorophenyl)-2-methylpropyl]-6-hydroxy-4-oxo-1,4-dihydropyrimidin-5-yl]methyl}-4-fluoro-[1,1'-biphenyl]-2-carboxamide (117), 5-{[3-fluoro-4-(2-fluoro-3-methylpyridin-4-yl)phenyl]methyl}-6-hydroxy-2-(4-methyl-1,3-thiazol-2-yl)-1-[(1S)-1-phenylpropyl]-1,4-dihydropyrimidin-4-one (118), 5-{[3-fluoro-4-(1-methyl-2-oxo-1,2-dihydropyridin-3-yl)phenyl]methyl}-6-hydroxy-2-(4-methyl-1,3-thiazol-2-yl)-1-[(1S)-1-phenylpropyl]-1,4-dihydropyrimidin-4-one (119), 2',4-difluoro-4'-{[6-hydroxy-2-(4-methyl-1,3-thiazol-2-yl)-4-oxo-1-[(1S)-1-phenylpropyl]-1,4-dihydropyrimidin-5-yl]methyl}-[1,1'-biphenyl]-2-carboxamide (120), 3-fluoro-5-[(1S)-1-(6-hydroxy-5-{[4-(2-methylpyridin-3-yl)phenyl]methyl}-4-oxo-2-[(propan-2-yloxy)methyl]-1,4-dihydropyrimidin-1-yl)-2-methylpropyl]benzonitrile (121), 1-[(1R)-1-(3,5-difluorophenyl)-2-methoxyethyl]-2-(ethoxymethyl)-6-hydroxy-5-{[4-(3-methylpyridin-4-yl)phenyl]methyl}-1,4-dihydropyrimidin-4-one (122), 1-[(1R)-1-(3,5-difluorophenyl)-2-methoxyethyl]-2-(ethoxymethyl)-6-hydroxy-5-{[4-(2-methylpyridin-3-yl)phenyl]methyl}-1,4-dihydropyrimidin-4-one (123), 1-[(1R)-1-(3,5-difluorophenyl)-2-methoxyethyl]-2-(ethoxymethyl)-5-{[4-(6-fluoro-2-methylpyridin-3-yl)phenyl]methyl}-6-hydroxy-1,4-dihydropyrimidin-4-one (124), 1-[(1R)-1-(3,5-difluorophenyl)-2-methoxyethyl]-2-(ethoxymethyl)-5-{[4-(6-fluoropyridin-3-yl)phenyl]methyl}-6-hydroxy-1,4-dihydropyrimidin-4-one (125), 1-[(1R)-1-(3,5-difluorophenyl)-2-methoxyethyl]-2-(ethoxymethyl)-5-{[4-(2-fluoro-3-methylpyridin-4-yl)phenyl]methyl}-6-hydroxy-1,4-dihydropyrimidin-4-one (126), 2-butyl-1-[(1S)-1-(3,5-difluorophenyl)propyl]-6-hydroxy-5-{[3-(3-methylpyridin-4-yl)phenyl]methyl}-1,4-dihydropyrimidin-4-one (127), 2-butyl-1-[(1S)-1-(3,5-difluorophenyl)propyl]-5-{[3-(2-fluoro-3-methylpyridin-4-yl)phenyl]methyl}-6-hydroxy-1,4-dihydropyrimidin-4-one (128), 2-butyl-1-[(1S)-1-(3,5-difluorophenyl)propyl]-6-hydroxy-5-{[3-(2-methylpyridin-3-yl)phenyl]methyl}-1,4-dihydropyrimidin-4-one (129), 2-butyl-1-[(1S)-1-(3,5-difluorophenyl)propyl]-5-{[3-(6-fluoro-2-methylpyridin-3-yl)phenyl]methyl}-6-hydroxy-1,4-dihydropyrimidin-4-one (130), 3'-({2-butyl-1-[(1S)-1-(3,5-difluorophenyl)propyl]-6-hydroxy-4-oxo-1,4-dihydropyrimidin-5-yl}methyl)-4-fluoro-[1,1'-biphenyl]-2-carboxamide (131), 1-[(1S)-1-(3,5-difluorophenyl)propyl]-2-(1-ethyl-1H-pyrazol-3-yl)-5-{[4-(2-fluoro-3-methylpyridin-4-yl)phenyl]methyl}-6-hydroxy-1,4-dihydropyrimidin-4-one (132), 1-[(1S)-1-(3,5-difluorophenyl)propyl]-2-(1-ethyl-1H-pyrazol-3-yl)-6-hydroxy-5-{[4-(2-methylpyridin-3-yl)phenyl]methyl}-1,4-dihydropyrimidin-4-one (133), 1-[(1S)-1-(3,5-difluorophenyl)propyl]-2-(1-ethyl-1H-pyrazol-3-yl)-5-{[4-(6-fluoro-2-methylpyridin-3-yl)phenyl]methyl}-6-hydroxy-1,4-dihydropyrimidin-4-one (134), 1-[(1S)-1-(3,5-difluorophenyl)propyl]-2-(1-ethyl-1H-pyrazol-3-yl)-5-{[4-(6-fluoropyridin-3-yl)phenyl]methyl}-6-hydroxy-1,4-dihydropyrimidin-4-one (135), and 1-[(1S)-1-(3,5-difluorophenyl)propyl]-2-(1-ethyl-1H-pyrazol-3-yl)-6-hydroxy-5-{[4-(3-methylpyridin-4-yl)phenyl]methyl}-1,4-dihydropyrimidin-4-one (136).

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements (including individual variable definitions) of an embodiment are meant to be combined with any and all other elements from any of the embodiments to describe additional embodiments. The present invention also provides a pharmaceutical composition comprising a compound of formula I, or an enantiomer, diastereomer, or a pharmaceutically-acceptable salt, and a pharmaceutically acceptable carrier therefore.

In another embodiment, the compounds of the present invention have $EC_{50}$ values ≤10 µM, using the APJ hcAMP assay disclosed herein, preferably, $EC_{50}$ values ≤5 µM, more preferably, $EC_{50}$ values ≤1 µM, even more preferably, $EC_{50}$ values ≤0.5 µM, even more preferably, $EC_{50}$ values ≤0.1 µM, even more preferably, $EC_{50}$ values ≤0.01 µM.

In another aspect, the present invention provides compounds selected from any subset list of compounds exemplified in the present application.

In another aspect, the present invention provides compounds selected from the subset in which the APJ hcAMP $EC_{50}$ potency range is A.

In another aspect, the present invention provides compounds selected from the subset in which the APJ hcAMP $EC_{50}$ potency range is B.

In another aspect, the present invention provides compounds selected from the subset in which the APJ hcAMP $EC_{50}$ potency range is C.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

The present invention provides a pharmaceutical composition further comprising additional therapeutic agent(s). In a preferred embodiment, the present invention provides pharmaceutical composition, wherein the additional therapeutic agent is, for example, angiotensin converting enzyme (ACE) inhibitor, β-adrenergic receptor blocker, angiotensin II receptor blocker, diuretic, aldosterone antagonist and digitalis compound.

In another embodiment, the present invention provides a method for the treatment and/or prophylaxis of multiple diseases or disorders associated with APJ or apelin activity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of the APJ and apelin that can be prevented, modulated, or treated according to the present invention include, but are not limited to heart failure such as acute decompensated heart failure (ADHF), atrial fibrillation, coronary artery disease, peripheral vascular disease, atherosclerosis, diabetes, metabolic syndrome, hypertension, pulmonary hypertension, cerebrovascular disorders and the sequelae thereof, cardiovascular disorders, angina, ischemia, stroke, myocardial infarction, acute coronary syndrome, reperfusion injury, angioplastic restenosis, vascular complications of diabetes and obesity.

In another embodiment, the present invention provides a method for the treatment and/or prophylaxis of heart failure, coronary artery disease, peripheral vascular disease, atherosclerosis, diabetes, metabolic syndrome, hypertension, pulmonary hypertension, atrial fibrillation, angina, ischemia, stroke, myocardial infarction, acute coronary syndrome, reperfusion injury, angioplastic restenosis, vascular complications of diabetes, obesity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of heart failure such as ADHF, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of diabetes and obesity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of pulmonary hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of acute coronary syndrome and cardiac ischemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of multiple diseases or disorders associated with APJ and apelin.

In another embodiment, the present invention also provides the use of a compound of the present invention for the manufacture of a medicament for the treatment and/or prophylaxis of multiple diseases or disorders associated with APJ and apelin.

In another embodiment, the present invention provides a method for the treatment and/or prophylaxis of multiple diseases or disorders associated with APJ and apelin, comprising administering to a patient in need thereof a therapeutically effective amount of a first and second therapeutic agent, wherein the first therapeutic agent is a compound of the present invention. Preferably, the second therapeutic agent, for example selected inotropic agent such as β-adrenergic agonist (for example dobutamine).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with APJ and apelin.

Where desired, the compound of the present invention may be used in combination with one or more other types of cardiovascular agents and/or one or more other types of therapeutic agents which may be administered orally in the same dosage form, in a separate oral dosage form or by injection. The other type of cardiovascular agents that may be optionally employed in combination with the APJ agonist of the present invention may be one, two, three or more cardiovascular agents administered orally in the same dosage form, in a separate oral dosage form, or by injection to produce an additional pharmacological benefit.

The compounds of the present invention may be employed in combination with additional therapeutic agent (s) selected from one or more, preferably one to three, of the following therapeutic agents: anti-hypertensive agents, ACE inhibitors, mineralocorticoid receptor antagonists, angiotensin receptor blockers, calcium channel blockers, β-adrenergic receptor blockers, diuretics, vasorelaxation agents such as nitrates, anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, calcium channel blockers, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating heart failure: ACE inhibitors, β-blockers, diuretics, mineralocorticoid receptor antagonists, renin inhibitors, calcium channel blockers, angiotensin II receptor antagonists, nitrates, digitalis compounds, inotropic agents.

The present invention may be embodied in other specific forms without parting from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For examples, "$C_1$ to $C_{12}$ alkyl" or "$C_{1-12}$ alkyl" (or alkylene), is intended to include $C_1$, $C_2$, $C_3$, $C_4$, $C_5$, $C_6$, $C_7$, $C_8$, $C_9$, $C_{10}$, $C_{11}$ and $C_{12}$ alkyl groups; "$C_4$ to $C_{18}$ alkyl" or "$C_{4-18}$ alkyl" (or alkylene), is intended to include $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, and $C_{18}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

When the term "hydrocarbon chain" is used, it is intended to include "alkyl", "alkenyl" and "alkynyl", unless otherwise specified.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable.

Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 15th Edition, John Wiley & Sons, Inc., New York (2007). "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3- triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., *Remington: The Science and Practice of Pharmacy*, 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2nd Edition, reproduced (2006)); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3rd Edition, Academic Press, San Diego, CA (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", "Z" and "ee" are stereochemical designations familiar to one skilled in the art.

AcOH or HOAc acetic acid
ACN Acetonitrile
Alk Alkyl
$BBr_3$ boron tribromide
Bn benzyl
Boc tert-butyloxycarbonyl
BOP reagent benzotriazol-1-yloxytris(dimethylamino)phosphonium hexafluorophosphate
Bu butyl
i-Bu isobutyl
t-Bu tert-butyl
BuOH n-butanol
t-BuOH tert-butanol
Cbz carbobenzyloxy
$CDCl_3$ deutero-chloroform
$CD_3OD$ deutero-methanol
$CH_2Cl_2$ Dichloromethane
$CH_3CN$ Acetonitrile
$CHCl_3$ Chloroform
DCM Dichloromethane
DIEA, DIPEA or diisopropylethylamine Hunig's base
DMF dimethyl formamide
DMSO dimethyl sulfoxide
Et Ethyl
$Et_3N$ or TEA triethylamine
$Et_2O$ diethyl ether
EtOAc ethyl acetate
EtOH ethanol
HCl hydrochloric acid
HOAt 1-Hydroxy-7-azabenzotriazole
HOBt 1-Hydroxybenzotriazole
HPLC high-performance liquid chromatography
$K_2CO_3$ potassium carbonate
$K_2HPO_4$ potassium hydrogenphosphate
LCMS liquid chromatography mass spectrometry
LiHMDS lithium bis(trimethylsilyl)amide
LG leaving group
Me methyl
MeOH methanol
$MgSO_4$ magnesium sulfate
MsOH or MSA methylsulfonic acid
NaCl sodium chloride
$Na_2CO_3$ sodium carbonate
$NaHCO_3$ sodium bicarbonate
NaOH sodium hydroxide
$Na_2SO_4$ sodium sulfate
$NH_3$ ammonia
$NH_4Cl$ ammonium chloride
$NH_4OAc$ ammonium acetate
$Pd(OAc)_2$ palladium(II) acetate
$Pd(PPh_3)_4$ tetrakis(triphenylphosphine)palladium(0)
PG protecting group
Ph phenyl
Pr Propyl
i-Pr isopropyl
i-PrOH or IPA Isopropanol
PyBOP benzotriazol-1-yl-oxytripyrrolidinophosphonium hexafluorophosphate
Rt retention time
$SiO_2$ silica oxide
SFC supercritical fluid chromatography
TBAI tetrabutylammonium iodide
TEA triethylamine
TFA trifluoroacetic acid
TFAA trifluoroacetic anhydride
THF tetrahydrofuran
$TiCl_4$ titanium tetrachloride
T3P 1-propanephosphonic acid cyclic anhydride The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and de-protection in the processes below may be carried out by procedures generally known in the art (see, for example, Wuts, P. G. M. et al., *Protecting Groups in Organic Synthesis,* 4th Edition, Wiley (2007)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, NY (1991); Smith, M. B. et al., *March's Advanced Organic Chemistry: Reactions, Mechanisms, and Structure*. 6th Edition, Wiley & Sons, New York, NY (2007); Katritzky, A. R. et al, eds., *Comprehensive Organic Functional Groups Transformations II*, 2nd Edition, Elsevier Science Inc., Tarrytown, NY (2004); Larock, R. C., *Comprehensive Organic Transformations*, VCH Publishers, Inc., New York, NY (1999), and references therein.

Scheme 1

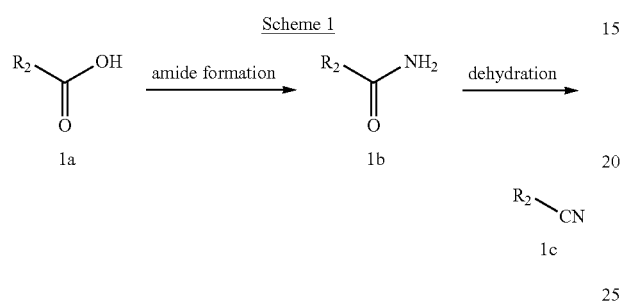

Cyano containing intermediate compound 1c is either commercially available or readily synthesized by those skilled in the art. One of such preparation from a corresponding commercially available carboxylic acid 1a is illustrated in Scheme 1. Formation of amides of general formula 1b from acid 1a is readily performed by those skilled in the art. One of such example is by reacting acid 1a and ammonium chloride with a base and a coupling agent under an inert environment. Preferred coupling agents include HOAt, HOBt, BOP, PyBOP and preferred bases include TEA, Hunig's base and pyridine. Preferred solvents are DCM, THF, dioxane, ether, DMF and N-Methyl-2-pyrrolidone. Alternatively, carboxylic acid 1a can react with oxalyl chloride or thionyl chloride to form an acid chloride intermediate, which then reacts with ammonia to provide amides of formula 1b. For conversion of amide 1b to cyano 1c, a variety of dehydrating agents such as TFAA, $POCl_3$ can be used. Preferred solvents are ethers and chlorinated solvents.

Scheme 2

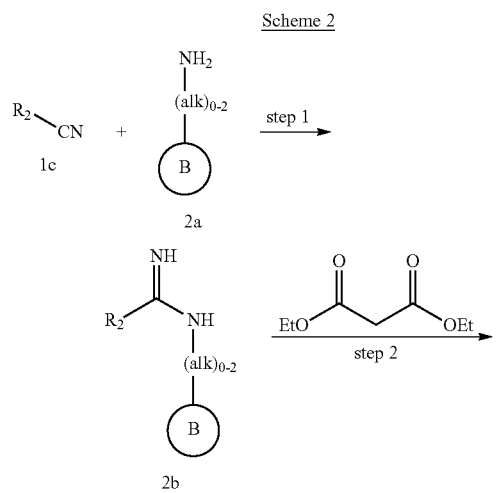

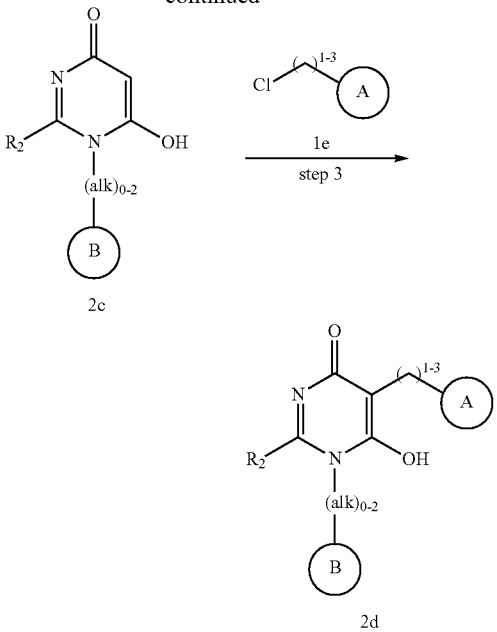

The construction of target compounds of formula 2d is generally described in scheme 2. Amine containing compounds of formula 2a are widely available from commercial sources. Step 1 describes the formation of intermediate amidine of formula 2b by reacting cyano of formula 1c (Scheme 1) and amines of formula of 2a typically mediated by a Lewis acid under an inert environment at ambient to elevated temperature. Preferred Lewis acids include trimethylsilyl triflate, aluminum and titanium based reagents, and preferred solvents are ethers, chlorinated and hydrocarbon solvents such as dioxane, THF, dichloroethane and toluene. Temperature can vary from ambient to 120° C. depending on $R_2$/ring B.

Step 2 describes the formation of hydroxypyrimidinone of formula 2c from reacting amidine of formula 2b with a malonate derivative such as diethyl malonate. Base is usually required for this transformation and preferred bases are NaH, hexamethyldisilazide-, tert-butoxide-, ethoxide- and methoxide-based bases. Preferred solvents are ethers, chlorinated or alcoholic solvents and temperature can vary from ambient to 200° C. depending on $R_2$/ring B.

Step 3 describes the formation of target substituted hydroxypyrimidinone of formula 2d by reacting 2c with an alkyl halide of general formula 1e. Alkyl halides are widely available from commercial sources and can be readily prepared by those skilled in the art. The formation of hydroxypyrimidinone 2d usually requires basic conditions and preferred bases are amine bases, carbonate bases, NaH, hexamethyldisilazide based bases, and phosphazene bases. O-alkylated products can also be formed under these reaction conditions. Preferred solvents used for this transformation are DMF, acetone, ether, chlorinated, alcoholic or aqueous solvents and temperature can vary from ambient to 160° C. depending on $R_2$/ring B.

An alternative method to construct the dihydroxypyrimidine core of interest 2d is shown in Scheme 3 and Scheme 4. Scheme 3 describes the generation of alkylated malonic acid of formula 3b.

Scheme 3

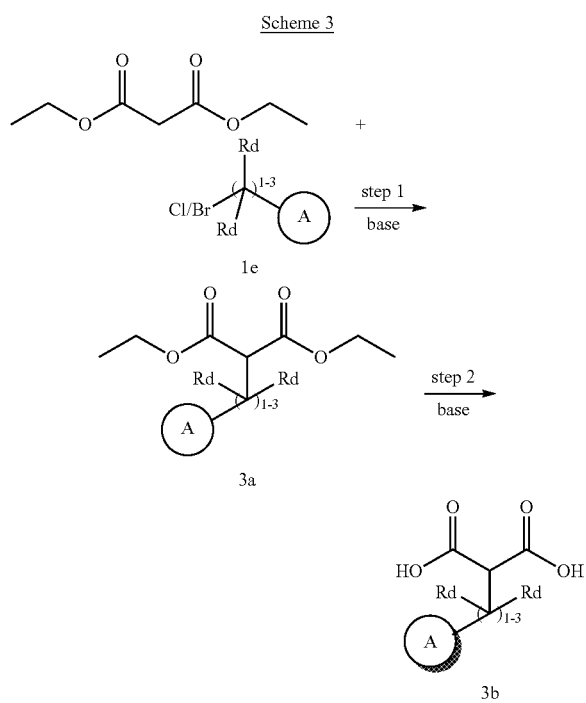

Alkyl halides of formula 1e are widely available from commercial sources and can be readily prepared by those skilled in the art. Alkylation of diethyl malonate with 1e under basic conditions leads to intermediate compounds of formula 3a. This can be performed by first deprotonating diethyl malonate with an appropriate base such as NaH, hexamethyldisilazide, alkyl lithiums, carbonate bases, phosphazene bases in an inert solvent such as THF, DMF, chlorinated and ethereal solvents at temperatures varying from −78° C. to 100° C. depending on solvents, bases, and ring A.

Step 2 describes hydrolysis of ester 3a to the corresponding diacid of formula 3b. This transformation is typically conducted under basic or acidic conditions and has been extensively described in the literature. Preferred reagents include hydroxide, carbonate, hydride bases and acids such as HCl, $H_2SO_4$. Preferred solvents include aqueous and alcohol solvents, most general organic solvents and temperatures can vary from 0° C. to 100° C. depending on solvents, acids/bases, and ring A.

Scheme 4

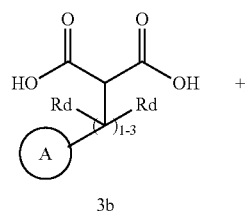

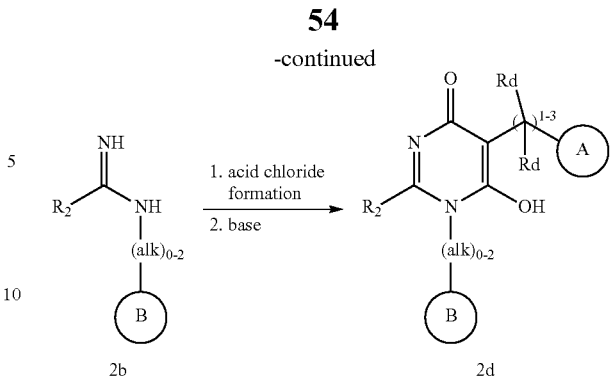

Scheme 4 describes an alternate method for the formation of dihydroxypyrimidines of formula 2d. Diacids of formula 3b are first converted to the corresponding diacid chloride. Preferred reagents for this transformation include oxalyl chloride, Ghosez reagent (*Org. Synth.* 1979, 59, 26), and preferred solvents are chlorinated, ethereal, and hydrocarbon solvents such as ether, dichloromethane, and hexane. Temperature can vary from 0° C. to 60° C. depending on ring A. When the acid chloride formation is completed, in the same reaction vessel, base and amidines of formula 2b can be added to allow the formation of dihydroxypyrimidines 2d. Preferred bases are non protic bases such as Hunig's base, phosphazenes, and temperature for this step can vary from 0° C. to 60° C.

IV. Biology

APJ receptor was discovered in 1993 as an orphan G protein-coupled receptor (GPCR) and was subsequently found to recognize apelin peptide as its endogenous ligand. It belongs to class A of GPCRs and has a classical 7-transmembrane domain structure, exhibiting greatest sequence homology to angiotensin AT1 receptor (for review see Pitkin, S. L. et al., *Pharmacol. Rev.*, 62(3):331-342 (2010)). APJ is expressed in wide variety of peripheral tissues and the CNS, and has relatively high expression in placenta, myocardium, vascular endothelial cells, smooth muscle cells as well as cardiac myocytes (Kleinz, J. M. et al., *Pharmacol. Ther.*, 107(2):198-211(2005)). Apelin peptide was originally identified in bovine stomach extract and remains to date the only known endogenous ligand and agonist of APJ receptor (Tatemoto, K. et al., *Biochem. Biophys. Res. Commun.*, 255:471-476 (1998)). Tissue expression of apelin gene mirrors closely the APJ expression pattern and has been postulated to act in an autocrine or paracrine manner, often exemplified by reference to "apelin-APJ system". Apelin gene encodes 77 amino acid precursor peptide that is cleaved to form mature secreted peptide undergoing further proteolytic cleavage forming shorter C-terminal fragments. Apelin-36, -17 and -13 represent the major active forms with the pyroglutamated form of apelin-13 being the most stable and the most abundant form present in the cardiac tissue (Maguire, J. J. et al., *Hypertension*, 54(3):598-604 (2009)). Apelin has very short half life in circulation, estimated to be less than 5 minutes (Japp, A. G. et al., *Circulation*, 121(16): 1818-1827 (2010)).

Activation of APJ receptor is known to inhibit forskolin-stimulated cyclic AMP (cAMP) levels in pertussis toxin-sensitive manner, indicating coupling to the Gi proteins. The binding affinity of apelin and the $EC_{50}$ values in the cAMP assay are reported to be in the sub-nanomolar range (for review see Pitkin, S. L. et al., *Pharmacol. Rev.*, 62(3):331-

342(2010)). In addition to cAMP inhibition, APJ receptor activation also leads to β-arrestin recruitment, receptor internalization and activation of extracellular-regulated kinases (ERKs) (for review see Kleinz, J. M. et al., *Pharmacol. Ther.*, 107(2):198-211 (2005)). Which of these signaling mechanisms contribute to modulation of downstream physiological effects of apelin is not clear at present. APJ receptor has been shown to interact with the AT1 receptor. While apelin does not bind AT1 and angiotensin II does not bind APJ, it has been postulated that certain physiological actions of apelin are mediated, at least in part, via functional antagonism of the angiotensin II and AT1 receptor pathway (Chun, A. J. et al., *J. Clin. Invest.*, 118(10):3343-3354 (2008)).

It is also desirable and preferable to find compounds with advantageous and improved characteristics compared with known HF treatment agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an APJ agonist. Exemplary subjects include human beings of any age with risk factors for development of heart failure and the sequelae thereof, angina, ischemia, cardiac ischemia, myocardial infarction, reperfusion injury, angioplastic restenosis, hypertension, vascular complications of diabetes, obesity or endotoxemia, stroke, as well as atherosclerosis, coronary artery disease, acute coronary syndrome, and/or dyslipidemias.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to modulate APJ and/or to prevent or treat the disorders listed herein. When applied to a combination, the term refers to combined amounts of the active ingredients that result in the preventive or therapeutic effect, whether administered in combination, serially, or simultaneously.

Assay Methods
Intracellular cAMP Accumulation Assay

HEK293 cells stably expressing human APJ receptor were used to assess the activity of compounds. Cultured cells were detached and resuspended in the cAMP Homogeneous Time-Resolved Fluorescence (HTRF) assay buffer (Cisbio cat; #62AM4PEJ). The assay was performed in 384-well assay plates (Perkin-Elmer; cat #6008289) according to assay protocol provided by the manufacturer. Serial dilutions of a compound together with assay buffer containing 0.2 nM IBMX and 2 µM forskolin were added to each well containing 5,000 cells and incubated for 30 minutes at room temperature. Subsequently, cAMP D2 reagent was added in the lysis buffer followed by the EuK antibody (Cisbio; cat #62AM4PEJ) and incubated for 60 min. The fluorescence emission ratio was measured using fluorometer. The intracellular cAMP concentrations (compound-stimulated inhibition of forskolin-mediated cAMP production) were calculated by extrapolation from a standard curve using known cAMP concentrations. The $EC_{50}$ values were obtained by fitting the data to a sigmoidal concentration-response curve with variable slope. The maximal achievable inhibition of forskolin-induced cAMP levels ($Y_{max}$) for each compound was expressed as relative percentage of inhibition attained using pyroglutamated apelin-13 ((Pyr1)apelin-13) peptide, which was set to 100%.

The examples disclosed below were tested in the APJ in vitro assays described above and were found having human APJ cyclic AMP (hcAMP) activity. The $EC_{50}$ value of each compound is presented at the end of the example description.

The compounds of the present invention possess activity as agonists of APJ receptor, and, therefore, may be used in the treatment of diseases associated with APJ activity. Accordingly, the compounds of the present invention can be administered to mammals, preferably humans, for the treatment of a variety of conditions and disorders, including, but not limited to, treating, preventing, or slowing the progression of heart failure, coronary artery disease, peripheral vascular disease, atherosclerosis, diabetes, metabolic syndrome and the sequelae of thereof, hypertension, pulmonary hypertension, cerebrovascular disorders, atrial fibrillation, angina, ischemia, stroke, myocardial infarction, acute coronary syndrome, reperfusion injury, angioplastic restenosis, vascular complications of diabetes and obesity.

The biological activity of the exemplified compounds of this invention determined by the assay described above is shown at the end of each example. The APJ cAMP $EC_{50}$ potency ranges are as follows: A=0.01-10 nM; B=10.01-100 nM; C=100.01-300 nM.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, Jr., L. V. et al., *Remington: The Science and Practice of Pharmacy* (2 Volumes), 22nd Edition, Pharmaceutical Press (2012), The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., agents used in treatment of heart failure or other pharmaceutically active material.

The compounds of the present invention may be employed in combination with other APJ agonists or one or more other suitable therapeutic agents useful in the treatment of the aforementioned disorders including: agents for treating heart failure, anti-hypertensive agents, anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, and agents for treating peripheral arterial disease.

The compounds of the present invention may be employed in combination with additional therapeutic agent(s) selected from one or more, preferably one to three, of the following therapeutic agents in treating heart failure and coronary artery disease: ACE inhibitors, β-blockers, diuretics, mineralocorticoid receptor antagonists, renin inhibitors, calcium channel blockers, angiotensin II receptor antagonists, nitrates, digitalis compounds, inotropic agents and β-receptor agonists, anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol), low density lipoprotein receptor inducers, clofibrate, fenofibrate, benzofibrate, cipofibrate, gemfibrizol, vitamin $B_6$, vitamin $B_{12}$, anti-oxidant vitamins, anti-diabetes agents, platelet aggregation inhibitors, fibrinogen receptor antagonists, aspirin and fibric acid derivatives.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-SO$_4$); anti-glucocorticoids; TNFα inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating heart failure and atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, β$_3$-adrenergic receptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine H$_3$ receptors, dopamine D$_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients but also to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the APJ receptor and apelin activity. Such compounds may be provided in a commercial kit, for example, for use in pharmaceutical research involving APJ and apelin or anti-heart failure activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving APJ and apelin.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof, and, (c) a package insert stating that the pharmaceutical composition can be used for the treatment and/or prophylaxis of multiple diseases or disorders associated with APJ and apelin (as defined previously). In another embodiment, the package insert states that the pharmaceutical composition can be used in combination (as defined previously) with a second therapeutic agent for the treatment and/or prophylaxis of multiple diseases or disorders associated with APJ and apelin. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

VI. Examples

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As a person of ordinary skill in the art would be able to understand that a hydroxypyrimidinone in a molecule may tautomerize to two different enol forms as shown in the following equation, wherein R1, R2 and R3 are as defined above, this disclosure is intended to cover all possible tautomers even when a structure depicts only one of them.

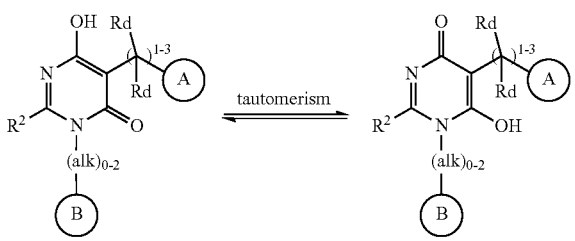

Description of Analytical LCMS Methods:

Method A: Column: Waters Acquity UPLC BEH C18, 2.1×50 mm, 1.7 μm particles; Mobile Phase A: 5:95 ACN: water with 10 mM NH$_4$OAc; Mobile Phase B: 95:5 ACN: water with 10 mM NH$_4$OAc; Temperature: 50° C.; Gradient: 0-100% B over 3 minutes, then a 0.75 minute hold at 100% B; Flow: 1.11 mL/min; Detection: UV at 220 nm.

Method B: Column: Waters Acquity UPLC BEH C18, 2.1×50 mm, 1.7 μm particles; Mobile Phase A: 5:95 ACN: water with 0.1% TFA; Mobile Phase B: 95:5 ACN:water with 0.1% TFA; Temperature: 50° C.; Gradient: 0-100% B over 3 minutes, then a 0.75 minute hold at 100% B; Flow: 1.11 mL/min; Detection: UV at 220 nm.

Method C: Column: PHENOMENEX® Luna 3 μm C18 (2.0×30 mm); Mobile Phase A: 10:90 MeOH:water with 0.1% TFA; Mobile Phase B: 90:10 MeOH:water with 0.1% TFA; Gradient: 0-100% B over 2 minutes, then a 1 minute hold at 100% B; Flow: 1 mL/min; Detection: UV at 220 nm.

Method D: Waters Acquity UPLC BEH C18, 2.1×50 mm, 1.7 μm particles; Mobile Phase A: water with 0.1% TFA; Mobile Phase B: ACN with 0.1% TFA; Gradient: 2-98% B over 1 minute, then a 0.5 minute hold at 98% B; Flow: 0.8 mL/min; Detection: UV at 220 nm.

Method E: A linear gradient using solvent A (10% MeOH, 90% water, 0.1% TFA) and solvent B (90% MeOH, 10% water, 0.1% TFA); 0-100% of solvent B over 4 min and then 100% of solvent B over 1 min. Column: PHENOMENEX® Luna 3 μm C18 (2.0×50 mm). Flow rate was 0.8 mL/min.

Example 1

3-(2,6-dimethoxyphenyl)-6-hydroxy-2-(3-methylbutyl)-5-{[4-(2-oxo-1,2-dihydropyridin-1-yl)phenyl]methyl}-3,4-dihydropyrimidin-4-one

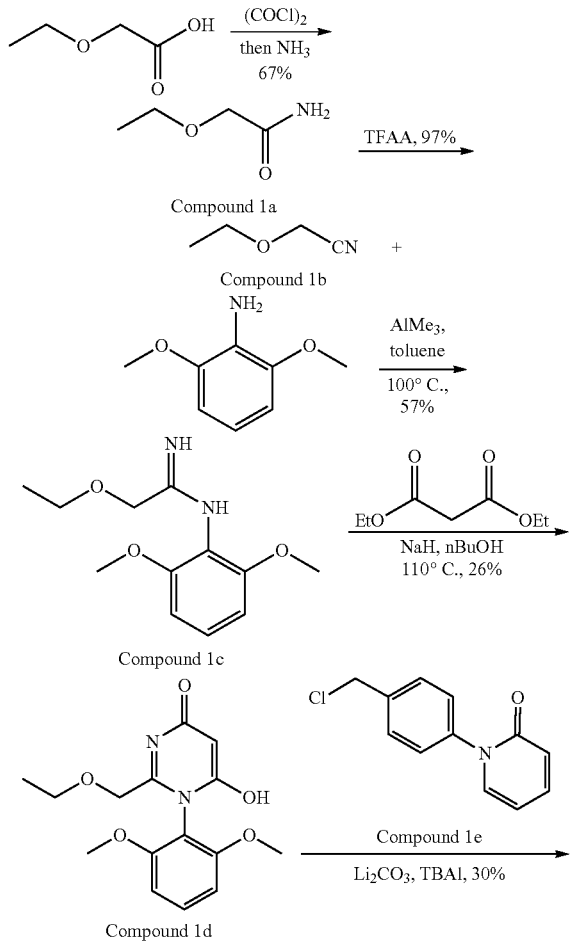

-continued

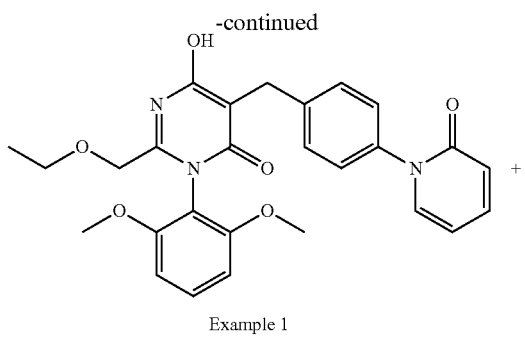

Example 1

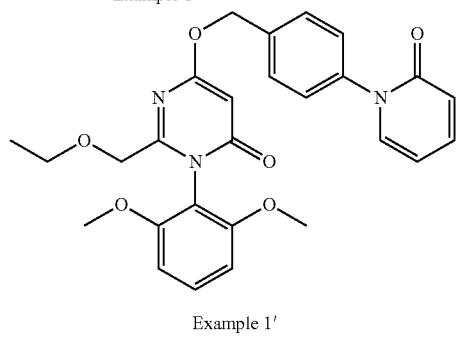

Example 1'

Compound 1a. 2-ethoxyacetamide

To a stirred solution of 2-ethoxyacetic acid (1.5 g, 14 mmol) in DCM (20 mL) at 0° C. was added oxalyl chloride (8.7 mL, 17 mmol), followed by DMF (2 drops). The reaction was allowed to reach RT and stirred for 3 hrs. The reaction mixture was concentrated under reduced pressure and dissolved in DCM (20 mL). Ammonia (20.6 mL, 144 mmol) (7 M in MeOH) was added slowly and the reaction mixture stirred for 16 hrs. The reaction mixture was concentrated under reduced pressure, dissolved in DCM, filtered and the solid further washed with DCM. The filtrate was concentrated to give Compound 1a (1 g, 9.7 mmol, 67% yield) as a white solid. 1H NMR (500 MHz, CDCl$_3$) δ 6.51 (br s, 1H), 5.46 (br s, 1H), 3.94 (s, 2H), 3.59 (q, J=6.8 Hz, 2H), 1.25 (t, J=7.2 Hz, 3H).

Compound 1b. 2-ethoxyacetonitrile

To a stirred solution of Compound 1a (1.0 g, 9.7 mmol) in THF (10 mL) at 0° C. was added pyridine (1.6 mL, 19 mmol) followed by TFAA (6.9 mL, 49 mmol). The reaction was stirred for 1 hr. Aqueous NaHCO$_3$ solution was added carefully to the reaction mixture until the pH=8. The reaction mixture was extracted with DCM (2×). The organic layers were separated, combined and further washed with 1N HCl. The organic layer was dried over MgSO$_4$, filtered and concentrated in vacuo to give Compound 1b (0.80 g, 9.4 mmol, 97% yield) as a yellow liquid. 1H NMR (500 MHz, CDCl$_3$) δ 4.24 (s, 2H), 3.66 (q, J=6.9 Hz, 2H), 1.27 (t, J=6.9 Hz, 3H).

Compound 1c.
N-(2,6-dimethoxyphenyl)-2-ethoxyacetimidamide

Trimethylaluminum (4.7 mL, 9.4 mmol) was added dropwise to a solution of 2,6-dimethoxyaniline (1.2 g, 7.8 mmol) and Compound 1b (0.80 g, 9.4 mmol) in toluene (10 mL) while cooling in an ice bath. After addition was complete, the reaction mixture was warmed to 110° C. and was stirred at this temperature for 14 hrs. The cooled reaction mixture was partitioned between a saturated solution of Rochelle's salt and EtOAc. The organic phase was separated, dried over MgSO$_4$, filtered and concentrated under reduced pressure. The resulting residue was added to a silica gel (120 g) column and was eluted with 0-20% of 20% MeOH/DCM in 0.5% TEA/DCM to give Compound 1c (1.1 g, 4.5 mmol, 57%) as a brown liquid. MS m/z=239.0 (M+H). 1H NMR (500 MHz, CDCl$_3$) δ 7.01 (t, J=8.3 Hz, 1H), 6.62 (d, J=7.7 Hz, 2H), 5.32 (s, 2H), 4.88 (br s, 2H), 4.31 (s, 2H), 3.82 (s, 6H), 3.62-3.73 (m, 2H), 1.19-1.33 (m, 3H).

Compound 1d. 1-(2,6-dimethoxyphenyl)-2-(ethoxymethyl)-6-hydroxypyrimidin-4(1H)-one To a solution of Compound 1c (300 mg, 1.3 mmol) and diethyl malonate (1.0 mL, 6.3 mmol) in BuOH (5 mL) was added NaH (252 mg, 6.30 mmol) portionwise. Evolution of gas was observed. After evolution of gas ceased, the reaction mixture was stirred at 110° C. for 2 hrs then 130° C. for 6 hrs. The reaction mixture was allowed to cool to RT and the residue concentrated under reduced pressure to reduce the volume of BuOH. The resulting residue was dissolved in water and DCM. The organic layer was separated, dried over MgSO$_4$, filtered and concentrated in vacuo. The residue was added to a silica gel (40 g) column and was eluted with 0-20% MeOH in DCM to give Compound 1d (100 mg, 0.30 mmol, 26% yield) as a light brown liquid. MS m/z=239.0 (M+H). 1H NMR (500 MHz, CD$_3$OD) δ 7.47 (t, J=8.5 Hz, 1H), 6.81 (d, J=8.5 Hz, 2H), 5.52 (s, 1H), 4.05 (s, 2H), 3.81 (s, 6H), 3.39 (q, J=6.9 Hz, 2H), 1.08 (t, J=6.9 Hz, 3H).

Compound 1e.
1-(4-(chloromethyl)phenyl)pyridin-2(1H)-one

To a stirred solution of 1-(4-(hydroxymethyl)phenyl)pyridin-2(1H)-one (150 mg, 0.7 mmol) in CHCl$_3$ (5 mL) was added thionyl chloride (0.16 mL, 2.2 mmol). The reaction mixture was heated to 78° C. for 2 hrs. The reaction mixture was allowed to cool and concentrated in vacuo. The residue was added to a silica gel (24 g) column and was eluted with 20-100% EtOAc in hexanes, then 0-20% MeOH in DCM to give Compound 1e (150 mg, 0.70 mmol, 92% yield) as a white solid. MS m/z=222.0 (M+H). 1H NMR (500 MHz, CDCl$_3$) δ 7.52 (d, J=8.5 Hz, 2H), 7.38-7.42 (m, 3H), 7.32 (dd, J=2.8, 6.3 Hz, 1H), 6.67 (d, J=8.8 Hz, 1H), 6.24 (t, J=8.0 Hz, 1H), 4.63 (s, 2H).

Example 1. 3-(2,6-dimethoxyphenyl)-6-hydroxy-2-(3-methylbutyl)-5-{[4-(2-oxo-1,2-dihydropyridin-1-yl)phenyl]methyl}-3,4-dihydropyrimidin-4-one To a suspension of Compound 1d (13 mg, 0.040 mmol) and Compound 1e (11.2 mg, 0.0500 mmol) in acetone (1 mL) and water (0.1 mL) was added lithium carbonate (6.3 mg, 0.090 mmol) and TBAI (7.8 mg, 0.02 mmol). The reaction mixture was heated at 50° C. for 20 hrs. The reaction mixture was filtered and concentrated under reduced pressure. The residue was purified via preparative LC/MS with the following conditions: Column: XBridge C18, 19×200 mm, 5-µm particles; Mobile Phase A: 5:95 acetonitrile:water with 10 mM ammonium acetate; Mobile Phase B: 95:5 acetonitrile:water with 10 mM ammonium acetate; Gradient: 10-55% B over 25 minutes, then a 5-minute hold at 100% B; Flow: 20 mL/min. Fractions containing the desired product were combined and dried via centrifugal evaporation to give Example 1 (6.4 mg, 31% yield) as a white solid. The estimated purity by LCMS analysis was 95%, HPLC method A, Rt=1.27 min, MS m/z=490.1 (M+H). 1H NMR (500 MHz, DMSO-d6) δ 7.63 (d, J=6.7 Hz, 1H), 7.48-7.51 (m, 1H), 7.41 (t, J=8.5 Hz, 1H), 7.35 (d, J=8.2 Hz, 2H), 7.25 (d, J=8.2 Hz, 2H), 6.80 (d, J=8.5 Hz, 2H), 6.47 (d, J=9.2 Hz, 1H), 6.29 (t, J=5.8 Hz, 1H), 3.90 (s, 2H), 3.75 (s, 6H), 3.66 (s, 2H), 3.26 (q, J=7.0 Hz, 2H), 0.97 (t, J=7.0 Hz, 3H). Human APJ cAMP $EC_{50}$ potency range: C. Example 1'. An O-alkylated product Example 1' (5.0 mg, 24%) was also isolated form the same reaction as a white solid. The estimated purity by LCMS analysis was 95%, HPLC method A, Rt=1.55 min, MS m/z=490.1 (M+H). The regiochemistry was determined by 2D NMR analysis. 1H NMR (500 MHz, DMSO-d6) δ 7.68 (d, J=8.2 Hz, 1H), 7.63 (d, J=8.2 Hz, 2H), 7.54 (dt, J=1.8, 7.0 Hz, 1H), 7.47 (d, J=8.5 Hz, 2H), 7.46 (t, J=8.6 Hz, 1H), 6.84 (d, J=8.5 Hz, 2H), 6.50 (d, J=9.2 Hz, 1H), 6.34 (t, J=7.3 Hz, 1H), 5.76 (s, 1H), 5.36 (s, 2H), 3.98 (s, 2H), 3.76 (s, 6H), 3.33 (q, J=7.0 Hz, 2H), 1.00 (t, J=7.0 Hz, 3H).

Examples 2 to 36 were prepared as described in the general procedure given for Example 1.

| Ex# | Structure | Name | NMR | Rt(min) method M + H | APJ cAMP Potency range |
|---|---|---|---|---|---|
| 2 | 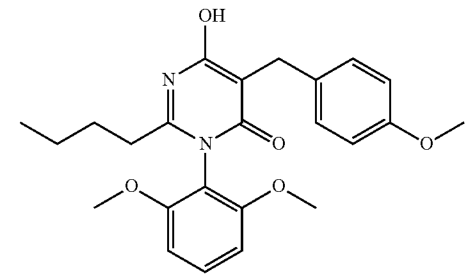 [SMILES: CCCCc1nc(O)c(Cc2ccc(OC)cc2)c(=O)n1-c1c(OC)cccc1OC] | 2-butyl-3-(2,6-dimethoxyphenyl)-6-hydroxy-5-[(4-methoxyphenyl)methyl]-3,4-dihydropyrimidin-4-one | 1H NMR (500 MHz, CHLOROFORM-d) d 7.45 (t, J = 8.5 Hz, 1H), 7.33 (d, J = 8.5 Hz, 2H), 6.79 (d, J = 8.5 Hz, 2H), 6.70 (d, J = 8.5 Hz, 2H), 3.79 (s, 6H), 3.77 (s, 3H), 3.73 (s, 2H), 2.51 (t, J = 8.0 Hz, 2H), 1.47 (m, 2H), 1.24 (m, 2H), 0.75 (t, J = 7.4 Hz, 3H) | 3.21 E 425.1 | B |
| 3 | 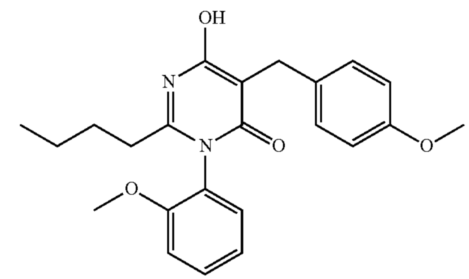 [SMILES: CCCCc1nc(O)c(Cc2ccc(OC)cc2)c(=O)n1-c1ccccc1OC] | 2-butyl-6-hydroxy-3-(2-methoxyphenyl)-5-[(4-methoxyphenyl)methyl]-3,4-dihydropyrimidin-4-one | 1H NMR (500 MHz, CHLOROFORM-d) d 7.57-7.51 (m, 1H), 7.36-7.32 (m, 2H), 7.15-7.12 (m, 2H), 7.10 (d, J = 8.5 Hz, 1H), 6.82-6.77 (m, 2H), 3.82 (s, 3H), 3.77 (s, 3H), 3.76-3.67 (m, 2H), 2.67-2.59 (m, 1H), 2.51-2.44 (m, 1H), 1.56-1.46 (m, 2H), 1.29-1.19 (m, 3H), 0.75 (t, J = 7.3 Hz, 3H) | 3.25 E 395.1 | C |
| 4 | 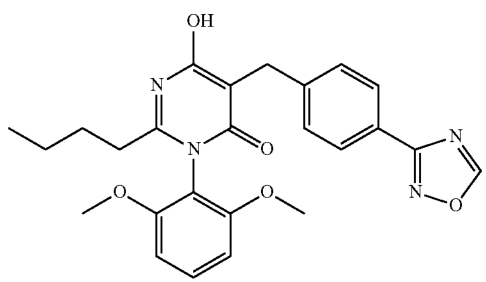 | 2-butyl-3-(2,6-dimethoxyphenyl)-6-hydroxy-5-[[4-(1,2,4-oxadiazol-3-yl)phenyl]methyl]-3,4-dihydropyrimidin-4-one | 1H NMR (500 MHz, DMSO-d6) d 9.67 (s, 1H), 7.93 (d, J = 8.2 Hz, 2H), 7.45 (t, J = 8.5 Hz, 2H), 7.42 (d, J = 8.2 Hz, 2H), 6.84 (d, J = 8.5 Hz, 2H), 3.75 (s, 6H), 3.69 (s, 2H), 2.20 (t, J = 7.6 Hz, 2H), 1.45 (m, 2H), 1.16 (m, 2H), 0.72 (t, J = 7.3 Hz, 3H) | 1.57 A 463.2 | A |

| Ex# | Structure | Name | NMR | Rt(min) method M + H | APJ cAMP Potency range |
|---|---|---|---|---|---|
| 5 | 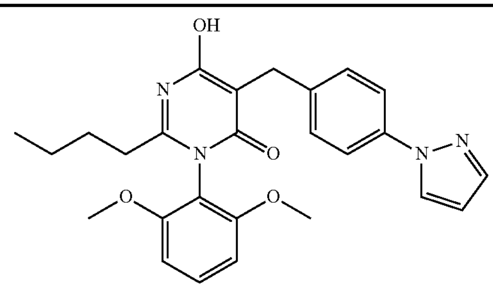 | 2-butyl-3-(2,6-dimethoxyphenyl)-6-hydroxy-5-{[4-(1H-pyrazol-1-yl)phenyl]methyl}-3,4-dihydropyrimidin-4-one | 1H NMR (500 MHz, DMSO-d6) d 8.40 (s, 1H), 7.71 (s, 1H), 7.68 (d, J = 7.7 Hz, 2H), 7.43 (t, J = 7.4 Hz, 1H), 7.34 (d, J = 7.3 Hz, 2H), 6.82 (d, J = 6.8 Hz, 2H), 6.51 (s, 1H), 3.76 (s, 6H), 3.61 (s, 2H), 2.16 (t, J = 7.6 Hz, 2H), 1.43 (m, 2H), 1.15 (m, 2H), 0.71 (t, J = 7.3 Hz, 3H) | 1.53 A 461.5 | A |
| 6 | 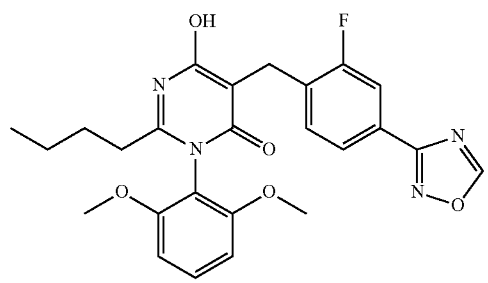 [SMILES: CCCCc1nc(O)c(Cc2ccc(-c3ncon3)cc2F)c(=O)n1-c1c(OC)cccc1OC] | 2-butyl-3-(2,6-dimethoxyphenyl)-5-{[2-fluoro-4-(1,2,4-oxadiazol-3-yl)phenyl]methyl}-6-hydroxy-3,4-dihydropyrimidin-4-one | 1H NMR (500 MHz, DMSO-d6) d 9.73 (s, 1H), 7.80 (d, J = 7.9 Hz, 1H), 7.72 (d, J = 9.5 Hz, 1H), 7.45 (t, J = 8.5 Hz, 1H), 7.32 (t, J = 7.9 Hz, 1H), 6.84 (d, J = 8.5 Hz, 2H), 3.77 (s, 6H), 3.71 (s, 2H), 2.23 (t, J = 7.6 Hz, 2H), 1.47 (m, 2H), 1.18 (m, 2H), 0.73 (t, J = 7.6 Hz, 3H) | 1.64 A 480.9 | A |
| 7 | 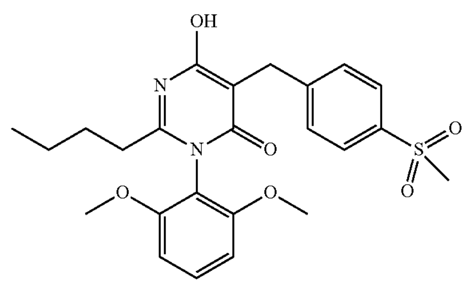 [SMILES: CCCCc1nc(O)c(Cc2ccc(S(C)(=O)=O)cc2)c(=O)n1-c1c(OC)cccc1OC] | 2-butyl-3-(2,6-dimethoxyphenyl)-6-hydroxy-5-[(4-methanesulfonylphenyl)methyl]-3,4-dihydropyrimidin-4-one | 1H NMR (500 MHz, DMSO-d6) d 7.81 (d, J = 8.2 Hz, 2H), 7.47 (d, J = 8.2 Hz, 2H), 7.45 (t, J = 8.5 Hz, 1H), 6.84 (d, J = 8.5 Hz, 2H), 3.75 (s, 6H), 3.70 (s, 2H), 3.17 (s, 3H), 2.20 (t, J = 7.6 Hz, 2H), 1.44 (m, 2H), 1.16 (m, 2H), 0.72 (t, J = 7.3 Hz, 3H) | 1.35 A 473.2 | B |

-continued

| Ex# | Structure | Name | NMR | Rt(min) method M + H | APJ cAMP Potency range |
|---|---|---|---|---|---|
| 8 | 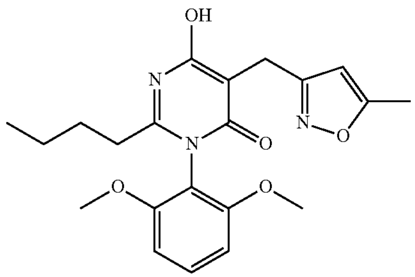 [SMILES: CCCCc1nc(O)c(Cc2cc(C)on2)c(=O)n1-c1c(OC)cccc1OC] | 2-butyl-3-(2,6-dimethoxyphenyl)-6-hydroxy-5-[(5-methyl-1,2-oxazol-3-yl)methyl]-3,4-dihydropyrimidin-4-one | 1H NMR (500 MHz, DMSO-d6) d 7.46 (t, J = 8.5 Hz, 1H), 6.85 (d, J = 8.2 Hz, 2H), 5.91 (s, 1H) 3.76 (s, 6H), 3.55 (s, 2H), 2.20 (t, J = 7.6 Hz, 2H), 1.45 (m, 2H), 1.16 (m, 2H), 0.72 (t, J = 7.6 Hz, 3H) | 1.29 A 400.1 | B |
| 9 | 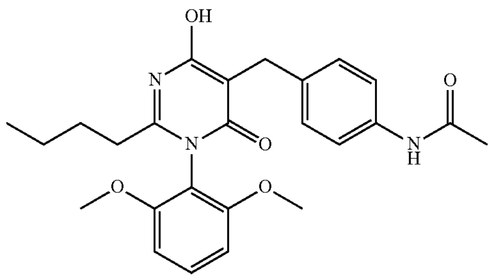 [SMILES: CCCCc1nc(O)c(Cc2ccc(NC(C)=O)cc2)c(=O)n1-c1c(OC)cccc1OC] | N-(4-{[2-butyl-1-(2,6-dimethoxyphenyl)-4-hydroxy-6-oxo-1,6-dihydropyrimidin-5-yl]methyl}phenyl)acetamide | 1H NMR (500 MHz, DMSO-d6) d 7.45 (t, J = 8.5 Hz, 1H), 7.41 (d, J = 8.2 Hz, 2H), 7.13 (d, J = 8.2 Hz, 2H), 6.84 (d, J = 8.2 Hz, 2H), 3.74 (s, 6H), 3.53 (s, 2H), 2.18 (t, J = 7.6 Hz, 2H), 2.02 (s, 3H), 1.44 (m, 2H), 1.15 (m, 2H), 0.72 (t, J = 7.0 Hz, 3H) | 1.32 A 452.1 | B |
| 10 | 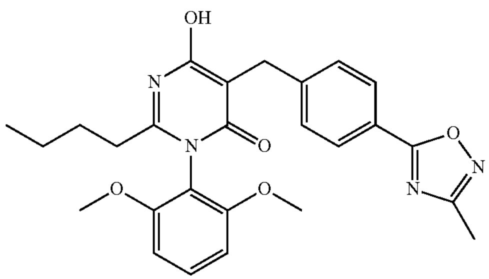 [SMILES: CCCCc1nc(O)c(Cc2ccc(-c3nc(C)no3)cc2)c(=O)n1-c1c(OC)cccc1OC] | 2-butyl-3-(2,6-dimethoxyphenyl)-6-hydroxy-5-{[4-(3-methyl-1,2,4-oxadiazol-5-yl)phenyl]methyl}-3,4-dihydropyrimidin-4-one | 1H NMR (500 MHz, DMSO-d6) d 7.98 (d, J = 8.2 Hz, 2H), 7.44-7.46 (m, 3H), 6.84 (d, J = 8.2 Hz, 2H), 3.74 (s, 6H), 3.70 (s, 2H), 2.41 (s 3H), 2.19 (t, J = 7.3 Hz, 2H), 1.44 (m, 2H), 1.15 (m, 2H), 0.71 (t, J = 7.3 Hz, 3H) | 1.65 A 477.1 | A |

| Ex# | Structure | Name | NMR | Rt(min) method M + H | APJ cAMP Potency range |
|---|---|---|---|---|---|
| 11 | 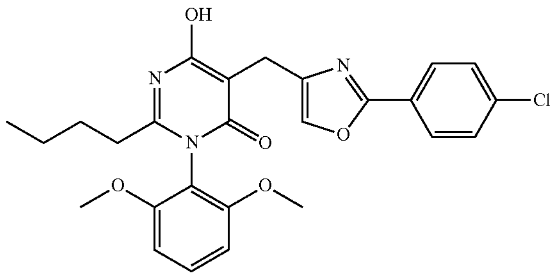 [SMILES: CCCCc1nc(O)c(Cc2coc(-c3ccc(Cl)cc3)n2)c(=O)n1-c1c(OC)cccc1OC] | 2-butyl-5-{[2-(4-chlorophenyl)-1,3-oxazol-4-yl]methyl}-3-(2,6-dimethoxyphenyl)-6-hydroxy-3,4-dihydropyrimidin-4-one | 1H NMR (500 MHz, DMSO-d6) d 7.95 (d, J = 8.5 Hz, 2H), 7.60 (s, 1H), 7.60 (d, J = 8.5 Hz, 2H), 7.45 (t, J = 8.5 Hz, 1H), 6.84 (d, J = 8.2 Hz, 2H), 3.76 (s, 6H), 3.56 (s, 2H), 2.21 (t, J = 7.3 Hz, 2H), 1.46 (m, 2H), 1.17 (m, 2H), 0.73 (t, J = 7.3 Hz, 3H) | 1.82 A 496.0 | A |
| 12 | 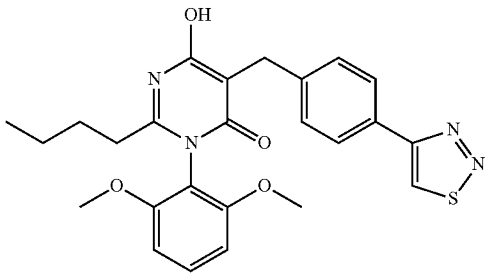 [SMILES: CCCCc1nc(O)c(Cc2ccc(-c3csnn3)cc2)c(=O)n1-c1c(OC)cccc1OC] | 2-butyl-3-(2,6-dimethoxyphenyl)-6-hydroxy-5-{[4-(1,2,3-thiadiazol-4-yl)phenyl]methyl}-3,4-dihydropyrimidin-4-one | 1H NMR (500 MHz, DMSO-d6) d 9.53 (s, 1H), 8.01 (d, J = 7.9 Hz, 2H), 7.46 (t, J = 8.5 Hz, 1H), 7.40 (d, J = 7.9 Hz, 2H), 6.85 (d, J = 8.2 Hz, 2H), 3.76 (s, 6H), 3.68 (s, 2H), 2.20 (t, J = 7.6 Hz, 2H), 1.45 (m, 2H), 1.16 (m, 2H), 0.72 (t, J = 7.3 Hz, 3H) | 1.64 A 479.1 | A |
| 13 | 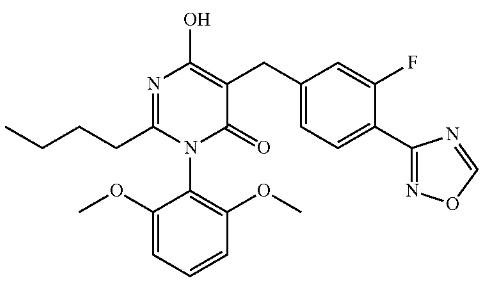 [SMILES: CCCCc1nc(O)c(Cc2ccc(-c3ncon3)c(F)c2)c(=O)n1-c1c(OC)cccc1OC] | 2-butyl-3-(2,6-dimethoxyphenyl)-5-{[3-fluoro-4-(1,2,4-oxadiazol-3-yl)phenyl]methyl}-6-hydroxy-3,4-dihydropyrimidin-4-one | 1H NMR (500 MHz, DMSO-d6) d 9.73 (s, 1H), 7.94 (t, J = 7.6 Hz, 1H), 7.46 (t, J = 8.5 Hz, 1H), 7.27 (d, J = 7.9 Hz, 1H), 7.21 (d, J = 11.9 Hz, 1H), 6.85 (d, J = 8.5 Hz, 2H), 3.76 (s, 6H), 3.70 (s, 2H), 2.22 (t, J = 7.6 Hz, 2H), 1.45 (m, 2H), 1.16 (m, 2H), 0.72 (t, J = 7.3 Hz, 3H) | 1.55 A 481.2 | A |

| Ex# | Structure | Name | NMR | Rt(min) method M + H | APJ cAMP Potency range |
|---|---|---|---|---|---|
| 14 | 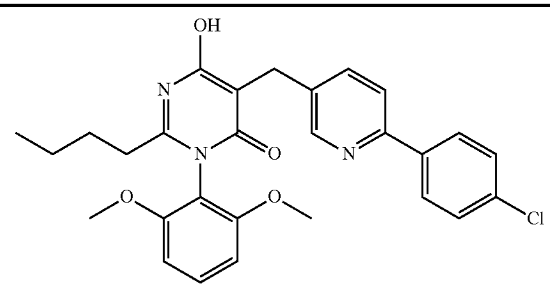 | 2-butyl-5-{[6-(4-chlorophenyl)pyridin-3-yl]methyl}-3-(2,6-dimethoxyphenyl)-6-hydroxy-3,4-dihydropyrimidin-4-one | 1H NMR (500 MHz, DMSO-d6) δ 8.53 (s, 1H), 8.08 (d, J = 8.2 Hz, 2H), 7.89 (d, J = 7.9 Hz, 1H), 7.68 (d, J = 7.9 Hz, 1H), 7.54 (d, J = 8.2 Hz, 2H), 7.46 (t, J = 8.5 Hz, 1H), 6.85 (d, J = 8.5 Hz, 2H), 3.75 (s, 6H), 3.65 (s, 2H), 2.21 (t, J = 7.6 Hz, 2H), 1.45 (m, 2H), 1.16 (m, 2H), 0.72 (t, J = 7.3 Hz, 3H) | 1.90 A 506.1 | A |
| 15 | 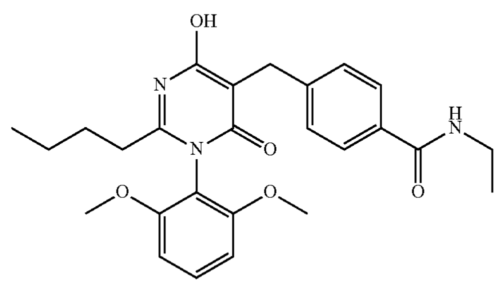 [SMILES: CCCCc1nc(O)c(Cc2ccc(C(=O)NCC)cc2)c(=O)n1-c1c(OC)cccc1OC] | 4-{[2-butyl-1-(2,6-dimethoxyphenyl)-4-hydroxy-6-oxo-1,6-dihydropyrimidin-5-yl]methyl}-N-ethylbenzamide | 1H NMR (500 MHz, DMSO-d6) δ 8.34 (t, J = 5.5 Hz, 1H), 7.71 (d, J = 8.2 Hz, 2H), 7.45 (t, J = 8.2 Hz, 1H), 7.28 (d, J = 7.9 Hz, 2H), 6.84 (d, J = 8.5 Hz, 2H), 3.75 (s, 6H), 3.64 (s, 2H), 3.25-3.33 (m, 2H), 2.19 (t, J = 7.6 Hz, 2H), 1.44 (m, 2H), 1.10-1.18 (m, 5H), 0.72 (t, J = 7.3 Hz, 3H) | 1.36 A 466.0 | B |
| 16 | 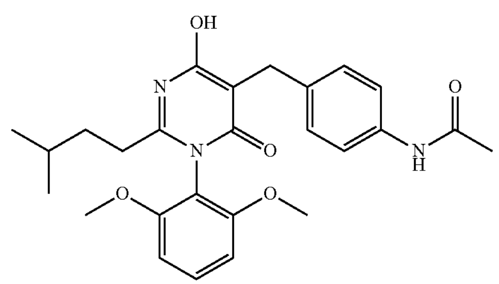 [SMILES: COc1cccc(OC)c1-n1c(CCC(C)C)nc(O)c(Cc2ccc(NC(C)=O)cc2)c1=O] | N-(4-{[1-(2,6-dimethoxyphenyl)-4-hydroxy-2-(3-methylbutyl)-6-oxo-1,6-dihydropyrimidin-5-yl]methyl}phenyl)acetamide | 1H NMR (500 MHz, DMSO-d6) δ 9.82 (s, 1H), 7.45 (t, J = 8.2 Hz, 1H), 7.41 (d, J = 7.9 Hz, 2H), 7.13 (d, J = 8.2 Hz, 2H), 6.84 (d, J = 8.5 Hz, 2H), 3.74 (s, 6H), 3.53 (s, 2H), 2.17 (t, J = 7.9 Hz, 2H), 2.01 (s, 3H), 1.32-1.37 (m, 3H), 0.67 (d, J = 5.5 Hz, 6H) | 1.46 A 466.2 | B |

| Ex# | Structure | Name | NMR | Rt(min) method M + H | APJ cAMP Potency range |
|---|---|---|---|---|---|
| 17 | 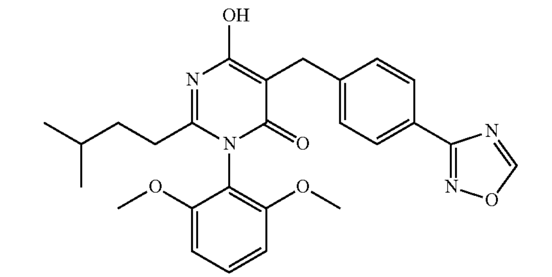 [SMILES: COc1cccc(OC)c1-n1c(CCC(C)C)nc(O)c(Cc2ccc(-c3ncon3)cc2)c1=O] | 3-(2,6-dimethoxyphenyl)-6-hydroxy-2-(3-methylbutyl)-5-{[4-(1,2,4-oxadiazol-3-yl)phenyl]methyl}-3,4-dihydropyrimidin-4-one | 1H NMR (500 MHz, DMSO-d6) δ 9.67 (s, 1H), 7.94 (d, J = 7.9 Hz, 2H), 7.73 (d, J = 7.9 Hz, 2H), 7.46 (t, J = 8.2 Hz, 1H), 6.85 (d, J = 8.5 Hz, 2H), 3.76 (s, 6H), 3.68 (s, 2H), 2.20 (m, 2H), 1.35 (m, 3H), 0.67 (d, J = 4.3 Hz, 6H) | 1.67 A 477.2 | B |
| 18 | 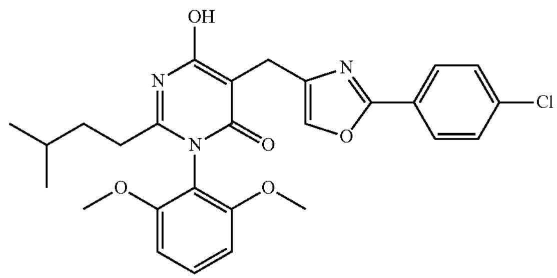 [SMILES: COc1cccc(OC)c1-n1c(CCC(C)C)nc(O)c(Cc2coc(-c3ccc(Cl)cc3)n2)c1=O] | 5-{[2-(4-chlorophenyl)-1,3-oxazol-4-yl]methyl}-3-(2,6-dimethoxyphenyl)-6-hydroxy-2-(3-methylbutyl)-3,4-dihydropyrimidin-4-one | 1H NMR (500 MHz, DMSO-d6) δ 7.95 (d, J = 8.2 Hz, 2H), 7.60 (s, 1H), 7.60 (d, J = 8.2 Hz, 2H), 7.45 (t, J = 8.5 Hz, 1H), 6.84 (d, J = 8.5 Hz, 2H), 3.76 (s, 6H), 3.56 (s, 2H), 2.20 (t, J = 7.6 Hz, 2H), 1.36 (m, 3H), 0.69 (d, J = 5.5 Hz, 6H) | 1.89 A 510.0 | B |
| 19 | 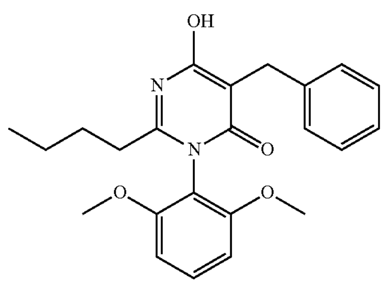 [SMILES: CCCCc1nc(O)c(Cc2ccccc2)c(=O)n1-c1c(OC)cccc1OC] | 5-benzyl-2-butyl-3-(2,6-dimethoxyphenyl)-6-hydroxy-3,4-dihydropyrimidin-4-one | 1H NMR (500 MHz, DMSO-d6) δ 7.45 (t, J = 8.5 Hz, 1H), 7.23 (m, 4H), 7.14 (m, 1H), 6.84 (d, J = 8.5 Hz, 2H), 3.75 (s, 6H), 3.60 (s, 2H), 2.19 (t, J = 7.6 Hz, 2H), 1.44 (m, 2H), 1.16 (m, 2H), 0.72 (t, J = 7.3 Hz, 3H) | 1.59 A 394.9 | B |

| Ex# | Structure | Name | NMR | Rt(min) method M + H | APJ cAMP Potency range |
|---|---|---|---|---|---|
| 20 | 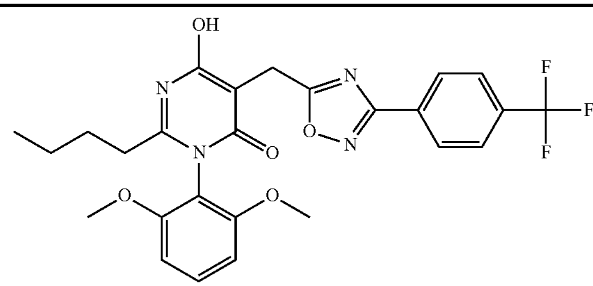 | 2-butyl-3-(2,6-dimethoxyphenyl)-6-hydroxy-5-({3-[4-(trifluoromethyl)phenyl]-1,2,4-oxadiazol-5-yl}methyl)-3,4-dihydropyrimidin-4-one | 1H NMR (500 MHz, DMSO-d6) d 8.29 (d, J = 8.2 Hz, 2H), 8.00 (d, J = 8.2 Hz, 2H), 7.45 (t, J = 8.2 Hz, 1H), 6.84 (d, J = 8.5 Hz, 2H), 3.82 (s, 2H), 3.75 (s, 6H), 2.23 (t, J = 7.3 Hz, 2H), 1.47 (m, 2H), 1.18 (m, 2H), 0.73 (t, J = 7.3 Hz, 3H) | 1.81 A 531.1 | A |
| 21 | 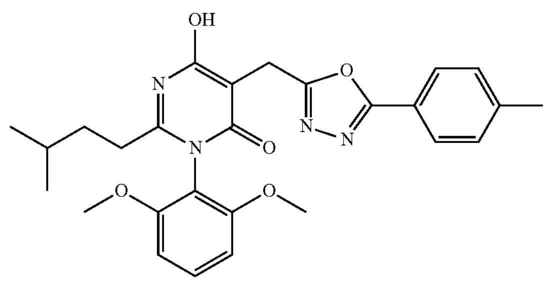 [SMILES: COc1cccc(OC)c1-n1c(CCC(C)C)nc(O)c(Cc2nnc(-c3ccc(C)cc3)o2)c1=O] | 3-(2,6-dimethoxyphenyl)-6-hydroxy-2-(3-methylbutyl)-5-{[5-(4-methylphenyl)-1,3,4-oxadiazol-2-yl]methyl}-3,4-dihydropyrimidin-4-one | 1H NMR (500 MHz, DMSO-d6) d 7.81 (d, J = 7.9 Hz, 2H), 7.45 (t, J = 8.5 Hz, 1H), 7.41 (d, J = 7.9 Hz, 2H), 6.84 (d, J = 8.5 Hz, 2H), 3.90 (s, 2H), 3.75 (s, 6H), 2.40 (s, 3H), 2.21 (m, 2H), 1.36 (m, 3H), 0.68 (d, J = 5.5 Hz, 6H) | 1.66 A 491.1 | B |
| 22 | 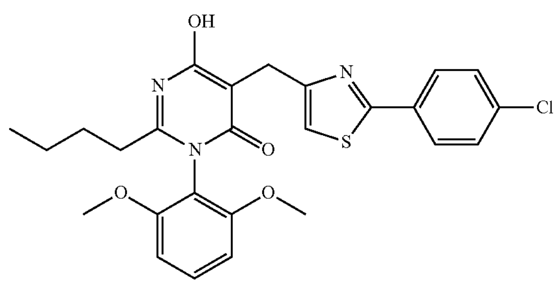 [SMILES: CCCCc1nc(O)c(Cc2csc(-c3ccc(Cl)cc3)n2)c(=O)n1-c1c(OC)cccc1OC] | 2-butyl-5-{[2-(4-chlorophenyl)-1,3-thiazol-4-yl]methyl}-3-(2,6-dimethoxyphenyl)-6-hydroxy-3,4-dihydropyrimidin-4-one | 1H NMR (500 MHz, DMSO-d6) d 7.93 (d, J = 7.9 Hz, 2H), 7.57 (d, J = 7.9 Hz, 2H), 7.46 (t, J = 8.5 Hz, 1H), 7.01 (s, 1H), 6.85 (d, J = 8.5 Hz, 2H), 3.80 (s, 2H), 3.77 (s, 6H), 2.22 (t, J = 7.6 Hz, 2H), 1.47 (m, 2H), 1.18 (m, 2H), 0.74 (t, J = 7.0 Hz, 3H) | 1.98 A 512.3 | B |

| Ex# | Structure | Name | NMR | Rt(min) method M + H | APJ cAMP Potency range |
|---|---|---|---|---|---|
| 23 | 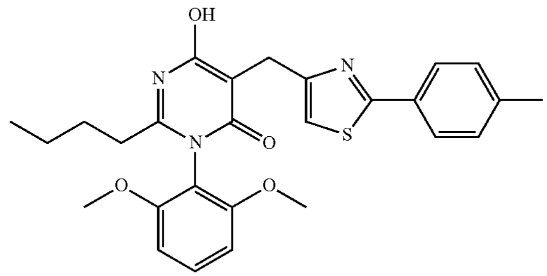 [SMILES: CCCCc1nc(O)c(Cc2csc(-c3ccc(C)cc3)n2)c(=O)n1-c1c(OC)cccc1OC] | 2-butyl-3-(2,6-dimethoxyphenyl)-6-hydroxy-5-{[2-(4-methylphenyl)-1,3-thiazol-4-yl]methyl}-3,4-dihydropyrimidin-4-one | 1H NMR (500 MHz, DMSO-d6) d 7.80 (d, J = 7.6 Hz, 2H), 7.45 (t, J = 8.2 Hz, 1H), 7.31 (d, J = 7.9 Hz, 2H), 6.91 (s, 1H), 6.85 (d, J = 8.5 Hz, 2H), 3.78 (s, 6H), 3.77 (s, 6H), 2.22 (t, J = 7.6 Hz, 2H), 1.47 (m, 2H), 1.18 (m, 2H), 0.73 (t, J = 7.0 Hz, 3H) | 1.88 B 492.0 | B |
| 24 | 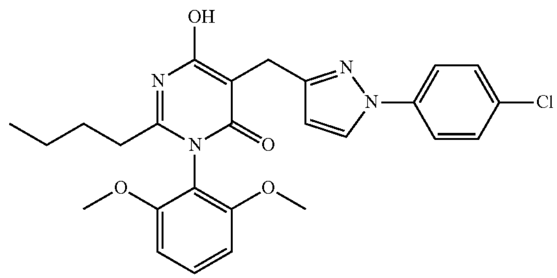 [SMILES: CCCCc1nc(O)c(Cc2ccn(-c3ccc(Cl)cc3)n2)c(=O)n1-c1c(OC)cccc1OC] | 2-butyl-5-{[1-(4-chlorophenyl)-1H-pyrazol-3-yl]methyl}-3-(2,6-dimethoxyphenyl)-6-hydroxy-3,4-dihydropyrimidin-4-one | 1H NMR (500 MHz, DMSO-d6) d 8.33 (s, 1H), 7.81 (d, J = 8.2 Hz, 2H), 7.53 (d, J = 8.2 Hz, 2H), 7.45 (t, J = 8.5 Hz, 1H), 6.84 (d, J = 8.2 Hz, 2H), 6.21 (s, 1H), 3.76 (s, 6H), 3.58 (s, 2H), 2.20 (t, J = 7.6 Hz, 2H), 1.45 (m, 2H), 1.16 (m, 2H), 0.72 (t, J = 7.3 Hz, 3H) | 1.94 B 495.0 | A |
| 25 | 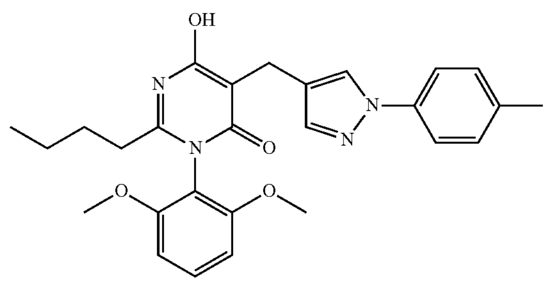 [SMILES: CCCCc1nc(O)c(Cc2cnn(-c3ccc(C)cc3)c2)c(=O)n1-c1c(OC)cccc1OC] | 2-butyl-3-(2,6-dimethoxyphenyl)-6-hydroxy-5-{[1-(4-methylphenyl)-1H-pyrazol-4-yl]methyl}-3,4-dihydropyrimidin-4-one | 1H NMR (500 MHz, DMSO-d6) d 8.07 (s, 1H), 7.63 (d, J = 7.9 Hz, 2H), 7.47 (s, 1H), 7.45 (t, J = 8.2 Hz, 1H), 7.27 (d, J = 7.9 Hz, 2H), 6.85 (d, J = 8.2 Hz, 2H), 3.75 (s, 6H), 3.48 (s, 2H), 2.33 (s, 3H), 2.19 (t, J = 7.3 Hz, 2H), 1.45 (m, 2H), 1.16 (m, 2H), 0.72 (t, J = 7.0 Hz, 3H) | 1.75 A 475.1 | A |

| Ex# | Structure | Name | NMR | Rt(min) method M + H | APJ cAMP Potency range |
|---|---|---|---|---|---|
| 26 | 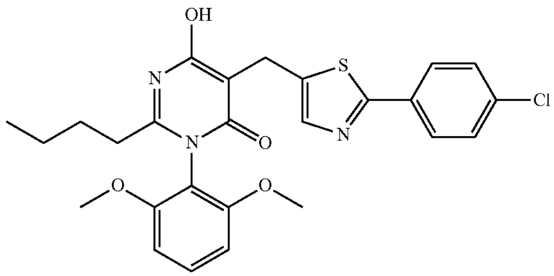 [SMILES: CCCCc1nc(O)c(Cc2cnc(-c3ccc(Cl)cc3)s2)c(=O)n1-c1c(OC)cccc1OC] | 2-butyl-5-{[2-(4-chlorophenyl)-1,3-thiazol-5-yl]methyl}-3-(2,6-dimethoxyphenyl)-6-hydroxy-3,4-dihydropyrimidin-4-one | 1H NMR (500 MHz, DMSO-d6) d 7.87 (d, J = 8.2 Hz, 2H), 7.59 (s, 1H), 7.54 (d, J = 8.2 Hz, 1H), 7.43 (t, J = 8.5 Hz, 1H), 6.82 (d, J = 8.5 Hz, 2H), 3.79 (s, 2H), 3.74 (s, 6H), 2.14 (t, J = 7.6 Hz, 2H), 1.42 (m, 2H), 1.14 (m, 2H), 0.71 (t, J = 7.0 Hz, 3H) | 1.96 A 511.9 | A |
| 27 | 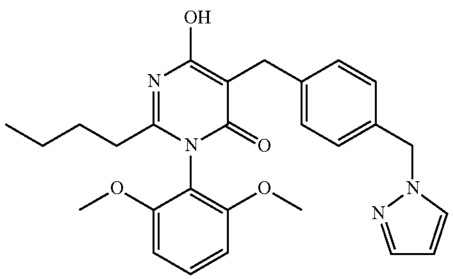 [SMILES: CCCCc1nc(O)c(Cc2ccc(Cn3cccn3)cc2)c(=O)n1-c1c(OC)cccc1OC] | 2-butyl-3-(2,6-dimethoxyphenyl)-6-hydroxy-5-{[4-((1H-pyrazol-1-yl)methyl)phenyl]methyl}-3,4-dihydropyrimidin-4-one | 1H NMR (500 MHz, DMSO-d6) d 7.78 (s, 1H), 7.45 (s, 1H), 7.45 (t, J = 8.2 Hz, 1H), 7.18 (d, J = 7.3 Hz, 2H), 7.10 (d, J = 7.6 Hz, 2H), 6.84 (d, J = 8.2 Hz, 2H), 6.26 (s, 1H), 5.26 (s, 2H), 3.74 (s, 6H), 3.57 (s, 2H), 2.18 (t, J = 7.3 Hz, 2H), 1.44 (m, 2H), 1.15 (m, 2H), 0.72 (t, J = 7.0 Hz, 3H) | 1.57 A 475.1 | A |
| 28 | 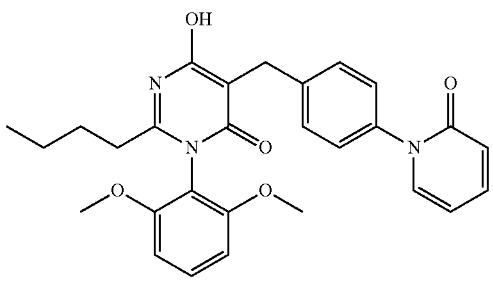 [SMILES: CCCCc1nc(O)c(Cc2ccc(-n3ccccc3=O)cc2)c(=O)n1-c1c(OC)cccc1OC] | 2-butyl-3-(2,6-dimethoxyphenyl)-6-hydroxy-5-{[4-(2-oxo-1,2-dihydropyridin-1-yl)phenyl]methyl}-3,4-dihydropyrimidin-4-one | 1H NMR (500 MHz, DMSO-d6) d 7.63 (d, J = 6.1 Hz, 1H), 7.50 (t, J = 7.3 Hz, 1H), 7.46 (t, J = 7.9 Hz, 1H), 7.34 (d, J = 8.2 Hz, 2H), 7.26 (d, J = 8.5 Hz, 2H), 6.85 (d, J = 7.9 Hz, 2H), 6.47 (d, J = 9.2 Hz, 1H), 6.30 (t, J = 5.5 Hz, 1H), 3.76 (s, 6H), 3.66 (s, 2H), 2.20 (t, J = 7.3 Hz, 2H), 1.45 (m, 2H), 1.16 (m, 2H), 0.72 (t, J = 7.0 Hz, 3H) | 1.43 A 488.1 | A |

| Ex# | Structure | Name | NMR | Rt(min) method M + H | APJ cAMP Potency range |
|---|---|---|---|---|---|
| 29 | 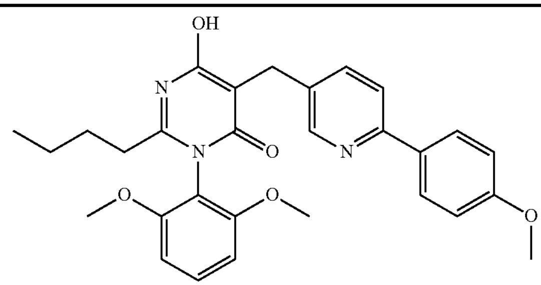 | 2-butyl-3-(2,6-dimethoxyphenyl)-6-hydroxy-5-{[6-(4-methoxyphenyl)pyridin-3-yl]methyl}-3,4-dihydropyrimidin-4-one | 1H NMR (500 MHz, DMSO-d6) d 8.45 (s, 1H), 7.98 (d, J = 8.2 Hz, 1H), 7.54 (d, J = 7.3 Hz, 2H), 7.46 (t, J = 8.5 Hz, 1H), 7.32 (d, J = 7.6 Hz, 2H), 6.91 (d, J = 8.5 Hz, 1H), 6.85 (d, J = 8.5 Hz, 2H), 3.90 (s, 3H), 3.76 (s, 6H), 3.64 (s, 2H), 2.20 (t, J = 7.6 Hz, 2H), 1.45 (m, 2H), 1.16 (m, 2H), 0.72 (t, J = 7.0 Hz, 3H) | 1.84 A 502.1 | A |
| 30 | 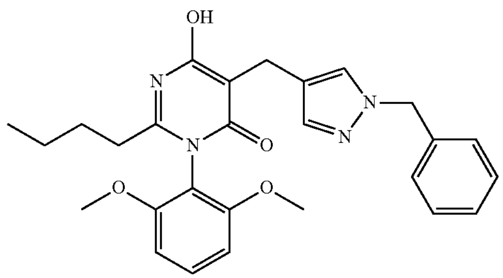 [SMILES: CCCCc1nc(O)c(Cc2cnn(Cc3ccccc3)c2)c(=O)n1-c1c(OC)cccc1OC] | 5-[(1-benzyl-1H-pyrazol-4-yl)methyl]-2-butyl-3-(2,6-dimethoxyphenyl)-6-hydroxy-3,4-dihydropyrimidin-4-one | 1H NMR (500 MHz, DMSO-d6) d 7.43-7.46 (m, 2H), 7.2-7.35 (m, 3H), 7.21-7.23 (m, 3H), 6.84 (d, J = 8.5 Hz, 2H), 3.73 (s, 8H), 2.17 (t, J = 7.3 Hz, 2H), 1.44 (m, 2H), 1.15 (m, 2H), 0.72 (t, J = 7.3 Hz, 3H) | 1.62 A 475.1 | A |
| 31 | 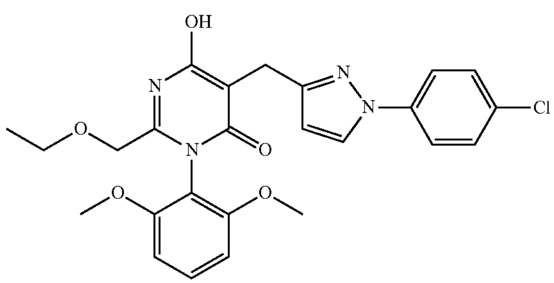 [SMILES: CCOCc1nc(O)c(Cc2ccn(-c3ccc(Cl)cc3)n2)c(=O)n1-c1c(OC)cccc1OC] | 5-{[1-(4-chlorophenyl)-1H-pyrazol-3-yl]methyl}-3-(2,6-dimethoxyphenyl)-2-(ethoxymethyl)-6-hydroxy-3,4-dihydropyrimidin-4-one | 1H NMR (500 MHz, DMSO-d6) d 8.36 (s, 1H), 7.82 (d, J = 8.2 Hz, 2H), 7.53 (d, J = 8.2 Hz, 2H), 7.45 (t, J = 8.5 Hz, 1H), 6.83 (d, J = 8.2 Hz, 2H), 6.22 (s, 1H), 3.95 (s, 2H), 3.76 (s, 6H), 3.68 (s, 2H), 3.29 (q, J = 7.0 Hz, 2H), 0.99 (t, J = 7.0 Hz, 3H) | 1.54 A 496.9 | B |

| Ex# | Structure | Name | NMR | Rt(min) method M + H | APJ cAMP Potency range |
|---|---|---|---|---|---|
| 32 | 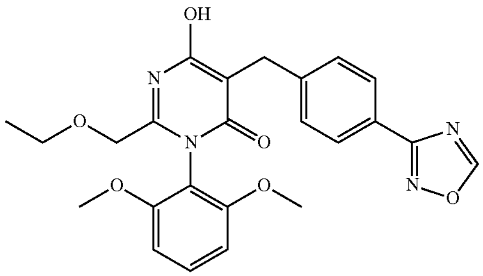 [SMILES: CCOCc1nc(O)c(Cc2ccc(-c3ncon3)cc2)c(=O)n1-c1c(OC)cccc1OC] | 3-(2,6-dimethoxyphenyl)-2-(ethoxymethyl)-6-hydroxy-5-{[4-(1,2,4-oxadiazol-3-yl)phenyl]methyl}-3,4-dihydropyrimidin-4-one | 1H NMR (500 MHz, DMSO-d6) d 9.68 (s, 1H), 7.95 (d, J = 7.6 Hz, 2H), 7.452-7.46 (m, 3H), 6.83 (d, J = 8.5 Hz, 2H), 3.95 (s, 2H), 3.76 (s, 6H), 3.72 (s, 2H), 3.26-3.34 (m, 2H), 0.98 (t, J = 6.7 Hz, 3H) | 1.36 A 465.3 | B |
| 33 | 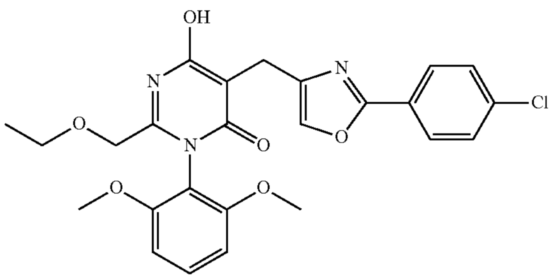 [SMILES: CCOCc1nc(O)c(Cc2coc(-c3ccc(Cl)cc3)n2)c(=O)n1-c1c(OC)cccc1OC] | 5-{[2-(4-chlorophenyl)-1,3-oxazol-4-yl]methyl}-3-(2,6-dimethoxyphenyl)-2-(ethoxymethyl)-6-hydroxy-3,4-dihydropyrimidin-4-one | 1H NMR (500 MHz, DMSO-d6) d 7.95 (d, J = 8.5 Hz, 2H), 7.63 (s, 1H), 7.60 (d, J = 8.5 Hz, 2H), 7.44 (t, J = 8.5 Hz, 1H), 6.83 (d, J = 8.5 Hz, 2H), 3.95 (s, 2H), 3.76 (s, 6H), 3.59 (s, 2H), 3.30 (q, J = 7.0 Hz, 2H), 0.99 (t, J = 7.0 Hz, 3H) | 1.6 A 498.0 | B |
| 34 | 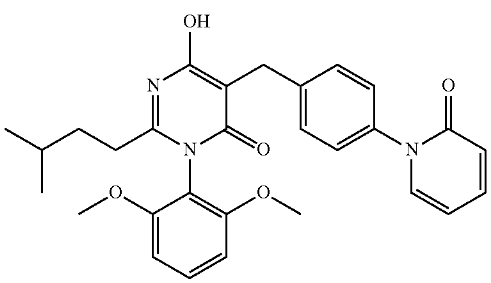 [SMILES: COc1cccc(OC)c1-n1c(CCC(C)C)nc(O)c(Cc2ccc(-n3ccccc3=O)cc2)c1=O] | 3-(2,6-dimethoxyphenyl)-6-hydroxy-2-(3-methylbutyl)-5-{[4-(2-oxo-1,2-dihydropyridin-1-yl)phenyl]methyl}-3,4-dihydropyrimidin-4-one | 1H NMR (500 MHz, DMSO-d6) d 7.62 (dd, J = 1.8, 6.7 Hz, 1H), 7.50 (dt, J = 1.8, 6.7 Hz, 1H), 7.44 (t, J = 8.5 Hz, 1H), 7.35 (d, J = 8.2 Hz, 2H), 7.25 (d, J = 8.2 Hz, 2H), 6.84 (d, J = 8.5 Hz, 2H), 6.47 (d, J = 9.2 Hz, 1H), 6.30 (t, J = 7.6 Hz, 1H), 3.75 (s, 6H), 3.65 (s, 2H), 2.17 (t, J = 7.0 Hz, 2H), 1.33-1.37 (m, 3H), 0.68 (d, J = 6.1 Hz, 6H) | 1.58 A 502.1 | A |

| Ex# | Structure | Name | NMR | Rt(min) method M + H | APJ cAMP Potency range |
|---|---|---|---|---|---|
| 35 | 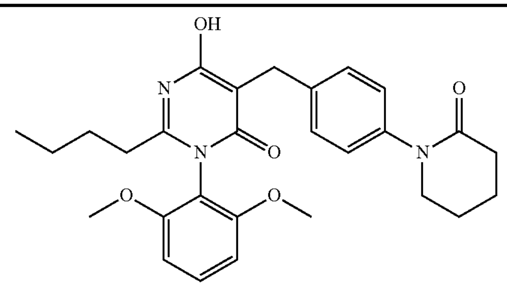 | 2-butyl-3-(2,6-dimethoxyphenyl)-6-hydroxy-5-{[4-(2-oxopiperidin-1-yl)phenyl]methyl}-3,4-dihydropyrimidin-4-one | 1H NMR (500 MHz, DMSO-d6) d 7.45 (t, J = 8.5 Hz, 1H), 7.21 (d, J = 8.2 Hz, 2H), 7.11 (d, J = 8.2 Hz, 2H), 6.84 (d, J = 8.5 Hz, 2H), 3.75 (s, 6H), 3.58 (s, 2H), 3.56 (t, J = 6.1 Hz, 2H), 2.36-2.40 (m, 2H), 2.19 (t, J = 7.6 Hz, 2H), 1.84 (m, 4H), 1.44 (m, 2H), 1.15 (m, 2H), 0.71 (t, J = 7.3 Hz, 3H) | 1.55 A 492.1 | A |
| 36 | 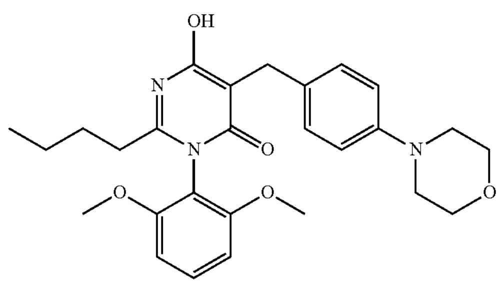 [SMILES: CCCCc1nc(O)c(Cc2ccc(N3CCOCC3)cc2)c(=O)n1-c1c(OC)cccc1OC] | 2-butyl-3-(2,6-dimethoxyphenyl)-6-hydroxy-5-{[4-(morpholin-4-yl)phenyl]methyl}-3,4-dihydropyrimidin-4-one | 1H NMR (500 MHz, DMSO-d6) d 7.41 (t, J = 8.2 Hz, 1H), 7.12 (d, J = 8.5 Hz, 2H), 6.81 (d, J = 8.2 Hz, 2H), 6.79 (d, J = 7.9 Hz, 2H), 3.74 (s, 6H), 3.72 (s, 2H), 3.16-3.20 (m, 2H), 3.01-3.03 (m, 2H), 2.11 (t, J = 7.6 Hz, 2H), 1.59 (m, 2H), 1.42 (m, 2H), 1.33 (m, 2H), 1.14 (m, 2H), 0.71 (t, J = 7.3 Hz, 3H) | 1.56 A 480.1 | A |

Example 37

3-(2,6-dimethoxyphenyl)-5-(4-(5-fluoro-2-oxopyridin-1(2H)-yl)benzyl)-2-(4-fluorophenyl)-6-hydroxypyrimidin-4(3H)-one

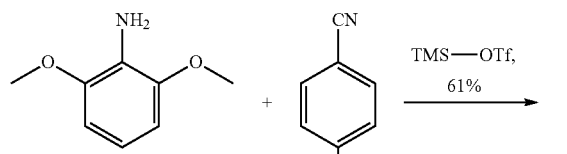

Example 37

Compound 37a. N-(2,6-dimethoxyphenyl)-4-fluorobenzimidamide

To a solution of 2,6-dimethoxyaniline (0.5 g, 3 mmol) and 4-fluorobenzonitrile (0.5 g, 4 mmol) in toluene (10 ml) at 0° C. was added dropwise TMS-OTf (0.65 ml, 3.6 mmol). The resulting mixture was stirred at 0° C. for 10 min and heated to 110° C. for 15 hrs. The reaction mixture was cooled to 0° C., quenched with 1.5 M $Na_2HPO_4$ (10 mL) solution and diluted with EtOAc. The organic layer was washed with 1.5 M $Na_2HPO_4$ solution and dried over sodium sulfate, concentrated to give a brown oil. The residue was purified by a silica gel (80 g) column and was eluted with 0-100% 0.5% TEA/EtOAc in DCM. Fractions containing compound 37a were combined and the solvent removed to give 37a (0.55 g, 2.0 mmol, 61% yield) an off white solid. 1H NMR (500 MHz, $CDCl_3$) δ 7.96 (br s, 2H), 7.10 (br s, 2H), 7.02 (t, J=8.0 Hz, 1H), 6.64 (d, J=7.7 Hz, 2H), 4.68 (br s, 2H), 3.80 (s, 6H).

Compound 37b. 1-(2,6-dimethoxyphenyl)-2-(4-fluorophenyl)-6-hydroxypyrimidin-4(1H)-one To a mixture of Compound 37a (50 mg, 0.18 mmol) and diethyl malonate (44 mg, 0.27 mmol) in TEA (1.0 ml, 7.3 mmol) was added TMS-Cl (0.35 ml, 2.7 mmol) at 0° C. The mixture was stirred at RT for 10 min and heated to 100° C. for 3 d. The reaction mixture was concentrated in vacuo and diluted with EtOAc. The organic layer was washed with 0.1M HCl. The organic layer was dried over $MgSO_4$, filtered and concentrated in vacuo. The residue was added to a silica gel (12 g) column and was eluted with 10-90% EtOAc in hexanes. Fractions containing Compound 37b were combined and the solvent removed to yield a yellow solid (25 mg, 0.07 mmol, 40% yield). 1H NMR (500 MHz, $CDCl_3$) δ 7.31 (dd, J=5.3, 8.8 Hz, 2H), 7.21 (t, J=8.6 Hz, 2H), 6.90 (t, J=8.6 Hz, 1H), 6.45 (d, J=8.6 Hz, 2H), 5.67 (s, 1H), 3.72 (s, 6H).

Compound 37c. 5-fluoro-1-(4-(hydroxymethyl)phenyl)pyridin-2(1H)-one

To a mixture of (4-iodophenyl)methanol (250 mg, 1.07 mmol) and 5-fluoropyridin-2-ol (121 mg, 1.07 mmol) in dioxane (2 mL) was added $Cs_2CO_3$ (696 mg, 2.14 mmol) and N, N-dimethylethylenediamine (141 mg, 1.60 mmol). The mixture was degassed with argon for 20 min. Copper (I) iodide (203 mg, 1.07 mmol) was added and the reaction mixture was heated to 115° C. for 16 hrs. The reaction mixture was allowed to cool to RT, filtered and concentrated in vacuo. The residue was added to a silica gel (40 g) column and was eluted with 0-20% MeOH in DCM. Fractions containing Compound 37c were combined and the solvent removed to yield an off white solid (46 mg, 0.21 mmol, 21% yield). 1H NMR (500 MHz, CDCl$_3$) δ 7.53 (d, J=8.6 Hz, 2H), 7.41 (d, J=8.4 Hz, 2H), 7.37-7.40 (m, 1H), 7.31 (t, J=4.0 Hz, 1H), 6.66 (dd, J=5.4, 9.5 Hz, 1H), 4.79 (s, 2H).

Compound 37d. 1-(4-(chloromethyl)phenyl)-5-fluoropyridin-2(1H)-one

To a stirred solution of Compound 37c (46 mg, 0.21 mmol) in CHCl$_3$ (5 mL) was added thionyl chloride (0.05 mL, 0.6 mmol). The reaction mixture was heated to 35° C. for 2 hrs. The reaction mixture was concentrated in vacuo and diluted with DCM. The organic layer was washed with sat NaHCO$_3$. The organic layer was dried over MgSO$_4$, filtered and concentrated in vacuo. The residue was added to a silica gel (12 g) column and was eluted with 0-100% EtOAc in hexanes. Fractions containing Compound 37c were combined and the solvent removed to yield a white solid (40 mg, 0.17 mmol, 80% yield). 1H NMR (500 MHz, CDCl$_3$) δ 7.55 (d, J=8.5 Hz, 2H), 7.42 (d, J=8.3 Hz, 2H), 7.39 (dd, J=3.5, 6.9 Hz, 1H), 7.28-7.31 (m, 1H), 6.67 (dd, J=4.7, 9.4 Hz, 1H), 4.65 (s, 2H).

Example 37. 3-(2,6-dimethoxyphenyl)-5-(4-(5-fluoro-2-oxopyridin-1(2H)-yl)benzyl)-2-(4-fluorophenyl)-6-hydroxypyrimidin-4(3H)-one To a suspension of Compound 37b (15 mg, 0.040 mmol) and Compound 37d (12.5 mg, 0.0530 mmol) in acetone (1 mL) and water (0.1 mL) was added lithium carbonate (6.48 mg, 0.0880 mmol) and TBAI (8.09 mg, 0.0220 mmol). The reaction mixture was stirred at RT for 5 d. The reaction mixture was concentrated under reduced pressure and filtered. The residue was purified via preparative LC/MS with the following conditions: Column: XBridge C18, 19×200 mm, 5-µm particles; Mobile Phase A: 5:95 acetonitrile:water with 10 mM ammonium acetate; Mobile Phase B: 95:5 acetonitrile:water with 10 mM ammonium acetate; Gradient: 10-55% B over 25 minutes, then a 5-minute hold at 100% B; Flow: 20 mL/min. Fractions containing Example 37 were combined and dried via centrifugal evaporation to give a white solid (2.2 mg, 10% yield). The estimated purity by LCMS analysis was 95%, HPLC method A, Rt=1.28 min, MS m/z=544.3 (M+H). 1H NMR (500 MHz, DMSO-d6) δ 7.90 (br s, 1H), 7.65 (br s, 1H), 7.41 (br s, 2H), 7.22-7.34 (m, 5H), 7.06 (br s, 2H), 6.60 (d, J=7.3 Hz, 2H), 6.50 (dd, J=4.9, 10.0 Hz, 1H), 3.72 (s, 2H), 3.66 (s, 6H). Human APJ cAMP EC$_{50}$ potency range: A.

Examples 38 to 60 were prepared as described in the general procedure given for Example 1.

| Ex # | Structure | Name | NMR | Rt(min) method M + H | APJ cAMP Potency range |
|---|---|---|---|---|---|
| 38 | 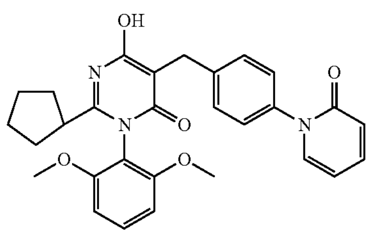 [SMILES: COc1cccc(OC)c1-n1c(C2CCCC2)nc(O)c(Cc2ccc(-n3ccccc3=O)cc2)c1=O] | 2-cyclopentyl-3-(2,6-dimethoxyphenyl)-6-hydroxy-5-{[4-(2-oxo-1,2-dihydropyridin-1-yl)phenyl]methyl}-3,4-dihydropyrimidin-4-one | 1H NMR (500 MHz, DMSO-d6) Shift 7.62 (br d, J = 6.7 Hz, 1H), 7.50 (br t, J = 7.2 Hz, 1H), 7.44 (t, J = 8.4 Hz, 1H), 7.35 (br d, J = 8.2 Hz, 2H), 7.26 (d, J = 8.2 Hz, 2H), 6.83 (d, J = 8.5 Hz, 2H), 6.47 (d, J = 9.2 Hz, 1H), 6.30 (t, J = 6.6 Hz, 1H), 3.75 (s, 6H), 3.67 (s, 2H), 3.26-3.08 (m, 1H), 1.89-1.50 (m, 4H), 1.46-1.22 (m, 4H) | 1.53, A, 500.1 | A |
| 39 | 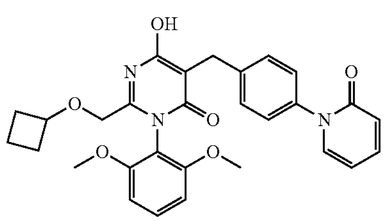 [SMILES: COc1cccc(OC)c1-n1c(COC2CCC2)nc(O)c(Cc2ccc(-n3ccccc3=O)cc2)c1=O] | 2-(cyclobutoxymethyl)-3-(2,6-dimethoxyphenyl)-6-hydroxy-5-{[4-(2-oxo-1,2-dihydropyridin-1-yl)phenyl]methyl}-3,4-dihydropyrimidin-4-one | 1H NMR (500 MHz, DMSO-d6) Shift 7.62 (br d, J = 6.4 Hz, 1H), 7.50 (br t, J = 7.2 Hz, 1H), 7.42 (br t, J = 8.4 Hz, 1H), 7.35 (br d, J = 7.9 Hz, 2H), 7.25 (br d, J = 8.2 Hz, 2H), 6.80 (d, J = 8.5 Hz, 2H), 6.46 (br d, J = 9.2 Hz, 1H), 6.29 (br t, J = 6.7 Hz, 1H), 3.80 (s, 2H), 3.74 (s, 7H), 3.66 (s, 2H), 2.05-1.86 (m, 2H), 1.68-1.46 (m, 3H), 1.43-1.24 (m, 1H) | 1.42, A, 516.1 | A |
| 40 | 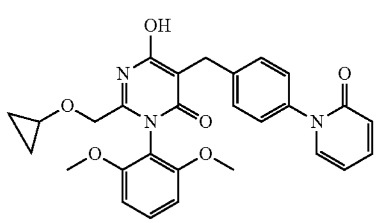 | 2-(cyclopropoxymethyl)-3-(2,6-dimethoxyphenyl)-6-hydroxy-5-{[4-(2-oxo-1,2-dihydropyridin-1-yl)phenyl]methyl}-3,4-dihydropyrimidin-4-one | 1H NMR (500 MHz, DMSO-d6) Shift 7.42 (br d, J = 6.7 Hz, 1H), 7.36-7.28 (m, 1H), 7.24 (t, J = 8.2 Hz, 1H), 7.15 (br d, J = 8.2 Hz, 2H), 7.05 (d, J = 8.2 Hz, 2H), 6.62 (d, J = 8.5 Hz, 2H), 6.27 (d, J = 9.5 Hz, 1H), 6.10 (t, J = 6.4 Hz, 1H), 3.74 (s, 2H), 3.55 (s, 6H), 3.48 (s, 2H), 3.09 (dt, J = 5.9, 3.0 Hz, 1H), 0.22-0.06 (m, 2H), 0.00 (br s, 2H) | 1.27, A, 502.1 | A |

-continued

| Ex # | Structure | Name | NMR | Rt(min) method M + H | APJ cAMP Potency range |
|---|---|---|---|---|---|
| 41 | 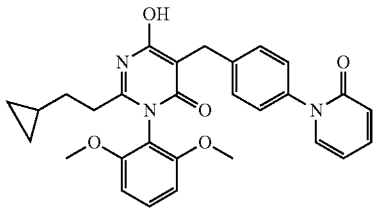 [SMILES: COc1cccc(OC)c1-n1c(COC2CC2)nc(O)c(Cc2ccc(-n3ccccc3=O)cc2)c1=O] | 2-(2-cyclopropylethyl)-3-(2,6-dimethoxyphenyl)-6-hydroxy-5-{[4-(2-oxo-1,2-dihydropyridin-1-yl)phenyl]methyl}-3,4-dihydropyrimidin-4-one | 1H NMR (500 MHz, DMSO-d6) Shift 7.82 (br d, J = 6.1 Hz, 1H), 7.77-7.62 (m, 2H), 7.55 (br d, J = 7.9 Hz, 2H), 7.46 (d, J = 7.9 Hz, 2H), 7.06 (d, J = 8.5 Hz, 2H), 6.69 (d, J = 9.2 Hz, 1H), 6.53 (t, J = 6.7 Hz, 1H), 3.96 (s, 6H), 3.86 (s, 2H), 2.49 (br t, J = 7.8 Hz, 2H), 1.67-1.47 (m, 2H), 0.80 (br s, 1H), 0.50 (br d, J = 7.6 Hz, 2H), 0.01 (br d, J = 4.6 Hz, 2H) | 1.76, A, 500.1 | A |
| 42 | 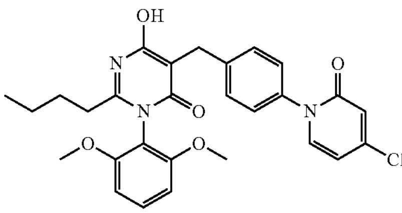 [SMILES: CCCCc1nc(O)c(Cc2ccc(-n3ccc(Cl)cc3=O)cc2)c(=O)n1-c1c(OC)cccc1OC] | 2-butyl-5-{[4-(4-chloro-2-oxo-1,2-dihydropyridin-1-yl)phenyl]methyl}-3-(2,6-dimethoxyphenyl)-6-hydroxy-3,4-dihydropyrimidin-4-one | 1H NMR (500 MHz, DMSO-d6) Shift 7.71 (d, J = 7.3 Hz, 1H), 7.50-7.32 (m, 3H), 7.20 (br d, J = 7.9 Hz, 2H), 6.79 (d, J = 8.5 Hz, 2H), 6.62 (s, 1H), 6.43 (br d, J = 6.1 Hz, 1H), 3.73 (s, 6H), 3.60 (s, 2H), 2.08 (br t, J = 7.6 Hz, 2H), 1.49-1.37 (m, 2H), 1.20-1.04 (m, 2H), 0.70 (t, J = 7.2 Hz, 3H) | 1.76, A, 522.0 | A |
| 43 | 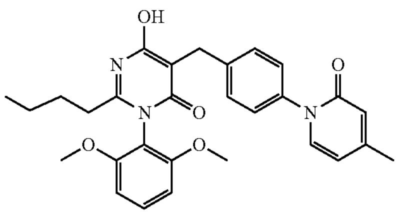 [SMILES: CCCCc1nc(O)c(Cc2ccc(-n3ccc(C)cc3=O)cc2)c(=O)n1-c1c(OC)cccc1OC] | 2-butyl-3-(2,6-dimethoxyphenyl)-6-hydroxy-5-{[4-(4-methyl-2-oxo-1,2-dihydropyridin-1-yl)phenyl]methyl}-3,4-dihydropyrimidin-4-one | 1H NMR (500 MHz, DMSO-d6) Shift 7.50 (d, J = 6.7 Hz, 1H), 7.45 (t, J = 8.4 Hz, 1H), 7.32 (br d, J = 7.9 Hz, 2H), 7.26-7.20 (m, 2H), 6.84 (d, J = 8.5 Hz, 2H), 6.28 (s, 1H), 6.17 (br d, J = 7.0 Hz, 1H), 3.75 (s, 6H), 3.65 (s, 2H), 2.28-2.14 (m, 5H), 1.44 (quin, J = 7.5 Hz, 2H), 1.15 (sxt, J = 7.3 Hz, 2H), 0.71 (t, J = 7.3 Hz, 3H) | 1.49, A, 502.0 | A |
| 44 | 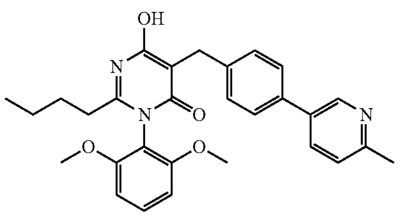 [SMILES: CCCCc1nc(O)c(Cc2ccc(-c3ccc(C)nc3)cc2)c(=O)n1-c1c(OC)cccc1OC] | 2-butyl-3-(2,6-dimethoxyphenyl)-6-hydroxy-5-{[4-(6-methylpyridin-3-yl)phenyl]methyl}-3,4-dihydropyrimidin-4-one | 1H NMR (500 MHz, DMSO-d6) Shift 8.88 (s, 1H), 8.29 (br d, J = 8.5 Hz, 1H), 7.75-7.57 (m, 3H), 7.46 (br t, J = 8.2 Hz, 1H), 7.37 (br d, J = 7.9 Hz, 2H), 6.85 (d, J = 8.5 Hz, 2H), 3.76 (s, 6H), 3.66 (s, 2H), 2.62 (s, 3H), 2.20 (br t, J = 7.3 Hz, 2H), 1.49-1.40 (m, 2H), 1.21-1.10 (m, 2H), 0.72 (t, J = 7.5 Hz, 3H) | 1.86, A, 485.9 | B |
| 45 | 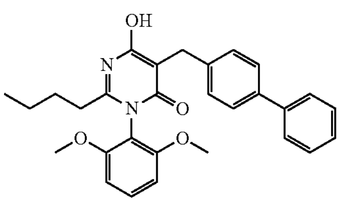 [SMILES: CCCCc1nc(O)c(Cc2ccc(-c3ccccc3)cc2)c(=O)n1-c1c(OC)cccc1OC] | 5-({[1,1'-biphenyl]-4-yl}methyl)-2-butyl-3-(2,6-dimethoxyphenyl)-6-hydroxy-3,4-dihydropyrimidin-4-one | 1H NMR (500 MHz, DMSO-d6) Shift 7.62 (br d, J = 7.6 Hz, 2H), 7.53 (br d, J = 7.9 Hz, 2H), 7.44 (br t, J = 7.3 Hz, 3H), 7.37-7.26 (m, 3H), 6.83 (d, J = 8.5 Hz, 2H), 3.74 (s, 6H), 3.56 (br s, 2H), 2.19 (br t, J = 7.6 Hz, 2H), 1.43 (quin, J = 7.4 Hz, 2H), 1.14 (sxt, J = 7.3 Hz, 2H), 0.70 (t, J = 7.2 Hz, 3H) | 1.95, A, 471.2 | A |
| 46 | 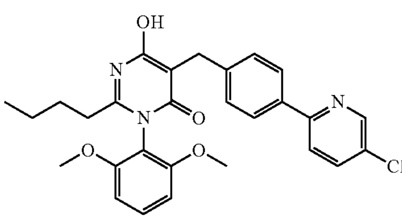 [SMILES: CCCCc1nc(O)c(Cc2ccc(-c3ccc(Cl)cn3)cc2)c(=O)n1-c1c(OC)cccc1OC] | 2-butyl-5-{[4-(5-chloropyridin-2-yl)phenyl]methyl}-3-(2,6-dimethoxyphenyl)-6-hydroxy-3,4-dihydropyrimidin-4-one | 1H NMR (500 MHz, CHLOROFORM-d) Shift 8.61 (dd, J = 2.5, 0.8 Hz, 1H), 7.84 (d, J = 8.5 Hz, 2H), 7.74-7.66 (m, 1H), 7.66-7.60 (m, 1H), 7.55-7.50 (m, 2H), 7.41 (t, J = 8.5 Hz, 1H), 6.69 (d, J = 8.5 Hz, 2H), 3.88 (s, 2H), 3.80 (s, 6H), 2.45-2.31 (m, 2H), 1.51-1.40 (m, 2H), 1.35-1.18 (m, 2H), 0.79 (t, J = 7.4 Hz, 3H) | 2.10, A, 506.1 | A |
| 47 | 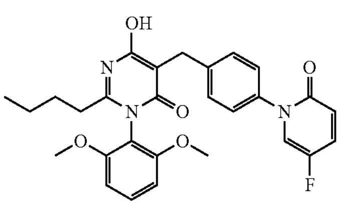 [SMILES: CCCCc1nc(O)c(Cc2ccc(-n3cc(F)ccc3=O)cc2)c(=O)n1-c1c(OC)cccc1OC] | 2-butyl-3-(2,6-dimethoxyphenyl)-5-{[4-(5-fluoro-2-oxo-1,2-dihydropyridin-1-yl)phenyl]methyl}-6-hydroxy-3,4-dihydropyrimidin-4-one | 1H NMR (500 MHz, DMSO-d6) Shift 7.87 (br s, 1H), 7.65 (br t, J = 8.2 Hz, 1H), 7.43 (br t, J = 8.2 Hz, 1H), 7.35 (br d, J = 7.6 Hz, 2H), 7.26 (br d, J = 7.9 Hz, 2H), 6.82 (br d, J = 8.5 Hz, 2H), 6.50 (br dd, J = 10.1, 5.5 Hz, 1H), 3.74 (s, 6H), 3.64 (s, 2H), 2.16 (br t, J = 7.5 Hz, 2H), 1.42 (quin, J = 7.5 Hz, 2H), 1.14 (dq, J = 14.7, 7.4 Hz, 2H), 0.70 (br t, J = 7.2 Hz, 3H) | 1.43, A, 505.9 | A |

-continued

| Ex # | Structure | Name | NMR | Rt(min) method M + H | APJ cAMP Potency range |
|---|---|---|---|---|---|
| 48 | 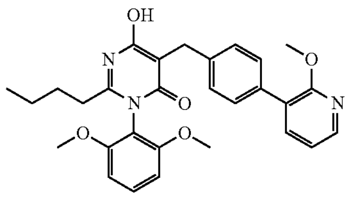 [SMILES: CCCCc1nc(O)c(Cc2ccc(-c3cccnc3OC)cc2)c(=O)n1-c1c(OC)cccc1OC] | 2-butyl-3-(2,6-dimethoxyphenyl)-6-hydroxy-5-{[4-(2-methoxypyridin-3-yl)phenyl]methyl}-3,4-dihydropyrimidin-4-one | 1H NMR (500 MHz, DMSO-d6) Shift 8.15 (dd, J = 4.9, 1.5 Hz, 1H), 7.70 (dd, J = 7.3, 1.8 Hz, 1H), 7.49-7.35 (m, 3H), 7.29 (br d, J = 8.2 Hz, 2H), 7.08 (dd, J = 7.2, 5.0 Hz, 1H), 6.82 (d, J = 8.5 Hz, 2H), 3.87 (s, 2H), 3.74 (s, 6H), 3.61 (s, 3H), 2.15 (br t, J = 7.6 Hz, 2H), 1.43 (quin, J = 7.6 Hz, 2H), 1.14 (sxt, J = 7.3 Hz, 2H), 0.71 (t, J = 7.3 Hz, 3H) | 1.80, A, 502.2 | A |
| 49 | 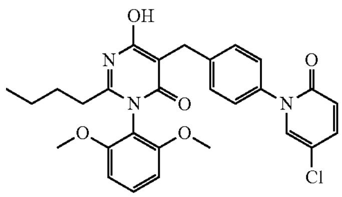 [SMILES: CCCCc1nc(O)c(Cc2ccc(-n3cc(Cl)ccc3=O)cc2)c(=O)n1-c1c(OC)cccc1OC] | 2-butyl-5-{[4-(5-chloro-2-oxo-1,2-dihydropyridin-1-yl)phenyl]methyl}-3-(2,6-dimethoxyphenyl)-6-hydroxy-3,4-dihydropyrimidin-4-one | 1H NMR (500 MHz, DMSO-d6) Shift 7.90 (d, J = 2.7 Hz, 1H), 7.56 (dd, J = 9.8, 3.1 Hz, 1H), 7.43 (t, J = 8.5 Hz, 1H), 7.35 (d, J = 8.2 Hz 2H), 7.26 (J = 8.2 Hz, 2H), 6.82 (d, J = 8.5 Hz, 2H), 6.51 (d, J = 9.8 Hz, 1H), 3.74 (s, 6H), 3.64 (s, 2H), 2.15 (br t, J = 7.6 Hz, 2H), 1.43 (quin, J = 7.5 Hz, 2H), 1.14 (sxt, J = 7.4 Hz, 2H), 0.71 (t, J = 7.3 Hz, 3H) | 1.55, A, 522.1 | A |
| 50 | 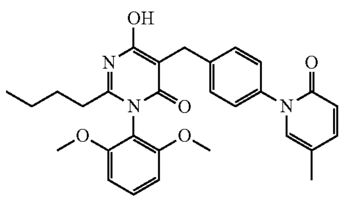 [SMILES: CCCCc1nc(O)c(Cc2ccc(-n3cc(C)ccc3=O)cc2)c(=O)n1-c1c(OC)cccc1OC] | 2-butyl-3-(2,6-dimethoxyphenyl)-6-hydroxy-5-{[4-(5-methyl-2-oxo-1,2-dihydropyridin-1-yl)phenyl]methyl}-3,4-dihydropyrimidin-4-one | 1H NMR (500 MHz, DMSO-d6) Shift 7.53-7.35 (m, 3H), 7.33 (d, J = 8.5 Hz, 2H), 7.24 (d, J = 8.2 Hz, 2H), 6.84 (d, J = 8.5 Hz, 2H), 6.41 (d, J = 9.2 Hz, 1H), 3.75 (s, 6H), 3.65 (s, 2H), 2.19 (t, J = 7.6 Hz, 2H), 1.92 (s, 3H), 1.44 (quin, J = 7.6 Hz, 2H), 1.15 (sxt, J = 7.4 Hz, 2H), 0.71 (t, J = 7.3 Hz, 3H) | 1.47, A, 501.9 | A |
| 51 | 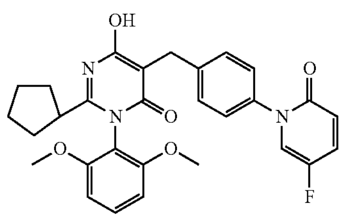 [SMILES: COc1cccc(OC)c1-n1c(C2CCCC2)nc(O)c(Cc2ccc(-n3cc(F)ccc3=O)cc2)c1=O] | 2-cyclopentyl-3-(2,6-dimethoxyphenyl)-5-{[4-(5-fluoro-2-oxo-1,2-dihydropyridin-1-yl)phenyl]methyl}-6-hydroxy-3,4-dihydropyrimidin-4-one | 1H NMR (500 MHz, DMSO-d6) Shift 7.87 (t, J = 4.0 Hz, 1H), 7.64 (ddd, J = 10.1, 7.0, 3.4 Hz, 1H), 7.44-7.30 (m, 3H), 7.20 (d, J = 8.2 Hz, 2H), 6.75 (d, J = 8.2 Hz, 2H), 6.49 (dd, J = 10.1, 5.5 Hz, 1H), 3.71 (s, 6H), 3.62-3.53 (m, 2H), 2.42 (quin, J = 8.3 Hz, 1H), 1.85-1.70 (m, 4H), 1.47 (br d, J = 7.6 Hz, 4H) | 1.59, A, 517.9 | A |
| 52 | 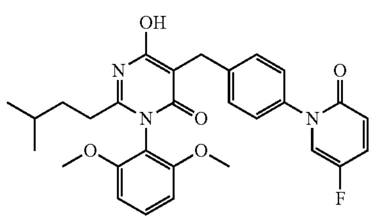 [SMILES: COc1cccc(OC)c1-n1c(CCC(C)C)nc(O)c(Cc2ccc(-n3cc(C)ccc3=O)cc2)c1=O] | 3-(2,6-dimethoxyphenyl)-5-{[4-(5-fluoro-2-oxo-1,2-dihydropyridin-1-yl)phenyl]methyl}-6-hydroxy-2-(3-methylbutyl)-3,4-dihydropyrimidin-4-one | 1H NMR (500 MHz, DMSO-d6) Shift 7.89 (t, J = 4.0 Hz, 1H), 7.65 (ddd, J = 10.1, 7.1, 3.2 Hz, 1H), 7.47-7.31 (m, 3H), 7.24 (d, J = 8.5 Hz, 2H), 6.80 (d, J = 8.5 Hz, 2H), 6.49 (dd, J = 10.1, 5.5 Hz, 1H), 3.74 (s, 6H), 3.61 (s, 2H), 2.16-2.01 (m, 2H), 1.68-1.50 (m, 2H), 1.32 (dq, J = 14.6, 7.1 Hz, 1H), 0.95 (t, J = 7.3 Hz, 6H) | 1.55, A, 520.2 | A |
| 53 | 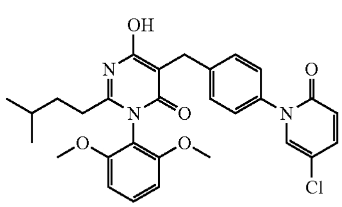 | 5-{[4-(5-chloro-2-oxo-1,2-dihydropyridin-1-yl)phenyl]methyl}-3-(2,6-dimethoxyphenyl)-6-hydroxy-2-(3-methylbutyl)-3,4-dihydropyrimidin-4-one | 1H NMR (500 MHz, DMSO-d6) Shift 7.89 (d, J = 2.7 Hz, 1H), 7.56 (dd, J = 9.8, 2.7 Hz, 1H), 7.41 (t, J = 8.4 Hz, 1H), 7.35 (br d, J = 8.2 Hz, 2H), 7.24 (d, J = 8.2 Hz, 2H), 6.81 (d, J = 8.5 Hz, 2H), 6.51 (d, J = 9.8 Hz, 1H), 3.74 (s, 6H), 3.62 (s, 2H), 2.21-2.05 (m, 2H), 1.56 (br d, J = 7.3 Hz, 2H), 1.40-1.23 (m, 1H), 0.94 (t, J = 7.3 Hz, 6H) | 1.66, A, 535.9 | A |
| 54 | 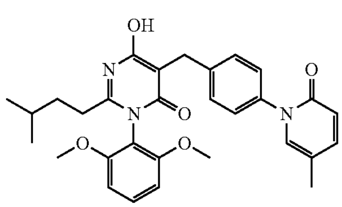 | 3-(2,6-dimethoxyphenyl)-6-hydroxy-5-{[4-(5-methyl-2-oxo-1,2-dihydropyridin-1-yl)phenyl]methyl}-2-(3-methylbutyl)-3,4-dihydropyrimidin-4-one | 1H NMR (500 MHz, DMSO-d6) Shift 7.50-7.31 (m, 5H), 7.18 (d, J = 7.9 Hz, 2H), 6.80 (d, J = 8.5 Hz, 2H), 6.41 (d, J = 9.2 Hz, 1H), 3.73 (s, 6H), 3.60 (s, 2H), 2.16-2.06 (m, 2H), 2.04 (s, 3H), 1.67-1.50 (m, 2H), 1.42-1.24 (m, 1H), 0.95 (t, J = 7.3 Hz, 6H) | 1.57, A, 516.2 | A |

-continued

| Ex # | Structure | Name | NMR | Rt(min) method M + H | APJ cAMP Potency range |
|---|---|---|---|---|---|
| 55 | 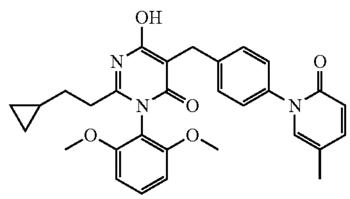 [SMILES: COc1cccc(OC)c1-n1c(CCC2CC2)nc(O)c(Cc2ccc(-n3cc(C)ccc3=O)cc2)c1=O] | 2-(2-cyclopropylethyl)-3-(2,6-dimethoxyphenyl)-6-hydroxy-5-{[4-(5-methyl-2-oxo-1,2-dihydropyridin-1-yl)phenyl]methyl}-3,4-dihydropyrimidin-4-one | 1H NMR (500 MHz, DMSO-d6) Shift 7.67 (t, J = 8.4 Hz, 1H), 7.63 (s, 1H), 7.59 (dd, J = 9.5, 2.1 Hz, 1H), 7.53 (br d, J = 8.2 Hz, 2H), 7.45 (d, J = 8.2 Hz, 2H), 7.06 (d, J = 8.5 Hz, 2H), 6.62 (d, J = 9.5 Hz, 1H), 3.96 (s, 6H), 3.86 (s, 2H), 2.50 (br t, J = 7.6 Hz, 2H), 2.25 (s, 3H), 1.63-1.50 (m, 2H), 0.89-0.73 (m, 1H), 0.56-0.44 (m, 2H), 0.00 (br d, J = 4.3 Hz, 2H) | 1.48, A, 514.2 | A |
| 56 | 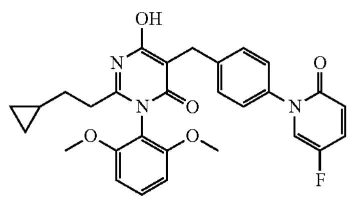 [SMILES: COc1cccc(OC)c1-n1c(CCC2CC2)nc(O)c(Cc2ccc(-n3cc(F)ccc3=O)cc2)c1=O] | 2-(2-cyclopropylethyl)-3-(2,6-dimethoxyphenyl)-5-{[4-(5-fluoro-2-oxo-1,2-dihydropyridin-1-yl)phenyl]methyl}-6-hydroxy-3,4-dihydropyrimidin-4-one | 1H NMR (500 MHz, DMSO-d6) Shift 8.11 (t, J = 4.0 Hz, 1H), 7.88 (ddd, J = 10.1, 7.0, 3.1 Hz, 1H), 7.66 (t, J = 8.4 Hz, 1H), 7.57 (br d, J = 8.2 Hz, 2H), 7.48 (d, J = 8.2 Hz, 2H), 7.05 (d, J = 8.5 Hz, 2H), 6.72 (dd, J = 10.1, 5.5 Hz, 1H), 3.96 (s, 6H), 3.85 (s, 2H), 2.54-2.40 (m, 2H), 1.79 (br d, J = 7.0 Hz, 2H), 0.91-0.72 (m, 1H), 0.61-0.43 (m, 2H), 0.00 (br d, J = 4.3 Hz, 2H) | 1.44, A, 518.2 | A |
| 57 | 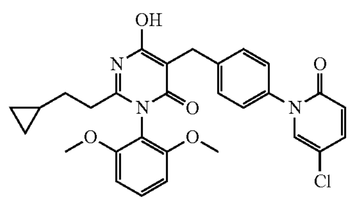 [SMILES: COc1cccc(OC)c1-n1c(CCC2CC2)nc(O)c(Cc2ccc(-n3cc(Cl)ccc3=O)cc2)c1=O] | 5-{[4-(5-chloro-2-oxo-1,2-dihydropyridin-1-yl)phenyl]methyl}-2-(2-cyclopropylethyl)-3-(2,6-dimethoxyphenyl)-6-hydroxy-3,4-dihydropyrimidin-4-one | 1H NMR (500 MHz, DMSO-d6) Shift 8.12 (d, J = 2.7 Hz, 1H), 7.80 (dd, J = 9.8, 2.7 Hz, 1H), 7.69-7.55 (m, 3H), 7.46 (d, J = 8.2 Hz, 2H), 7.04 (d, J = 8.5 Hz, 2H), 6.75 (d, J = 9.8 Hz, 1H), 3.97 (s, 6H), 3.85 (s, 2H), 2.50-2.36 (m, 2H), 1.91-1.73 (m, 2H), 0.91-0.72 (m, 1H), 0.59-0.44 (m, 2H), 0.00 (q, J = 4.7 Hz, 2H) | 1.55, A, 534.4 | A |
| 58 | 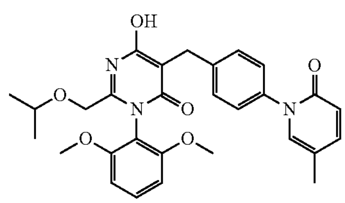 [SMILES: COc1cccc(OC)c1-n1c(COC(C)C)nc(O)c(Cc2ccc(-n3cc(C)ccc3=O)cc2)c1=O] | 3-(2,6-dimethoxyphenyl)-6-hydroxy-5-{[4-(5-methyl-2-oxo-1,2-dihydropyridin-1-yl)phenyl]methyl}-2-[(propan-2-yloxy)methyl]-3,4-dihydropyrimidin-4-one | 1H NMR (500 MHz, DMSO-d6) Shift 7.48-7.40 (m, 2H), 7.37 (dd, J = 9.3, 2.1 Hz, 1H), 7.32 (br d, J = 8.2 Hz, 2H), 7.24 (br d, J = 8.2 Hz, 2H), 6.80 (d, J = 8.6 Hz, 2H), 6.41 (d, J = 9.3 Hz, 1H), 3.90 (s, 2H), 3.73 (s, 6H), 3.67 (s, 2H), 3.32-3.21 (m, 1H), 2.03 (s, 3H), 0.87 (d, J = 6.1 Hz, 6H) | 1.24, A, 518.3 | A |
| 59 | 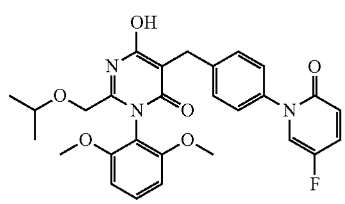 | 3-(2,6-dimethoxyphenyl)-5-{[4-(5-fluoro-2-oxo-1,2-dihydropyridin-1-yl)phenyl]methyl}-6-hydroxy-2-[(propan-2-yloxy)methyl]-3,4-dihydropyrimidin-4-one | 1H NMR (500 MHz, DMSO-d6) Shift 7.88 (br t, J = 3.7 Hz, 1H), 7.65 (ddd, J = 10.1, 7.0, 3.4 Hz, 1H), 7.43 (br t, J = 8.4 Hz, 1H), 7.36-7.30 (m, 2H), 7.30-7.25 (m, 2H), 6.80 (d, J = 8.5 Hz, 2H), 6.49 (dd, J = 10.0, 5.4 Hz, 1H), 3.90 (s, 2H), 3.73 (s, 6H), 3.67 (s, 2H), 3.26 (dt, J = 11.9, 6.0 Hz, 1H), 0.86 (d, J = 6.0 Hz, 6H) | 1.23, A, 522.1 | A |
| 60 | 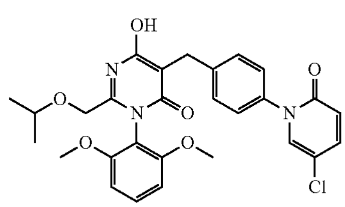 [SMILES: COc1cccc(OC)c1-n1c(COC(C)C)nc(O)c(Cc2ccc(-n3cc(Cl)ccc3=O)cc2)c1=O] | 5-{[4-(5-chloro-2-oxo-1,2-dihydropyridin-1-yl)phenyl]methyl}-3-(2,6-dimethoxyphenyl)-6-hydroxy-2-[(propan-2-yloxy)methyl]-3,4-dihydropyrimidin-4-one | 1H NMR (500 MHz, DMSO-d6) Shift 7.86 (d, J = 2.2 Hz, 1H), 7.55 (dd, J = 9.8, 2.4 Hz, 1H), 7.39 (br t, J = 8.4 Hz, 1H), 7.34 (br d, J = 7.9 Hz, 2H), 7.24 (br d, J = 8.1 Hz, 2H), 6.77 (d, J = 8.4 Hz, 2H), 6.51 (d, J = 9.8 Hz, 1H), 3.85 (s, 2H), 3.71 (s, 2H), 3.68 (br s, 6H), 3.29-3.19 (m, 1H), 0.84 (br d, J = 6.0 Hz, 6H) | 1.32, A, 538.3 | A |

Example 61

2-(1-cyclopropyl-1H-pyrazol-3-yl)-1-(2,6-diethylphenyl)-5-(3-fluoro-4-(2-fluoro-3-methylpyridin-4-yl)benzyl)-6-hydroxypyrimidin-4(1H)-one

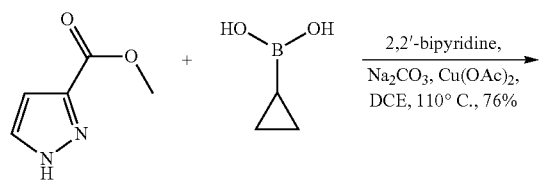

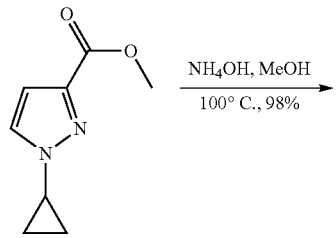

Compound 61a

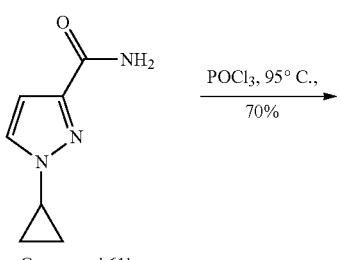

Compound 61b

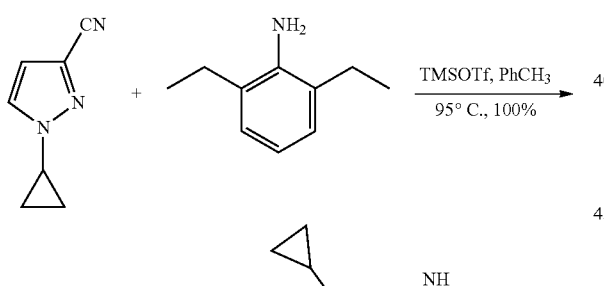

Compound 61d

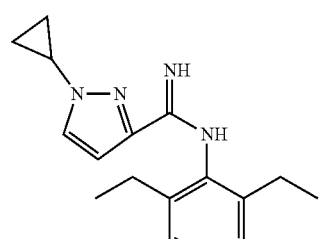

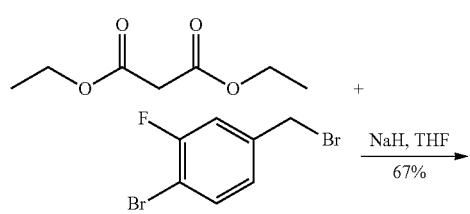

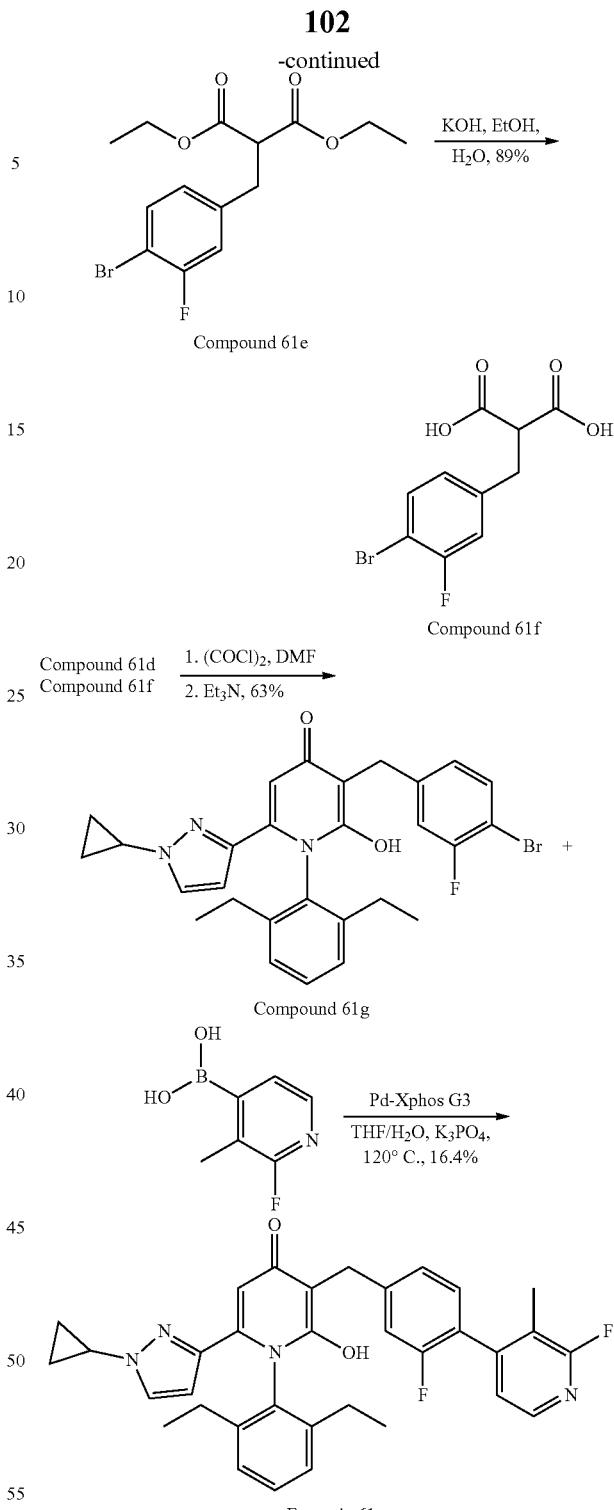

Compound 61e

Compound 61f

Compound 61g

Example 61

Compound 61a. methyl 1-cyclopropyl-1H-pyrazole-3-carboxylate

To a stirred solution of methyl 1H-pyrazole-3-carboxylate (1.04 g, 8.25 mmol), cyclopropylboronic acid (1.42 g, 16.5 mmol) and Na$_2$CO$_3$ (1.75 g, 16.5 mmol) in DCE (30 mL) at 70° C. was added 2,2'-bipyridine (1.29 g, 8.25 mmol) and copper (II) acetate (1.50 g, 8.25 mmol) under air. The reaction was heated to 70° C. for 8 hrs. The reaction was allowed to cool to RT. 1 mL AcOH was added and the reaction mixture was concentrated in vacuo and the residue diluted with EtOAc. The organic layer was washed with 1M HCl. The organic layer was dried over $MgSO_4$, filtered and concentrated in vacuo. The residue was added to a silica gel (120 g) column and eluted with 0-100% EtOAc in hexanes. Fractions containing Compound 61a were collected and the solvent removed in vacuo to yield a clear liquid (1.05 g, 6.29 mmol, 76% yield). MS m z=167.1 (M+H). $^1$H NMR (400 MHz, DMSO-$d_6$) δ 7.93 (d, J=2.4 Hz, 1H), 6.73 (d, J=2.4 Hz, 1H), 3.85 (tt, J=7.4, 3.8 Hz, 1H), 3.78 (s, 3H), 1.13-1.06 (m, 2H), 1.06-0.97 (m, 2H).

Compound 61b.
1-cyclopropyl-1H-pyrazole-3-carboxamide

To a stirred solution of Compound 61a (1.01 g, 6.02 mmol) in MeOH (10 mL) was added ammonium hydroxide (3.91 mL, 30.1 mmol). The reaction mixture was heated to 100° C. for 16 hrs. The reaction mixture was allowed to cool to RT. 1 mL AcOH was added and the reaction mixture was concentrated in vacuo and diluted with EtOAc. The organic layer was washed with sat $NH_4Cl$. The organic layer was dried over $MgSO_4$, filtered and concentrated in vacuo to give Compound 61b (0.89 g, 5.89 mmol, 98% yield) as a white solid. MS m/z=152.2 (M+H). $^1$H NMR (500 MHz, CHLOROFORM-d) δ 7.49 (d, J=2.5 Hz, 1H), 6.81 (d, J=2.5 Hz, 1H), 3.65 (tt, J=7.3, 3.7 Hz, 1H), 1.21-1.17 (m, 2H), 1.11-1.05 (m, 2H).

Compound 61c.
1-cyclopropyl-1H-pyrazole-3-carbonitrile

A stirred solution of Compound 1b (0.99 g, 6.55 mmol) in $POCl_3$ (6.10 ml, 65.5 mmol) was heated to 95° C. for 2 hrs. The reaction mixture was allowed to cool to RT and poured into ice-water. $NH_4OH$ was added until the pH was neutral. The reaction mixture was diluted with EtOAc. The organic layer was washed with $H_2O$. The organic layer was dried over $MgSO_4$, filtered and concentrated in vacuo. The residue was added to a silica gel (24 g) column and was eluted with 0-100% EtOAc in hexanes. Fractions containing Compound 61c were collected, combined and the solvent removed to yield a clear liquid (610 mg, 4.58 mmol, 70% yield). $^1$H NMR (400 MHz, CHLOROFORM-d) δ 7.52 (d, J=2.4 Hz, 1H), 6.63 (d, J=2.4 Hz, 1H), 3.67 (tt, J=7.4, 3.9 Hz, 1H), 1.25-1.16 (m, 2H), 1.13-1.03 (m, 2H).

Compound 61d. 1-cyclopropyl-N-(2,6-diethylphenyl)-1H-pyrazole-3-carboximidamide

To a solution of 2,6-diethylaniline (684 mg, 4.58 mmol) and Compound 61c (610 mg, 4.58 mmol) in toluene (5 ml) at 0° C. was added dropwise TMS-OTf (1.08 ml, 5.96 mmol). The resulting mixture was stirred at 0° C. for 10 min and allowed to warm to RT then heated to 110° C. for 16 hrs. The reaction mixture was cooled to 0° C. and water was added dropwise. The reaction mixture was diluted with EtOAc. The organic layer was washed with sat $NaHCO_3$. The organic layer was dried over $MgSO_4$, filtered and concentrated in vacuo. The residue was added to a silica gel (24 g) column and was eluted with 0-50% 1% TEA/EtOAc in DCM. Fractions containing Compound 61d were collected and the solvent removed in vacuo to yield a yellow solid (1.31 g, 4.60 mmol, 100% yield). MS m/z=152.2 (M+H). $^1$H NMR (500 MHz, CHLOROFORM-d) δ 7.53 (d, J=2.5 Hz, 1H), 7.16-7.10 (m, 2H), 7.09-7.02 (m, 1H), 6.99 (d, J=2.2 Hz, 1H), 3.66 (tt, J=7.4, 3.8 Hz, 1H), 2.71-2.42 (m, 4H), 1.20 (t, J=7.6 Hz, 6H), 1.23-1.15 (m, 2H), 1.13-1.04 (m, 2H).

Compound 61e. diethyl 2-(4-bromo-3-fluorobenzyl)malonate

NaH (0.537 g, 13.4 mmol) was slurried in THF (20 mL) in a 100 mL flask that was equipped with a magnetic stirrer and an $N_2$ inlet. Diethyl malonate (2.33 g, 14.6 mmol) was added dropwise which resulted in significant evolution of gas. The mixture was stirred at RT for 1 hr followed by a drop wise addition of 1-bromo-4-(bromomethyl)-2-fluorobenzene (3.01 g, 11.2 mmol) in THF (10 mL). The reaction mixture was stirred at RT for 16 hrs. A mix of mono- and bis-alkylated product observed by LCMS. The reaction mixture was concentrated in vacuo and diluted with EtOAc. The organic layer was washed with sat $NH_4Cl$. The organic layer was dried over $MgSO_4$, filtered and concentrated in vacuo. The residue was added to a silica gel (120 g) column and was eluted with 0-40% EtOAc in hexanes. Fractions containing Compound 61e were collected, combined and concentrated in vacuo to yield a clear liquid (2.62 g, 7.55 mmol, 67% yield). MS m/z=348.9 (M+H). $^1$H NMR (500 MHz, CHLOROFORM-d) δ 7.52-7.41 (m, 1H), 7.02 (dd, J=9.4, 1.9 Hz, 1H), 6.91 (dd, J=8.1, 1.8 Hz, 1H), 4.20 (d, J=1.4 Hz, 4H), 3.62 (t, J=7.8 Hz, 1H), 3.20 (d, J=7.7 Hz, 2H), 1.25 (t, J=7.2 Hz, 6H).

Compound 61f. 2-(4-bromo-3-fluorobenzyl)malonic acid

Compound 61e (2.62 g, 7.55 mmol) was dissolved in a mixture of ethanol (12.5 mL) and water (6.25 mL) in a 100 mL flask that was equipped with a magnetic stirrer. KOH (1.48 g, 26.4 mmol) was added and the reaction mixture was stirred for 2 hrs. The reaction mixture was acidified with 3N HCl and the aqueous portion extracted with $Et_2O$ (3×). The combined organic portions were dried over $MgSO_4$, filtered and the filtrate was concentrated in vacuo to give Compound 61f (1.95 g, 6.70 mmol, 89% yield) as a white solid. MS m/z=315.0 (M+Na). $^1$H NMR (400 MHz, METHANOL-$d_4$) δ 7.50 (t, J=7.8 Hz, 1H), 7.12 (dd, J=9.9, 1.8 Hz, 1H), 7.00 (dd, J=8.1, 1.8 Hz, 1H), 3.64 (t, J=7.7 Hz, 1H), 3.14 (d, J=7.9 Hz, 2H).

Compound 61g. 5-(4-bromo-3-fluorobenzyl)-2-(1-cyclopropyl-1H-pyrazol-3-yl)-1-(2,6-diethylphenyl)-6-hydroxypyrimidin-4(1H)-one Compound 61f (97.1 mg, 0.333 mmol) was slurried in DCM (5 mL) in a 25 mL flask that was equipped with a magnetic stirrer and a $N_2$ inlet. Oxalyl chloride (0.333 mL, 0.667 mmol) and DMF (1 drop) were added and the reaction mixture was stirred at RT for 1 hr. To the reaction mixture was added Compound 61d (94.2 mg, 0.333 mmol) in DCM (4 mL), followed by $Et_3N$ (0.186 mL, 1.333 mmol). The reaction mixture was stirred for 1 hr, then concentrated in vacuo and the residue diluted with EtOAc. The organic layer was washed with sat $NH_4Cl$. The organic layer was dried over $MgSO_4$, filtered and concentrated in vacuo. The residue was added to a silica gel (12 g) column and was eluted with 0-100% EtOAc in hexanes. Fractions containing Compound 61g were collected, combined and concentrated in vacuo to yield a light yellow liquid (112 mg, 0.208 mmol, 63% yield. MS m/z=536.9 (M+H). $^1$H NMR (500 MHz, CHLOROFORM-d) δ 7.48-7.43 (m, 1H), 7.41-7.35 (m, 1H), 7.27-7.22

(m, 5H), 7.14 (dd, J=8.3, 1.9 Hz, 1H), 3.84 (s, 2H), 3.66-3.54 (m, 1H), 2.45-2.33 (m, 2H), 2.26 (dq, J=15.1, 7.6 Hz, 2H), 1.09 (m, 2H), 1.07-1.05 (m, 2H), 1.05 (t, J=7.6 Hz, 6H).

Example 61. 2-(1-cyclopropyl-1H-pyrazol-3-yl)-1-(2,6-diethylphenyl)-5-(3-fluoro-4-(2-fluoro-3-methylpyridin-4-yl)benzyl)-6-hydroxypyrimidin-4(1H)-one A solution of Compound 61g (15 mg, 0.028 mmol), (2-fluoro-3-methylpyridin-4-yl)boronic acid (13 mg, 0.084 mmol) and Pd-XPhos G3 (1.772 mg, 2.093 μmol) in THF (1.8 mL) and phosphoric acid, potassium salt (0.5 M aq.) (0.14 mL, 0.070 mmol) was degassed with Ar for 1 min. The reaction mixture was sealed and heated in a microwave reactor at 120° C. for 45 min. The reaction mixture was filtered and concentrated under reduced pressure. The residue was purified via preparative LC/MS with the following conditions: Column: XBridge C18, 19×200 mm, 5-μm particles; Mobile Phase A: 5:95 acetonitrile:water with 10 mM ammonium acetate; Mobile Phase B: 95:5 acetonitrile:water with 10 mM ammonium acetate; Gradient: 10-55% B over 25 minutes, then a 5-minute hold at 100% B; Flow: 20 mL/min. Fractions containing Compound 61 were combined and dried via centrifugal evaporation to give a white solid (2.6 mg, 16.4% yield). The estimated purity by LCMS analysis was 100%, HPLC method A, Rt=2.08 min, MS m/z=568.3 (M+H). $^1$H NMR (500 MHz, DMSO-d$_6$) δ 8.11 (d, J=4.9 Hz, 1H), 7.73 (d, J=1.9 Hz, 1H), 7.40-7.26 (m, 2H), 7.26-7.02 (m, 5H), 6.20 (d, J=1.8 Hz, 1H), 3.79 (s, 2H), 3.67 (td, J=7.4, 3.8 Hz, 1H), 2.31-2.11 (m, 4H), 2.05 (s, 3H), 0.93 (t, J=7.5 Hz, 6H), 0.82-0.70 (m, 2H), 0.61 (br s, 2H). APJ cAMP EC$_{50}$ potency range: A.

Examples 62 to 94 were prepared as described in the general procedure given for Example 61.

| Ex # | Structure | Name | NMR | Rt (min) method M + H | APJ cAMP Potency range |
|---|---|---|---|---|---|
| 62 | 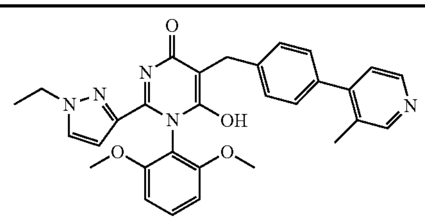 | 1-(2,6-dimethoxyphenyl)-2-(1-ethyl-1H-pyrazol-3-yl)-6-hydroxy-5-{[4-(3-methylpyridin-4-yl)phenyl]methyl}-1,4-dihydropyrimidin-4-one | 1H NMR (500 MHz, DMSO-d6) Shift 8.47 (s, 1H), 8.41 (d, J = 5.0 Hz, 1H), 7.51 (d, J = 1.9 Hz, 1H), 7.39 (br d, J = 7.9 Hz, 2H), 7.31-7.24 (m, 3H), 7.21 (d, J = 4.9 Hz, 1H), 6.64 (d, J = 8.4 Hz, 2H), 5.98 (d, J = 1.9 Hz, 1H), 4.05-3.84 (m, 2H), 3.67 (s, 2H), 3.60 (s, 6H), 2.27 (s, 3H), 1.13 (t, J = 7.2 Hz, 3H) | 1.36, A, 524.1 | A |
| 63 | 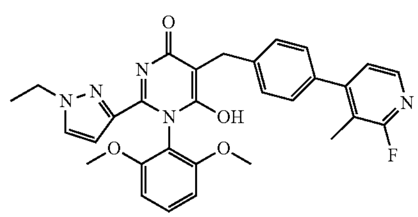 [SMILES: CCn1ccc(-c2nc(=O)c(Cc3ccc(-c4ccnc(F)c4C)cc3)c(O)n2-c2c(OC)cccc2OC)n1] | 1-(2,6-dimethoxyphenyl)-2-(1-ethyl-1H-pyrazol-3-yl)-5-{[4-(2-fluoro-3-methylpyridin-4-yl)phenyl]methyl}-6-hydroxy-1,4-dihydropyrimidin-4-one | 1H NMR (500 MHz, DMSO-d6) Shift 8.06 (d, J = 5.0 Hz, 1H), 7.55 (d, J = 1.9 Hz, 1H), 7.46-7.28 (m, 5H), 7.21 (br d, J = 5.0 Hz, 1H), 6.69 (d, J = 8.5 Hz, 2H), 6.01 (d, J = 1.9 Hz, 1H), 3.94 (q, J = 7.2 Hz, 2H), 3.78-3.69 (m, 2H), 3.61 (br s, 6H), 2.16 (s, 3H), 1.14 (t, J = 7.2 Hz, 3H) | 1.61, A, 542.2 | A |
| 64 | 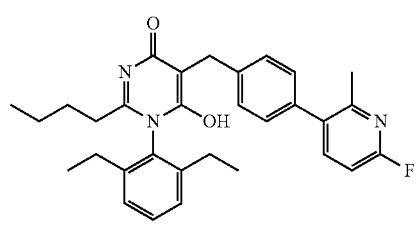 [SMILES: CCCCc1nc(=O)c(Cc2ccc(-c3ccc(F)nc3C)cc2)c(O)n1-c1c(CC)cccc1CC] | 2-butyl-1-(2,6-diethylphenyl)-5-{[4-(6-fluoro-2-methylpyridin-3-yl)phenyl]methyl}-6-hydroxy-1,4-dihydropyrimidin-4-one | 1H NMR (500 MHz, DMSO-d6) Shift 7.75 (t, J = 8.2 Hz, 1H), 7.47-7.35 (m, 1H), 7.29 (m, 7.8 Hz, 4H), 7.23 (m, 2H), 7.03 (dd, J = 7.9, 2.7 Hz, 1H), 3.69 (s, 2H), 2.34 (s, 3H), 2.30 (br dd, J = 15.0, 7.3 Hz, 2H), 2.21-2.11 (m, 2H), 2.07 (br t, J = 7.8 Hz, 2H), 1.55-1.45 (m, 2H), 1.19-1.10 (m, 2H), 1.04 (t, J = 7.5 Hz, 6H), 0.72 (t, J = 7.3 Hz, 3H) | 2.23, A, 500.3 | A |
| 65 | 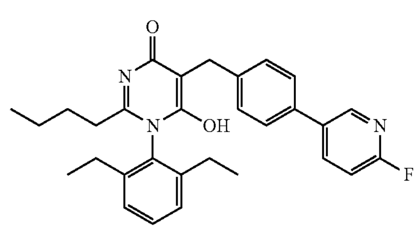 [SMILES: CCCCc1nc(=O)c(Cc2ccc(-c3ccc(F)nc3)cc2)c(O)n1-c1c(CC)cccc1CC] | 2-butyl-1-(2,6-diethylphenyl)-5-{[4-(6-fluoropyridin-3-yl)phenyl]methyl}-6-hydroxy-1,4-dihydropyrimidin-4-one | 1H NMR (600 MHz, DMSO-d6) Shift 8.50 (d, J = 1.0 Hz, 1H), 8.23 (td, J = 8.1, 2.2 Hz, 1H), 7.58 (d, J = 8.1 Hz, 2H), 7.46-7.39 (m, 1H), 7.35-7.27 (m, 4H), 7.25 (dd, J = 8.5, 2.4 Hz, 1H), 3.69 (s, 2H), 2.29 (dt, J = 14.6, 7.3 Hz, 2H), 2.21-2.11 (m, 2H), 2.11-2.03 (m, 2H), 1.51 (br t, J = 7.4 Hz, 2H), 1.20-1.10 (m, 2H), 1.06 (t, J = 7.5 Hz, 6H), 0.73 (t, J = 7.4 Hz, 3H) | 2.14, A, 486.2 | A |
| 66 | 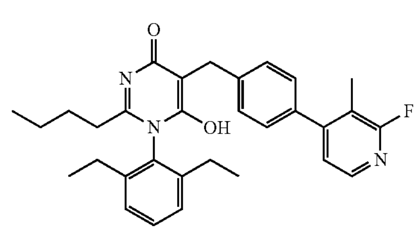 [SMILES: CCCCc1nc(=O)c(Cc2ccc(-c3ccnc(F)c3C)cc2)c(O)n1-c1c(CC)cccc1CC] | 2-butyl-1-(2,6-diethylphenyl)-5-{[4-(2-fluoro-3-methylpyridin-4-yl)phenyl]methyl}-6-hydroxy-1,4-dihydropyrimidin-4-one | 1H NMR (500 MHz, DMSO-d6) Shift 7.46-7.38 (m, 1H), 7.36-7.32 (m, 2H), 7.32-7.26 (m, 4H), 7.20 (br d, J = 4.8 Hz, 1H), 3.71 (s, 2H), 2.37-2.23 (m, 2H), 2.21-2.12 (m, 2H), 2.15 (s, 3H), 2.09 (br t, J = 7.7 Hz, 2H), 1.57-1.44 (m, 2H), 1.21-1.11 (m, 2H), 1.04 (t, J = 7.5 Hz, 6H), 0.73 (t, J = 7.3 Hz, 3H) | 2.24, A, 500.2 | A |

| Ex # | Structure | Name | NMR | Rt (min) method M + H | APJ cAMP Potency range |
|---|---|---|---|---|---|
| 67 | 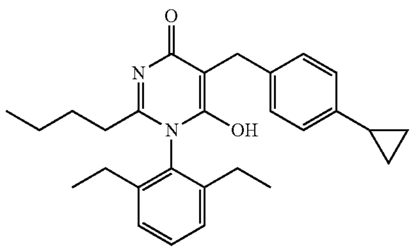 [SMILES: CCCCc1nc(=O)c(Cc2ccc(C3CC3)cc2)c(O)n1-c1c(CC)cccc1CC] | 2-butyl-5-[(4-cyclopropylphenyl)methyl]-1-(2,6-diethylphenyl)-6-hydroxy-1,4-dihydropyrimidin-4-one | 1H NMR (500 MHz, DMSO-d6) δ 7.46-7.35 (m, 1H), 7.27 (d, J = 7.7 Hz, 2H), 7.07 (d, J = 8.0 Hz, 2H), 6.90 (d, J = 8.0 Hz, 2H), 3.59 (s, 2H), 2.34-2.22 (m, 2H), 2.20-2.07 (m, 2H), 2.04 (m, 2H), 1.87-1.77 (m, 1H), 1.57-1.40 (m, 2H), 1.18-1.09 (m, 2H), 1.05 (t, J = 7.5 Hz, 6H), 0.87 (br dd, J = 8.3, 1.9 Hz, 2H), 0.72 (t, J = 7.3 Hz, 3H), 0.62-0.53 (m, 2H) | 2.33, B, 431.3 | A |
| 68 | 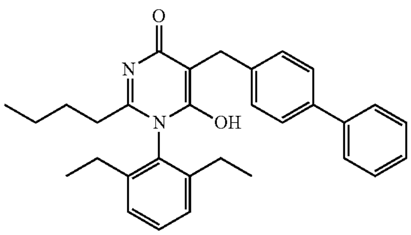 [SMILES: CCCCc1nc(=O)c(Cc2ccc(-c3ccccc3)cc2)c(O)n1-c1c(CC)cccc1CC] | 5-({[1,1'-biphenyl]-4-yl}methyl)-2-butyl-1-(2,6-diethylphenyl)-6-hydroxy-1,4-dihydropyrimidin-4-one | 1H NMR (500 MHz, DMSO-d6) δ 7.61 (br d, J = 7.6 Hz, 2H), 7.52 (br d, J = 7.9 Hz, 2H), 7.46-7.39 (m, 3H), 7.35-7.26 (m, 5H), 3.69 (s, 2H), 2.30 (dt, J = 14.8, 7.6 Hz, 2H), 2.22-2.12 (m, 2H), 2.12-2.03 (m, 2H), 1.57-1.47 (m, 2H), 1.21-1.11 (m, 2H), 1.07 (t, J = 7.5 Hz, 6H), 0.73 (t, J = 7.2 Hz, 3H) | 2.39, A, 467.3 | B |
| 69 | 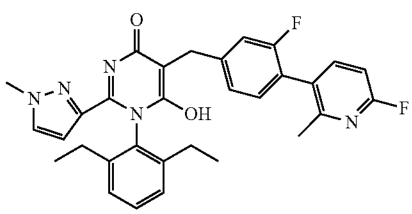 [SMILES: CCc1cccc(CC)c1-n1c(-c2ccn(C)n2)nc(=O)c(Cc2ccc(-c3ccc(F)nc3C)c(F)c2)c1O] | 1-(2,6-diethylphenyl)-5-{[3-fluoro-4-(6-fluoro-2-methylpyridin-3-yl)phenyl]methyl}-6-hydroxy-2-(1-methyl-1H-pyrazol-3-yl)-1,4-dihydropyrimidin-4-one | 1H NMR (500 MHz, DMSO-d6) Shift 7.80 (br t, J = 8.1 Hz, 1H), 7.57 (br t, J = 7.8 Hz, 1H), 7.51 (br s, 1H), 7.41-7.32 (m, 2H), 7.30-7.22 (m, 1H), 7.18 (br d, J = 7.0 Hz, 2H), 7.11-6.93 (m, 1H), 5.55 (dd, J = 9.0, 2.0 Hz, 1H), 3.79 (s, 2H), 3.69 (s, 3H), 2.25 (s, 3H), 2.23-2.12 (m, 4H), 0.96 (td, J = 7.4, 2.9 Hz, 6H) | 1.80, A, 542.1 | A |
| 70 | 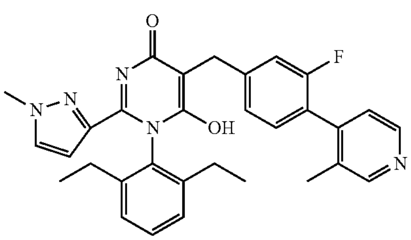 [SMILES: CCc1cccc(CC)c1-n1c(-c2ccn(C)n2)nc(=O)c(Cc2ccc(-c3ccncc3C)c(F)c2)c1O] | 1-(2,6-diethylphenyl)-5-{[3-fluoro-4-(3-methylpyridin-4-yl)phenyl]methyl}-6-hydroxy-2-(1-methyl-1H-pyrazol-3-yl)-1,4-dihydropyrimidin-4-one | 1H NMR (500 MHz, DMSO-d6) Shift 8.63 (br s, 1H), 7.65-7.55 (m, 1H), 7.52 (d, J = 1.8 Hz, 1H), 7.42-7.29 (m, 2H), 7.19 (br d, J = 7.6 Hz, 5H), 5.56 (s, 1H), 3.81 (s, 2H), 3.69 (s, 3H), 2.30-2.11 (m, 7H), 0.96 (t, J = 7.6 Hz, 6H) | 1.59, A, 524.0 | A |
| 71 | 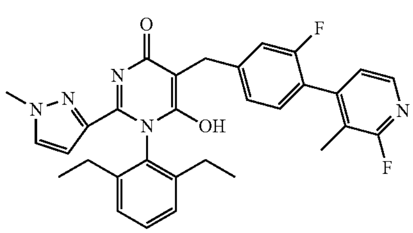 [SMILES: CCc1cccc(CC)c1-n1c(-c2ccn(C)n2)nc(=O)c(Cc2ccc(-c3ccnc(F)c3C)c(F)c2)c1O] | 1-(2,6-diethylphenyl)-5-{[3-fluoro-4-(2-fluoro-3-methylpyridin-4-yl)phenyl]methyl}-6-hydroxy-2-(1-methyl-1H-pyrazol-3-yl)-1,4-dihydropyrimidin-4-one | 1H NMR (500 MHz, DMSO-d6) Shift 8.10 (br d, J = 4.8 Hz, 1H), 7.50 (br s, 1H), 7.36 (s, 1H), 7.31-7.25 (m, 2H), 7.23-7.11 (m, 4H), 5.53 (s, 1H), 3.82-3.73 (m, 2H), 3.17 (s, 3H), 2.28-2.10 (m, 4H), 2.04 (s, 3H), 0.94 (br t, J = 7.4 Hz, 6H) | 1.83, A, 542.1 | A |
| 72 | 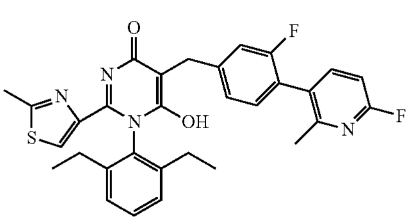 [SMILES: CCc1cccc(CC)c1-n1c(-c2csc(C)n2)nc(=O)c(Cc2ccc(-c3ccc(F)nc3C)c(F)c2)c1O] | 1-(2,6-diethylphenyl)-5-{[3-fluoro-4-(6-fluoro-2-methylpyridin-3-yl)phenyl]methyl}-6-hydroxy-2-(2-methyl-1,3-thiazol-4-yl)-1,4-dihydropyrimidin-4-one | 1H NMR (500 MHz, DMSO-d6) Shift 7.80 (br t, J = 8.2 Hz, 1H), 7.52 (s, 1H), 7.36-7.23 (m, 2H), 7.22-7.01 (m, 5H), 3.79 (s, 2H), 2.39 (s, 3H), 2.25 (s, 7H), 0.99 (br t, J = 7.4 Hz, 6H) | 1.90, A, 559.1 | A |

| Ex # | Structure | Name | NMR | Rt (min) method M + H | APJ cAMP Potency range |
|---|---|---|---|---|---|
| 73 | 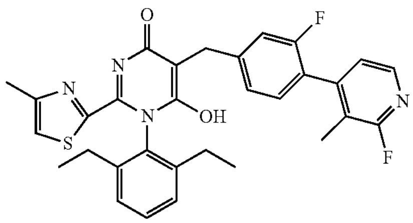 [SMILES: CCc1cccc(CC)c1-n1c(-c2nc(C)cs2)nc(=O)c(Cc2ccc(-c3ccnc(F)c3C)c(F)c2)c1O] | 1-(2,6-diethylphenyl)-5-{[3-fluoro-4-(2-fluoro-3-methylpyridin-4-yl)phenyl]methyl}-6-hydroxy-2-(4-methyl-1,3-thiazol-2-yl)-1,4-dihydropyrimidin-4-one | 1H NMR (500 MHz, DMSO-d6) Shift 8.11 (br d, J = 4.9 Hz, 1H), 7.43 (s, 1H), 7.35 (s, 1H), 7.29 (br d, J = 7.9 Hz, 1H), 7.25-7.06 (m, 5H), 3.82 (s, 2H), 2.33-2.13 (m, 4H), 2.08-2.05 (m, 3H), 2.05 (br s, 3H), 0.94 (br t, J = 7.5 Hz, 6H) | 1.93, A, 559.3 | A |
| 74 | 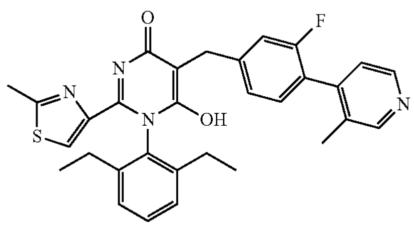 [SMILES: CCc1cccc(CC)c1-n1c(-c2csc(C)n2)nc(=O)c(Cc2ccc(-c3ccncc3C)c(F)c2)c1O] | 1-(2,6-diethylphenyl)-5-{[3-fluoro-4-(3-methylpyridin-4-yl)phenyl]methyl}-6-hydroxy-2-(2-methyl-1,3-thiazol-4-yl)-1,4-dihydropyrimidin-4-one | 1H NMR (500 MHz, DMSO-d6) Shift 8.75-8.44 (m, 1H), 7.53 (s, 1H), 7.43 (br d, J = 4.0 Hz, 1H), 7.34-7.27 (m, 2H), 7.25 (s, 2H), 7.15-7.08 (m, 2H), 7.04 (s, 1H), 3.82 (s, 2H), 2.40 (s, 3H), 2.32 (dt, J = 15.0, 7.5 Hz, 2H), 2.27-2.20 (m, 2H), 2.18 (s, 3H), 1.00 (br t, J = 7.6 Hz, 6H) | 1.74, A, 541.1 | A |
| 75 | 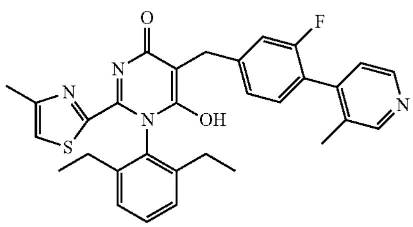 [SMILES: CCc1cccc(CC)c1-n1c(-c2nc(C)cs2)nc(=O)c(Cc2ccc(-c3ccncc3C)c(F)c2)c1O] | 1-(2,6-diethylphenyl)-5-{[3-fluoro-4-(3-methylpyridin-4-yl)phenyl]methyl}-6-hydroxy-2-(4-methyl-1,3-thiazol-2-yl)-1,4-dihydropyrimidin-4-one | 1H NMR (500 MHz, DMSO-d6) Shift 8.58-8.49 (m, 1H), 8.45 (br d, J = 4.6 Hz, 1H), 7.44 (s, 1H), 7.39-7.31 (m, 1H), 7.25 (br d, J = 7.6 Hz, 1H), 7.22 (br s, 2H), 7.19-7.14 (m, 3H), 3.81 (s, 2H), 2.22 (dquin, J = 14.9, 7.4 Hz, 4H), 2.12 (s, 3H), 2.06 (s, 3H), 0.94 (t, J = 7.5 Hz, 6H) | 1.62, A, 541.2 | A |
| 76 | 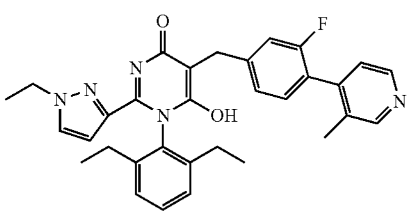 [SMILES: CCc1cccc(CC)c1-n1c(-c2ccn(CC)n2)nc(=O)c(Cc2ccc(-c3ccncc3C)c(F)c2)c1O] | 1-(2,6-diethylphenyl)-2-(1-ethyl-1H-pyrazol-3-yl)-5-{[3-fluoro-4-(3-methylpyridin-4-yl)phenyl]methyl}-6-hydroxy-1,4-dihydropyrimidin-4-one | 1H NMR (500 MHz, DMSO-d6) Shift 8.52 (br s, 1H), 8.45 (br d, J = 4.0 Hz, 1H), 7.58 (br s, 1H), 7.38-7.30 (m, 1H), 7.29-7.19 (m, 3H), 7.16 (br d, J = 7.6 Hz, 1H), 5.90 (br s, 1H), 3.94 (q, J = 7.1 Hz, 2H), 3.79 (s, 2H), 2.31-2.17 (m, 4H), 2.13 (s, 3H), 1.11 (brt, J = 7.2 Hz, 3H), 0.95 (br t, J = 7.5 Hz, 6H) | 1.61, A, 538.3 | A |
| 77 | 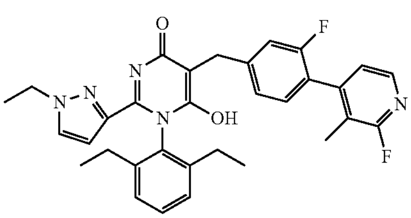 | 1-(2,6-diethylphenyl)-2-(1-ethyl-1H-pyrazol-3-yl)-5-{[3-fluoro-4-(2-fluoro-3-methylpyridin-4-yl)phenyl]methyl}-6-hydroxy-1,4-dihydropyrimidin-4-one | 1H NMR (500 MHz, DMSO-d6) Shift 8.11 (br d, J = 4.9 Hz, 1H), 7.57 (br s, 1H), 7.31 (dt, J = 15.8, 7.8 Hz, 2H), 7.26-7.09 (m, 5H), 5.91 (br s, 1H), 3.93 (q, J = 7.1 Hz, 2H), 3.80 (s, 2H), 2.36-2.14 (m, 4H), 2.05 (s, 3H), 1.10 (br t, J = 7.2 Hz, 3H), 0.95 (br t, J = 7.5 Hz, 6H) | 1.98, A, 556.1 | A |
| 78 | 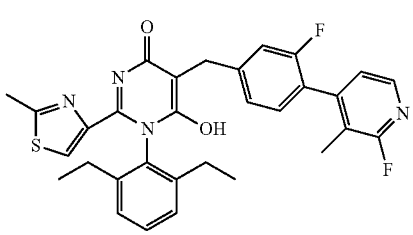 [SMILES: CCc1cccc(CC)c1-n1c(-c2csc(C)n2)nc(=O)c(Cc2ccc(-c3ccnc(F)c3C)c(F)c2)c1O] | 1-(2,6-diethylphenyl)-5-{[3-fluoro-4-(2-fluoro-3-methylpyridin-4-yl)phenyl]methyl}-6-hydroxy-2-(2-methyl-1,3-thiazol-4-yl)-1,4-dihydropyrimidin-4-one | 1H NMR (500 MHz, DMSO-d6) Shift 8.10 (br d, J = 4.6 Hz, 1H), 7.51 (s, 1H), 7.34-7.25 (m, 2H), 7.24-7.15 (m, 3H), 7.13-7.05 (m, 2H), 3.89 (s, 2H), 2.38 (s, 3H), 2.30 (dt, J = 14.7, 7.2 Hz, 2H), 2.24-2.13 (m, 2H), 2.04 (s, 3H), 0.98 (br t, J = 7.4 Hz, 6H) | 1.93, A, 559.1 | A |

| Ex # | Structure | Name | NMR | Rt (min) method M + H | APJ cAMP Potency range |
|---|---|---|---|---|---|
| 79 | 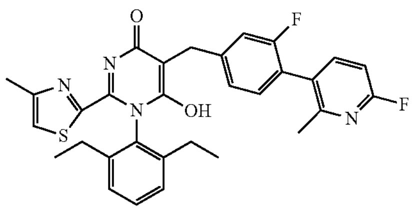 [SMILES: CCc1cccc(CC)c1-n1c(-c2nc(C)cs2)nc(=O)c(Cc2ccc(-c3ccc(F)nc3C)c(F)c2)c1O] | 1-(2,6-diethylphenyl)-5-{[3-fluoro-4-(6-fluoro-2-methylpyridin-3-yl)phenyl]methyl}-6-hydroxy-2-(4-methyl-1,3-thiazol-2-yl)-1,4-dihydropyrimidin-4-one | 1H NMR (500 MHz, DMSO-d6) Shift 7.79 (br t, J = 8.0 Hz, 1H), 7.42 (br s, 1H), 7.38-7.31 (m, 1H), 7.30-7.23 (m, 1H), 7.22-7.11 (m, 4H), 7.10-7.03 (m, 1H), 3.79 (br s, 2H), 2.24 (s, 3H), 2.22-2.12 (m, 4H), 2.05 (s, 3H), 0.93 (br t, J = 7.4 Hz, 6H) | 1.81, A, 559.3 | A |
| 80 | 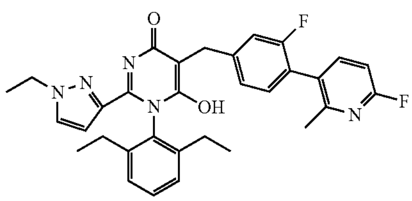 [SMILES: CCc1cccc(CC)c1-n1c(-c2ccn(CC)n2)nc(=O)c(Cc2ccc(-c3ccc(F)nc3C)c(F)c2)c1O] | 1-(2,6-diethylphenyl)-2-(1-ethyl-1H-pyrazol-3-yl)-5-{[3-fluoro-4-(6-fluoro-2-methylpyridin-3-yl)phenyl]methyl}-6-hydroxy-1,4-dihydropyrimidin-4-one | 1H NMR (500 MHz, DMSO-d6) Shift 7.80 (br t, J = 8.1 Hz, 1H), 7.58 (br s, 1H), 7.32 (br d, J = 7.6 Hz, 1H), 7.31-7.24 (m, 1H), 7.23-7.12 (m, 4H), 7.08 (br dd, J = 8.1, 2.3 Hz, 1H), 5.90 (s, 1H), 3.94 (q, J = 7.0 Hz, 2H), 3.79 (s, 1H), 2.29-2.25 (m, 3H), 2.24-2.16 (m, 4H), 1.10 (br t, J = 7.2 Hz, 3H), 0.95 (br t, J = 7.5 Hz, 7H) | 1.82, A, 556.3 | A |
| 81 | 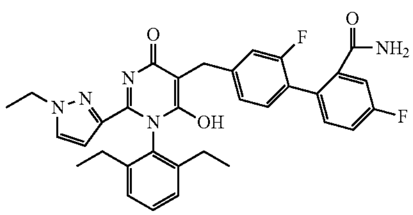 [SMILES: CCc1cccc(CC)c1-n1c(-c2ccn(CC)n2)nc(=O)c(Cc2ccc(-c3ccc(F)cc3C(N)=O)c(F)c2)c1O] | 4'-{1-(2,6-diethylphenyl)-2-(1-ethyl-1H-pyrazol-3-yl)-6-hydroxy-4-oxo-1,4-dihydropyrimidin-5-yl]methyl}-2',5-difluoro-[1,1'-biphenyl]-2-carboxamide | 1H NMR (500 MHz, DMSO-d6) Shift 7.70 (br s, 1H), 7.64-7.45 (m, 2H), 7.35 (br d, J = 7.3 Hz, 3H), 7.17 (br d, J = 7.6 Hz, 2H), 7.12-6.96 (m, 2H), 5.91 (br s, 1H), 3.93 (q, J = 7.1 Hz, 2H), 3.75 (br s, 2H), 2.23 (q, J = 7.2 Hz, 4H), 1.10 (br t, J = 6.9 Hz, 3H), 0.97 (br t, J = 7.5 Hz, 6H) | 1.56, A, 584.2 | A |
| 82 | 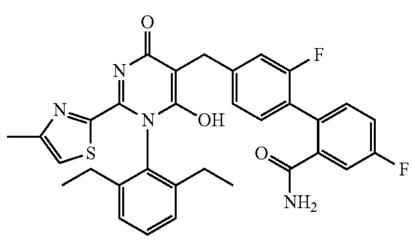 [SMILES: CCc1cccc(CC)c1-n1c(-c2nc(C)cs2)nc(=O)c(Cc2ccc(-c3ccc(F)cc3C(N)=O)c(F)c2)c1O] | 4'-{[1-(2,6-diethylphenyl)-6-hydroxy-2-(4-methyl-1,3-thiazol-2-yl)-4-oxo-1,4-dihydropyrimidin-5-yl]methyl}-2',4-difluoro-[1,1'-biphenyl]-2-carboxamide | 1H NMR (500 MHz, DMSO-d6) Shift 7.76-7.66 (m, 1H), 7.42 (s, 1H), 7.34 (br d, J = 5.5 Hz, 2H), 7.27 (br s, 1H), 7.22 (br t, J = 7.9 Hz, 1H), 7.16 (d, J = 7.6 Hz, 2H), 7.09 (br d, J = 7.9 Hz, 1H), 7.01 (br d, J = 11.3 Hz, 1H), 3.76 (s, 2H), 2.22 (q, J = 7.3 Hz, 4H), 2.06 (s, 3H), 0.96 (t, J = 7.5 Hz, 6H) | 1.73, A, 587.2 | A |
| 83 | 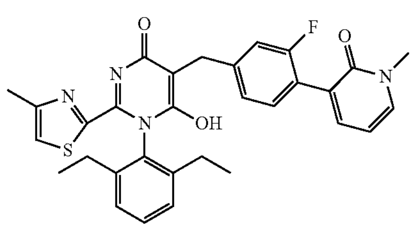 | 1-(2,6-diethylphenyl)-5-{[3-fluoro-4-(1-methyl-2-oxo-1,2-dihydropyridin-3-yl)phenyl]methyl}-6-hydroxy-2-(4-methyl-1,3-thiazol-2-yl)-1,4-dihydropyrimidin-4-one | 1H NMR (500 MHz, DMSO-d6) Shift 7.75 (br d, J = 6.1 Hz, 1H), 7.51-7.39 (m, 2H), 7.39-7.26 (m, 2H), 7.16 (br d, J = 7.3 Hz, 2H), 7.10 (br d, J = 7.9 Hz, 1H), 7.05 (br d, J = 11.6 Hz, 1H), 6.29 (br t, J = 6.6 Hz, 1H), 3.76 (br s, 2H), 3.49 (s, 3H), 2.23 (q, J = 7.1 Hz, 4H), 2.06 (s, 3H), 0.97 (br t, J = 7.3 Hz, 6H) | 1.50, A, 557.2 | A |
| 84 | 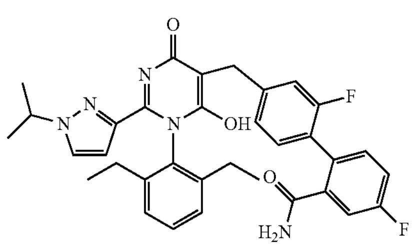 [SMILES: CCc1cccc(CC)c1-n1c(-c2ccn(C(C)C)n2)nc(=O)c(Cc2ccc(-c3ccc(F)cc3C(N)=O)c(F)c2)c1O] | 4'-{[1-(2,6-diethylphenyl)-6-hydroxy-4-oxo-2-[1-(propan-2-yl)-1H-pyrazol-3-yl]-1,4-dihydropyrimidin-5-yl]methyl}-2',4-difluoro-[1,1'-biphenyl]-2-carboxamide | 1H NMR (500 MHz, DMSO-d6) Shift 7.58 (s, 1H), 7.35 (br d, J = 4.3 Hz, 2H), 7.31-7.25 (m, 2H), 7.23-7.16 (m, 1H), 7.15-7.06 (m, 3H), 7.02 (br d, J = 11.3 Hz, 1H), 6.22 (s, 1H), 4.28 (dt, J = 13.0, 6.4 Hz, 1H), 3.73 (s, 2H), 2.25 (q, J = 7.3 Hz, 4H), 1.09 (d, J = 6.4 Hz, 6H), 0.97 (t, J = 7.5 Hz, 6H) | 1.74, A, 598.1 | A |

-continued

| Ex # | Structure | Name | NMR | Rt (min) method M + H | APJ cAMP Potency range |
|---|---|---|---|---|---|
| 85 | 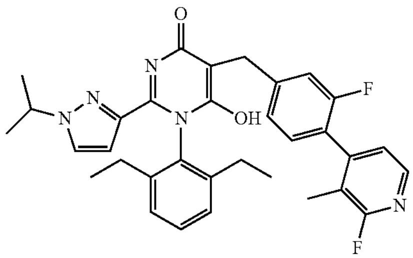 [SMILES: CCc1cccc(CC)c1-n1c(-c2ccn(C(C)C)n2)nc(=O)c(Cc2ccc(-c3ccnc(F)c3C)c(F)c2)c1O] | 1-(2,6-diethylphenyl)-5-{[3-fluoro-4-(2-fluoro-3-methylpyridin-4-yl)phenyl]methyl}-6-hydroxy-2-[1-(propan-2-yl)-1H-pyrazol-3-yl]-1,4-dihydropyrimidin-4-one | 1H NMR (500 MHz, DMSO-d6) Shift 8.10 (br d, J = 4.9 Hz, 1H), 7.59 (br s, 1H), 7.34-7.25 (m, 2H), 7.25-7.16 (m, 3H), 7.13 (br d, J = 7.6 Hz, 2H), 6.22 (br s, 1H), 4.28 (dt, J = 13.0, 6.4 Hz, 1H), 3.79 (s, 2H), 2.22 (q, J = 7.0 Hz, 4H), 2.05 (s, 3H), 1.09 (br d, J = 6.4 Hz, 6H), 0.93 (br t, J = 7.3 Hz, 6H) | 2.11, A, 570.2 | A |
| 86 | 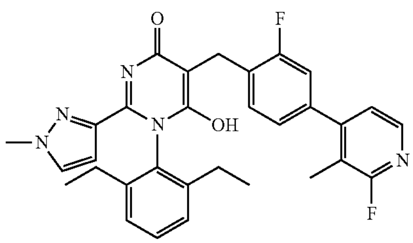 [SMILES: CCc1cccc(CC)c1-n1c(-c2ccn(C)n2)nc(=O)c(Cc2ccc(-c3ccnc(F)c3C)cc2F)c1O] | 1-(2,6-diethylphenyl)-5-{[2-fluoro-4-(2-fluoro-3-methylpyridin-4-yl)phenyl]methyl}-6-hydroxy-2-(1-methyl-1H-pyrazol-3-yl)-1,4-dihydropyrimidin-4-one | 1H NMR (500 MHz, DMSO-d6) Shift 8.09 (br d, J = 4.9 Hz, 1H), 7.53 (s, 1H), 7.42-7.34 (m, 1H), 7.32-7.21 (m, 2H), 7.22-7.11 (m, 4H), 5.54 (s, 1H), 3.79 (s, 2H), 3.70 (s, 3H), 2.32-2.19 (m, 4H), 2.16 (s, 3H), 0.96 (t, J = 7.5 Hz, 6H) | 1.78, A, 542.0 | A |
| 87 | 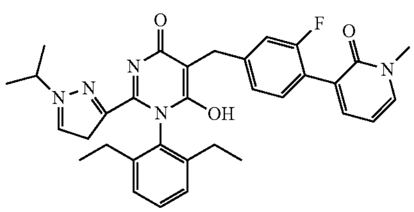 | 1-(2,6-diethylphenyl)-5-{[3-fluoro-4-(1-methyl-2-oxo-1,2-dihydropyridin-3-yl)phenyl]methyl}-6-hydroxy-2-[1-(propan-2-yl)-1H-pyrazol-3-yl]-1,4-dihydropyrimidin-4-one | 1H NMR (500 MHz, DMSO-d6) Shift 7.74 (br d, J = 6.7 Hz, 1H), 7.60 (d, J = 1.8 Hz, 1H), 7.45 (br d, J = 6.1 Hz, 1H), 7.36-7.25 (m, 2H), 7.14 (d, J = 7.6 Hz, 2H), 7.11-7.06 (m, 1H), 7.04 (br d, J = 11.3 Hz, 1H), 6.29 (t, J = 6.9 Hz, 1H), 6.23 (d, J = 1.8 Hz, 1H), 4.29 (dt, J = 13.1, 6.6 Hz, 1H), 3.74 (s, 2H), 3.48 (s, 3H), 2.24 (q, J = 7.4 Hz, 4H), 1.10 (d, J = 6.7 Hz, 6H), 0.96 (t, J = 7.6 Hz, 6H) | 1.66, A, 568.1 | A |
| 88 | 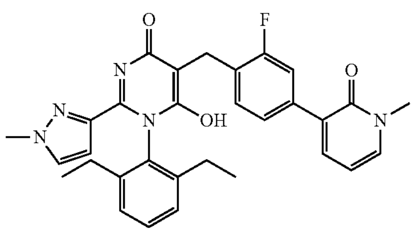 | 1-(2,6-diethylphenyl)-5-{[2-fluoro-4-(1-methyl-2-oxo-1,2-dihydropyridin-3-yl)phenyl]methyl}-6-hydroxy-2-(1-methyl-1H-pyrazol-3-yl)-1,4-dihydropyrimidin-4-one | 1H NMR (500 MHz, DMSO-d6) Shift 7.74 (br d, J = 6.4 Hz, 1H), 7.66 (br d, J = 6.7 Hz, 1H), 7.60-7.53 (m, 1H), 7.50 (s, 1H), 7.43-7.37 (m, 1H), 7.36-7.27 (m, 1H), 7.16 (br d, J = 7.3 Hz, 3H), 6.32 (t, J = 6.9 Hz, 1H), 5.58 (s, 1H), 3.73 (s, 2H), 3.68 (s, 3H), 3.50 (s, 3H), 2.26 (q, J = 7.3 Hz, 4H), 0.99 (t, J = 7.6 Hz, 6H) | 1.35, A, 540.2 | A |
| 89 | 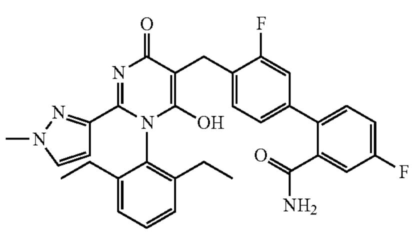 [SMILES: CCc1cccc(CC)c1-n1c(-c2ccn(C)n2)nc(=O)c(Cc2ccc(-c3ccc(F)cc3C(N)=O)cc2F)c1O] | 4'-{[1-(2,6-diethylphenyl)-6-hydroxy-2-(1-methyl-1H-pyrazol-3-yl)-4-oxo-1,4-dihydropyrimidin-5-yl]methyl}-3',4-difluoro-[1,1'-biphenyl]-2-carboxamide | 1H NMR (500 MHz, DMSO-d6) Shift 7.77 (br s, 1H), 7.52 (s, 1H), 7.46-7.39 (m, 2H), 7.39-7.34 (m, 1H), 7.34-7.28 (m, 1H), 7.25 (br d, J = 7.9 Hz, 1H), 7.22-7.06 (m, 5H), 5.56 (s, 1H), 3.90 (s, 2H), 3.70 (s, 3H), 2.24 (q, J = 7.5 Hz, 4H), 0.99 (br t, J = 7.5 Hz, 6H) | 1.57, A, 570.1 | A |
| 90 | 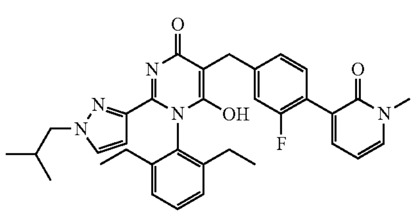 [SMILES: CCc1cccc(CC)c1-n1c(-c2ccn(CC(C)C)n2)nc(=O)c(Cc2ccc(-c3cccn(C)c3=O)c(F)c2)c1O] | 1-(2,6-diethylphenyl)-5-{[3-fluoro-4-(1-methyl-2-oxo-1,2-dihydropyridin-3-yl)phenyl]methyl}-6-hydroxy-2-[1-(2-methylpropyl)-1H-pyrazol-3-yl]-1,4-dihydropyrimidin-4-one | 1H NMR (500 MHz, DMSO-d6) Shift 7.73 (br d, J = 6.1 Hz, 1H), 7.55 (br s, 1H), 7.44 (br d, J = 6.4 Hz, 1H), 7.37-7.22 (m, 2H), 7.13 (br d, J = 7.0 Hz, 2H), 7.10-6.97 (m, 2H), 6.29 (br t, J = 6.7 Hz, 1H), 6.02 (br s, 1H), 3.74 (br s, 2H), 3.69 (br d, J = 6.7 Hz, 2H), 3.44 (br s, 3H), 2.23 (br d, J = 6.7 Hz, 4H), 1.79 (br d, J = 5.2 Hz, 1H), 0.97 (br t, J = 7.2 Hz, 6H), 0.59 (br d, J = 6.1 Hz, 6H) | 1.78, A, 582.0 | A |

-continued

| Ex # | Structure | Name | NMR | Rt (min) method M + H | APJ cAMP Potency range |
|---|---|---|---|---|---|
| 91 | 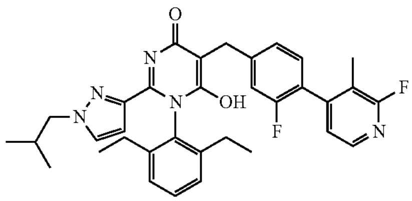 [SMILES: CCc1cccc(CC)c1-n1c(-c2ccn(CC(C)C)n2)nc(=O)c(Cc2ccc(-c3ccnc(F)c3C)c(F)c2)c1O] | 1-(2,6-diethylphenyl)-5-{[3-fluoro-4-(2-fluoro-3-methylpyridin-4-yl)phenyl]methyl}-6-hydroxy-2-[1-(2-methylpropyl)-1H-pyrazol-3-yl]-1,4-dihydropyrimidin-4-one | 1H NMR (500 MHz, DMSO-d6) Shift 8.08 (br d, J = 5.0 Hz, 1H), 7.52 (s, 1H), 7.37-7.24 (m, 2H), 7.21 (br d, J = 7.9 Hz, 2H), 7.18-7.06 (m, 3H), 5.97 (s, 1H), 3.76 (br s, 4H), 2.29-2.11 (m, 4H), 2.03 (br s, 3H), 1.86-1.71 (m, 1H), 0.93 (br t, J = 7.4 Hz, 6H), 0.57 (br d, J = 6.5 Hz, 6H) | 2.14, A, 584.1 | C |
| 92 | 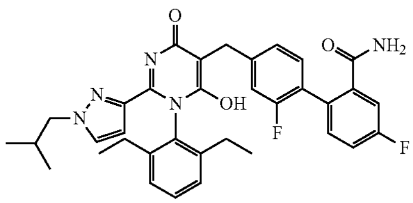 [SMILES: CCc1cccc(CC)c1-n1c(-c2ccn(CC(C)C)n2)nc(=O)c(Cc2ccc(-c3ccc(F)cc3C(N)=O)c(F)c2)c1O] | 4'-{[1-(2,6-diethylphenyl)-6-hydroxy-2-[1-(2-methylpropyl)-1H-pyrazol-3-yl]-4-oxo-1,4-dihydropyrimidin-5-yl]methyl}-2',4-difluoro-[1,1'-biphenyl]-2-carboxamide | 1H NMR (500 MHz, DMSO-d6) Shift 7.73 (br s, 1H), 7.56 (s, 1H), 7.42-7.27 (m, 3H), 7.21 (br t, J = 7.8 Hz, 1H), 7.13 (br d, J = 7.5 Hz, 2H), 7.11-7.05 (m, 1H), 7.00 (br d, J = 11.4 Hz, 1H), 6.01 (s, 1H), 3.89 (s, 2H), 3.69 (br d, J = 7.2 Hz, 2H), 2.31-2.16 (m, 4H), 1.85-1.72 (m, 1H), 0.98 (br t, J = 7.4 Hz, 6H), 0.59 (br d, J = 6.5 Hz, 6H) | 1.86, A, 612.0 | B |
| 93 | 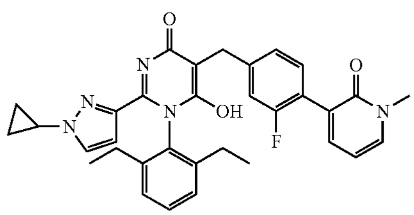 [SMILES: CCc1cccc(CC)c1-n1c(-c2ccn(C3CC3)n2)nc(=O)c(Cc2ccc(-c3cccn(C)c3=O)c(F)c2)c1O] | 2-(1-cyclopropyl-1H-pyrazol-3-yl)-1-(2,6-diethylphenyl)-5-{[3-fluoro-4-(1-methyl-2-oxo-1,2-dihydropyridin-3-yl)phenyl]methyl}-6-hydroxy-1,4-dihydropyrimidin-4-one | 1H NMR (500 MHz, DMSO-d6) Shift 7.70 (br d, J = 6.7 Hz, 1H), 7.67 (d, J = 1.8 Hz, 1H), 7.44 (br d, J = 6.7 Hz, 1H), 7.36-7.24 (m, 2H), 7.14 (br d, J = 7.6 Hz, 2H), 7.07 (br d, J = 7.9 Hz, 1H), 7.01 (br d, J = 11.6 Hz, 1H), 6.30 (t, J = 6.9 Hz, 1H), 6.21 (s, 1H), 3.72 (s, 2H), 3.62 (br d, J = 9.5 Hz, 1H), 3.47 (s, 3H), 2.19 (q, J = 7.3 Hz, 4H), 0.94 (t, J = 7.6 Hz, 6H), 0.80-0.70 (m, 2H), 0.59 (br s, 2H) | 1.62, A, 566.0 | A |
| 94 | 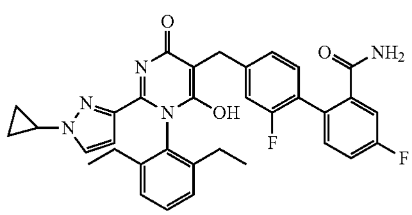 [SMILES: CCc1cccc(CC)c1-n1c(-c2ccn(C3CC3)n2)nc(=O)c(Cc2ccc(-c3ccc(F)cc3C(N)=O)c(F)c2)c1O] | 4'-{[2-(1-cyclopropyl-1H-pyrazol-3-yl)-1-(2,6-diethylphenyl)-6-hydroxy-4-oxo-1,4-dihydropyrimidin-5-yl]methyl}-2',4-difluoro-[1,1'-biphenyl]-2-carboxamide | 1H NMR (500 MHz, DMSO-d6) Shift 7.72 (br s, 1H), 7.68 (s, 1H), 7.42-7.26 (m, 3H), 7.19 (s, 1H), 7.14 (br d, J = 7.6 Hz, 2H), 7.07 (br d, J = 7.7 Hz, 1H), 6.99 (br d, J = 11.7 Hz, 1H), 6.21 (br s, 1H), 3.68-3.48 (m, 3H), 2.20 (q, J = 7.3 Hz, 4H), 0.94 (br t, J = 7.5 Hz, 6H), 0.75 (br d, J = 6.3 Hz, 2H), 0.59 (br s, 2H) | 1.72, A, 596.2 | A |

Example 95

(S)-3-(1-(2-butyl-5-(4-(6-fluoro-2-methylpyridin-3-yl)benzyl)-6-hydroxy-4-oxopyrimidin-1(4H)-yl)propyl)benzonitrile

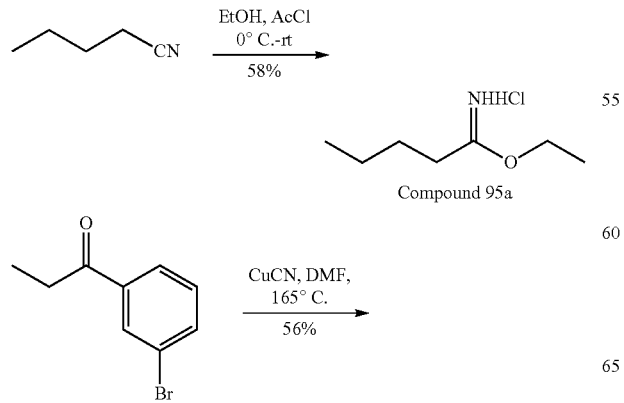

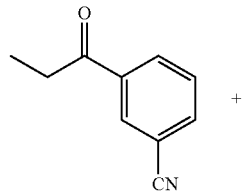

117
-continued

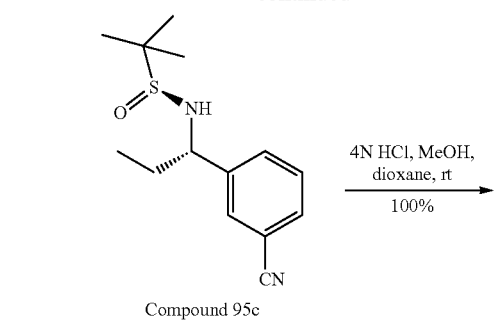

Compound 95c

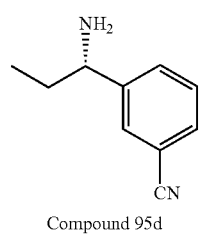

Compound 95d

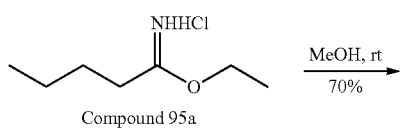

Compound 95a

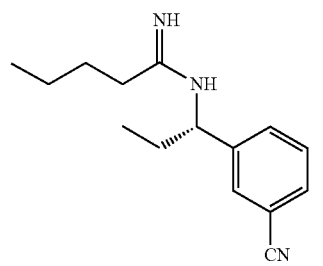

Compound 95e

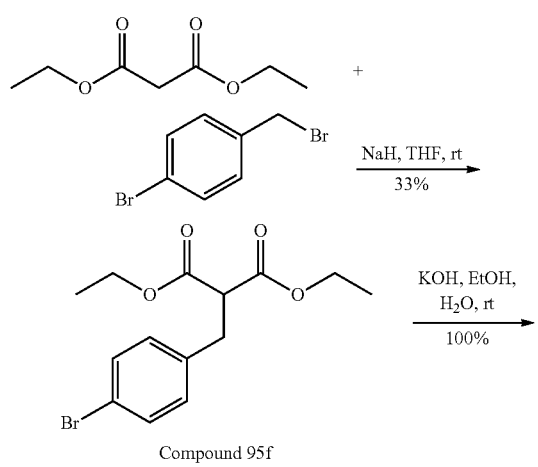

Compound 95f

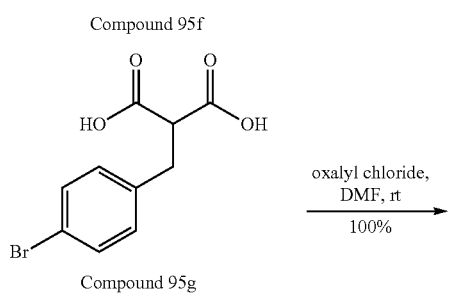

Compound 95g

118
-continued

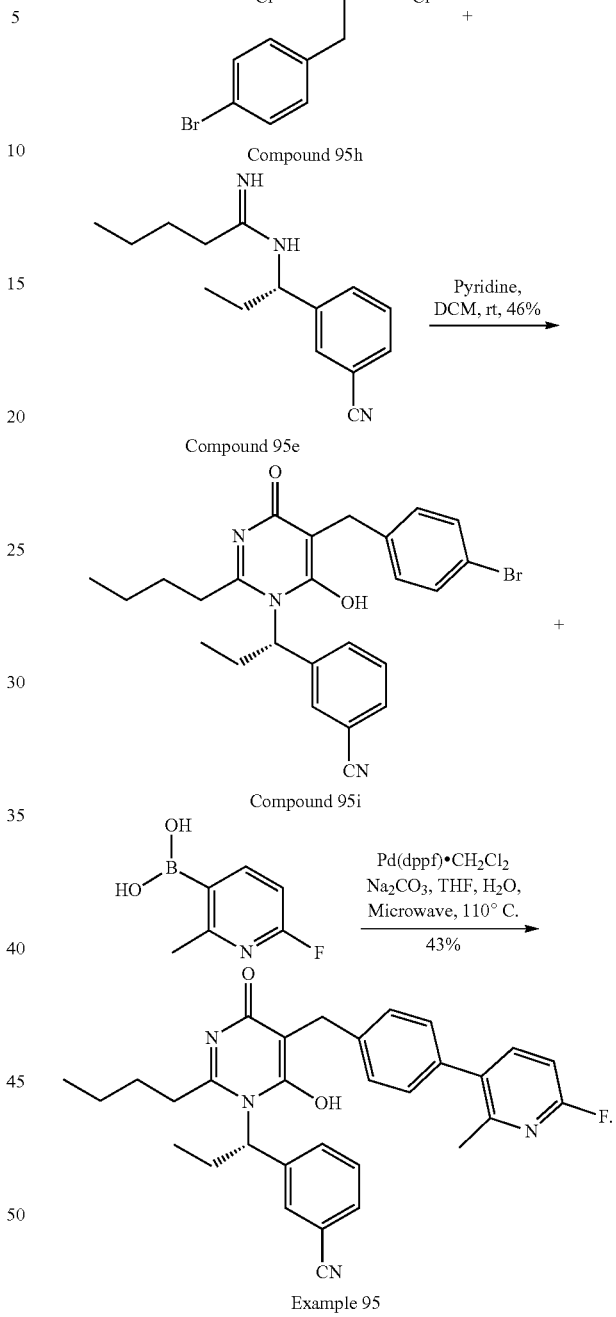

Compound 95a. Ethyl Pentanimidate Hydrochloride

To a solution of pentanenitrile (7.11 g, 86.1 mmol) in ethanol (60 ml) at 0° C. was added acetyl chloride (30.4 mL, 428 mmol) dropwise. The cooling bath was removed and the reaction mixture was stirred overnight at RT. The reaction solvent was removed under vacuum and the residue was triturated with Et$_2$O. The resultant slurry was filtered and the filter cake was washed with Et$_2$O and dried under vacuum to give Compound 95a (8.21 g, 58% yield) as a white solid. $^1$H NMR (500 MHz, CHLOROFORM-d) δ 12.36 (br s, 1H), 11.47 (br s, 1H), 4.64 (q, J=7.2 Hz, 2H), 2.74 (t, J=7.7 Hz, 2H), 1.76-1.66 (m, 2H), 1.49 (t, J=7.0 Hz, 3H), 1.45-1.37 (m, 2H), 0.95 (t, J=7.4 Hz, 3H).

Compound 95b. 3-propionylbenzonitrile

To a solution of 1-(3-bromophenyl)propan-1-one (950 mg, 4.46 mmol) in DMF (10 ml) was added copper(I) cyanide (998 mg, 11.2 mmol). The reaction vessel was sealed and the reaction mixture was stirred at 165° C. overnight. The reaction mixture was quenched by the addition of 30% $NH_4OH$ and extracted with EtOAc (2×). The EtOAc layers were combined and the composite was washed with brine, dried over $MgSO_4$, filtered and concentrated under reduced pressure. The residue was purified by silica gel chromatography eluting with 0 to 60% EtOAc in hexane to give Compound 95b (400 mg, 56% yield) as an off-white solid. MS m/z=160.0 (M+H). $^1$H NMR (CHLOROFORM-d) δ: 8.26 (s, 1H), 8.21 (dt, J=7.9, 1.4 Hz, 1H), 7.86 (dt, J=7.7, 1.2 Hz, 1H), 7.63 (t, J=7.8 Hz, 1H), 3.04 (q, J=7.2 Hz, 2H), 1.58-1.61 (m, 1H), 1.28 (t, J=7.3 Hz, 3H).

Compound 95c. (S)—N—((S)-1-(3-cyanophenyl)propyl)-2-methylpropane-2-sulfinamide

To a solution of Compound 95b (400 mg, 2.51 mmol) in THF (10 ml) was added titanium(IV) ethoxide (1.15 g, 5.03 mmol) and (S)-2-methylpropane-2-sulfinamide (335 mg, 2.76 mmol). The reaction mixture was stirred at 75° C. for 4 hrs. The reaction mixture was cooled to −48° C. and was added dropwise to a −48° C. solution of sodium borohydride (380 mg, 10.1 mmol) in THF (4 mL). The reaction mixture was allowed to warm to RT over 3 hrs and was then carefully quenched by the addition of MeOH. With rapid stirring, the reaction mixture was poured into an equal volume of brine, the resulting suspension was filtered through celite and the celite cake was washed with EtOAc. The two-phase filtrate was split and the organic phase was dried over $MgSO_4$ and concentrated under reduced pressure. The residue was purified by silica gel chromatography eluting with 0 to 100% EtOAc in hexane to give Compound 95c (450 mg, 68% yield) as a white solid. MS m/z=265.1 (M+H). $^1$H NMR (CHLOROFORM-d) δ: 7.57-7.65 (m, 2H), 7.46-7.52 (m, 1H), 7.22-7.33 (m, 1H), 4.31-4.39 (m, 1H), 3.32-3.54 (m, 1H), 1.74-2.12 (m, 2H), 1.26 (s, 9H), 0.85 (t, J=7.3 Hz, 3H).

Compound 95d. (S)-3-(1-aminopropyl)benzonitrile

To a solution of Compound 95c (450 mg, 1.70 mmol) in MeOH (5 ml) was added 4N HCl in dioxane (0.85 mL, 3.4 mmol), and the reaction mixture was stirred at RT for 1 hr. The reaction mixture was concentrated under reduced pressure to give Compound 95d (335 mg, 100% yield) as a white solid. MS m/z=161.0 (M+H). $^1$H NMR (METHANOL-$d_4$) δ: 7.82-7.88 (m, 2H), 7.77-7.81 (m, 1H), 7.67-7.73 (m, 1H), 4.20-4.34 (m, 1H), 1.95-2.13 (m, 2H), 0.93 (t, J=7.4 Hz, 3H).

Compound 95e. (S)—N-(1-(3-cyanophenyl)propyl)pentanimidamide

To a solution of Compound 95d (1.61 g, 8.19 mmol) in MeOH (20 ml) was added Compound 95a (2.44 g, 14.2 mmol), and DIEA (4.23 g, 32.7 mmol) the reaction mixture was stirred at RT for 14 h. The reaction mixture was concentrated under reduced pressure and the residue was purified via preparative HPLC with the following conditions: Column: Phen Luna AXIA C18, 30×100 mm, 5-µm particles; Mobile Phase A: 10:90 MeOH:water with 0.1% TFA; Mobile Phase B: 90:10 MeOH:water with 0.1% TFA; Gradient: 0-100% B over 10 minutes, then a 2-minute hold at 100% B; Flow: 40 mL/min. Fractions containing the 95e were combined, concentrated under reduced pressure and the residue was partitioned between DCM and 1N NaOH. Compound 95e was extracted with DCM (2×), the organic phases were combined and the composite was dried over $MgSO_4$ and concentrate under reduced pressure to give a white solid (1.4 g, 70% yield). MS m/z=244.2 (M+H). $^1$H NMR (CHLOROFORM-d) δ: 7.61-7.63 (m, 1H), 7.56-7.60 (m, 1H), 7.51-7.56 (m, 1H), 7.40-7.47 (m, 1H), 5.32 (s, 1H), 2.24 (t, J=7.8 Hz, 2H), 1.66-1.86 (m, 2H), 1.54-1.62 (m, 2H), 1.23-1.44 (m, 2H), 0.87-0.97 (m, 6H), 0.01-0.03 (m, 1H).

Compound 95f. diethyl 2-(4-bromobenzyl)malonate3-propionylbenzonitrile

To a slurry of 60% NaH (699 mg, 17.5 mmol) in THF (20 ml) was added diethyl malonate (2.0 g, 13 mmol) dropwise and the reaction mixture was stirred at RT for 1 hr. The reaction mixture cooled to 0° C. and a solution of 1-bromo-4-(bromomethyl)benzene (3.13 g, 12.5 mmol) in THF (5 mL) was added dropwise. The reaction mixture was allowed to warm and stir for 14 h at RT. The reaction mixture was quenched by the addition of EtOH, filtered through celite and the celite cake was washed with EtOAc. The filtrate was concentrated under reduced pressure and the residue was purified by silica gel chromatography eluting with 0 to 70% EtOAc in hexane to give Compound 95f (1.35 g, 33% yield) as a colorless oil. MS m/z=329.0 (M+H). $^1$H NMR (CHLOROFORM-d) δ: 7.38-7.52 (m, 2H), 7.07-7.20 (m, 2H), 4.09-4.37 (m, 4H), 3.59 (t, J=7.8 Hz, 1H), 3.16 (d, J=7.9 Hz, 2H), 1.56 (s, 1H), 1.22 (t, J=7.2 Hz, 6H), −0.01-0.05 (m, 1H).

Compound 95g. 2-(4-bromobenzyl)malonic acid

To a solution of Compound 95f (500 mg, 1.52 mmol) in a mixture of EtOH (2.5 ml) and water (1.25 mL) was added KOH (298 mg, 5.32 mmol) and the reaction mixture was stirred at RT for 14 h. The reaction mixture was acidified with 3N HCl and the product was extracted with $Et_2O$ (3×). The organic phases were combined and the composite was dried over $MgSO_4$ and concentrated under reduced pressure to give Compound 395g (420 mg, 100% yield) as a white solid. MS m/z=272.9 (M+H). $^1$H NMR (CHLOROFORM-d) δ: 7.42-7.47 (m, 2H), 7.07-7.16 (m, 2H), 3.76 (t, J=7.4 Hz, 1H), 3.28 (d, J=7.4 Hz, 2H).

Compound 95h. 2-(4-bromobenzyl)malonyl dichloride

To a solution of Compound 95g (802 mg, 2.94 mmol) in DCM (25 ml) was added 2M oxalyl chloride in DCM (2.94 mL, 5.87 mmol) and DMF (3 drops). The reaction mixture was stirred at RT for 1 hr. The reaction mixture was used without further purification in the next reaction step.

Compound 95i. (S)-3-(1-(5-(4-bromobenzyl)-2-butyl-6-hydroxy-4-oxopyrimidin-1(4H)-yl)propyl)benzonitrile To Compound 95h (911 mg, 2.94 mmol) was added a solution of Compound 38e (550 mg, 2.26 mmol) in DCM (8 mL) and TEA (915 mg, 904 mmol) and the reaction mixture was stirred at RT for 2 hrs. The reaction mixture was concentrated under reduced pressure and the residue was purified by silica gel chromatography eluting with 0 to 60% EtOAc in hexane to give Compound 95i (501 mg, 46% yield) as a pale yellow solid. MS m/z=480.2 (M+H). $^1$H NMR (CHLOROFORM-d) δ: 7.62 (br s, 1H), 7.52-7.59 (m, 2H), 7.43-7.52 (m, 2H), 7.30-7.39 (m, 2H), 4.84-4.96 (m, 1H), 3.73 (br s, 2H), 2.21-2.35 (m, 2H), 1.77-1.87 (m, 2H), 1.57-1.70 (m, 2H), 1.41-1.49 (m, 2H), 1.02 (t, J=6.9 Hz, 3H), 0.91-0.97 (m, 3H). Human APJ cAMP $EC_{50}$ potency range: B.

Example 95. (S)-3-(1-(2-butyl-5-(4-(6-fluoro-2-methylpyridin-3-yl)benzyl)-6-hydroxy-4-oxopyrimidin-1(4H)-yl)propyl)benzonitrile To a 5 mL microwave vial were added Compound 95i (30.1 mg, 0.0620 mmol), (6-fluoro-2-methylpyridin-3-yl) boronic acid (29.1 mg, 0.187 mmol), Pd(dppf)Cl$_2$·CH$_2$Cl$_2$ (5 mg, 0.006 mmol), 1.5 M Na$_2$CO$_3$ (0.125 mL, 0.187 mmol), and THF (1 mL). The reaction mixture was degassed with argon and stirred at 110° C. under microwave irradiation for 1 hr. The reaction mixture was filtered and concentrated under reduced pressure. The residue was purified via preparative LC/MS with the following conditions: Column: XBridge C18, 19×200 mm, 5-μm particles; Mobile Phase A: 5:95 acetonitrile:water with 10 mM ammonium acetate; Mobile Phase B: 95:5 acetonitrile:water with 10 mM ammonium acetate; Gradient: 30-70% B over 20 minutes, then a 5-minute hold at 100% B; Flow: 20 mL/min. Fractions containing Compound 95 were combined and dried via centrifugal evaporation (13.9 mg, 43% yield) a white solid. The estimated purity by LCMS analysis was 99.2%, HPLC method B, RT=2.03 min, MS m/z=511.2 (M+H). $^1$H NMR (DMSO-d$_6$) δ: 7.70-7.80 (m, 2H), 7.62-7.70 (m, 1H), 7.49-7.62 (m, 2H), 7.14-7.35 (m, 4H), 6.98-7.08 (m, 1H), 5.23-5.59 (m, 1H), 3.38 (br s, 2H), 2.77-2.96 (m, 2H), 2.28-2.48 (m, 5H), 1.57-1.72 (m, 2H), 1.31-1.47 (m, 2H), 0.79-1.01 (m, 6H). Human APJ cAMP $EC_{50}$ potency range: A.

Examples 96 to 136 were prepared as described in the general procedure given for Example 95.

| Ex # | Structure | Name | NMR | Rt (min) method M + H | APJ cAMP Potency range |
|---|---|---|---|---|---|
| 96 | 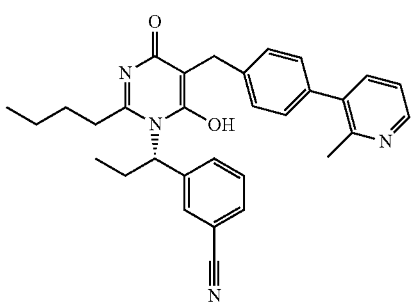 [SMILES: CCCCc1nc(=O)c(Cc2ccc(-c3cccnc3C)cc2)c(O)n1[C@@H](CC)c1cccc(C#N)c1] | 3-[(1S)-1-(2-butyl-6-hydroxy-5-{[4-(2-methylpyridin-3-yl)phenyl]methyl}-4-oxo-1,4-dihydropyrimidin-1-yl)propyl]benzonitrile | 1H NMR (DMSO-d6) Shift: 8.42 (br s, 1H), 7.63-7.77 (m, 2H), 7.55 (br s, 2H), 7.24-7.39 (m, 3H), 7.17-7.24 (m, 3H), 5.36-5.47 (m, 1H), 3.81-3.98 (m, 2H), 2.76-2.93 (m, 2H), 2.53-2.56 (m, 5H), 2.33-2.47 (m, 5H), 1.53-1.71 (m, 2H), 1.28-1.50 (m, 2H), 0.85 (s, 6H) | 1.77, A, 493.0 | A |
| 97 | 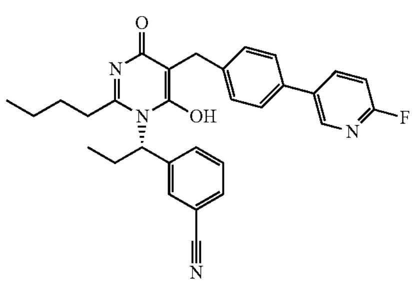 [SMILES: CCCCc1nc(=O)c(Cc2ccc(-c3ccc(F)nc3)cc2)c(O)n1[C@@H](CC)c1cccc(C#N)c1] | 3-[(1S)-1-(2-butyl-5-{[4-(6-fluoropyridin-3-yl)phenyl]methyl}-6-hydroxy-4-oxo-1,4-dihydropyrimidin-1-yl)propyl]benzonitrile | 1H NMR (DMSO-d6) Shift: 8.48 (br s, 1H), 8.17-8.26 (m, 1H), 7.69-7.77 (m, 1H), 7.67 (br s, 1H), 7.51-7.62 (m, 3H), 7.16-7.31 (m, 4H), 5.30-5.57 (m, 1H), 3.80-3.96 (m, 2H), 2.79-2.93 (m, 2H), 2.05-2.20 (m, 2H), 1.58-1.71 (m, 2H), 1.34-1.43 (m, 2H), 0.80-0.93 (m, 6H) | 1.91, A, 497.0 | A |
| 98 | 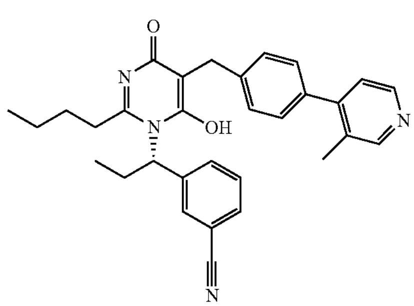 [SMILES: CCCCc1nc(=O)c(Cc2ccc(-c3ccncc3C)cc2)c(O)n1[C@@H](CC)c1cccc(C#N)c1] | 3-[(1S)-1-(2-butyl-6-hydroxy-5-{[4-(3-methylpyridin-4-yl)phenyl]methyl}-4-oxo-1,4-dihydropyrimidin-1-yl)propyl]benzonitrile | 1H NMR (DMSO-d6) Shift: 8.47 (s, 1H), 8.36-8.41 (m, 1H), 7.62-7.75 (m, 2H), 7.48-7.60 (m, 2H), 7.13-7.30 (m, 5H), 5.18-5.66 (m, 1H), 3.44-3.66 (m, 2H), 2.74-2.92 (m, 2H), 2.16-2.28 (m, 5H), 1.56-1.72 (m, 2H), 1.28-1.46 (m, 2H), 0.76-0.95 (m, 6H) | 1.78, A, 493.2 | A |

-continued

| Ex # | Structure | Name | NMR | Rt (min) method M + H | APJ cAMP Potency range |
|---|---|---|---|---|---|
| 99 | 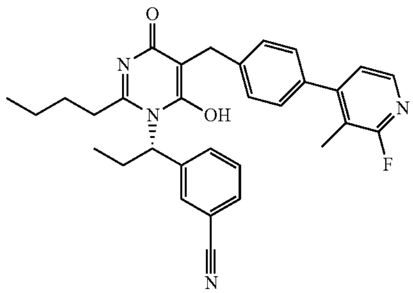 [SMILES: CCCCc1nc(=O)c(Cc2ccc(-c3ccnc(F)c3C)cc2)c(O)n1[C@@H](CC)c1cccc(C#N)c1] | 3-[(1S)-1-(2-butyl-5-{[4-(2-fluoro-3-methylpyridin-4-yl)phenyl]methyl}-6-hydroxy-4-oxo-1,4-dihydropyrimidin-1-yl)propyl]benzonitrile | 1H NMR (DMSO-d6) Shift: 7.93-8.19 (m, 1H), 7.63-7.78 (m, 2H), 7.47-7.62 (m, 2H), 7.14-7.32 (m, 5H), 5.27-5.59 (m, 1H), 3.36-3.52 (m, 2H), 2.76-2.97 (m, 2H), 2.10-2.21 (m, 5H), 1.54-1.74 (m, 2H), 1.29-1.46 (m, 2H), 0.73-0.96 (m, 6H) | 1.98, A, 511.3 | A |
| 100 | 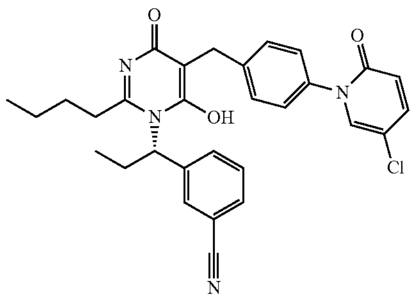 [SMILES: CCCCc1nc(=O)c(Cc2ccc(-n3cc(Cl)ccc3=O)cc2)c(O)n1[C@@H](CC)c1cccc(C#N)c1] | 3-[(1S)-1-(2-butyl-5-{[4-(5-chloro-2-oxo-1,2-dihydropyridin-1-yl)phenyl]methyl}-6-hydroxy-4-oxo-1,4-dihydropyrimidin-1-yl)propyl]benzonitrile | 1H NMR (DMSO-d6) Shift: 7.81-7.90 (m, 1H), 7.62-7.75 (m, 2H), 7.46-7.60 (m, 3H), 7.29-7.40 (m, 1H), 7.15-7.28 (m, 3H), 6.43-6.57 (m, 1H), 5.28-5.50 (m, 1H), 3.51-3.61 (m, 2H), 2.75-2.94 (m, 2H), 1.96-2.21 (m, 2H), 1.56-1.70 (m, 2H), 1.30-1.43 (m, 2H), 0.72-0.97 (m, 6H) | 1.77, A, 529.2 | A |
| 101 | 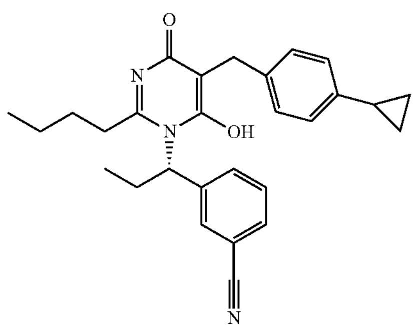 [SMILES: CCCCc1nc(=O)c(Cc2ccc(C3CC3)cc2)c(O)n1[C@@H](CC)c1cccc(C#N)c1] | 3-[(1S)-1-{2-butyl-5-[(4-cyclopropylphenyl)methyl]-6-hydroxy-4-oxo-1,4-dihydropyrimidin-1-yl}propyl]benzonitrile | 1H NMR (DMSO-d6) Shift: 7.67-7.75 (m, 1H), 7.60-7.66 (m, 1H), 7.48-7.61 (m, 1H), 6.78-7.02 (m, 5H), 5.31-5.55 (m, 1H), 3.79-3.96 (m, 2H), 2.75-2.89 (m, 2H), 2.33-2.45 (m, 2H), 1.76-1.87 (m, 1H), 1.52-1.71 (m, 2H), 1.28-1.43 (m, 2H), 0.87 (br d, J = 6.5 Hz, 4H), 0.79-0.85 (m, 6H) | 2.04 min, A, 442.3 | A |
| 102 | 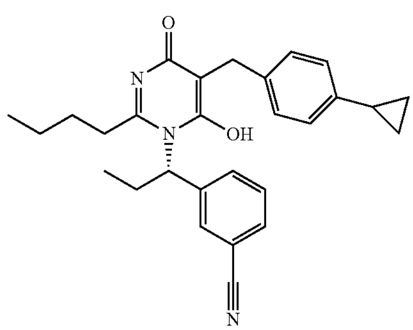 [SMILES: CCCCc1nc(=O)c(Cc2ccc(C3CC3)cc2)c(O)n1[C@@H](CC)c1cccc(C#N)c1] | 3-[(1S)-1-{2-butyl-5-[(4-cyclopropylphenyl)methyl]-6-hydroxy-4-oxo-1,4-dihydropyrimidin-1-yl}propyl]benzonitrile | 1H NMR (DMSO-d6) Shift: 7.65-7.77 (m, 1H), 7.50-7.62 (m, 1H), 7.12-7.25 (m, 1H), 6.96-7.11 (m, 1H), 6.29-6.39 (m, 1H), 6.27-6.40 (m, 1H), 6.20 (br d, J = 6.6 Hz, 1H), 5.22-5.57 (m, 1H), 3.25-3.38 (m, 2H), 2.73-2.91 (m, 2H), 2.26-2.42 (m, 2H), 2.03-2.13 (m, 1H), 1.58-1.74 (m, 2H), 1.30-1.44 (m, 2H), 0.86-0.93 (m, 4H), 0.78-0.86 (m, 6H) | 2.09, A, 442.0 | B |
| 103 | 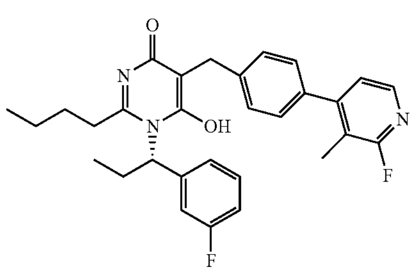 [SMILES: CCCCc1nc(=O)c(Cc2ccc(-c3ccnc(F)c3C)cc2)c(O)n1[C@@H](CC)c1cccc(F)c1] | 2-butyl-5-{[4-(2-fluoro-3-methylpyridin-4-yl)phenyl]methyl}-1-[(1S)-1-(3-fluorophenyl)propyl]-6-hydroxy-1,4-dihydropyrimidin-4-one | 1H NMR (DMSO-d6) Shift: 7.93-8.21 (m, 1H), 7.33-7.44 (m, 2H), 7.23-7.33 (m, 3H), 7.16-7.21 (m, 1H), 7.05-7.15 (m, 1H), 6.95-7.06 (m, 1H), 5.15-5.52 (m, 1H), 3.41-3.65 (m, 2H), 2.66-3.00 (m, 2H), 2.10-2.22 (m, 5H), 1.46-1.76 (m, 2H), 1.25-1.45 (m, 2H), 0.77-0.91 (m, 6H) | 2.14, A, 504.0 | A |

| Ex # | Structure | Name | NMR | Rt (min) method M + H | APJ cAMP Potency range |
|---|---|---|---|---|---|
| 104 | 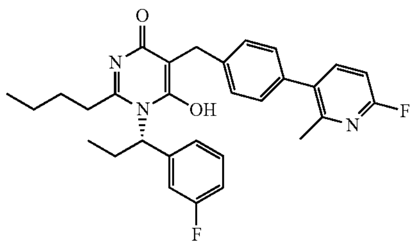 [SMILES: CCCCc1nc(=O)c(Cc2ccc(-c3ccc(F)nc3C)cc2)c(O)n1[C@@H](CC)c1cccc(F)c1] | 2-butyl-5-{[4-(6-fluoro-2-methylpyridin-3-yl)phenyl]methyl}-1-[(1S)-1-(3-fluorophenyl)propyl]-6-hydroxy-1,4-dihydropyrimidin-4-one | 1H NMR (DMSO-d6) Shift: 7.75 (t, J = 7.6 Hz, 2H), 7.33-7.46 (m, 2H), 7.15-7.32 (m, 3H), 7.06-7.16 (m, 1H), 6.97-7.06 (m, 2H), 5.20-5.58 (m, 1H), 3.38-3.65 (m, 2H), 2.67-2.96 (m, 2H), 2.27-2.45 (m, 5H), 1.46-1.73 (m, 2H), 1.22-1.47 (m, 2H), 0.73-0.97 (m, 6H) | 2.10, A, 504.3 | A |
| 105 | 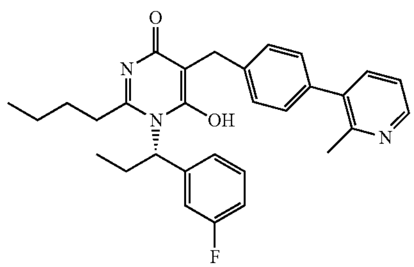 [SMILES: CCCCc1nc(=O)c(Cc2ccc(-c3cccnc3C)cc2)c(O)n1[C@@H](CC)c1cccc(F)c1] | 2-butyl-1-[(1S)-1-(3-fluorophenyl)propyl]-6-hydroxy-5-{[4-(2-methylpyridin-3-yl)phenyl]methyl}-1,4-dihydropyrimidin-4-one | 1H NMR (DMSO-d6) Shift: 8.28-8.52 (m, 1H), 7.56 (br d, J = 6.7 Hz, 1H), 7.15-7.49 (m, 6H), 6.96-7.13 (m, 3H), 5.20-5.60 (m, 1H), 3.45-3.74 (m, 2H), 2.71-3.00 (m, 2H), 2.40 (s, 5H), 1.48-1.76 (m, 2H), 1.21-1.50 (m, 2H), 0.80-0.89 (m, 6H) | 1.94, A, 486.3 | A |
| 106 | 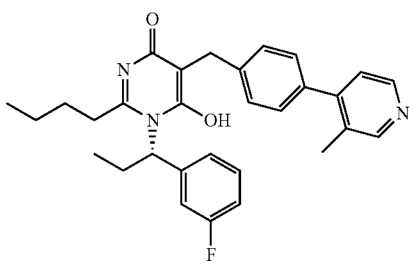 [SMILES: CCCCc1nc(=O)c(Cc2ccc(-c3ccncc3C)cc2)c(O)n1[C@@H](CC)c1cccc(F)c1] | 2-butyl-1-[(1S)-1-(3-fluorophenyl)propyl]-6-hydroxy-5-{[4-(3-methylpyridin-4-yl)phenyl]methyl}-1,4-dihydropyrimidin-4-one | 1H NMR (DMSO-d6) Shift: 8.26-8.59 (m, 2H), 7.15-7.47 (m, 6H), 6.96-7.14 (m, 3H), 5.26-5.47 (m, 1H), 3.83-3.97 (m, 2H), 2.73-2.93 (m, 2H), 2.18-2.30 (m, 5H), 1.49-1.75 (m, 2H), 1.28-1.50 (m, 2H), 0.77-0.92 (m, 6H) | 1.93, A, 486.2 | A |
| 107 | 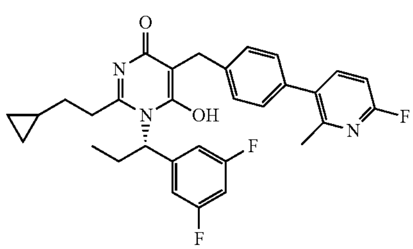 [SMILES: CC[C@@H](c1cc(F)cc(F)c1)n1c(CCC2CC2)nc(=O)c(Cc2ccc(-c3ccc(F)nc3C)cc2)c1O] | 2-(2-cyclopropylethyl)-1-[(1S)-1-(3,5-difluorophenyl)propyl]-5-{[4-(6-fluoro-2-methylpyridin-3-yl)phenyl]methyl}-6-hydroxy-1,4-dihydropyrimidin-4-one | 1H NMR (DMSO-d6) Shift: 7.60-7.76 (m, 1H), 7.07-7.33 (m, 4H), 6.93-7.05 (m, 2H), 6.75-6.90 (m, 2H), 5.15-5.55 (m, 1H), 3.34-3.48 (m, 2H), 2.73-3.03 (m, 2H), 2.29 (s, 5H), 1.39-1.63 (m, 2H), 0.78 (t, J = 7.2 Hz, 3H), 0.26-0.45 (m, 2H), 0.10-0.27 (m, 1H), -0.10-0.10 (m, 2H) | 2.25, A, 534.0 | A |
| 108 | 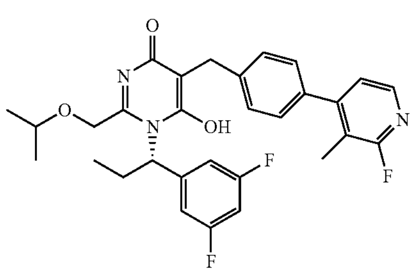 [SMILES: CC[C@@H](c1cc(F)cc(F)c1)n1c(COC(C)C)nc(=O)c(Cc2ccc(-c3ccnc(F)c3C)cc2)c1O] | 1-[(1S)-1-(3,5-difluorophenyl)propyl]-5-{[4-(2-fluoro-3-methylpyridin-4-yl)phenyl]methyl}-6-hydroxy-2-[(propan-2-yloxy)methyl]-1,4-dihydropyrimidin-4-one | 1H NMR (DMSO-d6) Shift: 8.02-8.11 (m, 1H), 7.22-7.29 (m, 4H), 7.15-7.21 (m, 1H), 7.04-7.12 (m, 1H), 6.92-7.05 (m, 2H), 5.19-5.37 (m, 1H), 4.51-4.66 (m, 2H), 4.28-4.47 (m, 2H), 3.47-3.68 (m, 1H), 2.32-2.46 (m, 2H), 2.14 (s, 3H), 0.98-1.16 (m, 6H), 0.85 (brt, J = 7.2 Hz, 3H) | 2.16, A, 538.0 | A |

| Ex # | Structure | Name | NMR | Rt (min) method M + H | APJ cAMP Potency range |
|---|---|---|---|---|---|
| 109 | 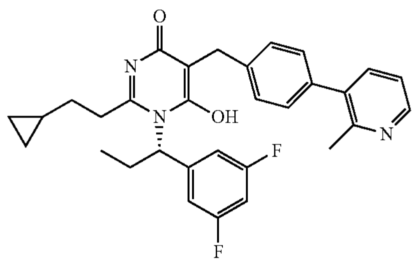 [SMILES: CC[C@@H](c1cc(F)cc(F)c1)n1c(CCC2CC2)nc(=O)c(Cc2ccc(-c3cccnc3C)cc2)c1O] | 2-(2-cyclopropylethyl)-1-[(1S)-1-(3,5-difluorophenyl)propyl]-6-hydroxy-5-{[4-(2-methylpyridin-3-yl)phenyl]methyl}-1,4-dihydropyrimidin-4-one | 1H NMR (DMSO-d6) Shift: 8.31-8.43 (m, 1H), 7.38-7.55 (m, 1H), 7.07-7.33 (m, 4H), 6.97-7.07 (m, 1H), 6.74-6.91 (m, 3H), 5.09-5.49 (m, 1H), 3.10 (s, 2H), 2.73-2.96 (m, 2H), 2.20-2.39 (m, 5H), 1.35-1.65 (m, 2H), 0.77 (t, J = 7.2 Hz, 3H), 0.26-0.44 (m, 2H), 0.08-0.26 (m, 1H), −0.10-0.07 (m, 2H) | 2.04, A, 516.2 | A |
| 110 | 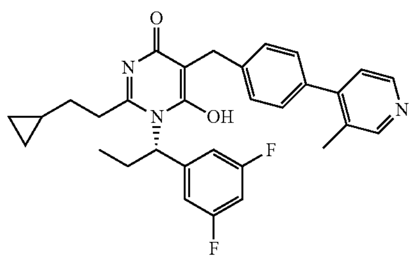 [SMILES: CC[C@@H](c1cc(F)cc(F)c1)n1c(CCC2CC2)nc(=O)c(Cc2ccc(-c3ccncc3C)cc2)c1O] | 2-(2-cyclopropylethyl)-1-[(1S)-1-(3,5-difluorophenyl)propyl]-6-hydroxy-5-{[4-(3-methylpyridin-4-yl)phenyl]methyl}-1,4-dihydropyrimidin-4-one | 1H NMR (DMSO-d6) Shift: 8.29-8.48 (m, 2H), 6.96-7.37 (m, 5H), 6.78-6.91 (m, 3H), 5.21-5.51 (m, 1H), 3.45-3.69 (m, 2H), 2.72-2.93 (m, 2H), 2.21-2.41 (m, 2H), 2.13-2.23 (m, 3H), 1.35-1.64 (m, 2H), 0.77 (t, J = 7.0 Hz, 3H), 0.27-0.40 (m, 2H), 0.11-0.25 (m, 1H), −0.13-0.08 (m, 2H) | 1.99, A, 516.3 | A |
| 111 | 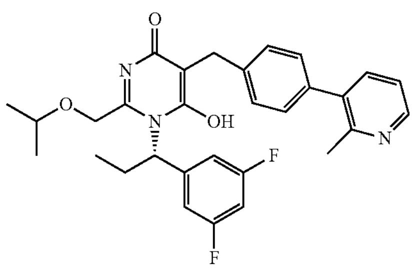 [SMILES: CC[C@@H](c1cc(F)cc(F)c1)n1c(COC(C)C)nc(=O)c(Cc2ccc(-c3cccnc3C)cc2)c1O] | 1-[(1S)-1-(3,5-difluorophenyl)propyl]-6-hydroxy-5-{[4-(2-methylpyridin-3-yl)phenyl]methyl}-2-[(propan-2-yloxy)methyl]-1,4-dihydropyrimidin-4-one | 1H NMR (DMSO-d6) Shift: 8.54-8.63 (m, 1H), 7.85-7.96 (m, 1H), 7.56 (br t, J = 6.1 Hz, 1H), 7.19-7.32 (m, 4H), 7.16 (s, 1H), 7.04-7.12 (m, 1H), 6.98-7.04 (m, 1H), 5.25-5.45 (m, 1H), 4.33-4.74 (m, 1H), 3.63 (s, 2H), 3.38-3.51 (m, 1H), 2.38-2.50 (m, 5H), 1.02-1.14 (m, 6H), 0.86 (t, J = 7.2 Hz, 3H) | 2.00, A, 520.0 | A |
| 112 | 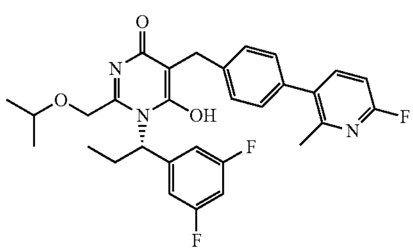 [SMILES: CC[C@@H](c1cc(F)cc(F)c1)n1c(COC(C)C)nc(=O)c(Cc2ccc(-c3ccc(F)nc3C)cc2)c1O] | 1-[(1S)-1-(3,5-difluorophenyl)propyl]-5-{[4-(6-fluoro-2-methylpyridin-3-yl)phenyl]methyl}-6-hydroxy-2-[(propan-2-yloxy)methyl]-1,4-dihydropyrimidin-4-one | 1H NMR (DMSO-d6) Shift: 7.70-7.78 (m, 1H), 7.18-7.25 (m, 3H), 6.94-7.12 (m, 5H), 5.13-5.46 (m, 1H), 4.31-4.64 (m, 2H), 3.52-3.67 (m, 2H), 3.33-3.52 (m, 1H), 2.35-2.46 (m, 2H), 2.31-2.36 (m, 3H), 1.01-1.14 (m, 6H), 0.78-0.92 (m, 3H) | 2.10, A, 538.0 | A |
| 113 | 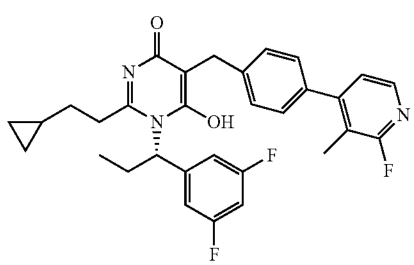 [SMILES: CC[C@@H](c1cc(F)cc(F)c1)n1c(CCC2CC2)nc(=O)c(Cc2ccc(-c3ccnc(F)c3C)cc2)c1O] | 2-(2-cyclopropylethyl)-1-[(1S)-1-(3,5-difluorophenyl)propyl]-5-{[4-(2-fluoro-3-methylpyridin-4-yl)phenyl]methyl}-6-hydroxy-1,4-dihydropyrimidin-4-one | 1H NMR (DMSO-d6) Shift: 7.96-8.06 (m, 1H), 6.99-7.35 (m, 6H), 6.78-6.93 (m, 2H), 5.15-5.51 (m, 1H), 3.55 (br s, 2H), 2.71-2.95 (m, 2H), 2.14-2.41 (m, 2H), 2.03-2.17 (m, 3H), 1.36-1.64 (m, 2H), 0.78 (t, J = 7.2 Hz, 3H), 0.09-0.41 (m, 3H), −0.19-0.08 (m, 2H) | 2.20, A, 534.1 | A |

-continued

| Ex # | Structure | Name | NMR | Rt (min) method M + H | APJ cAMP Potency range |
|---|---|---|---|---|---|
| 114 | 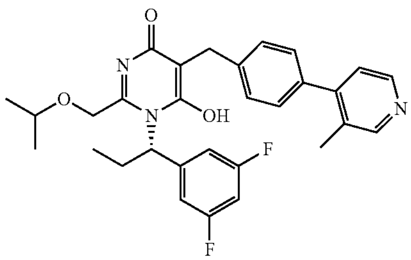 [SMILES: CC[C@@H](c1cc(F)cc(F)c1)n1c(COC(C)C)nc(=O)c(Cc2ccc(-c3ccncc3C)cc2)c1O] | 1-[(1S)-1-(3,5-difluorophenyl)propyl]-6-hydroxy-5-{[4-(3-methylpyridin-4-yl)phenyl]methyl}-2-[(propan-2-yloxy)methyl]-1,4-dihydropyrimidin-4-one | 1H NMR (DMSO-d6) Shift: 7.20-7.35 (m, 4H), 7.10-7.17 (m, 2H), 7.02-7.10 (m, 3H), 6.98-7.02 (m, 1H), 5.21-5.48 (m, 1H), 3.89 (s, 2H), 3.17 (s, 2H), 2.77-3.02 (m, 1H), 2.40-2.46 (m, 2H), 2.26 (s, 3H), 1.07 (br s, 6H), 0.85 (br t, J = 7.0 Hz, 3H) | 2.00, A, 520.0 | A |
| 115 | 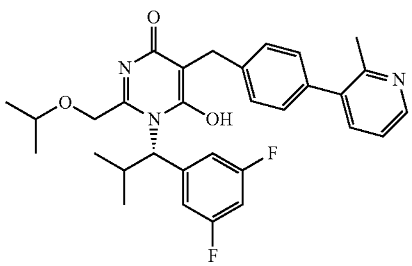 [SMILES: Cc1ncccc1-c1ccc(Cc2c(O)n([C@H](c3cc(F)cc(F)c3)C(C)C)c(COC(C)C)nc2=O)cc1] | 1-[(1S)-1-(3,5-difluorophenyl)-2-methylpropyl]-6-hydroxy-5-{[4-(2-methylpyridin-3-yl)phenyl]methyl}-2-[(propan-2-yloxy)methyl]-1,4-dihydropyrimidin-4-one | 1H NMR (DMSO-d6) Shift: 8.42 (br d, J = 3.7 Hz, 1H), 7.54 (br d, J = 7.6 Hz, 1H), 7.37 (br d, J = 7.9 Hz, 2H), 7.22-7.29 (m, 1H), 7.17-7.22 (m, 4H), 7.10-7.17 (m, 1H), 4.92 (br d, J = 10.4 Hz, 1H), 4.48-4.66 (m, 2H), 3.55-3.63 (m, 2H), 2.38 (s, 3H), 1.20 (br d, J = 5.8 Hz, 6H), 1.00 (br d, J = 6.1 Hz, 1H), 0.94 (br d, J = 6.1 Hz, 3H), 0.82 (br d, J = 6.4 Hz, 3H) | 2.13, A, 534.3 | A |
| 116 | 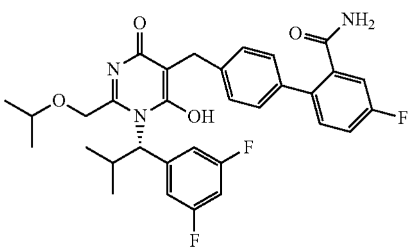 [SMILES: CC(C)OCc1nc(=O)c(Cc2ccc(-c3ccc(F)cc3C(N)=O)cc2)c(O)n1[C@H](c1cc(F)cc(F)c1)C(C)C] | 4'-({1-[(1S)-1-(3,5-difluorophenyl)-2-methylpropyl]-6-hydroxy-4-oxo-2-[(propan-2-yloxy)methyl]-1,4-dihydropyrimidin-5-yl}methyl)-4-fluoro-[1,1'-biphenyl]-2-carboxamide | 1H NMR (DMSO-d6) Shift: 7.70 (br s, 1H), 7.32-7.43 (m, 3H), 7.30 (br d, J = 7.7 Hz, 1H), 7.22 (br d, J = 7.5 Hz, 2H), 7.06-7.18 (m, 3H), 4.91 (br d, J = 10.0 Hz, 1H), 4.46-4.69 (m, 2H), 3.74-3.96 (m, 2H), 3.55 (br s, 1H), 1.15-1.24 (m, 6H), 1.00 (br d, J = 6.0 Hz, 1H), 0.94 (br d, J = 5.2 Hz, 3H), 0.84 (br d, J = 5.4 Hz, 3H) | 2.13, A, 579.9 | A |
| 117 | 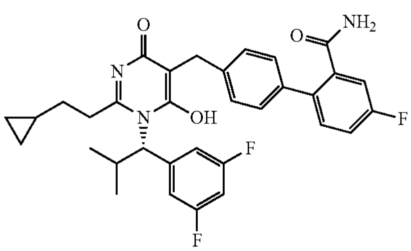 [SMILES: CC(C)[C@@H](c1cc(F)cc(F)c1)n1c(CCC2CC2)nc(=O)c(Cc2ccc(-c3ccc(F)cc3C(N)=O)cc2)c1O] | 4'-{[2-(2-cyclopropylethyl)-1-[(1S)-1-(3,5-difluorophenyl)-2-methylpropyl]-6-hydroxy-4-oxo-1,4-dihydropyrimidin-5-yl]methyl}-4-fluoro-[1,1'-biphenyl]-2-carboxamide | 1H NMR (DMSO-d6) Shift: 7.66 (br s, 1H), 7.18-7.31 (m, 5H), 7.13 (br d, J = 7.1 Hz, 3H), 7.03 (br d, J = 7.0 Hz, 2H), 6.93 (br s, 1H), 4.79 (br d, J = 9.3 Hz, 1H), 3.04-3.15 (m, 2H), 2.80-3.00 (m, 2H), 1.46-1.63 (m, 2H), 0.99-1.12 (m, 1H), 0.85 (br d, J = 5.6 Hz, 3H), 0.72 (br d, J = 5.7 Hz, 3H), 0.23-0.38 (m, 2H), 0.07-0.22 (m, 1H), −0.12-0.05 (m, 2H) | 2.05, A, 576.1 | A |
| 118 | 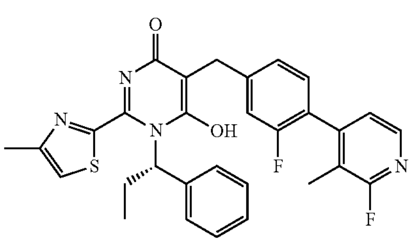 [SMILES: CC[C@@H](c1ccccc1)n1c(-c2nc(C)cs2)nc(=O)c(Cc2ccc(-c3ccnc(F)c3C)c(F)c2)c1O] | 5-{[3-fluoro-4-(2-fluoro-3-methylpyridin-4-yl)phenyl]methyl}-6-hydroxy-2-(4-methyl-1,3-thiazol-2-yl)-1-[(1S)-1-phenylpropyl]-1,4-dihydropyrimidin-4-one | 1H NMR (500 MHz, DMSO-d6) Shift 8.07 (d, J = 4.9 Hz, 1H), 7.61 (s, 1H), 7.31-7.14 (m, 6H), 7.07 (br d, J = 7.9 Hz, 1H), 7.01 (br d, J = 11.0 Hz, 1H), 6.91 (br t, J = 7.3 Hz, 1H), 3.78-3.55 (m, 3H), 2.62-2.44 (m, 2H), 2.40 (s, 3H), 2.02 (s, 3H), 0.84 (br t, J = 7.3 Hz, 3H) | 2.28, A, 545.1 | A |
| 119 | 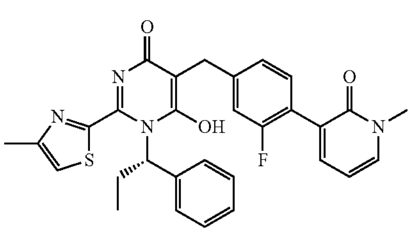 | 5-{[3-fluoro-4-(1-methyl-2-oxo-1,2-dihydropyridin-3-yl)phenyl]methyl}-6-hydroxy-2-(4-methyl-1,3-thiazol-2-yl)-1-[(1S)-1-phenylpropyl]-1,4-dihydropyrimidin-4-one | 1H NMR (500 MHz, DMSO-d6) Shift 7.73 (br d, J = 6.7 Hz, 1H), 7.65 (s, 1H), 7.43 (br d, J = 6.1 Hz, 1H), 7.33-7.15 (m, 5H), 6.99-6.84 (m, 3H), 6.28 (t, J = 6.6 Hz, 1H), 3.70-3.54 (m, 1H), 3.47 (s, 3H), 3.43-3.37 (m, 2H), 2.63-2.48 (m, 2H), 2.43 (s, 3H), 0.86 (br t, J = 7.2 Hz, 3H) | 1.88, A, 560.2 | A |

| Ex # | Structure | Name | NMR | Rt (min) method M + H | APJ cAMP Potency range |
|---|---|---|---|---|---|
| 120 | 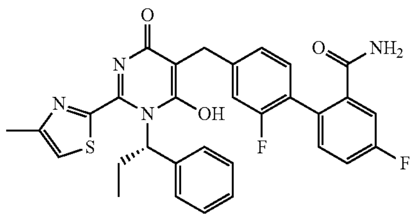 [SMILES: CC[C@@H](c1ccccc1)n1c(-c2nc(C)cs2)nc(=O)c(Cc2ccc(-c3ccc(F)cc3C(N)=O)c(F)c2)c1O] | 2',4-difluoro-4'-{[6-hydroxy-2-(4-methyl-1,3-thiazol-2-yl)-4-oxo-1-[(1S)-1-phenylpropyl]-1,4-dihydropyrimidin-5-yl]methyl}-[1,1'-biphenyl]-2-carboxamide | $^1$H NMR (500 MHz, DMSO-d$_6$) δ 7.68 (br d, J = 15.9 Hz, 2H), 7.34 (br d, J = 7.6 Hz, 2H), 7.29 (br s, 3H), 7.22-7.12 (m, 2H), 6.95 (br d, J = 7.6 Hz, 2H), 6.88 (br d, J = 11.3 Hz, 1H), 3.71-3.54 (m, 3H), 3.34 (br s, 1H), 2.65-2.46 (m, 2H), 2.45-2.39 (m, 3H), 0.88 (br t, J = 7.2 Hz, 3H) | 2.06, B, 570.9 (M − H) | A |
| 121 | 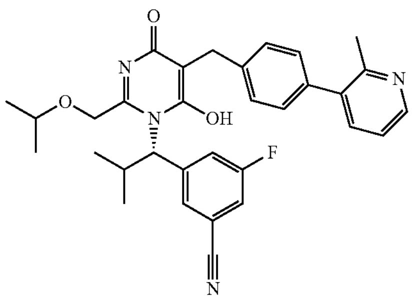 [SMILES: Cc1ncccc1-c1ccc(Cc2c(O)n([C@H](c3cc(F)cc(C#N)c3)C(C)C)c(COC(C)C)nc2=O)cc1] | 3-fluoro-5-[(1S)-1-(6-hydroxy-5-{[4-(2-methylpyridin-3-yl)phenyl]methyl}-4-oxo-2-[(propan-2-yloxy)methyl]-1,4-dihydropyrimidin-1-yl)-2-methylpropyl]benzonitrile | 1H NMR (DMSO-d6) Shift: 7.92-7.97 (m, 1H), 7.75 (br d, J = 7.3 Hz, 1H), 7.43-7.65 (m, 2H), 7.15-7.37 (m, 5H), 7.08 (s, 1H), 4.97 (br d, J = 10.4 Hz, 1H), 4.50-4.74 (m, 2H), 3.81-3.94 (m, 1H), 3.54 (br s, 2H), 2.46-2.50 (m, 3H), 1.21 (br t, J = 6.1 Hz, 6H), 1.00 (br d, J = 6.1 Hz, 1H), 0.94 (br d, J = 6.1 Hz, 3H), 0.83 (br d, J = 6.1 Hz, 3H) | 1.65, B, 541.1 | B |
| 122 | 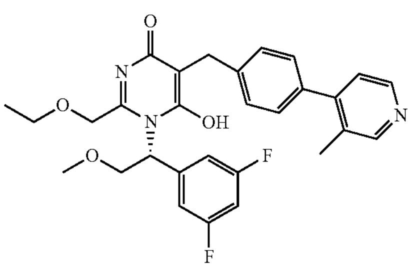 [SMILES: CCOCc1nc(=O)c(Cc2ccc(-c3ccncc3C)cc2)c(O)n1[C@@H](COC)c1cc(F)cc(F)c1] | 1-[(1R)-1-(3,5-difluorophenyl)-2-methoxyethyl]-2-(ethoxymethyl)-6-hydroxy-5-{[4-(3-methylpyridin-4-yl)phenyl]methyl}-1,4-dihydropyrimidin-4-one | 1H NMR (DMSO-d6) Shift: 8.68 (br s, 1H), 8.59-8.65 (m, 1H), 7.24-7.37 (m, 4H), 7.06-7.12 (m, 2H), 6.89-6.95 (m, 2H), 5.45-5.85 (m, 1H), 4.30-4.36 (m, 2H), 4.03-4.16 (m, 2H), 3.58-3.73 (m, 2H), 3.30 (s, 2H), 2.47-2.51 (m, 3H), 2.32 (s, 3H), 1.04 (br t, J = 6.9 Hz, 3H) | 1.98, A, 522.0 | A |
| 123 | 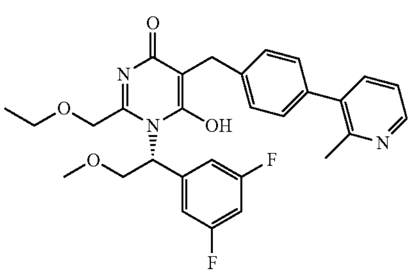 [SMILES: CCOCc1nc(=O)c(Cc2ccc(-c3cccnc3C)cc2)c(O)n1[C@@H](COC)c1cc(F)cc(F)c1] | 1-[(1R)-1-(3,5-difluorophenyl)-2-methoxyethyl]-2-(ethoxymethyl)-6-hydroxy-5-{[4-(2-methylpyridin-3-yl)phenyl]methyl}-1,4-dihydropyrimidin-4-one | 1H NMR (DMSO-d6) Shift: 8.57-8.67 (m, 1H), 7.89-8.02 (m, 1H), 7.52-7.69 (m, 1H), 7.22-7.32 (m, 4H), 7.10-7.15 (m, 1H), 6.94 (br d, J = 7.4 Hz, 2H), 5.60 (br s, 1H), 4.37-4.70 (m, 2H), 4.07-4.36 (m, 2H), 3.61 (br s, 2H), 3.54 (br s, 2H), 3.31 (s, 3H), 2.44-2.51 (m, 3H), 1.05 (br t, J = 6.6 Hz, 3H) | 1.57, A, 522.1 | A |
| 124 | 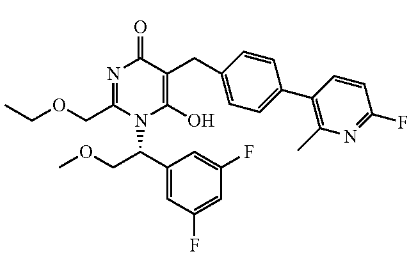 [SMILES: CCOCc1nc(=O)c(Cc2ccc(-c3ccc(F)nc3C)cc2)c(O)n1[C@@H](COC)c1cc(F)cc(F)c1] | 1-[(1R)-1-(3,5-difluorophenyl)-2-methoxyethyl]-2-(ethoxymethyl)-5-{[4-(6-fluoro-2-methylpyridin-3-yl)phenyl]methyl}-6-hydroxy-1,4-dihydropyrimidin-4-one | 1H NMR (DMSO-d6) Shift: 7.73 (br t, J = 8.2 Hz, 1H), 7.20 (s, 4H), 7.06-7.16 (m, 1H), 7.02 (br d, J = 6.1 Hz, 1H), 6.92 (br d, J = 7.3 Hz, 2H), 5.59 (br s, 1H), 4.36-4.68 (m, 2H), 4.02-4.35 (m, 2H), 3.44-3.55 (m, 2H), 3.30 (s, 2H), 2.33 (s, 3H), 1.04 (t, J = 6.9 Hz, 3H) | 2.16, A, 540.2 | A |

-continued

| Ex # | Structure | Name | NMR | Rt (min) method M + H | APJ cAMP Potency range |
|---|---|---|---|---|---|
| 125 | 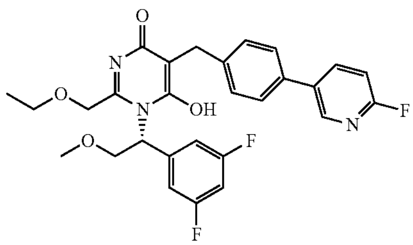 [SMILES: CCOCc1nc(=O)c(Cc2ccc(-c3ccc(F)nc3)cc2)c(O)n1[C@@H](COC)c1cc(F)cc(F)c1] | 1-[(1R)-1-(3,5-difluorophenyl)-2-methoxyethyl]-2-(ethoxymethyl)-5-{[4-(6-fluoropyridin-3-yl)phenyl]methyl}-6-hydroxy-1,4-dihydropyrimidin-4-one | 1H NMR (DMSO-d6) Shift: 8.44 (br s, 1H), 8.19 (t, J = 8.1 Hz, 1H), 7.51 (br d, J = 7.9 Hz, 2H), 7.22 (br d, J = 7.9 Hz, 3H), 7.08 (br t, J = 9.0 Hz, 1H), 6.90 (br d, J = 7.6 Hz, 2H), 5.58 (br s, 1H), 4.29-4.39 (m, 2H), 3.65-3.72 (m, 4H), 3.52-3.60 (m, 2H), 3.30 (s, 3H), 1.03 (br t, J = 6.9 Hz, 3H) | 1.71, A, 526.2 | B |
| 126 | 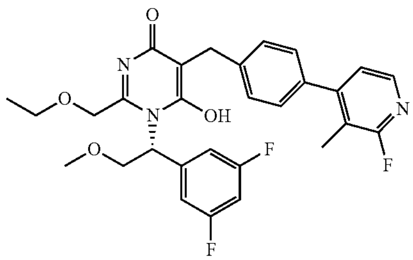 [SMILES: CCOCc1nc(=O)c(Cc2ccc(-c3ccnc(F)c3C)cc2)c(O)n1[C@@H](COC)c1cc(F)cc(F)c1] | 1-[(1R)-1-(3,5-difluorophenyl)-2-methoxyethyl]-2-(ethoxymethyl)-5-{[4-(2-fluoro-3-methylpyridin-4-yl)phenyl]methyl}-6-hydroxy-1,4-dihydropyrimidin-4-one | 1H NMR (DMSO-d6) Shift: 8.05 (br d, J = 4.9 Hz, 1H), 7.24-7.37 (m, 2H), 7.13-7.24 (m, 3H), 6.98-7.11 (m, 1H), 6.89 (br d, J = 7.3 Hz, 2H), 5.44 (br s, 1H), 4.25-4.39 (m, 2H), 3.95-4.09 (m, 2H), 3.41-3.52 (m, 2H), 3.32 (s, 2H), 2.54-2.56 (m, 3H), 2.15 (s, 3H), 1.02 (br t, J = 6.6 Hz, 3H) | 1.82, A, 540.2 | A |
| 127 | 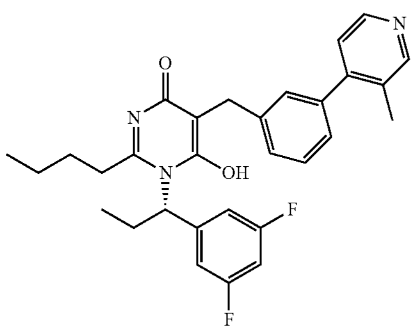 [SMILES: CCCCc1nc(=O)c(Cc2cccc(-c3ccncc3C)c2)c(O)n1[C@@H](CC)c1cc(F)cc(F)c1] | 2-butyl-1-[(1S)-1-(3,5-difluorophenyl)propyl]-6-hydroxy-5-{[3-(3-methylpyridin-4-yl)phenyl]methyl}-1,4-dihydropyrimidin-4-one | 1H NMR (DMSO-d6) Shift: 8.46 (br s, 1H), 8.38-8.43 (m, 1H), 6.94-7.48 (m, 6H), 6.84-6.91 (m, 2H), 5.15-5.55 (m, 1H), 3.53 (br s, 2H), 2.48-2.50 (m, 3H), 2.31-2.46 (m, 2H), 2.11-2.22 (m, 2H), 1.53-1.68 (m, 2H), 1.27-1.42 (m, 2H), 0.72-0.90 (m, 6H) | 1.97, A, 503.9 | B |
| 128 | 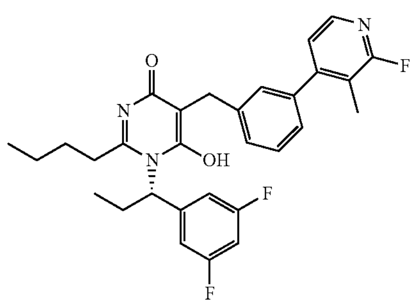 [SMILES: CCCCc1nc(=O)c(Cc2cccc(-c3ccnc(F)c3C)c2)c(O)n1[C@@H](CC)c1cc(F)cc(F)c1] | 2-butyl-1-[(1S)-1-(3,5-difluorophenyl)propyl]-5-{[3-(2-fluoro-3-methylpyridin-4-yl)phenyl]methyl}-6-hydroxy-1,4-dihydropyrimidin-4-one | 1H NMR (DMSO-d6) Shift: 8.06 (br d, J = 4.5 Hz, 1H), 6.97-7.47 (m, 6H), 6.87 (br s, 2H), 5.34 (br s, 1H), 3.49-3.58 (m, 2H), 2.72-2.86 (m, 2H), 2.06 (br s, 3H), 1.56-1.73 (m, 2H), 1.35 (br s, 2H), 1.17-1.29 (m, 2H), 0.72-0.91 (m, 6H) | 2.21, A, 522.2 | B |
| 129 | 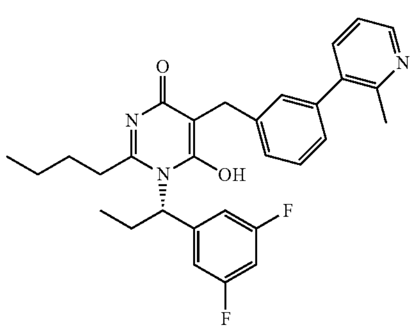 [SMILES: CCCCc1nc(=O)c(Cc2cccc(-c3cccnc3C)c2)c(O)n1[C@@H](CC)c1cc(F)cc(F)c1] | 2-butyl-1-[(1S)-1-(3,5-difluorophenyl)propyl]-6-hydroxy-5-{[3-(2-methylpyridin-3-yl)phenyl]methyl}-1,4-dihydropyrimidin-4-one | 1H NMR (DMSO-d6) Shift: 8.36-8.40 (m, 1H), 7.43-7.54 (m, 1H), 6.89-7.40 (m, 6H), 6.80 (br d, J = 7.0 Hz, 2H), 5.15-5.44 (m, 1H), 3.45-3.79 (m, 2H), 2.44 (br s, 2H), 2.30 (br s, 3H), 1.44-1.62 (m, 2H), 1.25-1.43 (m, 2H), 1.16-1.25 (m, 2H), 0.71-0.83 (m, 6H) | 2.00, A, 504.0 | B |

| Ex # | Structure | Name | NMR | Rt (min) method M + H | APJ cAMP Potency range |
|---|---|---|---|---|---|
| 130 | 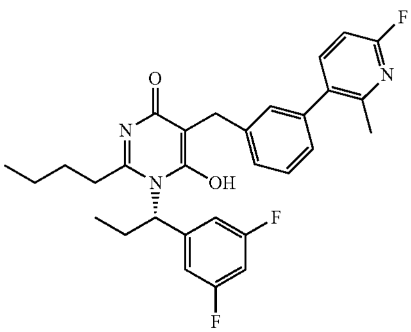 [SMILES: CCCCc1nc(=O)c(Cc2cccc(-c3ccc(F)nc3C)c2)c(O)n1[C@@H](CC)c1cc(F)cc(F)c1] | 2-butyl-1-[(1S)-1-(3,5-difluorophenyl)propyl]-5-{[3-(6-fluoro-2-methylpyridin-3-yl)phenyl]methyl}-6-hydroxy-1,4-dihydropyrimidin-4-one | 1H NMR (DMSO-d6) Shift: 7.62-7.72 (m, 1H), 6.94-7.43 (m, 7H), 6.85 (br d, J = 7.0 Hz, 2H), 5.34 (br s, 1H), 3.61-3.69 (m, 2H), 2.31-2.44 (m, 2H), 2.25 (br s, 3H), 1.44-1.66 (m, 2H), 1.27-1.41 (m, 2H), 1.15-1.27 (m, 2H), 0.64-0.97 (m, 6H) | 2.20, A, 522.3 | A |
| 131 | 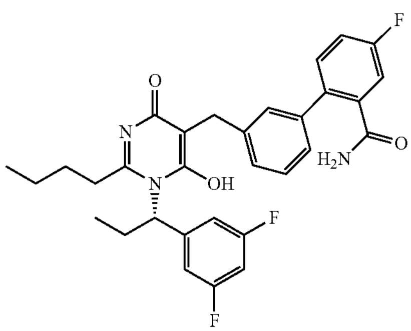 [SMILES: CCCCc1nc(=O)c(Cc2cccc(-c3ccc(F)cc3C(N)=O)c2)c(O)n1[C@@H](CC)c1cc(F)cc(F)c1] | 3'-({2-butyl-1-[(1S)-1-(3,5-difluorophenyl)propyl]-6-hydroxy-4-oxo-1,4-dihydropyrimidin-5-yl}methyl)-4-fluoro-[1,1'-biphenyl]-2-carboxamide | 1H NMR (DMSO-d6) Shift: 7.70 (br s, 1H), 6.98-7.40 (m, 8H), 6.85-6.92 (m, 1H), 5.15-5.49 (m, 1H), 3.61 (br s, 2H), 2.63-2.93 (m, 2H), 2.29-2.47 (m, 2H), 1.46-1.67 (m, 2H), 1.26-1.42 (m, 2H), 0.69-0.95 (m, 6H) | 1.89, A, 550.2 | B |
| 132 | 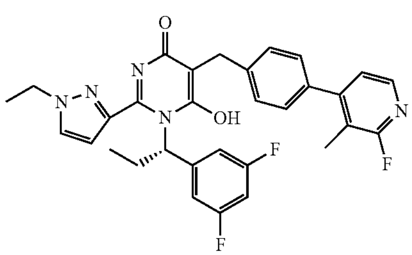 [SMILES: CC[C@@H](c1cc(F)cc(F)c1)n1c(-c2ccn(CC)n2)nc(=O)c(Cc2ccc(-c3ccnc(F)c3C)cc2)c1O] | 1-[(1S)-1-(3,5-difluorophenyl)propyl]-2-(1-ethyl-1H-pyrazol-3-yl)-5-{[4-(2-fluoro-3-methylpyridin-4-yl)phenyl]methyl}-6-hydroxy-1,4-dihydropyrimidin-4-one | 1H NMR (DMSO-d6) Shift: 8.05 (br d, J = 4.9 Hz, 1H), 7.88 (br s, 1H), 7.26 (s, 4H), 7.18 (br d, J = 4.9 Hz, 1H), 7.01-7.11 (m, 1H), 6.92-7.01 (m, 2H), 6.70 (br s, 1H), 5.98-6.18 (m, 1H), 4.16 (q, J = 7.0 Hz, 2H), 3.53-3.67 (m, 2H), 2.19-2.35 (m, 2H), 2.13 (s, 3H), 1.33 (t, J = 7.2 Hz, 3H), 0.75 (br t, J = 7.2 Hz, 3H) | 2.11, A, 560.3 | A |
| 133 | 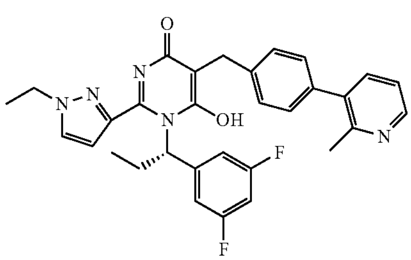 [SMILES: CC[C@@H](c1cc(F)cc(F)c1)n1c(-c2ccn(CC)n2)nc(=O)c(Cc2ccc(-c3cccnc3C)cc2)c1O] | 1-[(1S)-1-(3,5-difluorophenyl)propyl]-2-(1-ethyl-1H-pyrazol-3-yl)-6-hydroxy-5-{[4-(2-methylpyridin-3-yl)phenyl]methyl}-1,4-dihydropyrimidin-4-one | 1H NMR (DMSO-d6) Shift: 8.40 (br d, J = 3.2 Hz, 1H), 7.87 (br s, 1H), 7.55 (br d, J = 7.4 Hz, 2H), 7.24-7.41 (m, 2H), 7.19-7.24 (m, 4H), 7.04 (br t, J = 8.3 Hz, 1H), 6.70 (br s, 1H), 5.98-6.16 (m, 1H), 4.12-4.28 (m, 2H), 3.50-3.69 (m, 2H), 2.38 (s, 3H), 2.27 (dt, J = 13.8, 6.8 Hz, 2H), 1.33 (br t, J = 7.2 Hz, 3H), 0.75 (br t, J = 7.2 Hz, 3H) | 2.09, A, 542.4 | A |
| 134 | 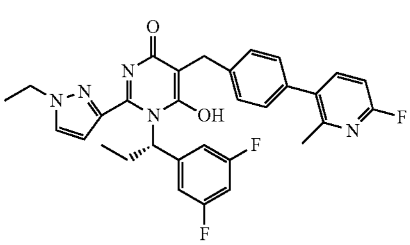 [SMILES: CC[C@@H](c1cc(F)cc(F)c1)n1c(-c2ccn(CC)n2)nc(=O)c(Cc2ccc(-c3ccc(F)nc3C)cc2)c1O] | 1-[(1S)-1-(3,5-difluorophenyl)propyl]-2-(1-ethyl-1H-pyrazol-3-yl)-5-{[4-(6-fluoro-2-methylpyridin-3-yl)phenyl]methyl}-6-hydroxy-1,4-dihydropyrimidin-4-one | 1H NMR (DMSO-d6) Shift: 7.89 (br s, 1H), 7.74 (br t, J = 8.0 Hz, 1H), 7.17-7.30 (m, 4H), 6.92-7.12 (m, 4H), 6.69 (br s, 1H), 5.95-6.15 (m, 1H), 4.08-4.28 (m, 2H), 3.77-3.96 (m, 2H), 2.31-2.47 (m, 3H), 1.76-1.97 (m, 2H), 1.26-1.42 (m, 3H), 0.70-0.83 (m, 3H) | 2.08, A, 560.3 | A |

| Ex # | Structure | Name | NMR | Rt (min) method M + H | APJ cAMP Potency range |
|---|---|---|---|---|---|
| 135 | 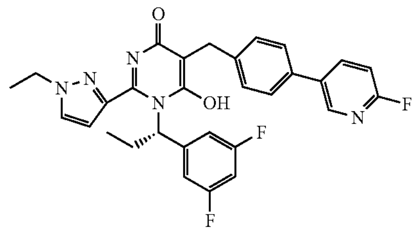 [SMILES: CC[C@@H](c1cc(F)cc(F)c1)n1c(-c2ccn(CC)n2)nc(=O)c(Cc2ccc(-c3ccc(F)nc3)cc2)c1O] | 1-[(1S)-1-(3,5-difluorophenyl)propyl]-2-(1-ethyl-1H-pyrazol-3-yl)-5-{[4-(6-fluoropyridin-3-yl)phenyl]methyl}-6-hydroxy-1,4-dihydropyrimidin-4-one | 1H NMR (DMSO-d6) Shift: 8.45 (s, 1H), 8.12-8.27 (m, 1H), 7.87 (s, 1H), 7.53 (d, J = 7.9 Hz, 2H), 7.19-7.31 (m, 3H), 7.04 (br t, J = 8.4 Hz, 1H), 6.97 (br d, J = 7.3 Hz, 2H), 6.69 (br s, 1H), 5.98-6.08 (m, 1H), 4.16 (q, J = 7.0 Hz, 2H), 3.70 (br s, 2H), 2.26 (dt, J = 13.7, 6.8 Hz, 2H), 1.33 (t, J = 7.2 Hz, 3H), 0.75 (t, J = 7.3 Hz, 3H) | 1.93, A, 546.4 | A |
| 136 | 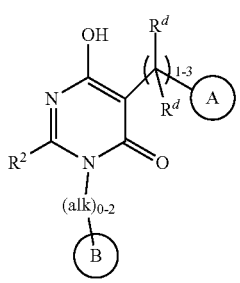 | 1-[(1S)-1-(3,5-difluorophenyl)propyl]-2-(1-ethyl-1H-pyrazol-3-yl)-6-hydroxy-5-{[4-(3-methylpyridin-4-yl)phenyl]methyl}-1,4-dihydropyrimidin-4-one | 1H NMR (DMSO-d6) Shift: 8.32-8.55 (m, 2H), 7.85 (br s, 1H), 7.11-7.39 (m, 5H), 7.00-7.12 (m, 1H), 6.82-7.00 (m, 2H), 6.61 (br s, 1H), 5.91 (br s, 1H), 4.07-4.28 (m, 2H), 3.57 (br s, 2H), 2.49 (s, 3H), 2.16-2.30 (m, 2H), 1.27-1.42 (m, 3H), 0.69-0.89 (m, 3H) | 1.89, A, 540.1 | A |

What is claimed is:

1. A compound of Formula (I):

(I)

or a stereoisomer, a tautomer, or a pharmaceutically acceptable salt thereof, wherein:

alk is $C_{1-6}$ alkyl substituted with 1-5 $R^4$;

ring A is independently selected from 5- or 6-membered aryl and heteroaryl consisting of carbon atoms and 1-4 heteroatoms selected from N, $NR^{3a}$, O, and S, each substituted with 1-3 $R^3$;

ring B is independently selected from aryl, heteroaryl, and cycloalkyl, each substituted with 1-4 $R^1$;

$R^1$ is independently selected from H, halogen, $NO_2$, $-(CH_2)_nOR^b$, $(CH_2)_nS(O)_pR_c$, $-(CH_2)_nC(=O)R^b$, $-(CH_2)_nNR^aR^a$, $-(CH_2)_nCN$, $-(CH_2)_nC(=O)NR^aR^a$, $-(CH_2)_nNR^aC(=O)R^b$, $-(CH_2)_nNR^aC(=O)NR^aR^a$, $-(CH_2)_nNR^aC(=O)OR^b$, $-(CH_2)_nOC(=O)NR^aR^a$, $-(CH_2)_nC(=O)OR^b$, $-(CH_2)_nS(O)_pNR^aR^a$, $-(CH_2)_nNR^aS(O)_pNR^aR^a$, $-(CH_2)_nNR^aS(O)_pR^c$, $C_{1-4}$ alkyl substituted with 0-3 $R^e$, $-(CH_2)_n-C_{3-6}$ carbocyclyl substituted with 0-3 $R^e$, and $-(CH_2)_n$-heterocyclyl substituted with 0-3 $R^e$;

$R^2$ is independently selected from $C_{2-5}$ alkyl substituted with 0-3 $R^e$; $C_{2-5}$ alkenyl substituted with 0-3 $R^e$, aryl substituted with 1-3 $R^e$, heterocyclyl substituted with 0-3 $R^e$, and $C_{3-6}$ cycloalkyl substituted with 0-3 $R^e$;

provided when $R^2$ is $C_{2-5}$ alkyl, the carbon atom and the groups attached thereto except the one attached to the pyrimidine ring may be replaced by O, N, and S;

$R^3$ is independently selected from H, halogen, $-(CH_2)_nOR^b$, $-(CH_2)_nS(O)_pR_c$, $-(CH_2)_nC(=O)R^b$, $-(CH_2)_nNR^aR^a$, $-(CH_2)_nCN$, $-(CH_2)_nC(=O)NR^aR^a$, $-(CH_2)_nNR^aC(=O)R^b$, $-(CH_2)_nNR^aC(=O)NR^aR^a$, $-(CH_2)_nNR^aC(=O)OR^b$, $-(CH_2)_nOC(=O)NR^aR^a$, $-(CH_2)_nC(=O)OR^b$, $-(CH_2)_nS(O)_pNR^aR^a$, $-(CH_2)_nNR^aS(O)_pNR^aR^a$, $-(CH_2)_nNR^aS(O)_pR^c$, $C_{1-5}$ alkyl substituted with 0-3 $R^e$, $(CH_2)_n-C_{3-6}$ carbocyclyl substituted with 0-3 $R^e$, and $-(CH_2)_n$-heterocyclyl consisting of carbon atoms and 1-4 heteroatoms selected from N, $NR^{3a}$, O, S, and substituted with 0-3 $R^e$;

$R^{3a}$ is independently selected from H, $-S(O)_pR_c$, $-C(=O)R^b$, $-C(=O)NR^aR^a$, $-C(=O)OR^b$, $-S(O)_pNR^aR^a$, $C_{1-5}$ alkyl substituted with 0-3 $R^e$, $-(CH_2)_n-C_{3-6}$ carbocyclyl substituted with 0-3 $R^e$, and $-(CH_2)_n$-heterocyclyl substituted with 0-3 $R^e$;

$R^4$ is independently selected from $C_{1-5}$ alkyl substituted with 0-3 $R^e$, $(CH_2)_n-C_{3-6}$ carbocyclyl substituted with 0-3 $R^e$, and $-(CH_2)_n$-heterocyclyl substituted with 0-3 $R^e$;

$R^a$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, $-(CH_2)_n-C_{3-10}$ carbocyclyl substituted with 0-5 $R^e$, and $-(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, $-(CH_2)_n-C_{3-10}$ carbocyclyl substituted with 0-5 $R^e$, and $-(CH_2)_n$-heterocyclyl substituted with 0-5 $R^e$;

$R^c$, at each occurrence, is independently selected from $C_{1-6}$ alkyl substituted with 0-5 $R^e$, $C_{2-6}$ alkenyl substituted with 0-5 R$^e$, C$_{2-6}$alkynyl substituted with 0-5 R$^e$, C$_{3-6}$carbocyclyl, and heterocyclyl;

R$^d$, at each occurrence, is independently selected from H and C$_{1-6}$ alkyl substituted with 0-5 R$^e$;

R$^e$, at each occurrence, is independently selected from C$_{1-6}$ alkyl (optionally substituted with halogen, OH, and CN), C$_{2-6}$ alkenyl, C$_{2-6}$ alkynyl, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H, —(CH$_2$)$_n$OR$^f$, S(O)$_p$R$^f$, C(=O)NR$^f$R$^f$, NR$^f$C(=O)R$^f$, S(O)$_p$NR$^f$R$^f$, NR$^f$S(O)$_p$R$^f$, NR$^f$C(=O)OR$^f$, OC(=O)NR$^f$R$^f$ and —(CH$_2$)$_n$NR$^f$R$^f$;

R$^f$, at each occurrence, is independently selected from H, C$_{1-5}$alkyl (optionally substituted with halogen and OH), C$_{3-6}$ cycloalkyl, and phenyl, or R$^f$ and R$^f$ together with the nitrogen atom to which they are both attached form a heterocyclic ring optionally substituted with C$_{1-4}$alkyl;

n is independently selected from zero, 1, 2, and 3; and
p, at each occurrence, is independently selected from zero, 1, and 2.

2. The compound according to claim 1, or a stereoisomer a tautomer, or a pharmaceutically acceptable salt thereof, wherein: ring A is independently selected from

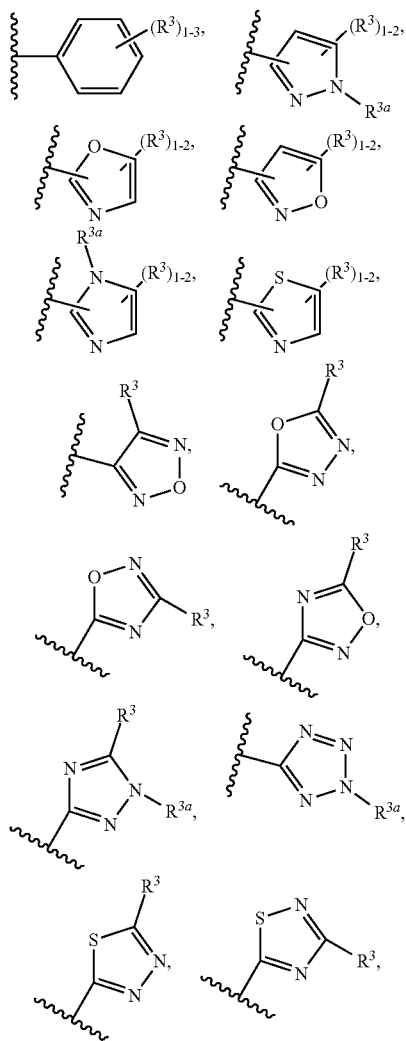

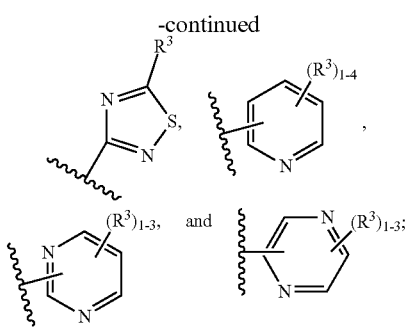

ring B is independently selected from

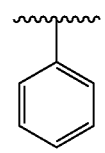

and 6-membered heteroaryl, each substituted with 1-4 R$^1$;

R$^1$ is independently selected from H, F, Cl, Br, NO$_2$, —(CH$_2$)$_n$OR$^b$, (CH$_2$)$_n$S(O)$_p$R$_c$, —(CH$_2$)$_n$C(=O)R$^b$, —(CH$_2$)$_n$NR$^a$R$^a$, —(CH$_2$)$_n$C(=O)NR$^a$R$^a$, —(CH$_2$)$_n$NR$^a$C(=O)R$^b$, C$_{1-4}$ alkyl substituted with 0-3 R$^e$ and C$_{3-6}$ cycloalkyl substituted with 0-3 R$^e$;

R$^2$ is independently selected from C$_{2-5}$ alkyl substituted with 0-3 R$^e$; C$_{2-5}$ alkenyl, aryl substituted with 1-3 R$^e$, heterocyclyl substituted with 0-3 R$^e$, and C$_{3-6}$ cycloalkyl; provided when R$^2$ is C$_{1-5}$ alkyl, the carbon atom and the groups attached thereto except the one attached to the pyrimidine ring may be replaced by O, N, and S;

R$^3$ is independently selected from H, halogen, —(CH$_2$)$_n$OR$^b$, (CH$_2$)$_n$S(O)$_p$R$_c$, —(CH$_2$)$_n$C(=O)R$^b$, —(CH$_2$)$_n$NR$^a$R$^a$, —(CH$_2$)$_n$CN, —(CH$_2$)$_n$C(=O)NR$^a$R$^a$, —(CH$_2$)$_n$NHC(=O)R$^b$, —(CH$_2$)$_n$NHC(=O)NR$^a$R$^a$, —(CH$_2$)$_n$NHC(=O)OR$^b$, —(CH$_2$)$_n$OC(=O)NR$^a$R$^a$, —(CH$_2$)$_n$C(=O)OR$^b$, —(CH$_2$)$_m$S(O)$_p$NR$^a$R$^a$, —(CH$_2$)$_n$NHS(O)$_p$NR$^a$R$^a$, —(CH$_2$)$_n$NHS(O)$_p$R$^c$, C$_{1-5}$ alkyl substituted with 0-3 R$^e$, (CH$_2$)$_n$—C$_{3-6}$ carbocyclyl substituted with 0-3 R$^e$, and —(CH$_2$)$_n$-heterocyclyl consisting of carbon atoms and 1-4 heteroatoms selected from N, NR$^{3a}$, O, S, and substituted with 0-3 R$^e$;

R$^{3a}$ is independently selected from H, C$_{1-4}$ alkyl, —(CH$_2$)$_n$-aryl substituted with 0-3 R$^e$, and —(CH$_2$)$_n$-heterocyclyl substituted with 0-3 R$^e$;

R$^a$, at each occurrence, is independently selected from H, C$_{1-6}$ alkyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;

R$^b$, at each occurrence, is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;

R$^e$, at each occurrence, is independently selected from C$_{1-6}$ alkyl (optionally substituted with halogen, OH, and CN), C$_{2-6}$ alkenyl, C$_{2-6}$ alkynyl, —(CH$_2$)$_n$—C$_{3-6}$ cycloalkyl, —(CH$_2$)$_n$—C$_{4-6}$ heterocyclyl, —(CH$_2$)$_n$- aryl, —(CH$_2$)$_n$-heteroaryl, F, Cl, Br, CN, NO$_2$, =O, CO$_2$H, —(CH$_2$)$_n$OR$_f$, S(O)$_p$R$^f$, C(=O)NR$^f$R$^f$, NR$^f$C (=O)R$^f$, S(O)$_p$NR$^f$R$^f$, NR$^f$S(O)$_p$R$^f$, NR$^f$C(=O)OR$_f$, OC(=O)NR$^f$R$^f$ and —(CH$_2$)$_n$NR$^f$R$^f$;

R$^f$, at each occurrence, is independently selected from H, C$_{1-5}$alkyl (optionally substituted with halogen and OH), C$_{3-6}$ cycloalkyl, and phenyl;

n is independently selected from zero, 1, 2, and 3; and p, at each occurrence, is independently selected from zero, 1, and 2.

3. The compound according to claim 2 having Formula (II):

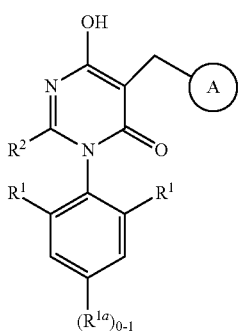

(II)

or a stereoisomer, a tautomer, or a pharmaceutically acceptable salt thereof, wherein:
ring A is independently selected from

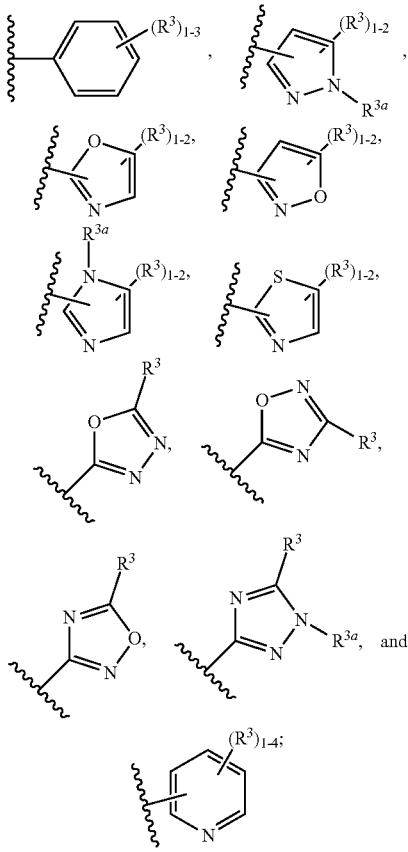

R$^1$ is independently selected from F, Cl, OH, C$_{1-3}$ alkyl, and OC$_{1-3}$ alkyl;

R$^{1a}$ is independently selected from F, Cl, and C$_{1-2}$ alkyl;

R$^2$ is independently selected from C$_{2-5}$ alkyl substituted with 0-3 R$^e$; C$_{2-5}$ alkenyl, aryl substituted with 1-3 R$^e$, heteroaryl substituted with 0-3 R$^e$, C$_{3-6}$ cycloalkyl and —(CH$_2$)$_{1-4}$OC$_{1-5}$alkyl, and —(CH$_2$)$_{1-3}$OC$_{3-6}$cycloalkyl;

R$^3$ is independently selected from H, F, Cl, Br, —OR$^b$, —(CH$_2$)$_n$C(=O)R$^b$, (CH$_2$)$_n$S(O)$_p$R$_c$, —(CH$_2$)$_n$C(=O)OR$^b$, —(CH$_2$)$_n$NR$^a$R$^a$, CN, —(CH$_2$)$_n$C(=O)NR$^a$R$^a$, —(CH$_2$)$_n$NHC(=O)R$^b$, C$_{1-4}$ alkyl substituted with 0-3 R$^e$, (CH$_2$)$_n$—C$_{3-6}$ carbocyclyl substituted with 0-3 R$^e$, and —(CH$_2$)$_n$-heterocyclyl consisting of carbon atoms and 1-4 heteroatoms selected from N, NR$^{3a}$, O, S, and substituted with 0-3 R$^e$;

R$^{3a}$ is independently selected from H, CH$_3$, —(CH$_2$)$_n$-aryl substituted with 0-3 R$^e$, and —(CH$_2$)$_n$-heterocyclyl substituted with 0-3 R$^e$;

R$^a$, at each occurrence, is independently selected from H, C$_{1-6}$ alkyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;

R$^b$, at each occurrence, is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;

R$^e$, at each occurrence, is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, and CO$_2$H; and n is independently selected from zero, 1, 2, and 3.

4. The compound according to claim 3 having Formula (III):

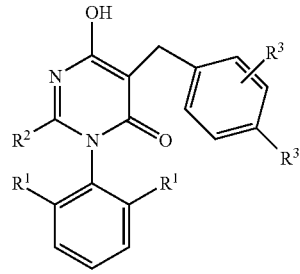

(III)

or a stereoisomer, a tautomer, or a pharmaceutically acceptable salt thereof, wherein:

R$^1$ is independently selected from C$_{1-3}$ alkyl and —OC$_{1-3}$ alkyl;

R$^2$ is independently selected from C$_{2-5}$ alkyl substituted with 0-3 R$^e$; C$_{2-5}$ alkenyl, aryl substituted with 1-3 R$^e$, heteroaryl substituted with 0-3 R$^e$, C$_{3-6}$ cycloalkyl, —(CH$_2$)$_{1-4}$C$_{1-5}$alkyl, and —(CH$_2$)$_{1-3}$OC$_{3-6}$cycloalkyl;

R$^3$ is independently selected from H, F, Cl, Br, —OC$_{1-4}$alkyl, S(O)$_2$C$_{1-4}$alkyl R$_c$, —(CH$_2$)$_n$C(=O)R$^b$, —(CH$_2$)$_n$C(=O)OR$^b$, —(CH$_2$)$_n$NR$^a$R$^a$, —C(=O)NR$^a$R$^a$, —NHC(=O)R$^b$, C$_{1-4}$ alkyl substituted with 0-3 R$^e$, C$_{3-6}$ carbocyclyl selected from

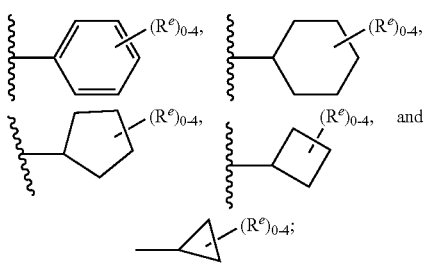

and heterocyclyl selected from

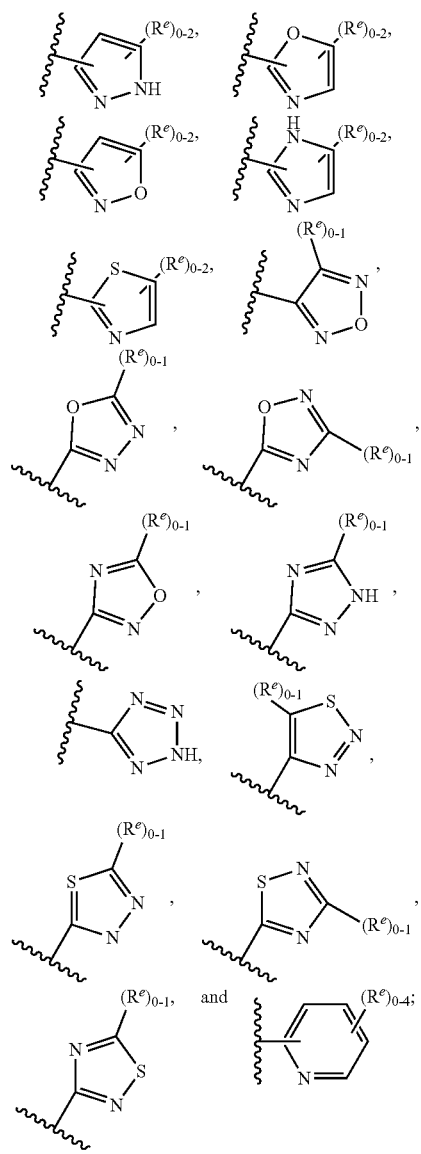

$R^a$, at each occurrence, is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$, and $CONH_2$; and n is independently selected from zero, 1, 2, and 3.

5. The compound according to claim 4 having Formula (IIIa):

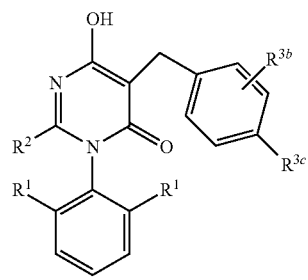

(IIIa)

or a stereoisomer, a tautomer, or a pharmaceutically acceptable salt thereof, wherein:

$R^1$ is independently selected from $C_{1-3}$ alkyl and —$OC_{1-3}$ alkyl;

$R^2$ is independently selected from $C_{2-5}$ alkyl substituted with 0-3 $R^e$, phenyl substituted with 1-3 $R^e$, 5-membered heteroaryl substituted with 0-3 $R^e$, $C_{3-6}$ cycloalkyl, —$(CH_2)_{1-4}OC_{1-5}$alkyl, and —$(CH_2)_{1-3}OC_{3-6}$cycloalkyl;

$R^{3b}$ is independently selected from H, F, Cl, and Br;

$R^{3c}$ is independently selected from H, —$(CH_2)_nNR^aR^a$,

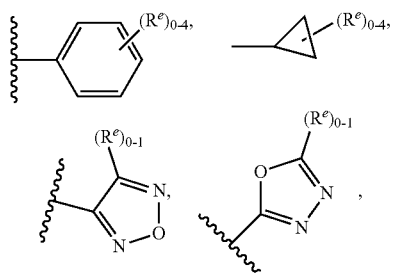

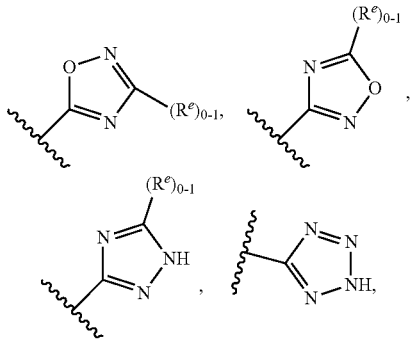

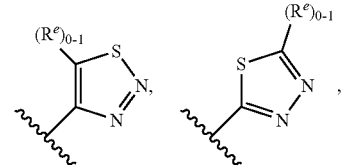

-continued

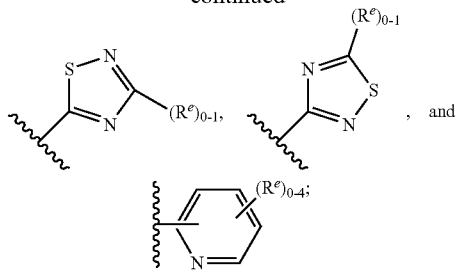

, and

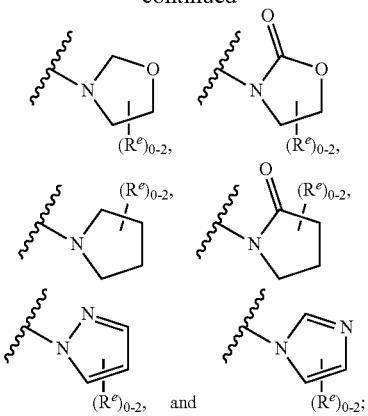

$R^a$, at each occurrence, is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$ and $CONH_2$; and n is independently selected from zero, 1, 2, and 3.

6. The compound according to claim 5 or a stereoisomer, a tautomer, or a pharmaceutically acceptable salt thereof, wherein:

$R^2$ is independently selected from $C_{2-5}$ alkyl substituted with 0-3 $R^e$; $C_{2-5}$ alkenyl, phenyl substituted with 1-3 $R^e$, 5-membered heteroaryl substituted with 0-3 R, $C_{3-6}$ cycloalkyl and $CH_2O(CH_2)_{1-3}CH_3$;

$R^3$ is independently selected from H and —$(CH_2)_{0-1}NR^aR^a$;

$R^a$ and $R^a$ together with the nitrogen atom to which they are both attached form a heterocyclic ring selected from

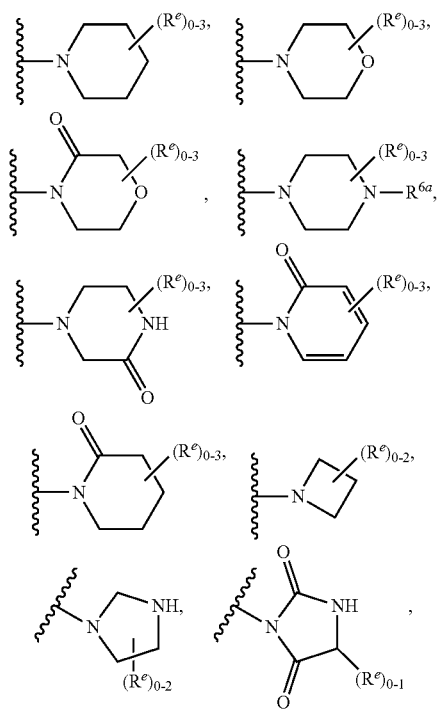

-continued

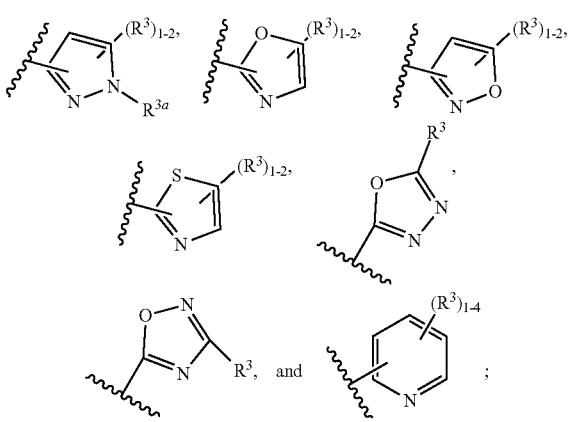

$R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$, and $CONH_2$.

7. A compound according to claim 3, or a stereoisomer, a tautomer, or a pharmaceutically acceptable salt thereof, wherein: ring A is independently selected from $R^1$ is independently selected from F, Cl, OH, and $OC_{1-4}$ alkyl;

$R^{1a}$ is independently selected from F, Cl, and $C_{1-2}$ alkyl;

$R^2$ is independently selected from $C_{2-5}$ alkyl substituted with 0-3 $R^e$; $C_{2-5}$ alkenyl, phenyl substituted with 1-3 $R^e$, 5- or 6-membered heteroaryl substituted with 0-3 $R^e$, $C_{3-6}$ cycloalkyl, and $CH_2O(CH_2)_{1-3}CH_3$;

$R^3$ is independently selected from H, $C_{1-4}$ alkyl substituted with 0-3 $R^e$, and phenyl substituted with 0-3 $R^e$;

$R^{3a}$ is independently selected from H, $CH_3$, and —$(CH_2)_n$-phenyl substituted with 0-3 $R^e$; and $R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, and $CO_2H$.

8. The compound according to claim 1 having Formula (IV):

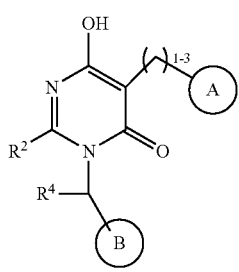

(IV)

or a stereoisomer, a tautomer, or a pharmaceutically acceptable salt thereof, wherein:

ring A is independently selected from

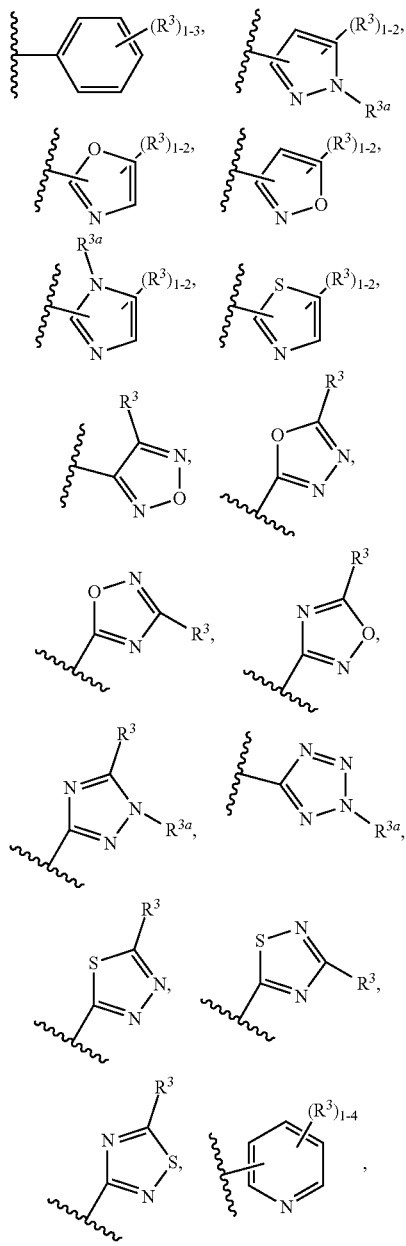

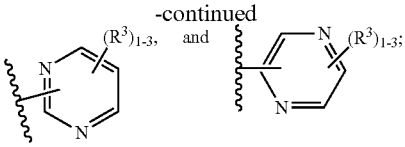

ring B is independently selected from

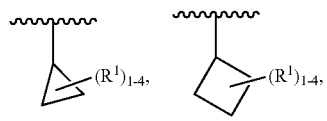

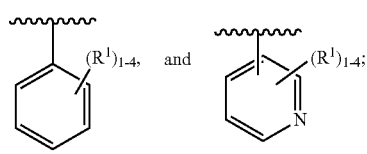

$R^1$ is independently selected from H, F, Cl, Br, $OC_{1-4}$ alkyl, CN, and $C_{1-4}$ alkyl;

$R^2$ is independently selected from $C_{2-5}$ alkyl substituted with 0-3 $R^e$; $C_{2-5}$ alkenyl, phenyl substituted with 1-3 $R^e$, 5- or 6-membered heteroaryl substituted with 0-3 $R^e$, $C_{3-6}$ cycloalkyl and $CH_2O(CH_2)_{1-3}CH_3$;

$R^3$ is independently selected from H, F, Cl, Br, $—OR^b$, $—(CH_2)_nC(=O)R^b$, $(CH_2)_nS(O)_pR_c$, $—(CH_2)_nC(=O)OR^b$, $—(CH_2)_nNR^aR^a$, CN, $—(CH_2)_nC(=O)NR^aR^a$, $—(CH_2)_nNHC(=O)R^b$, $C_{1-4}$ alkyl substituted with 0-3 $R^e$, $(CH_2)_n—C_{3-6}$ carbocyclyl substituted with 0-3 $R^e$, and $—(CH_2)_n$-heterocyclyl substituted with 0-3 $R^e$;

$R^{3a}$ is independently selected from H, $CH_3$, $—(CH_2)_n$-aryl substituted with 0-3 $R^e$, and $—(CH_2)_n$-heterocyclyl substituted with 0-3 $R^e$;

$R^4$ is independently selected from $CH_3$, $CH_2CH_3$, $CH_2CH_2CH_3$, $CH(CH_3)_2$, and $CH_2OCH_3$;

$R^a$, at each occurrence, is independently selected from H, $C_{1-6}$ alkyl substituted with 0-5 $R^e$, $—(CH_2)_n—C_{3-10}$carbocyclyl substituted with 0-5 $R^e$, and $—(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, $—(CH_2)_n—C_{3-10}$carbocyclyl substituted with 0-5 $R^e$, and $—(CH_2)_n$-heterocyclyl substituted with 0-5 $R^e$;

$R^e$, at each occurrence, is independently selected from $C_{1-6}$ alkyl (optionally substituted with F and Cl), OH, $OCH_3$, $OCF_3$, $—(CH_2)_n—C_{3-6}$ cycloalkyl, $—(CH_2)_n—C_{4-6}$ heterocyclyl, $—(CH_2)_n$-aryl, $—(CH_2)_n$-heteroaryl, F, Cl, Br, CN, $NO_2$, =O, $CO_2H$, and $CONH_2$; and n is independently selected from zero, 1, 2, and 3.

9. The compound according to claim 8 having Formula (V):

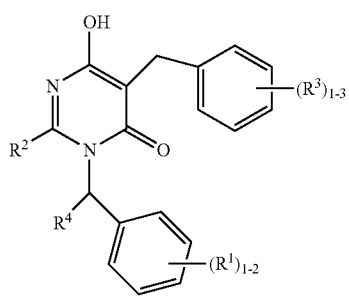

(V)

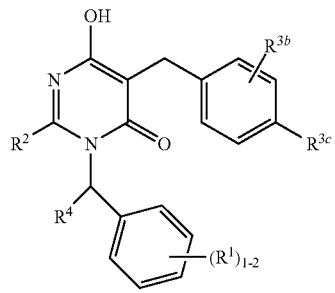

(VI)

or a stereoisomer, a tautomer, or a pharmaceutically acceptable salt thereof, wherein:

R¹ is independently selected from H, F, Cl, Br, OC$_{1-4}$ alkyl, CN, and C$_{1-4}$ alkyl;

R² is independently selected from —CH$_2$(CH$_2$)$_{1-3}$CH$_3$, —CH$_2$OCH(CH$_3$)$_2$, —(CH$_2$)$_{1-3}$C$_{3-6}$cycloalkyl,

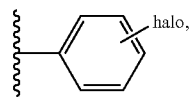

5-membered heteroaryl selected from

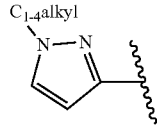 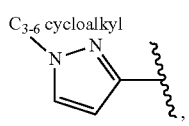 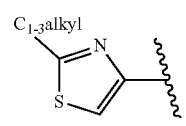

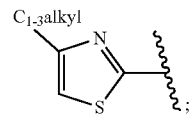

and CH$_2$O(CH$_2$)$_{1-3}$CH$_3$;

R³ is independently selected from H, F, Cl, Br, C$_{3-6}$ cycloalkyl, phenyl substituted with 0-3 R$^e$, and 5- or 6-membered heteroaryl substituted with 0-3 R$^e$;

R⁴ is independently selected from CH$_3$, CH$_2$CH$_3$, CH$_2$CH$_2$CH$_3$, CH(CH$_3$)$_2$, and CH$_2$OCH$_3$;

R$^e$, at each occurrence, is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H, and CONH$_2$; and n is independently selected from zero, 1, 2, and 3.

10. The compound according to claim 9 having Formula (VI):

or a stereoisomer, a tautomer, or a pharmaceutically acceptable salt thereof, wherein:

R¹ is independently selected from H, F, Cl, Br, OC$_{1-4}$ alkyl, CN, and C$_{1-4}$ alkyl;

R$^{3b}$ is independently selected from H and F;

R$^{3c}$ is independently selected from

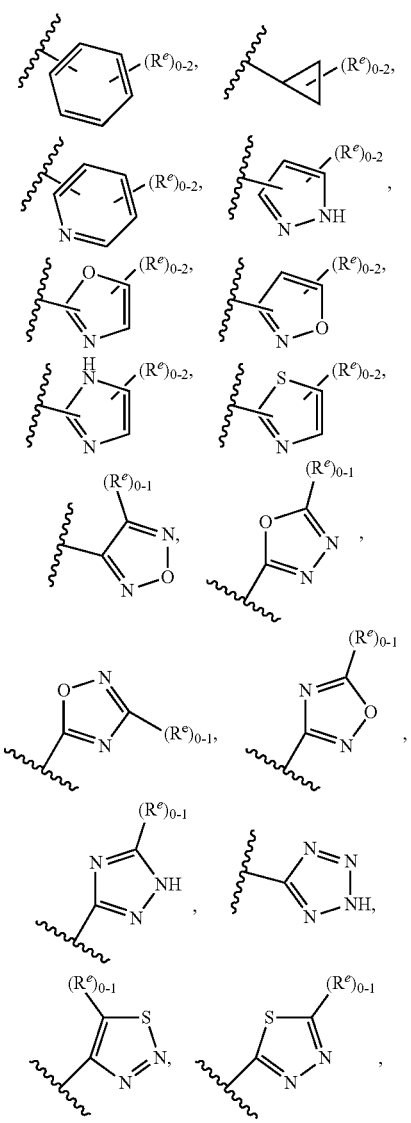

-continued

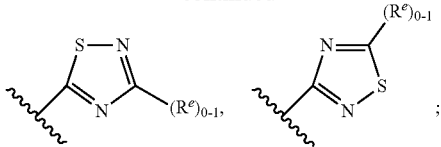

R⁴ is independently selected from CH₃, CH₂CH₃, CH₂CH₂CH₃, CH(CH₃)₂, and CH₂OCH₃;

R$^e$, at each occurrence, is independently selected from C$_{1-6}$ alkyl (optionally substituted with F and Cl), OH, OCH₃, OCF₃, —(CH₂)$_n$—C$_{3-6}$ cycloalkyl, —(CH₂)$_n$—C$_{4-6}$ heterocyclyl, —(CH₂)$_n$-aryl, —(CH₂)$_n$-heteroaryl, F, Cl, Br, CN, NO₂, =O, CO₂H, and CONH₂; and n is independently selected from zero, 1, 2, and 3.

11. A compound according claim 1, wherein the compound is selected from 3-(2,6-dimethoxyphenyl)-6-hydroxy-2-(3-methylbutyl)-5-{[4-(2-oxo-1,2-dihydropyridin-1-yl)phenyl]methyl}-3,4-dihydropyrimidin-4-one (1), 2-butyl-3-(2,6-dimethoxyphenyl)-6-hydroxy-5-[(4-methoxyphenyl)methyl]-3,4-dihydropyrimidin-4-one (2), 2-butyl-6-hydroxy-3-(2-methoxyphenyl)-5-[(4-methoxyphenyl)methyl]-3,4-dihydropyrimidin-4-one (3), 2-butyl-3-(2,6-dimethoxyphenyl)-6-hydroxy-5-{[4-(1,2,4-oxadiazol-3-yl)phenyl]methyl}-3,4-dihydropyrimidin-4-one (4), 2-butyl-3-(2,6-dimethoxyphenyl)-6-hydroxy-5-{[4-(1H-pyrazol-1-yl)phenyl]methyl}-3,4-dihydropyrimidin-4-one (5), 2-butyl-3-(2,6-dimethoxyphenyl)-5-{[2-fluoro-4-(1,2,4-oxadiazol-3-yl)phenyl]methyl}-6-hydroxy-3,4-dihydropyrimidin-4-one (6), 2-butyl-3-(2,6-dimethoxyphenyl)-6-hydroxy-5-[(4-methanesulfonylphenyl)methyl]-3,4-dihydropyrimidin-4-one (7), 2-butyl-3-(2,6-dimethoxyphenyl)-6-hydroxy-5-[(5-methyl-1,2-oxazol-3-yl)methyl]-3,4-dihydropyrimidin-4-one (8), N-(4-{[2-butyl-1-(2,6-dimethoxyphenyl)-4-hydroxy-6-oxo-1,6-dihydropyrimidin-5-yl]methyl}phenyl)acetamide (9), 2-butyl-3-(2,6-dimethoxyphenyl)-6-hydroxy-5-{[4-(3-methyl-1,2,4-oxadiazol-5-yl)phenyl]methyl}-3,4-dihydropyrimidin-4-one (10), 2-butyl-5-{[2-(4-chlorophenyl)-1,3-oxazol-4-yl]methyl}-3-(2,6-dimethoxyphenyl)-6-hydroxy-3,4-dihydropyrimidin-4-one (11), 2-butyl-3-(2,6-dimethoxyphenyl)-6-hydroxy-5-{[4-(1,2,3-thiadiazol-4-yl)phenyl]methyl}-3,4-dihydropyrimidin-4-one (12), 2-butyl-3-(2,6-dimethoxyphenyl)-5-{[3-fluoro-4-(1,2,4-oxadiazol-3-yl)phenyl]methyl}-6-hydroxy-3,4-dihydropyrimidin-4-one (13), 2-butyl-5-{[6-(4-chlorophenyl)pyridin-3-yl]methyl}-3-(2,6-dimethoxyphenyl)-6-hydroxy-3,4-dihydropyrimidin-4-one (14), 4-{[2-butyl-1-(2,6-dimethoxyphenyl)-4-hydroxy-6-oxo-1,6-dihydropyrimidin-5-yl]methyl}-N-ethylbenzamide (15), N-(4-{[1-(2,6-dimethoxyphenyl)-4-hydroxy-2-(3-methylbutyl)-6-oxo-1,6-dihydropyrimidin-5-yl]methyl}phenyl)acetamide (16), 3-(2,6-dimethoxyphenyl)-6-hydroxy-2-(3-methylbutyl)-5-{[4-(1,2,4-oxadiazol-3-yl)phenyl]methyl}-3,4-dihydropyrimidin-4-one (17), 5-{[2-(4-chlorophenyl)-1,3-oxazol-4-yl]methyl}-3-(2,6-dimethoxyphenyl)-6-hydroxy-2-(3-methylbutyl)-3,4-dihydropyrimidin-4-one (18), 5-benzyl-2-butyl-3-(2,6-dimethoxyphenyl)-6-hydroxy-3,4-dihydropyrimidin-4-one (19), 2-butyl-3-(2,6-dimethoxyphenyl)-6-hydroxy-5-({3-[4-(trifluoromethyl)phenyl]-1,2,4-oxadiazol-5-yl}methyl)-3,4-dihydropyrimidin-4-one (20), 3-(2,6-dimethoxyphenyl)-6-hydroxy-2-(3-methylbutyl)-5-{[5-(4-methylphenyl)-1,3,4-oxadiazol-2-yl]methyl}-3,4-dihydropyrimidin-4-one (21), 2-butyl-5-{[2-(4-chlorophenyl)-1,3-thiazol-4-yl]methyl}-3-(2,6-dimethoxyphenyl)-6-hydroxy-3,4-dihydropyrimidin-4-one (22), 2-butyl-3-(2,6-dimethoxyphenyl)-6-hydroxy-5-{[2-(4-methylphenyl)-1,3-thiazol-4-yl]methyl}-3,4-dihydropyrimidin-4-one (23), 2-butyl-5-{[1-(4-chlorophenyl)-1H-pyrazol-3-yl]methyl}-3-(2,6-dimethoxyphenyl)-6-hydroxy-3,4-dihydropyrimidin-4-one (24), 2-butyl-3-(2,6-dimethoxyphenyl)-6-hydroxy-5-{[1-(4-methylphenyl)-1H-pyrazol-4-yl]methyl}-3,4-dihydropyrimidin-4-one (25), 2-butyl-5-{[2-(4-chlorophenyl)-1,3-thiazol-5-yl]methyl}-3-(2,6-dimethoxyphenyl)-6-hydroxy-3,4-dihydropyrimidin-4-one (26), 2-butyl-3-(2,6-dimethoxyphenyl)-6-hydroxy-5-f{[4-(1H-pyrazol-1-ylmethyl)phenyl]methyl}-3,4-dihydropyrimidin-4-one (27), 2-butyl-3-(2,6-dimethoxyphenyl)-6-hydroxy-5-{[4-(2-oxo-1,2-dihydropyridin-1-yl)phenyl]methyl}-3,4-dihydropyrimidin-4-one (28), 2-butyl-3-(2,6-dimethoxyphenyl)-6-hydroxy-5-{[6-(4-methoxyphenyl)pyridin-3-yl]methyl}-3,4-dihydropyrimidin-4-one (29), 5-[(1-benzyl-1H-pyrazol-4-yl)methyl]-2-butyl-3-(2,6-dimethoxyphenyl)-6-hydroxy-3,4-dihydropyrimidin-4-one (30), 5-{[1-(4-chlorophenyl)-1H-pyrazol-3-yl]methyl}-3-(2,6-dimethoxyphenyl)-2-(ethoxymethyl)-6-hydroxy-3,4-dihydropyrimidin-4-one (31), 3-(2,6-dimethoxyphenyl)-2-(ethoxymethyl)-6-hydroxy-5-{[4-(1,2,4-oxadiazol-3-yl)phenyl]methyl}-3,4-dihydropyrimidin-4-one (32), 5-{[2-(4-chlorophenyl)-1,3-oxazol-4-yl]methyl}-3-(2,6-dimethoxyphenyl)-2-(ethoxymethyl)-6-hydroxy-3,4-dihydropyrimidin-4-one (33), 3-(2,6-dimethoxyphenyl)-6-hydroxy-2-(3-methylbutyl)-5-{[4-(2-oxo-1,2-dihydropyridin-1-yl)phenyl]methyl}-3,4-dihydropyrimidin-4-one (34), 2-butyl-3-(2,6-dimethoxyphenyl)-6-hydroxy-5-{[4-(2-oxopiperidin-1-yl)phenyl]methyl}-3,4-dihydropyrimidin-4-one (35), 2-butyl-3-(2,6-dimethoxyphenyl)-6-hydroxy-5-{[4-(morpholin-4-yl)phenyl]methyl}-3,4-dihydropyrimidin-4-one (36), 3-(2,6-dimethoxyphenyl)-5-(4-(5-fluoro-2-oxopyridin-1(2H)-yl)benzyl)-2-(4-fluorophenyl)-6-hydroxypyrimidin-4(3H)-one (37), 2-cyclopentyl-3-(2,6-dimethoxyphenyl)-6-hydroxy-5-{[4-(2-oxo-1,2-dihydropyridin-1-yl)phenyl]methyl}-3,4-dihydropyrimidin-4-one (38), 2-(cyclobutoxymethyl)-3-(2,6-dimethoxyphenyl)-6-hydroxy-5-{[4-(2-oxo-1,2-dihydropyridin-1-yl)phenyl]methyl}-3,4-dihydropyrimidin-4-one (39), 2-(cyclopropoxymethyl)-3-(2,6-dimethoxyphenyl)-6-hydroxy-5-{[4-(2-oxo-1,2-dihydropyridin-1-yl)phenyl]methyl}-3,4-dihydropyrimidin-4-one (40), 2-(2-cyclopropylethyl)-3-(2,6-dimethoxyphenyl)-6-hydroxy-5-{[4-(2-oxo-1,2-dihydropyridin-1-yl)phenyl]methyl}-3,4-dihydropyrimidin-4-one (41), 2-butyl-5-{[4-(4-chloro-2-oxo-1,2-dihydropyridin-1-yl)phenyl]methyl}-3-(2,6-dimethoxyphenyl)-6-hydroxy-3,4-dihydropyrimidin-4-one (42), 2-butyl-3-(2,6-dimethoxyphenyl)-6-hydroxy-5-{[4-(4-methyl-2-oxo-1,2-dihydropyridin-1-yl)phenyl]methyl}-3,4-dihydropyrimidin-4-one (43), 2-butyl-3-(2,6-dimethoxyphenyl)-6-hydroxy-5-{[4-(6-methylpyridin-3-yl)phenyl]methyl}-3,4-dihydropyrimidin-4-one (44), 5-({[1,1'-biphenyl]-4-yl}methyl)-2-butyl-3-(2,6-dimethoxyphenyl)-6-hydroxy-3,4-dihydropyrimidin-4-one (45), 2-butyl-5-{[4-(5-chloropyridin-2-yl)phenyl]methyl}-3-(2,6-dimethoxyphenyl)-6-hydroxy-3,4-dihydropyrimidin-4-one (46), 2-butyl-3-(2,6-dimethoxyphenyl)-5-{[4-(5-fluoro-2-oxo-1,2-dihydropyridin-1-yl)phenyl]methyl}-6-hydroxy-3,4-dihydropyrimidin-4-one (47), 2-butyl-3-(2,6-dimethoxyphenyl)-6-hydroxy-5-{[4-(2-methoxypyridin-3-yl)phenyl]methyl}-3,4-dihydropyrimidin-4-one (48), 2-butyl-5-{[4-(5-chloro-2-oxo-1,2-dihydropyridin-1-yl)phenyl]methyl}-3-(2,6-dimethoxyphenyl)-6-hydroxy-3,4-dihydropyrimidin-4-one (49), 2-butyl-3-(2,6-dimethoxyphenyl)-6-hydroxy-5-{[4-(5-methyl-2-oxo-1,2-dihydropyridin-1-yl)phenyl]methyl}-3,4-dihydropyrimidin-4-one (50), 2-cyclopentyl-3-(2,6-dimethoxyphenyl)-5-{[4-(5-fluoro-2-oxo-1,2-dihydropyridin-1-yl)phenyl]methyl}-6-hydroxy-3,4-dihydropyrimidin-4-one (51), 3-(2,6-dimethoxyphenyl)-5-{[4-(5-fluoro-2-oxo-1,2-dihydropyridin-1-yl)phenyl]methyl}-6-hydroxy-2-(3-methylbutyl)-3,4-dihydropyrimidin-4-one (52), 5-{[4-(5-chloro-2-oxo-1,2-dihydropyridin-1-yl)phenyl]methyl}-3-(2,6-dimethoxyphenyl)-6-hydroxy-2-(3-methylbutyl)-3,4-dihydropyrimidin-4-one (53), 3-(2,6-dimethoxyphenyl)-6-hydroxy-5-{[4-(5-methyl-2-oxo-1,2-dihydropyridin-1-yl)phenyl]methyl}-2-(3-methylbutyl)-3,4-dihydropyrimidin-4-one (54), 2-(2-cyclopropylethyl)-3-(2,6-dimethoxyphenyl)-6-hydroxy-5-{[4-(5-methyl-2-oxo-1,2-dihydropyridin-1-yl)phenyl]methyl}-3,4-dihydropyrimidin-4-one (55), 2-(2-cyclopropylethyl)-3-(2,6-dimethoxyphenyl)-5-{[4-(5-fluoro-2-oxo-1,2-dihydropyridin-1-yl)phenyl]methyl}-6-hydroxy-3,4-dihydropyrimidin-4-one (56), 5-{[4-(5-chloro-2-oxo-1,2-dihydropyridin-1-yl)phenyl]methyl}-2-(2-cyclopropylethyl)-3-(2,6-dimethoxyphenyl)-6-hydroxy-3,4-dihydropyrimidin-4-one (57), 3-(2,6-dimethoxyphenyl)-6-hydroxy-5-{[4-(5-methyl-2-oxo-1,2-dihydropyridin-1-yl)phenyl]methyl}-2-[(propan-2-yloxy)methyl]-3,4-dihydropyrimidin-4-one (58), 3-(2,6-dimethoxyphenyl)-5-1{[4-(5-fluoro-2-oxo-1,2-dihydropyridin-1-yl)phenyl]methyl}-6-hydroxy-2-[(propan-2-yloxy)methyl]-3,4-dihydropyrimidin-4-one (59), 5-{[4-(5-chloro-2-oxo-1,2-dihydropyridin-1-yl)phenyl]methyl}-3-(2,6-dimethoxyphenyl)-6-hydroxy-2-[(propan-2-yloxy)methyl]-3,4-dihydropyrimidin-4-one (60), 2-(1-cyclopropyl-1H-pyrazol-3-yl)-1-(2,6-diethylphenyl)-5-(3-fluoro-4-(2-fluoro-3-methylpyridin-4-yl)benzyl)-6-hydroxypyrimidin-4(1H)-one (61), 1-(2,6-dimethoxyphenyl)-2-(1-ethyl-1H-pyrazol-3-yl)-6-hydroxy-5-{[4-(3-methylpyridin-4-yl)phenyl]methyl}-1,4-dihydropyrimidin-4-one (62), 1-(2,6-dimethoxyphenyl)-2-(1-ethyl-1H-pyrazol-3-yl)-5-{[4-(2-fluoro-3-methylpyridin-4-yl)phenyl]methyl}-6-hydroxy-1,4-dihydropyrimidin-4-one (63), 2-butyl-1-(2,6-diethylphenyl)-5-{[4-(6-fluoro-2-methylpyridin-3-yl)phenyl]methyl}-6-hydroxy-1,4-dihydropyrimidin-4-one (64), 2-butyl-1-(2,6-diethylphenyl)-5-{[4-(6-fluoropyridin-3-yl)phenyl]methyl}-6-hydroxy-1,4-dihydropyrimidin-4-one (65), 2-butyl-1-(2,6-diethylphenyl)-5-{[4-(2-fluoro-3-methylpyridin-4-yl)phenyl]methyl}-6-hydroxy-1,4-dihydropyrimidin-4-one (66), 2-butyl-5-[(4-cyclopropylphenyl)methyl]-1-(2,6-diethylphenyl)-6-hydroxy-1,4-dihydropyrimidin-4-one (67), 5-({[1,1'-biphenyl]-4-yl}methyl)-2-butyl-1-(2,6-diethylphenyl)-6-hydroxy-1,4-dihydropyrimidin-4-one (68), 1-(2,6-diethylphenyl)-5-{[3-fluoro-4-(6-fluoro-2-methylpyridin-3-yl)phenyl]methyl}-6-hydroxy-2-(1-methyl-1H-pyrazol-3-yl)-1,4-dihydropyrimidin-4-one (69), 1-(2,6-diethylphenyl)-5-{[3-fluoro-4-(3-methylpyridin-4-yl)phenyl]methyl}-6-hydroxy-2-(1-methyl-1H-pyrazol-3-yl)-1,4-dihydropyrimidin-4-one (70), 1-(2,6-diethylphenyl)-5-{[3-fluoro-4-(2-fluoro-3-methylpyridin-4-yl)phenyl]methyl}-6-hydroxy-2-(1-methyl-1H-pyrazol-3-yl)-1,4-dihydropyrimidin-4-one (71), 1-(2,6-diethylphenyl)-5-{[3-fluoro-4-(6-fluoro-2-methylpyridin-3-yl)phenyl]methyl}-6-hydroxy-2-(2-methyl-1,3-thiazol-4-yl)-1,4-dihydropyrimidin-4-one (72), 1-(2,6-diethylphenyl)-5-{[3-fluoro-4-(2-fluoro-3-methylpyridin-4-yl)phenyl]methyl}-6-hydroxy-2-(4-methyl-1,3-thiazol-2-yl)-1,4-dihydropyrimidin-4-one (73), 1-(2,6-diethylphenyl)-5-{[3-fluoro-4-(3-methylpyridin-4-yl)phenyl]methyl}-6-hydroxy-2-(2-methyl-1,3-thiazol-4-yl)-1,4-dihydropyrimidin-4-one (74), 1-(2,6-diethylphenyl)-5-{[3-fluoro-4-(3-methylpyridin-4-yl)phenyl]methyl}-6-hydroxy-2-(4-methyl-1,3-thiazol-2-yl)-1,4-dihydropyrimidin-4-one (75), 1-(2,6-diethylphenyl)-2-(1-ethyl-1H-pyrazol-3-yl)-5-{[3-fluoro-4-(3-methylpyridin-4-yl)phenyl]methyl}-6-hydroxy-1,4-dihydropyrimidin-4-one (76), 1-(2,6-diethylphenyl)-2-(1-ethyl-1H-pyrazol-3-yl)-5-{[3-fluoro-4-(2-fluoro-3-methylpyridin-4-yl)phenyl]methyl}-6-hydroxy-1,4-dihydropyrimidin-4-one (77), 1-(2,6-diethylphenyl)-5-{[3-fluoro-4-(2-fluoro-3-methylpyridin-4-yl)phenyl]methyl}-6-hydroxy-2-(2-methyl-1,3-thiazol-4-yl)-1,4-dihydropyrimidin-4-one (78), 1-(2,6-diethylphenyl)-5-{[3-fluoro-4-(6-fluoro-2-methylpyridin-3-yl)phenyl]methyl}-6-hydroxy-2-(4-methyl-1,3-thiazol-2-yl)-1,4-dihydropyrimidin-4-one (79), 1-(2,6-diethylphenyl)-2-(1-ethyl-1H-pyrazol-3-yl)-5-{[3-fluoro-4-(6-fluoro-2-methylpyridin-3-yl)phenyl]methyl}-6-hydroxy-1,4-dihydropyrimidin-4-one (80), 4'-{[1-(2,6-diethylphenyl)-2-(1-ethyl-1H-pyrazol-3-yl)-6-hydroxy-4-oxo-1,4-dihydropyrimidin-5-yl]methyl}-2',5-difluoro-[1,1'-biphenyl]-2-carboxamide (81), 4'-{[1-(2,6-diethylphenyl)-6-hydroxy-2-(4-methyl-1,3-thiazol-2-yl)-4-oxo-1,4-dihydropyrimidin-5-yl]methyl}-2',4-difluoro-[1,1'-biphenyl]-2-carboxamide (82), 1-(2,6-diethylphenyl)-5-{[3-fluoro-4-(1-methyl-2-oxo-1,2-dihydropyridin-3-yl)phenyl]methyl}-6-hydroxy-2-(4-methyl-1,3-thiazol-2-yl)-1,4-dihydropyrimidin-4-on (83), 4'-{[1-(2,6-diethylphenyl)-6-hydroxy-4-oxo-2-[1-(propan-2-yl)-1H-pyrazol-3-yl]-1,4-dihydropyrimidin-5-yl]methyl}-2',4-difluoro-[1,1'-biphenyl]-2-carboxamide (84), 1-(2,6-diethylphenyl)-5-{[3-fluoro-4-(2-fluoro-3-methylpyridin-4-yl)phenyl]methyl}-6-hydroxy-2-[1-(propan-2-yl)-1H-pyrazol-3-yl]-1,4-dihydropyrimidin-4-one (85), 1-(2,6-diethylphenyl)-5-{[2-fluoro-4-(2-fluoro-3-methylpyridin-4-yl)phenyl]methyl}-6-hydroxy-2-(i-methyl-1H-pyrazol-3-yl)-1,4-dihydropyrimidin-4-one (86), 1-(2,6-diethylphenyl)-5-{[3-fluoro-4-(1-methyl-2-oxo-1,2-dihydropyridin-3-yl)phenyl]methyl}-6-hydroxy-2-[1-(propan-2-yl)-1H-pyrazol-3-yl]-1,4-dihydropyrimidin-4-one (87), 1-(2,6-diethylphenyl)-5-{[2-fluoro-4-(1-methyl-2-oxo-1,2-dihydropyridin-3-yl)phenyl]methyl}-6-hydroxy-2-(1-methyl-1H-pyrazol-3-yl)-1,4-dihydropyrimidin-4-one (88), 4'-{[1-(2,6-diethylphenyl)-6-hydroxy-2-(1-methyl-1H-pyrazol-3-yl)-4-oxo-1,4-dihydropyrimidin-5-yl]methyl}-3',4-difluoro-[1,1'-biphenyl]-2-carboxamide (89), 1-(2,6-diethylphenyl)-5-{[3-fluoro-4-(1-methyl-2-oxo-1,2-dihydropyridin-3-yl)phenyl]methyl}-6-hydroxy-2-[1-(2-methylpropyl)-1H-pyrazol-3-yl]-1,4-dihydropyrimidin-4-one (90), 1-(2,6-diethylphenyl)-5-{[3-fluoro-4-(2-fluoro-3-methylpyridin-4-yl)phenyl]methyl}-6-hydroxy-2-[1-(2-methylpropyl)-1H-pyrazol-3-yl]-1,4-dihydropyrimidin-4-one (91), 4'-{[1-(2,6-diethylphenyl)-6-hydroxy-2-[1-(2-methylpropyl)-1H-pyrazol-3-yl]-4-oxo-1,4-dihydropyrimidin-5-yl]methyl}-2',4-difluoro-[1,1'-biphenyl]-2-carboxamide (92), 2-(1-cyclopropyl-1H-pyrazol-3-yl)-1-(2,6-diethylphenyl)-5-{[3-fluoro-4-(1-methyl-2-oxo-1,2-dihydropyridin-3-yl)phenyl]methyl}-6-hydroxy-1,4-dihydropyrimidin-4-one (93), 4'-{[2-(1-cyclopropyl-1H-pyrazol-3-yl)-1-(2,6-diethylphenyl)-6-hydroxy-4-oxo-1,4-dihydropyrimidin-5-yl]methyl}-2',4-difluoro-[1,1'-biphenyl]-2-carboxamide (94), (S)-3-(1-(2-butyl-5-(4-(6-fluoro-2-methylpyridin-3-yl)benzyl)-6-hydroxy-4-oxopyrimidin-1(4H)-yl)propyl)benzonitrile (95), 3-[(1S)-1-(2-butyl-6-hydroxy-5-{[4-(2-methylpyridin-3-yl)phenyl]methyl}-4-oxo-1,4-dihydropyrimidin-1-yl)propyl]benzonitrile (96), 3-[(1S)-1-(2-butyl-5-{[4-(6-fluoropyridin-3-yl)phenyl]methyl}-6-hydroxy-4-oxo-1,4-dihydropyrimidin-1-yl)propyl]benzonitrile (97), 3-[(1S)-1-(2-butyl-6-hydroxy-5-{[4-(3-methylpyridin-4-yl)phenyl]methyl}-4-oxo-1,4-dihydropyrimidin-1-yl)propyl]benzonitrile (98), 3-[(1S)-1-(2-butyl-5-{[4-(2-fluoro-3-methylpyridin-4-yl)phenyl]methyl}-6-hydroxy-4-oxo-1,4-dihydropyrimidin-1-yl)propyl]benzonitrile (99), 3-[(1S)-1-(2-butyl-5-{[4-(5-chloro-2-oxo-1,2-dihydropyridin-1-yl)phenyl]methyl}-6-hydroxy-4-oxo-1,4-dihydropyrimidin-1-yl)propyl]benzonitrile (100), 3-[(1S)-1-{2-butyl-5-[(4-cyclopropylphenyl)methyl]-6-hydroxy-4-oxo-1,4-dihydropyrimidin-1-yl}propyl]benzonitrile (101), 3-[(1S)-1-{2-butyl-5-[(4-cyclopropylphenyl)methyl]-6-hydroxy-4-oxo-1,4-dihydropyrimidin-1-yl}propyl]benzonitrile (102), 2-butyl-5-{[4-(2-fluoro-3-methylpyridin-4-yl)phenyl]methyl}-1-[(1S)-1-(3-fluorophenyl)propyl]-6-hydroxy-1,4-dihydropyrimidin-4-one (103), 2-butyl-5-{[4-(6-fluoro-2-methylpyridin-3-yl)phenyl]methyl}-1-[(1S)-1-(3-fluorophenyl)propyl]-6-hydroxy-1,4-dihydropyrimidin-4-one (104), 2-butyl-1-[(1S)-1-(3-fluorophenyl)propyl]-6-hydroxy-5-{[4-(2-methylpyridin-3-yl)phenyl]methyl}-1,4-dihydropyrimidin-4-one (105), 2-butyl-1-[(1S)-1-(3-fluorophenyl)propyl]-6-hydroxy-5-{[4-(3-methylpyridin-4-yl)phenyl]methyl}-1,4-dihydropyrimidin-4-one (106), 2-(2-cyclopropylethyl)-1-[(1S)-1-(3,5-difluorophenyl)propyl]-5-{[4-(6-fluoro-2-methylpyridin-3-yl)phenyl]methyl}-6-hydroxy-1,4-dihydropyrimidin-4-one (107), 1-[(1S)-1-(3,5-difluorophenyl)propyl]-5-{[4-(2-fluoro-3-methylpyridin-4-yl)phenyl]methyl}-6-hydroxy-2-[(propan-2-yloxy)methyl]-1,4-dihydropyrimidin-4-one (108), 2-(2-cyclopropylethyl)-1-[(1S)-1-(3,5-difluorophenyl)propyl]-6-hydroxy-5-{[4-(2-methylpyridin-3-yl)phenyl]methyl}-1,4-dihydropyrimidin-4-one (109), 2-(2-cyclopropylethyl)-1-[(1S)-1-(3,5-difluorophenyl)propyl]-6-hydroxy-5-{[4-(3-methylpyridin-4-yl)phenyl]methyl}-1,4-dihydropyrimidin-4-one (110), 1-[(1S)-1-(3,5-difluorophenyl)propyl]-6-hydroxy-5-{[4-(2-methylpyridin-3-yl)phenyl]methyl}-2-[(propan-2-yloxy)methyl]-1,4-dihydropyrimidin-4-one (111), 1-[(1S)-1-(3,5-difluorophenyl)propyl]-5-{[4-(6-fluoro-2-methylpyridin-3-yl)phenyl]methyl}-6-hydroxy-2-[(propan-2-yloxy)methyl]-1,4-dihydropyrimidin-4-one (112), 2-(2-cyclopropylethyl)-1-[(1S)-1-(3,5-difluorophenyl)propyl]-5-{[4-(2-fluoro-3-methylpyridin-4-yl)phenyl]methyl}-6-hydroxy-1,4-dihydropyrimidin-4-one (113), 1-[(1S)-1-(3,5-difluorophenyl)propyl]-6-hydroxy-5-{[4-(3-methylpyridin-4-yl)phenyl]methyl}-2-[(propan-2-yloxy)methyl]-1,4-dihydropyrimidin-4-one (114), 1-[(1S)-1-(3,5-difluorophenyl)-2-methylpropyl]-6-hydroxy-5-{[4-(2-methylpyridin-3-yl)phenyl]methyl}-2-[(propan-2-yloxy)methyl]-1,4-dihydropyrimidin-4-one (115), 4'-({1-[(1S)-1-(3,5-difluorophenyl)-2-methylpropyl]-6-hydroxy-4-oxo-2-[(propan-2-yloxy)methyl]-1,4-dihydropyrimidin-5-yl}methyl)-4-fluoro-[1,1'-biphenyl]-2-carboxamide (116), 4'-{[2-(2-cyclopropylethyl)-1-[(1S)-1-(3,5-difluorophenyl)-2-methylpropyl]-6-hydroxy-4-oxo-1,4-dihydropyrimidin-5-yl]methyl}-4-fluoro-[1,1'-biphenyl]-2-carboxamide (117), 5-{[3-fluoro-4-(2-fluoro-3-methylpyridin-4-yl)phenyl]methyl}-6-hydroxy-2-(4-methyl-1,3-thiazol-2-yl)-1-[(1S)-1-phenylpropyl]-1,4-dihydropyrimidin-4-one (118), 5-{[3-fluoro-4-(1-methyl-2-oxo-1,2-dihydropyridin-3-yl)phenyl]methyl}-6-hydroxy-2-(4-methyl-1,3-thiazol-2-yl)-1-[(1S)-1-phenylpropyl]-1,4-dihydropyrimidin-4-one (119), 2',4-difluoro-4'-{[6-hydroxy-2-(4-methyl-1,3-thiazol-2-yl)-4-oxo-1-[(1S)-1-phenylpropyl]-1,4-dihydropyrimidin-5-yl]methyl}-[1,1'-biphenyl]-2-carboxamide (120), 3-fluoro-5-[(1S)-1-(6-hydroxy-5-{[4-(2-methylpyridin-3-yl)phenyl]methyl}-4-oxo-2-[(propan-2-yloxy)methyl]-1,4-dihydropyrimidin-1-yl)-2-methylpropyl]benzonitrile (121), 1-[(1R)-1-(3,5-difluorophenyl)-2-methoxyethyl]-2-(ethoxymethyl)-6-hydroxy-5-{[4-(3-methylpyridin-4-yl)phenyl]methyl}-1,4-dihydropyrimidin-4-one (122), 1-[(1R)-1-(3,5-difluorophenyl)-2-methoxyethyl]-2-(ethoxymethyl)-6-hydroxy-5-{[4-(2-methylpyridin-3-yl)phenyl]methyl}-1,4-dihydropyrimidin-4-one (123), 1-[(1R)-1-(3,5-difluorophenyl)-2-methoxyethyl]-2-(ethoxymethyl)-5-{[4-(6-fluoro-2-methylpyridin-3-yl)phenyl]methyl}-6-hydroxy-1,4-dihydropyrimidin-4-one (124), 1-[(1R)-1-(3,5-difluorophenyl)-2-methoxyethyl]-2-(ethoxymethyl)-5-{[4-(6-fluoropyridin-3-yl)phenyl]methyl}-6-hydroxy-1,4-dihydropyrimidin-4-one (125), 1-[(1R)-1-(3,5-difluorophenyl)-2-methoxyethyl]-2-(ethoxymethyl)-5-{[4-(2-fluoro-3-methylpyridin-4-yl)phenyl]methyl}-6-hydroxy-1,4-dihydropyrimidin-4-one (126), 2-butyl-1-[(1S)-1-(3,5-difluorophenyl)propyl]-6-hydroxy-5-{[3-(3-methylpyridin-4-yl)phenyl]methyl}-1,4-dihydropyrimidin-4-one (127), 2-butyl-1-[(1S)-1-(3,5-difluorophenyl)propyl]-5-{[3-(2-fluoro-3-methylpyridin-4-yl)phenyl]methyl}-6-hydroxy-1,4-dihydropyrimidin-4-one (128), 2-butyl-1-[(1S)-1-(3,5-difluorophenyl)propyl]-6-hydroxy-5-{[3-(2-methylpyridin-3-yl)phenyl]methyl}-1,4-dihydropyrimidin-4-one (129), 2-butyl-1-[(1S)-1-(3,5-difluorophenyl)propyl]-5-{[3-(6-fluoro-2-methylpyridin-3-yl)phenyl]methyl}-6-hydroxy-1,4-dihydropyrimidin-4-one (130), 3'-({2-butyl-1-[(1S)-1-(3,5-difluorophenyl)propyl]-6-hydroxy-4-oxo-1,4-dihydropyrimidin-5-yl}methyl)-4-fluoro-[1,1'-biphenyl]-2-carboxamide (131), 1-[(1S)-1-(3,5-difluorophenyl)propyl]-2-(1-ethyl-1H-pyrazol-3-yl)-5-{[4-(2-fluoro-3-methylpyridin-4-yl)phenyl]methyl}-6-hydroxy-1,4-dihydropyrimidin-4-one (132), 1-[(1S)-1-(3,5-difluorophenyl)propyl]-2-(1-ethyl-1H-pyrazol-3-yl)-6-hydroxy-5-{[4-(2-methylpyridin-3-yl)phenyl]methyl}-1,4-dihydropyrimidin-4-one (133), 1-[(1S)-1-(3,5-difluorophenyl)propyl]-2-(1-ethyl-1H-pyrazol-3-yl)-5-{[4-(6-fluoro-2-methylpyridin-3-yl)phenyl]methyl}-6-hydroxy-1,4-dihydropyrimidin-4-one (134), 1-[(1S)-1-(3,5-difluorophenyl)propyl]-2-(1-ethyl-1H-pyrazol-3-yl)-5-{[4-(6-fluoropyridin-3-yl)phenyl]methyl}-6-hydroxy-1,4-dihydropyrimidin-4-one (135), and 1-[(1S)-1-(3,5-difluorophenyl)propyl]-2-(1-ethyl-1H-pyrazol-3-yl)-6-hydroxy-5-{[4-(3-methylpyridin-4-yl)phenyl]methyl}-1,4-dihydropyrimidin-4-one (136), or a stereoisomer, a tautomer, or a pharmaceutically acceptable salt thereof.

12. A pharmaceutical composition, comprising a pharmaceutically acceptable carrier and a compound of claim 1, or a stereoisomer, a tautomer, or a pharmaceutically acceptable salt thereof.

13. A method of treating cardiovascular diseases, comprising administering to a patient in need there of a therapeutically effective amount of the pharmaceutical composition of claim 12.

14. The method of claim 13 wherein said cardiovascular diseases are coronary heart disease, stroke, heart failure, systolic heart failure, diastolic heart failure, diabetic heart failure, heart failure with preserved ejection fraction, cardiomyopathy, myocardial infarction, left ventricular dysfunction, left ventricular dysfunction after myocardial infarction, cardiac hypertrophy, myocardial remodeling, myocardial remodeling after infarction or after cardiac surgery and valvular heart diseases.

* * * * *